(12) United States Patent
Lombardi Borgia et al.

(10) Patent No.: US 9,616,059 B2
(45) Date of Patent: *Apr. 11, 2017

(54) SUBSTITUTED INDAZOLE DERIVATIVES ACTIVE AS KINASE INHIBITORS

(71) Applicant: NERVIANO MEDICAL SCIENCES S.R.L., Nerviano (MI) (IT)

(72) Inventors: Andrea Lombardi Borgia, Paullo (IT); Maria Menichincheri, Milan (IT); Paolo Orsini, Legnano (IT); Achille Panzeri, Merate (IT); Ettore Perrone, Boffalora Sopra Ticino (IT); Ermes Vanotti, Milan (IT); Marcella Nesi, Saronno (IT); Chiara Marchionni, Milan (IT)

(73) Assignee: NERVIANO MEDICAL SCIENCES S.R.L., Nerviano (MI) (IT)

( * ) Notice: Subject to any disclaimer, the term of this patent is extended or adjusted under 35 U.S.C. 154(b) by 0 days.

This patent is subject to a terminal disclaimer.

(21) Appl. No.: 14/971,372

(22) Filed: Dec. 16, 2015

(65) Prior Publication Data
US 2016/0095856 A1    Apr. 7, 2016

Related U.S. Application Data

(63) Continuation of application No. 14/534,617, filed on Nov. 6, 2014, now Pat. No. 9,255,087, which is a continuation of application No. 14/212,256, filed on Mar. 14, 2014, now Pat. No. 9,029,356, which is a continuation of application No. 13/611,679, filed on Sep. 12, 2012, now Pat. No. 8,673,893, which is a continuation of application No. 12/668,745, filed as application No. PCT/EP2008/058861 on Jul. 8, 2008, now Pat. No. 8,299,057.

(30) Foreign Application Priority Data

Jul. 20, 2007    (EP) .................................. 07112881

(51) Int. Cl.
*A61K 31/496*    (2006.01)
*A61K 45/06*    (2006.01)
*C07D 405/12*    (2006.01)
*C07D 231/56*    (2006.01)
*C07D 401/12*    (2006.01)
*C07D 401/14*    (2006.01)
*C07D 403/14*    (2006.01)
*C07D 405/04*    (2006.01)
*C07D 405/14*    (2006.01)

(52) U.S. Cl.
CPC .......... *A61K 31/496* (2013.01); *A61K 45/06* (2013.01); *C07D 231/56* (2013.01); *C07D 401/12* (2013.01); *C07D 401/14* (2013.01); *C07D 403/14* (2013.01); *C07D 405/04* (2013.01); *C07D 405/12* (2013.01); *C07D 405/14* (2013.01)

(58) Field of Classification Search
CPC .............................. A61K 31/496; A61K 45/06
USPC ....................... 514/253.09, 254.06, 322, 407
See application file for complete search history.

(56) References Cited

U.S. PATENT DOCUMENTS

| | | | |
|---|---|---|---|
| 8,114,865 B2 | 2/2012 | Bandiera et al. |
| 8,299,057 B2 | 10/2012 | Borgia et al. |
| 8,354,399 B2 | 1/2013 | Menichincheri et al. |
| 8,673,893 B2 | 3/2014 | Borgia et al. |
| 9,029,356 B2 | 5/2015 | Borgia et al. |
| 2004/0014802 A1 | 1/2004 | Dutruc-Rosset et al. |
| 2013/0018036 A1 | 1/2013 | Borgia et al. |
| 2014/0228351 A1 | 8/2014 | Borgia et al. |
| 2015/0065520 A1 | 3/2015 | Borgia et al. |

FOREIGN PATENT DOCUMENTS

| | | |
|---|---|---|
| WO | WO 03/051847 A1 | 6/2003 |
| WO | WO 03/078403 A2 | 9/2003 |

OTHER PUBLICATIONS

Banker G.S. et al., "Modern Pharmaceutics", 3rd Ed., p. 596 (1996).
Shaw A.T. et al., "Targeting Anaplastic Lymphoma Kinase in Lung Cancer", Clinical Cancer Research 17 (8):2081-2086 (2011).
Voskoglou-Nomikos T. et al., "Clinical Predictive Value of the In Vitro Cell Line, Human Xenograft, and Mouse Allograft Preclinical Cancer Models", Clinical Cancer Research 9:4227-4239 (Sep. 15, 2003).
Warner S.L. et al., "Targeting Aurora-2 Kinase in Cancer", Molecular Cancer Therapeutics 2:589-595 (Jun. 2003).
Weroha S.J. et al., "IGF-1 Receptor Inhibitors in Clinical Trials-Early Lessons", J. Mammary Gland Biol. Neoplasia 13(4):471-483 (Dec. 2008).
Wolff M.E., "Burger's Medicinal Chemistry and Drug Discovery", 5th Ed. Part 1, pp. 975-977 (1995).
U.S. Office Action dated Jul. 16, 2015 issued in corresponding U.S. Appl. No. 14/534,617.
U.S. Office Action dated Mar. 12, 2015 issued in corresponding U.S. Appl. No. 14/534,617.
U.S. Office Action dated Jun. 26, 2013 issued in corresponding U.S. Appl. No. 13/611,679.
U.S. Office Action dated Dec. 7, 2011 issued in corresponding U.S. Appl. No. 12/668,745.
International Search Report dated Oct. 2, 2008 issued in corresponding Application No. PCT/EP2008/058861.

*Primary Examiner* — Alexander R Pagano
*Assistant Examiner* — Ebenezer O Sackey
(74) *Attorney, Agent, or Firm* — Scully, Scott, Murphy & Presser, P.C.

(57) ABSTRACT

Substituted indazole derivatives of formula (I) and pharmaceutically acceptable salts thereof, as defined in the specification; the compounds of the invention may be useful in therapy in the treatment of diseases associated with a deregulated protein kinase activity, like cancer.

13 Claims, No Drawings

SUBSTITUTED INDAZOLE DERIVATIVES ACTIVE AS KINASE INHIBITORS

CROSS REFERENCE TO RELATED APPLICATIONS

The present application is a continuation of a co-pending application having U.S. Ser. No. 14/534,617, filed on Nov. 6, 2014, which is a continuation of application having U.S. Ser. No. 14/212,256, filed on Mar. 14, 2014, now U.S. Pat. No. 9,029,356, which is a continuation of application having U.S. Ser. No. 13/611,679, filed on Sep. 12, 2012, now U.S. Pat. No. 8,673,893, which is a continuation of the application having U.S. Ser. No. 12/668,745, filed on Feb. 8, 2010, now U.S. Pat. No. 8,299,057, which is a 371 of International application having Serial No. PCT/EP08/058861, filed on Jul. 8, 2008, which claims benefit of European Patent Application No. 07112881.3, filed on Jul. 20, 2007, the contents of all of which are incorporated herein by reference.

INCORPORATION BY REFERENCE OF SEQUENCE LISTING

The Sequence Listing in the ASCII text file, named as 24846_sequencelisting.txt of 2 KB, created on May 25, 2010, and submitted to the United States Patent and Trademark Office via EFS-Web, is incorporated herein by reference.

BACKGROUND OF THE INVENTION

The present invention relates to certain substituted indazole compounds, which modulate the activity of protein kinases. The compounds of this invention are therefore useful in treating diseases caused by deregulated protein kinase activity. The present invention also provides methods for preparing these compounds, pharmaceutical compositions comprising these compounds, and methods of treating diseases utilizing pharmaceutical compositions comprising these compounds.

The malfunctioning of protein kinases (PKs) is the hallmark of numerous diseases. A large share of the oncogenes and proto-oncogenes involved in human cancers encode for PKs. The enhanced activities of PKs are also implicated in many non-malignant diseases, such as benign prostate hyperplasia, familial adenomatosis, polyposis, neuro-fibromatosis, psoriasis, vascular smooth cell proliferation associated with atherosclerosis, pulmonary fibrosis, arthritis glomerulonephritis and post-surgical stenosis and restenosis.

PKs are also implicated in inflammatory conditions and in the multiplication of viruses and parasites. PKs may also play a major role in the pathogenesis and development of neurodegenerative disorders.

For a general reference to PKs malfunctioning or deregulation see, for instance, Current Opinion in Chemical Biology 1999, 3, 459-465. A subset of PK is a group of membrane receptors with intrinsic protein-tyrosine kinase activity (RPTK). Upon binding of grow factors, RPTKs become activated and phosphorylate themselves and a series of substrates in the cytoplasm. Through this mechanism, they can transduce intracellular signalings for proliferation, differentiation or other biological changes. Structural abnormalities, over-expression and activation of RTPKs are frequently observed in human tumors, suggesting that constitutive ignition of the signal transduction leading to cell proliferation can result in malignant transformation. Anaplastic lymphoma kinase (ALK) is a tyrosine kinase receptor belonging to the insulin receptor subfamily of RTKs: the ALK gene is located on chromosome 2 and is expressed mainly in neuronal cells, especially during development. The ALK gene is involved in a balanced chromosomal translocation with the Nucleophosmin (NPM) gene on chromosome 5 in a large subset of Anaplastic Large Cell Lymphomas (ALCL). In the ALK+ALCL, as a result of the translocation, the NPM ubiquitous promoter drives an ectopic expression of the fusion protein in which the NPM moiety dimerizes and the ALK kinase domain undergoes auto-phosphorylation and becomes constitutively active.

Many data from the literature have demonstrated that the NPM-ALK fusion protein has a strong oncogenic potential and its ectopic expression is responsible for cellular transformation. Moreover, the constitutive expression of human NPM-ALK in mouse T-cell lymphocytes is sufficient for the development of lymphoid neoplasia in transgenic animals with a short period of latency.

ALCL is a defined disease characterized by the surface expression of the CD30 antigen (Ki-1), and accounts for 2% of adult and 13% of pediatric non-Hodgkin's lymphomas, affecting predominantly young male patients. ALK+ALCL accounts for 70% of all ALCLs and is an aggressive disease with systemic signs, and frequent extranodal involvement (bone marrow, skin, bone, soft tissues).

About 15-20% of ALK-expressing ALCLs were found to bear a different chromosomal translocation, involving the cytoplasmic portion of ALK, with different N-terminal moieties, all resulting in constitutive activation of the ALK kinase domain. Moreover, cell lines established from solid tumors of ectodermal origin like melanomas, breast carcinomas, as well as neuroblastomas, glioblastomas, Ewings sarcomas, retinoblastomas, were found to express the ALK receptor.

In conclusion, interfering with the ALK signalling likely represents a specific and effective way to block tumor cell proliferation in ALCL and possibly other indications.

The insulin-like growth factor 1 receptor (IGF-1R, IGF1R) is also a member of the insulin receptor subfamily of RTKs.

There exist several lines of evidence suggesting that IGF-1R signaling can contribute to tumorigenesis, and that interfering with IGF-1R function represents a valid therapeutic option in cancer. For an overview of IGFs and IGF-1R signalling, physiological function, and detailed description of the evidence supporting involvement of this system in human cancer that is summarised above, as well as in other pathologies, the reader is directed to the many reviews on the subject and references contained therein, for example Baserga R. et al, Biochim Biophys Acta vol. 1332, pages F105-F126, 1997; Khandwala H. M. et al, Endocr Rev vol. 21, pages 215-44, 2000; Le Roith D. et al, Endocr Rev vol. 22, pages 53-74, 2001; Valentinis B. et al, Mol Pathol vol. 54, pages 133-7, 2001; Wang Y. et al, Curr Cancer Drug Targets vol. 2, pages 191-207, 2002; Laron, Z. J Clin Endocrinol Metab vol. 89, pages 1031-1044, 2004; Hofmann F et al, Drug Discov Today vol. 10, pages 1041-7, 2005.

SUMMARY OF THE INVENTION

3-Amino and 3-acylamino indazole derivatives for the treatment of neurodegenerative diseases, cerebrovascular accidents, obesity, cardiovascular diseases and cancer are disclosed in WO2006003276, WO2004022544 and WO 2003078403 in the name of Aventis Pharma SA.

Indazolylamide derivatives for the treatment of diabetes, neurodegenerative conditions such as Alzheimer's disease and Parkinson's disease are disclosed in WO2003051847 in the name of SmithKline Beecham P. L. C.

Indazole derivatives for the treatment of tumor disease, viral disease, immunosuppression in transplantation, cystic fibrosis and diseases associated with angiogenesis are disclosed in WO2008003396 in the name of Merck GMBH. Despite these developments, there is still a need for more effective agents for the treatment of such diseases We have now discovered that a series of indazoles are potent protein kinase inhibitors and are thus useful in anticancer therapy.

Accordingly, a first object of the present invention is to provide a substituted indazole compound represented by formula (I),

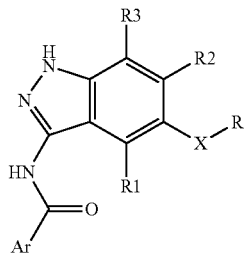

wherein:

X is —$CH_2$—, —CH(OH)—, —CH(OR')— or —C(R'R")—, wherein:

R' is an optionally further substituted straight or branched $C_1$-$C_6$ alkyl and R" is hydrogen or an optionally further substituted straight or branched $C_1$-$C_6$ alkyl;

Ar is aryl or heteroaryl optionally substituted with one or more substituents independently selected from halogen, $C_2$-$C_6$ alkenyl, $C_2$-$C_6$ alkynyl, cyano, nitro, NHCOR4, COR4, NR5R6, NR5COR4, OR7, SR7, SOR10, $SO_2$R10, NHSOR10, NHSO$_2$R10, R8R9N—$C_1$-$C_6$ alkyl, R8O—$C_1$-$C_6$ alkyl, an optionally further substituted straight or branched $C_1$-$C_6$ alkyl, $C_3$-$C_6$ cycloalkyl, heterocyclyl, aryl and heteroaryl, wherein:

R4 is hydrogen, $C_2$-$C_6$ alkenyl, $C_2$-$C_6$ alkynyl, NR5R6, OR7, SR7, R8R9N—$C_1$-$C_6$ alkyl, R8O—$C_1$-$C_6$ alkyl, an optionally further substituted straight or branched $C_1$-$C_6$ alkyl, $C_3$-$C_6$ cycloalkyl, heterocyclyl, aryl or heteroaryl;

R5 and R6 are independently hydrogen, $C_2$-$C_6$ alkenyl, $C_2$-$C_6$ alkynyl, R8R9N—$C_2$-$C_6$ alkyl, R8O—$C_2$-$C_6$ alkyl, an optionally further substituted straight or branched $C_1$-$C_6$ alkyl, $C_3$-$C_6$ cycloalkyl, heterocyclyl, aryl or heteroaryl, or R5 and R6, taken together with the nitrogen atom to which they are bonded, may form an optionally substituted heterocyclyl group;

R7 is hydrogen, $C_2$-$C_6$ alkenyl, $C_2$-$C_6$ alkynyl, COR4, SOR10, $SO_2$R10, R8R9N—$C_2$-$C_6$ alkyl, R8O—$C_2$-$C_6$ alkyl, an optionally further substituted straight or branched $C_1$-$C_6$ alkyl, $C_3$-$C_6$ cycloalkyl, heterocyclyl, aryl or heteroaryl, wherein R4 is as defined above;

R8 and R9 are independently hydrogen, $C_2$-$C_6$ alkenyl, $C_2$-$C_6$ alkynyl, COR4, an optionally further substituted straight or branched $C_1$-$C_6$ alkyl, $C_3$-$C_6$ cycloalkyl, heterocyclyl, aryl or heteroaryl, or R8 and R9, taken together with the nitrogen atom to which they are bonded, may form an optionally substituted heterocyclyl group, wherein R4 is as defined above;

R10 is hydrogen, $C_2$-$C_6$ alkenyl, $C_2$-$C_6$ alkynyl, NR5R6, OR7, R8R9N—$C_1$-$C_6$ alkyl, R8O—$C_1$-$C_6$ alkyl, an optionally further substituted straight or branched $C_1$-$C_6$ alkyl, $C_3$-$C_6$ cycloalkyl, heterocyclyl, aryl or heteroaryl, wherein R5, R6, R7, R8 and R9 are as defined above;

R is an optionally substituted straight or branched $C_1$-$C_6$ alkyl, $C_3$-$C_6$ cycloalkyl, heterocyclyl, aryl or heteroaryl;

R1, R2 and R3 are independently hydrogen, halogen, nitro, an optionally substituted straight or branched $C_1$-$C_6$ alkyl, NR5R6, or OR7, wherein R5, R6 and R7 are as defined above;

or isomers, tautomers, prodrugs or pharmaceutically acceptable salt thereof.

The present invention also provides methods of synthesizing the substituted indazole derivatives of formula (I) prepared through a process consisting of standard synthetic transformations.

The present invention also provides a method for treating diseases caused by and/or associated with deregulated protein kinase activity, particularly PLK family, protein kinase C in different isoforms, Met, PAK-4, PAK-5, ZC-1, STLK-2, DDR-2, Aurora 1, Aurora 2, Bub-1, Chk1, Chk2, HER2, raf1, MEK1, MAPK, EGF-R, PDGF-R, FGF-R, FLT3, JAK2, IGF-R, ALK, PI3K, weel kinase, Src, Abl, Akt, MAPK, ILK, MK-2, IKK-2, Cdc7, Nek, Cdk/cyclin kinase family, more particularly Aurora 2, IGF-1R and ALK activity, and further more particularly ALK activity, which comprises administering to a mammal in need thereof an effective amount of a substituted indazole compound represented by formula (I) as defined above.

A preferred method of the present invention is to treat a disease caused by and/or associated with dysregulated protein kinase activity selected from the group consisting of cancer and cell proliferative disorders.

Another preferred method of the present invention, is to treat specific types of cancer including carcinoma, squamous cell carcinoma, hematopoietic tumors of myeloid or lymphoid lineage, tumors of mesenchymal origin, tumors of the central and peripheral nervous system, melanoma, seminoma, teratocarcinoma, osteosarcoma, xeroderma pigmentosum, keratocanthomas, thyroid follicular cancer and Kaposi's sarcoma.

Another preferred method of the present invention, is to treat specific types of cancer such as, but not restricted to, breast cancer, lung cancer, colorectal cancer, prostate cancer, ovarian cancer, endometrial cancer, gastric cancer, clear cell renal cell carcinoma, uveal melanoma, multiple myeloma, rhabdomyosarcoma, Ewing's sarcoma, Kaposi's sarcoma, and medulloblastoma.

Another preferred method of the present invention, is to treat ALK+Anaplastic Large Cell Lymphomas (ALCL) and possibly other indications in which the ALK activity might play a role, like Neuroblastoma, Rhabdomyosarcoma, Glioblastoma, Inflammatory MyofibroblasticTumor, and some kind of Melanomas, Breast Carcinomas, Ewings sarcomas, Retinoblastomas and Non Small Cell Lung Carcinomas (NSCLC).

Another preferred method of the present invention, is to treat cell proliferative disorders such as, but not restricted to, benign prostate hyperplasia, familial adenomatosis polyposis, neuro-fibromatosis, psoriasis, atherosclerosis and conditions involving vascular smooth muscle proliferation or neointimal formation such as restenosis following angioplasty or surgery, pulmonary fibrosis, arthritis, glomerulonephritis, retinopathies including diabetic and neonatal retinopathies and age related macular degeneration, graft vessel disease, such as can occur following vessel or organ transplantation, acromegaly and disorders secondary to acromegaly as well as other hypertrophic conditions in which IGF/IGF-1R signalling is implicated, such as fibrotic lung disease, pathologies related to chronic or acute oxidative stress or hyperoxia induced tissue damage, and metabolic disorders in which elevated IGF levels or IGF-1R activity are implicated, such as obesity.

In addition, the method of the present invention also provides tumor angiogenesis and metastasis inhibition.

In a further preferred embodiment, the method of the present invention further comprises subjecting the mammal in need thereof to a radiation therapy or chemotherapy regimen in combination with at least one cytostatic or cytotoxic agent.

Moreover the invention provides a method for inhibiting the activity ALK protein which comprises contacting the said protein with an effective amount of a compound of formula (I).

The present invention also provides a pharmaceutical composition comprising one or more compounds of formula (I) or a pharmaceutically acceptable salt thereof and a pharmaceutically acceptable excipient, carrier or diluent.

The present invention further provides a pharmaceutical composition comprising a compound of formula (I) in combination with one or more chemotherapeutic agents or radiotherapy. Such agents can include, but are not limited to, antihormonal agents such as antiestrogens, antiandrogens and aromatase inhibitors, topoisomerase I inhibitors, topoisomerase II inhibitors, agents that target microtubules, platin-based agents, alkylating agents, DNA damaging or intercalating agents, antineoplastic antimetabolites, other kinase inhibitors, other anti-angiogenic agents, inhibitors of kinesins, therapeutic monoclonal antibodies, inhibitors of mTOR, histone deacetylase inhibitors, farnesyl transferase inhibitors, and inhibitors of hypoxic response.

Additionally, the invention provides a product or kit comprising a compound of formula (I) or a pharmaceutically acceptable salt thereof, as defined above, or pharmaceutical compositions thereof and one or more chemotherapeutic agents, as a combined preparation for simultaneous, separate or sequential use in anticancer therapy.

In yet another aspect the invention provides a compound of formula (I) or a pharmaceutically acceptable salt thereof, as defined above, for use as a medicament. Moreover the invention provides the use of a compound of formula (I) or a pharmaceutically acceptable salt thereof, as defined above, in the manufacture of a medicament with antitumor activity.

Finally, the invention provides a compound of formula (I) or a pharmaceutically acceptable salt thereof, as defined above, for use in a method of treating cancer.

DETAILED DESCRIPTION OF THE INVENTION

The compounds of formula (I) may have one or more asymmetric centres, and may therefore exist as individual optical isomers or racemic mixtures. Accordingly, all the possible isomers, and their mixtures, of the compounds of formula (I) are within the scope of the present invention.

Derivatives of compounds of formula (I) originating from metabolism in a mammal, and the pharmaceutically acceptable bio-precursors (otherwise referred to as pro-drugs) of the compounds of formula (I) are also within the scope of the present invention.

In addition to the above, as known to those skilled in the art, the unsubstituted nitrogen on the pyrazole ring of the compounds of formula (I) rapidly equilibrates in solution to form a mixture of tautomers, as depicted below:

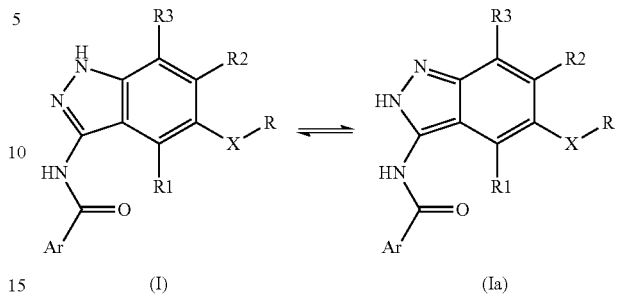

wherein X, Ar, R, R1, R2 and R3 are as defined above.

Accordingly, in the present invention, where only one tautomer is indicated for the compounds of formula (I), the other tautomer (Ia) is also within the scope of the present invention, unless specifically noted otherwise.

The general terms as used herein, unless otherwise specified, have the meaning reported below.

The term "straight or branched $C_1$-$C_6$ alkyl" refers to a saturated aliphatic hydrocarbon radical, including straight chain and branched chain groups of from 1 to 6 carbon atoms, e.g. methyl, ethyl, propyl, 2-propyl, n-butyl, isobutyl, tert-butyl, pentyl and the like. The alkyl group may be substituted or unsubstituted. When substituted, the substituent groups are preferably one to three, independently selected from the group consisting of halogen, $C_2$-$C_6$ alkenyl, $C_2$-$C_6$ alkynyl, cyano, nitro, NHCOR4, COR4, NR5R6, NR5COR4, OR7, SR7, SOR10, $SO_2$R10, NHSOR10, $NHSO_2$R10, R8R9N—$C_1$-$C_6$ alkyl, R8O—$C_1$-$C_6$ alkyl, an optionally further substituted $C_3$-$C_6$ cycloalkyl, heterocyclyl and aryl, wherein R4, R5, R6, R7, R8, R9 and R10 are as defined above.

The term "$C_3$-$C_6$ cycloalkyl" refers to a 3- to 6-membered all-carbon monocyclic ring, which may contain one or more double bonds but does not have a completely conjugated π-electron system. Examples of cycloalkyl groups, without limitation, are cyclopropyl, cyclobutyl, cyclopentyl, cyclopentenyl, cyclohexyl, cyclohexenyl and cyclohexadienyl. A cycloalkyl group may be substituted or unsubstituted. When substituted, the substituent groups are preferably one or two substituents, independently selected from the group consisting of halogen, $C_2$-$C_6$ alkenyl, $C_2$-$C_6$ alkynyl, cyano, nitro, NHCOR4, COR4, NR5R6, NR5COR4, OR7, SR7, SOR10, $SO_2$R10, NHSOR10, $NHSO_2$R10, R8R9N—$C_1$-$C_6$ alkyl, R8O—$C_1$-$C_6$ alkyl, an optionally further substituted straight or branched $C_1$-$C_6$ alkyl, $C_3$-$C_6$ cycloalkyl, heterocyclyl and aryl, wherein R4, R5, R6, R7, R5, R9 and R10 are as defined above.

The term "heterocyclyl" refers to a 3- to 7-membered, saturated or partially unsaturated carbocyclic ring where one or more carbon atoms are replaced by heteroatoms such as nitrogen, oxygen and sulfur. Not limiting examples of heterocyclyl groups are, for instance, oxiranyl, aziridinyl, oxetanyl, azetidinyl, tetrahydrofuranyl, dihydrofuranyl, tetrahydrothiophenyl, dihydrothiophenyl, pyrrolidinyl, dihydropyrrolyl, pyranyl, dihydropyranyl, tetrahydropyranyl, tetrahydrothiopyranyl, piperidinyl, pyrazolinyl, isoxazolidinyl, isoxazolinyl, thiazolidinyl, thiazolinyl, isothiazolinyl, dioxanyl, piperazinyl, morpholinyl, thiomorpholinyl, examethyleneiminyl, homopiperazinyl and the like. A heterocyclyl group may be substituted or unsubstituted. When substituted, the substituent groups are preferably one or two substituents, independently selected from the group consisting of halogen, $C_2$-$C_6$ alkenyl, $C_2$-$C_6$ alkynyl, cyano, nitro, NHCOR4, COR4, NR5R6, NR5COR4, OR7, SR7, SOR10, $SO_2R10$, NHSOR10, $NHSO_2R10$, R8R9N—$C_1$-$C_6$ alkyl, R8O—$C_1$-$C_6$ alkyl, an optionally further substituted straight or branched $C_1$-$C_6$ alkyl, $C_3$-$C_6$ cycloalkyl, heterocyclyl and aryl, wherein R4, R5, R6, R7, R8, R9 and R10 are as defined above.

The term "aryl" refers to a mono-, bi- or poly-carbocyclic hydrocarbon with from 1 to 4 ring systems, optionally further fused or linked to each other by single bonds, wherein at least one of the carbocyclic rings is "aromatic", wherein the term "aromatic" refers to completely conjugated pi-electron bond system. Non limiting examples of such aryl groups are phenyl, α- or β-naphthyl or biphenyl groups.

The term "heteroaryl" refers to aromatic heterocyclic rings, typically 5- to 7-membered heterocycles with from 1 to 3 heteroatoms selected among N, O or S; the heteroaryl ring can be optionally further fused or linked to aromatic and non-aromatic carbocyclic and heterocyclic rings. Not limiting examples of such heteroaryl groups are, for instance, pyridyl, pyrazinyl, pyrimidinyl, pyridazinyl, indolyl, imidazolyl, thiazolyl, isothiazolyl, pyrrolyl, phenyl-pyrrolyl, furyl, phenyl-furyl, oxazolyl, isoxazolyl, pyrazolyl, thienyl, benzothienyl, isoindolinyl, benzoimidazolyl, quinolinyl, isoquinolinyl, 1,2,3-triazolyl, 1-phenyl-1,2,3-triazolyl, 2,3-dihydroindolyl, 2,3-dihydrobenzofuranyl, 2,3-dihydrobenzothiophenyl; benzopyranyl, 2,3-dihydrobenzoxazinyl, 2,3-dihydroquinoxalinyl and the like.

The aryl and heteroaryl groups can be optionally substituted by one or more, preferably one, two or three substituents independently selected from halogen, $C_2$-$C_6$ alkenyl, $C_2$-$C_6$ alkynyl, cyano, nitro, NHCOR4, COR4, NR5R6, NR5COR4, OR7, SR7, SOR10, $SO_2R10$, NHSOR10, $NHSO_2R10$, R8R9N—$C_1$-$C_6$ alkyl, R8O—$C_1$-$C_6$ alkyl, an optionally further substituted straight or branched $C_1$-$C_6$ alkyl, $C_3$-$C_6$ cycloalkyl, heterocyclyl and aryl, wherein R4, R5, R6, R7, R8, R9 and R10 are as defined above.

The term "halogen" indicates fluorine, chlorine, bromine or iodine.

The term "$C_2$-$C_6$ alkenyl" indicates an aliphatic $C_2$-$C_6$ hydrocarbon chain containing at least one carbon-carbon double bond and which can be straight or branched. Representative examples include, but are not limited to, ethenyl, 1-propenyl, 2-propenyl, 1- or 2-butenyl, and the like.

The term "$C_2$-$C_6$ alkynyl" indicates an aliphatic $C_2$-$C_6$ hydrocarbon chain containing at least one carbon-carbon double bond and which can be straight or branched. Representative examples include, but are not limited to, ethynyl, 1-propynyl, 2-propynyl, 1- or 2-butynyl, and the like.

The term "cyano" indicates a —CN residue.

The term "nitro" indicates a —$NO_2$ group.

The term "pharmaceutically acceptable salt" of compounds of formula (I) refers to those salts that retain the biological effectiveness and properties of the parent compound. Such salts include acid addition salts with inorganic acids such as hydrochloric, hydrobromic, nitric, phosphoric, sulfuric, perchloric acid and the like, or with organic acids such as acetic, trifluoroacetic, propionic, glycolic, lactic, (D) or (L) malic, maleic, methanesulfonic, ethanesulfonic, benzoic, p-toluenesulfonic, salicylic, cinnamic, mandelic, tartaric, citric, succinic, malonic acid and the like; salts formed when an acidic proton present in a compound of formula (I) is either replaced by a metal ion, e.g., an alkali metal ion such as sodium or potassium, or an alkaline earth ion such as calcium or magnesium, or coordinates with an organic base such as ethanolamine, diethanolamine, triethanolamine, tromethamine, N-methylglucamine, and the like.

Compounds of formula (I) wherein X is —$CH_2$—, are represented by the general formula ($I_A$):

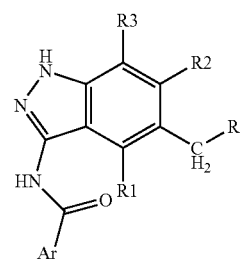

(I$_A$)

Compounds of formula (I) wherein X is —CH(OH)—, are represented by the general formula ($I_B$):

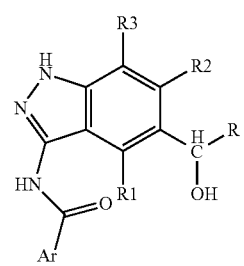

(I$_B$)

Compounds of formula (I) wherein X is —CH(OR')—, are represented by the general formula ($I_C$):

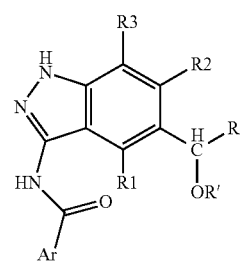

(I$_C$)

Compounds of formula (I) wherein X is —C(R'R")—, are represented by the general formula ($I_D$):

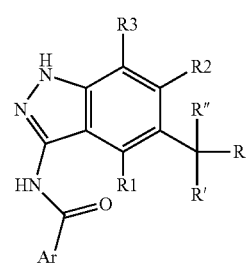

(I$_D$)

A preferred class of compounds of formula (I) are the compounds wherein:

X is —CH$_2$—, —CH(OH)—, —CH(OR')— or —C(R'R")—, wherein R' is C$_1$-C$_3$ alkyl and R" is hydrogen or C$_1$-C$_3$ alkyl;

R is an optionally substituted C$_3$-C$_6$ cycloalkyl, heterocyclyl, aryl or heteroaryl, and R1, R2 and R3 are independently hydrogen, halogen or hydroxy.

Another preferred class of compounds of formula (I) are the compounds wherein:

X is —CH$_2$—, —CH(OH)—, —CH(OR')— or —C(R'R")—, wherein R' is methyl and R" is hydrogen or methyl, and R1, R2 and R3 are hydrogen.

A further preferred class of compounds of formula (I) are the compounds wherein R is an optionally substituted aryl or heteroaryl.

A more preferred class of compounds of formula (I) are the compounds wherein Ar is a group of formula:

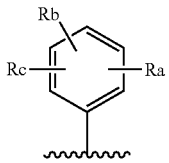

wherein Ra, Rb and Rc are independently hydrogen, halogen, C$_2$-C$_6$ alkenyl, C$_2$-C$_6$ alkynyl, cyano, nitro, NHCOR4, COR4, NR5R6, NR5COR4, OR7, SR7, SOR10, SO$_2$R10, NHSOR10, NHSO$_2$R10, R8R9N—C$_1$-C$_6$ alkyl, R8O—C$_1$-C$_6$ alkyl, an optionally further substituted straight or branched C$_1$-C$_6$ alkyl, C$_3$-C$_6$ cycloalkyl, heterocyclyl, aryl or heteroaryl, wherein R4, R5, R6, R7, R8, R9 and R10 are as defined above and R is an optionally substituted aryl.

A further more preferred class of compounds of formula (I) are the compounds wherein:

Ar is a group of formula:

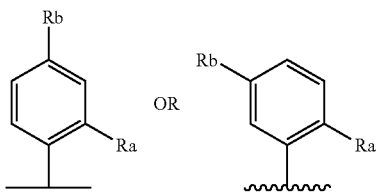

wherein Ra and Rb are as defined above.

A most preferred class of compounds of formula (I) are the compounds wherein:

Ar is a group of formula:

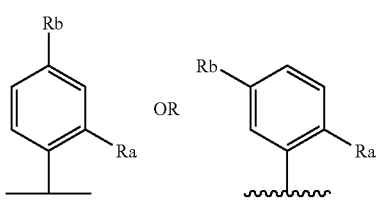

wherein Ra is hydrogen, halogen, nitro, NHCOR4 or NR5R6 and Rb is hydrogen, nitro, NR5R6, OR7 or R8R9N—C$_1$-C$_6$ alkyl wherein R4, R5, R6, R7, R8 and R9 are as defined above.

Specific compounds (cpd.) of the invention are listed below:

1. N-(5-benzyl-1H-indazol-3-yl)-4-(4-methyl-piperazin-1-yl)-benzamide;
2. N-[5-(3-fluoro-benzyl)-1H-indazol-3-yl]-4-(4-methyl-piperazin-1-yl)-benzamide;
3. N-[5-(2,5-difluoro-benzyl)-1H-indazol-3-yl]-4-(4-methyl-piperazin-1-yl)benzamide;
4. N-[5-(3,5-difluoro-benzyl)-1H-indazol-3-yl]-4-(4-methyl-piperazin-1-yl)benzamide;
5. N-[5-(3-fluoro-benzyl)-1H-indazol-3-yl]-4-(4-methyl-piperazin-1-yl)-2-nitrobenzamide;
6. N-[5-(3,5-difluoro-benzyl)-1H-indazol-3-yl]-4-(4-methyl-piperazin-1-yl)-2-nitro-benzamide;
7. 2-Amino-N-[5-(3-fluoro-benzyl)-1H-indazol-3-yl]-4-(4-methyl-piperazin-1-yl)-benzamide;
8. 2-Amino-N-[5-(3,5-difluoro-benzyl)-1H-indazol-3-yl]-4-(4-methyl-piperazin-1-yl)-benzamide;
9. N-[5-(3-fluoro-benzyl)-1H-indazol-3-yl]-4-(4-methyl-piperazin-1-yl)-2-(tetrahydro-pyran-4-ylamino)-benzamide;
10. N-[5-(2,5-difluoro-benzyl)-1H-indazol-3-yl]-4-(4-methyl-piperazin-1-yl)-2-(tetrahydro-pyran-4-ylamino)-benzamide;
11. N-[5-(3,5-difluoro-benzyl)-1H-indazol-3-yl]-4-(4-methyl-piperazin-1-yl)-2-(tetrahydro-pyran-4-ylamino)-benzamide;
12. N-[5-(3-fluoro-benzyl)-1H-indazol-3-yl]-4-(4-methyl-piperazin-1-yl)-2-(1-methyl-piperidin-4-ylamino)-benzamide;
13. N-[5-(3,5-difluoro-benzyl)-1H-indazol-3-yl]-4-(4-methyl-piperazin-1-yl)-2-(1-methyl-piperidin-4-ylamino)-benzamide;
14. N-[5-(3-fluoro-benzyl)-1H-indazol-3-yl]-2-(2-methoxy-1-methoxymethyl-ethylamino)-4-(4-methyl-piperazin-1-yl)-benzamide;
15. N-[5-(2,5-difluoro-benzyl)-1H-indazol-3-yl]-2-(2-methoxy-1-methoxymethyl-ethylamino)-4-(4-methyl-piperazin-1-yl)-benzamide;
16. N-[5-(3,5-difluoro-benzyl)-1H-indazol-3-yl]-2-(2-methoxy-1-methoxymethyl-ethylamino)-4-(4-methyl-piperazin-1-yl)-benzamide;
17. 2-cyclohexylamino-N-[5-(3-fluoro-benzyl)-1H-indazol-3-yl]-4-(4-methyl-piperazin-1-yl)-benzamide;
18. 2-cyclohexylamino-N-[5-(3,5-difluoro-benzyl)-1H-indazol-3-yl]-4-(4-methyl-piperazin-1-yl)-benzamide;
19. N-[5-(3-fluoro-benzyl)-1H-indazol-3-yl]-2-(4-hydroxy-cyclohexylamino)-4-(4-methyl-piperazin-1-yl)-benzamide;
20. N-[5-(3,5-difluoro-benzyl)-1H-indazol-3-yl]-2-(4-hydroxy-cyclohexylamino)-4-(4-methyl-piperazin-1-yl)-benzamide;
21. N-[5-(3-fluoro-benzyl)-1H-indazol-3-yl]-2-isobutylamino-4-(4-methyl-piperazin-1-yl)-benzamide;
22. N-[5-(3,5-difluoro-benzyl)-1H-indazol-3-yl]-2-isobutylamino-4-(4-methyl-piperazin-1-yl)-benzamide;
23. 2-benzylamino-N-[5-(3-fluoro-benzyl)-1H-indazol-3-yl]-4-(4-methyl-piperazin-1-yl)-benzamide;
24. 2-benzylamino-N-[5-(3,5-difluoro-benzyl)-1H-indazol-3-yl]-4-(4-methyl-piperazin-1-yl)-benzamide;
25. N-[5-(3-fluoro-benzyl)-1H-indazol-3-yl]-2-(2-methoxy-ethylamino)-4-(4-methyl-piperazin-1-yl)-benzamide;
26. N-[5-(3,5-difluoro-benzyl)-1H-indazol-3-yl]-2-(2-methoxy-ethylamino)-4-(4-methyl-piperazin-1-yl)-benzamide;

27. N-[5-(3-fluoro-benzyl)-1H-indazol-3-yl]-2-(2-methoxy-1-methyl-ethylamino)-4-(4-methyl-piperazin-1-yl)-benzamide;
28. N-[5-(3,5-difluoro-benzyl)-1H-indazol-3-yl]-2-(2-methoxy-1-methyl-ethylamino)-4-(4-methyl-piperazin-1-yl)-benzamide;
29. N-[5-(3-fluoro-benzyl)-1H-indazol-3-yl]-2-((S)-2-methoxy-1-methyl-ethylamino)-4-(4-methyl-piperazin-1-yl)-benzamide;
30. N-[5-(3,5-difluoro-benzyl)-1H-indazol-3-yl]-2-((S)-2-methoxy-1-methyl-ethylamino)-4-(4-methyl-piperazin-1-yl)-benzamide;
31. N-[5-(3-fluoro-benzyl)-1H-indazol-3-yl]-2-((R)-2-methoxy-1-methyl-ethylamino)-4-(4-methyl-piperazin-1-yl)-benzamide;
32. N-[5-(3,5-difluoro-benzyl)-1H-indazol-3-yl]-2-((R)-2-methoxy-1-methyl-ethylamino)-4-(4-methyl-piperazin-1-yl)-benzamide;
33. N-[5-(3-fluoro-benzyl)-1H-indazol-3-yl]-2-(2-methoxy-1,1-dimethyl-ethylamino)-4-(4-methyl-piperazin-1-yl)-benzamide;
34. N-[5-(3,5-difluoro-benzyl)-1H-indazol-3-yl]-2-(2-methoxy-1,1-dimethyl-ethylamino)-4-(4-methyl-piperazin-1-yl)-benzamide;
35. N-[5-(3-fluoro-benzyl)-1H-indazol-3-yl]-2-(3-methoxy-propylamino)-4-(4-methyl-piperazin-1-yl)-benzamide;
36. N-[5-(3,5-difluoro-benzyl)-1H-indazol-3-yl]-2-(3-methoxy-propylamino)-4-(4-methyl-piperazin-1-yl)-benzamide;
37. N-[5-(3-fluoro-benzyl)-1H-indazol-3-yl]-2-(2-fluoro-ethylamino)-4-(4-methyl-piperazin-1-yl)-benzamide;
38. N-[5-(3,5-difluoro-benzyl)-1H-indazol-3-yl]-2-(2-fluoro-ethylamino)-4-(4-methyl-piperazin-1-yl)-benzamide;
39. N-[5-(3-fluoro-benzyl)-1H-indazol-3-yl]-2-(3-fluoro-propylamino)-4-(4-methyl-piperazin-1-yl)-benzamide;
40. N-[5-(3,5-difluoro-benzyl)-1H-indazol-3-yl]-2-(3-fluoro-propylamino)-4-(4-methyl-piperazin-1-yl)-benzamide;
41. N-[5-(3-fluoro-benzyl)-1H-indazol-3-yl]-4-(4-methyl-piperazin-1-yl)-2-phenylamino-benzamide;
42. N-[5-(3,5-difluoro-benzyl)-1H-indazol-3-yl]-4-(4-methyl-piperazin-1-yl)-2-phenylamino-benzamide;
43. 1H-pyrrole-2-carboxylic acid [2-[5-(3-fluoro-benzyl)-1H-indazol-3-ylcarbamoyl]-5-(4-methyl-piperazin-1-yl)-phenyl]-amide;
44. 1H-pyrrole-2-carboxylic acid [2-[5-(3,5-difluoro-benzyl)-1H-indazol-3-ylcarbamoyl]-5-(4-methyl-piperazin-1-yl)-phenyl]-amide;
45. 1H-pyrrole-3-carboxylic acid [2-[5-(3-fluoro-benzyl)-1H-indazol-3-ylcarbamoyl]-5-(4-methyl-piperazin-1-yl)-phenyl]-amide;
46. 1H-pyrrole-3-carboxylic acid [2-[5-(3,5-difluoro-benzyl)-1H-indazol-3-ylcarbamoyl]-5-(4-methyl-piperazin-1-yl)-phenyl]-amide;
47. N-[5-(3-fluoro-benzyl)-1H-indazol-3-yl]-2-methanesulfonylamino-4-(4-methyl-piperazin-1-yl)-benzamide;
48. N-[5-(3,5-difluoro-benzyl)-1H-indazol-3-yl]-2-methanesulfonylamino-4-(4-methyl-piperazin-1-yl)-benzamide;
49. 2-fluoro-N-[5-(3-fluoro-benzyl)-1H-indazol-3-yl]-5-(tetrahydro-pyran-4-ylamino)-benzamide;
50. N-[5-(3,5-difluoro-benzyl)-1H-indazol-3-yl]-2-fluoro-5-(tetrahydro-pyran-4-ylamino)-benzamide;
51. 2-fluoro-N-[5-(3-fluoro-benzyl)-1H-indazol-3-yl]-5-(2-methoxy-ethylamino)-benzamide;
52. N-[5-(3,5-difluoro-benzyl)-1H-indazol-3-yl]-2-fluoro-5-(2-methoxy-ethylamino)-benzamide;
53. 4-[(3-dimethylamino-propyl)-methyl-amino]-N-[5-(3-ethoxy-benzyl)-1H-indazol-3-yl]-2-nitro-benzamide;
54. 2-amino-4-[(3-dimethylamino-propyl)-methyl-amino]-N-[5-(3-ethoxy-benzyl)-1H-indazol-3-yl]-benzamide;
55. N-[5-(3,5-difluoro-benzyl)-1H-indazol-3-yl]-4-[(3-dimethylamino-propyl)-methyl-amino]-2-(tetrahydro-pyran-4-ylamino)-benzamide;
56. N-[5-(3,5-difluoro-benzyl)-1H-indazol-3-yl]-4-[(3-dimethylamino-propyl)-methyl-amino]-2-(2-methoxy-1-methoxymethyl-ethylamino)-benzamide;
57. 2-amino-N-[5-(3,5-difluoro-benzyl)-1H-indazol-3-yl]-4-[(3-dimethylamino-propyl)-methyl-amino]-benzamide;
58. N-[5-(3,5-difluoro-benzyl)-1H-indazol-3-yl]-4-[(3-dimethylamino-propyl)-methyl-amino]-benzamide;
59. N-[5-(3,5-difluoro-benzyl)-1-indazol-3-yl]-4-[(3-dimethylamino-propyl)-methyl-amino]-2-nitro-benzamide;
60. N-{5-[(3,5-difluoro-phenyl)-hydroxy-methyl]-1H-indazol-3-yl}-4-(4-methyl-piperazin-1-yl)-2-(tetrahydro-pyran-4-ylamino)-benzamide;
61. N-{5-[(3,5-difluoro-phenyl)-hydroxy-methyl]-1H-indazol-3-yl}-2-(2-methoxy-1-methoxymethyl-ethylamino)-4-(4-methyl-piperazin-1-yl)-benzamide;
62. N-{5-[(3,5-difluoro-phenyl)-hydroxy-methyl]-1H-indazol-3-yl}-4-(4-methyl-piperazin-1-yl)-benzamide;
63. N-{5-[(3,5-difluoro-phenyl)-hydroxy-methyl]-1H-indazol-3-yl}-2-(2-methoxy-ethylamino)-4-(4-methyl-piperazin-1-yl)-benzamide;
64. N-{5-[(3,5-difluoro-phenyl)-hydroxy-methyl]-1H-indazol-3-yl}-2-(3-methoxy-propylamino)-4-(4-methyl-piperazin-1-yl)-benzamide;
65. N-{5-[(3,5-difluoro-phenyl)-hydroxy-methyl]-1H-indazol-3-yl}-2-(2-methoxy-1,1-dimethyl-ethylamino)-4-(4-methyl-piperazin-1-yl)-benzamide;
66. N-{5-[(3,5-difluoro-phenyl)-hydroxy-methyl]-1H-indazol-3-yl}-2-(2-fluoro-ethylamino)-4-(4-methyl-piperazin-1-yl)-benzamide;
67. N-{5-[(3-ethoxy-phenyl)-hydroxy-methyl]-1H-indazol-3-yl}-4-(4-methyl-piperazin-1-yl)-2-nitro-benzamide;
68. N-{5-[(3,5-difluoro-phenyl)-methoxy-methyl]-1H-indazol-3-yl}-4-(4-methyl-piperazin-1-yl)-2-(tetrahydro-pyran-4-ylamino)-benzamide;
69. N-{5-[(3,5-difluoro-phenyl)-methoxy-methyl]-1H-indazol-3-yl}-2-(2-methoxy-1-methoxymethyl-ethylamino)-4-(4-methyl-piperazin-1-yl)-benzamide;
70. N-{5-[(3,5-difluoro-phenyl)-methoxy-methyl]-1H-indazol-3-yl}-4-(4-methyl-piperazin-1-yl)-benzamide;
71. N-{5-[(3,5-difluoro-phenyl)-methoxy-methyl]-1H-indazol-3-yl}-2-(2-methoxy-ethylamino)-4-(4-methyl-piperazin-1-yl)-benzamide;
72. N-{5-[(3,5-difluoro-phenyl)-methoxy-methyl]-1H-indazol-3-yl}-2-(3-methoxy-propylamino)-4-(4-methyl-piperazin-1-yl)-benzamide;
73. N-{5-[(3,5-difluoro-phenyl)-methoxy-methyl]-1H-indazol-3-yl}-2-(2-methoxy-1,1-dimethyl-ethylamino)-4-(4-methyl-piperazin-1-yl)-benzamide;
74. N-{5-[(3,5-difluoro-phenyl)-methoxy-methyl]-1H-indazol-3-yl}-2-(2-fluoro-ethylamino)-4-(4-methyl-piperazin-1-yl)-benzamide;
75. N-{5-[1-(3,5-difluoro-phenyl)-ethyl]-1H-indazol-3-yl}-4-(4-methyl-piperazin-1-yl)-2-(tetrahydro-pyran-4-ylamino)-benzamide;
76. N-{5-[1-(3,5-difluoro-phenyl)-ethyl]-1H-indazol-3-yl}-2-(2-methoxy-1-methoxymethyl-ethylamino)-4-(4-methyl-piperazin-1-yl)-benzamide;

77. N-{5-[(3,5-difluoro-phenyl)-ethyl]-1H-indazol-3-yl}-4-(4-methyl-piperazin-1-yl)-benzamide;
78. N-{5-[(3,5-difluoro-phenyl)-ethyl]-1H-indazol-3-yl}-2-(2-methoxy-ethylamino)-4-(4-methyl-piperazin-1-yl)-benzamide;
79. N-({5-[(3,5-difluoro-phenyl)-ethyl]-1H-indazol-3-yl}-2-(3-methoxy-propylamino)-4-(4-methyl-piperazin-1-yl)-benzamide;
80. N-{5-[(3,5-difluoro-phenyl)-ethyl]-1H-indazol-3-yl}-2-(2-methoxy-1,1-dimethyl-ethylamino)-4-(4-methyl-piperazin-1-yl)-benzamide;
81. N-{5-[(3,5-difluoro-phenyl)-ethyl]-1H-indazol-3-yl}-2-(2-fluoro-ethylamino)-4-(4-methyl-piperazin-1-yl)-benzamide;
82. N-{5-[1-(3,5-difluoro-phenyl)-1-methyl-ethyl]-1H-indazol-3-yl}-4-(4-methyl-piperazin-1-yl)-2-(tetrahydro-pyran-4-ylamino)-benzamide;
83. N-{5-[1-(3,5-difluoro-phenyl)-1-methyl-ethyl]-1H-indazol-3-yl}-2-(2-methoxy-1-methoxymethyl-ethylamino)-4-(4-methyl-piperazin-1-yl)-benzamide;
84. N-{5-[1-(3,5-difluoro-phenyl)-1-methyl-ethyl]-1H-indazol-3-yl}-4-(4-methyl-piperazin-1-yl)-benzamide;
85. N-{5-[1-(3,5-difluoro-phenyl)-1-methyl-ethyl]-1H-indazol-3-yl}-2-(2-methoxy-ethylamino)-4-(4-methyl-piperazin-1-yl)-benzamide;
86. N-{5-[1-(3,5-difluoro-phenyl)-1-methyl-ethyl]-1H-indazol-3-yl}-2-(3-methoxy-propylamino)-4-(4-methyl-piperazin-1-yl)-benzamide;
87. N-{5-[1-(3,5-difluoro-phenyl)-1-methyl-ethyl]-1H-indazol-3-yl}-2-(2-methoxy-1,1-dimethyl-ethylamino)-4-(4-methyl-piperazin-1-yl)-benzamide;
88. N-{5-[1-(3,5-difluoro-phenyl)-1-methyl-ethyl]-1H-indazol-3-yl}-2-(2-fluoro-ethylamino)-4-(4-methyl-piperazin-1-yl)-benzamide;
89. N-[5-(3,5-difluorobenzyl)-1H-indazol-3-yl]-4-(4-methyl-1,4-diazepan-1-yl)-2-(tetrahydro-2H-pyran-4-ylamino)benzamide;
90. N-[5-(3,5-Difluoro-benzyl)-1H-indazol-3-yl]-4-[(2-dimethylamino-ethyl)-methyl-amino]-2-(tetrahydro-pyran-4-ylamino)-benzamide;
91. N-[5-(3,5-difluorobenzyl)-1H-indazol-3-yl]-4-[4-(dimethylamino)piperidin-1-yl]-2-(tetrahydro-2H-pyran-4-ylamino)benzamide;
92. N-[5-(3,5-difluorobenzyl)-1H-indazol-3-yl]-4-[(2S)-2-(pyrrolidin-1-ylmethyl)pyrrolidin-1-yl]-2-(tetrahydro-2H-pyran-4-ylamino)benzamide;
93. N-[5-(3,5-difluorobenzyl)-1H-indazol-3-yl]-3-(4-methylpiperazin-1-yl)benzamide;
94. N-[5-(3,5-difluorobenzyl)-1H-indazol-3-yl]-4-{[(2S)-1-methylpyrrolidin-2-yl]methoxy}-2-(tetrahydro-2H-pyran-4-ylamino)benzamide;
95. N-[5-(3,5-difluorobenzyl)-1H-indazol-3-yl]-4-[(1-methylpiperidin-4-yl)oxy]-2-(tetrahydro-2H-pyran-4-ylamino)benzamide;
96. N-[5-(3,5-difluorobenzyl)-1H-indazol-3-yl]-4-[2-(dimethylamino)ethoxy]-2-(tetrahydro-2H-pyran-4-ylamino)benzamide;
97. N-[5-(3,5-difluorobenzyl)-1H-indazol-3-yl]-4-{[(3S)-1-methylpyrrolidin-3-yl]oxy}-2-(tetrahydro-2H-pyran-4-ylamino)benzamide;
98. N-[5-(3,5-difluorobenzyl)-1H-indazol-3-yl]-4-(piperazin-1-yl)-2-(tetrahydro-2H-pyran-4-ylamino)benzamide;
99. N-[5-(3,5-difluorobenzyl)-1H-indazol-3-yl]-4-(4-methylpiperazin-1-yl)-2-{[cis-4-(trifluoromethyl)cyclohexyl]amino}benzamide;
100. N-[5-(3,5-difluorobenzyl)-1H-indazol-3-yl]-4-(4-methylpiperazin-1-yl)-2-{[trans-4-(trifluoromethyl)cyclohexyl]amino}benzamide;
101. N-[5-(3,5-difluorobenzyl)-1H-indazol-3-yl]-2-fluoro-4-(4-methylpiperazin-1-yl)benzamide;
102. N-[5-(3,5-difluorobenzyl)-1H-indazol-3-yl]-1-(piperidin-4-yl)-1H-pyrazole-4-carboxamide;
103. N-[5-(3,5-difluorobenzyl)-1H-indazol-3-yl]-2-[(cis-4-hydroxycyclohexyl)amino]-4-(4-methylpiperazin-1-yl)benzamide;
104. N-[5-(3,5-difluorobenzyl)-1H-indazol-3-yl]-2-[(trans-4-hydroxycyclohexyl)amino]-4-(4-methylpiperazin-1-yl)benzamide;
105. N-[5-(3,5-difluorobenzyl)-1H-indazol-3-yl]-2-[(2-hydroxyethyl)amino]-4-(4-methylpiperazin-1-yl)benzamide;
106. 2-[(azetidin-3-ylmethyl)amino]-N-[5-(3,5-difluorobenzyl)-1H-indazol-3-yl]-4-(4-methylpiperazin-1-yl)benzamide;
107. N-[5-(3,5-difluorobenzyl)-1H-indazol-3-yl]-2-{[(1-methylazetidin-3-yl)methyl]amino}-4-(4-methylpiperazin-1-yl)benzamide;
108. N-[5-(3,5-difluorobenzyl)-1H-indazol-3-yl]-4-[(1-methylpiperidin-4-yl)amino]-2-[tetrahydro-2H-pyran-4-ylamino]benzamide;
109. 4-[(azetidin-3-ylmethyl)amino]-N-[5-(3,5-difluorobenzyl)-1H-indazol-3-yl]-2-(tetrahydro-2H-pyran-4-ylamino)benzamide;
110. N-[5-(3,5-difluorobenzyl)-1H-indazol-3-yl]-2-[(1-methylpiperidin-4-yl)amino]benzamide;
111. N-[5-(3,5-difluorobenzyl)-1H-indazol-3-yl]-2-[(1-methylpiperidin-4-yl)amino]-4-(morpholin-4-yl)benzamide;
112. N-[5-(3,5-difluorobenzyl)-1H-indazol-3-yl]-2-methoxy-4-(4-methylpiperazin-1-yl)benzamide;
113. N-[5-(3,5-difluorobenzyl)-1H-indazol-3-yl]-5-(4-methylpiperazin-1-yl)-3-(tetrahydro-2H-pyran-4-ylamino)pyridine-2-carboxamide;
114. N-[5-(3,5-difluorobenzyl)-1H-indazol-3-yl]-6-(4-methylpiperazin-1-yl)-2-(tetrahydro-2H-pyran-4-ylamino)pyridine-3-carboxamide;
115. 1-[4-{[5-(3,5-difluorobenzyl)-1H-indazol-3-yl]carbamoyl}-3-(tetrahydro-2H-pyran-4-ylamino)benzyl]piperidine;
116. N-[5-(3,5-difluorobenzyl)-1H-indazol-3-yl]-4-{[(2-methoxyethyl)(methyl)amino]methyl}-2-(tetrahydro-2H-pyran-4-ylamino)benzamide;
117. N-[5-(3,5-difluorobenzyl)-1H-indazol-3-yl]-4-(pyrrolidin-1-ylmethyl)-2-(tetrahydro-2H-pyran-4-ylamino)benzamide;
118. N-[5-(3,5-difluorobenzyl)-1H-indazol-3-yl]-4-(morpholin-4-ylmethyl)-2-(tetrahydro-2H-pyran-4-ylamino)benzamide;
119. 4-(azetidin-1-ylmethyl)-N-[5-(3,5-difluorobenzyl)-1H-indazol-3-yl]-2-(tetrahydro-2H-pyran-4-ylamino)benzamide;
120. N-[5-(3,5-Difluoro-benzyl)-1H-indazol-3-yl]-2-fluoro-5-(4-methyl-piperazin-1-ylmethyl)-benzamide;
121. N-[5-(3,5-difluorobenzyl)-1H-indazol-3-yl]-2-fluoro-5-{[(2S)-2-(pyrrolidin-1-ylmethyl)pyrrolidin-1-yl]methyl}benzamide;
122. N-[5-(3,5-difluorobenzyl)-1H-indazol-3-yl]-2-fluoro-5-(morpholin-4-ylmethyl)benzamide;
123. N-[5-(3,5-Difluoro-benzyl)-1H-indazol-3-yl]-2-fluoro-5-((S)-2-pyrrolidin-1-ylmethyl-pyrrolidine-1-carbonyl)-benzamide;

124. N-[5-(3,5-difluorobenzyl)-1H-indazol-3-yl]-4-{[(2R)-2-(pyrrolidin-1-ylmethyl)pyrrolidin-1-yl]carbonyl}benzamide;
125. N-[5-(3,5-difluorobenzyl)-1H-indazol-3-yl]-4-{[(2S)-2-(pyrrolidin-1-ylmethyl)pyrrolidin-1-yl]carbonyl}benzamide;
126. N-[5-(3,5-difluorobenzyl)-1H-indazol-3-yl]-4 {[4-pyrrolidin-1-yl)piperidin-1-yl]carbonyl}benzamide;
127. N-[5-(3,5-difluorobenzyl)-1H-indazol-3-yl]-4-{[(2S)-2-(pyrrolidin-1-ylmethyl)pyrrolidin-1-yl]carbonyl}-2-(tetrahydro-2H-pyran-4-ylamino)benzamide;
128. N-[5-(3,5-difluorobenzyl)-1H-indazol-3-yl]-4-4{[(2R)-2-(pyrrolidin-1-ylmethyl)pyrrolidin-1-yl]carbonyl}-2-(tetrahydro-2H-pyran-4-ylamino)benzamide;
129. $N^1$-[5-(3,5-difluorobenzyl)-1H-indazol-3-yl]-$N^4$-[2-(dimethylamino)ethyl]-$N^4$-methyl-2-(tetrahydro-2H-pyran-4-ylamino)benzene-1,4-dicarboxamide;
130. N-[5-(3,5-difluorobenzyl)-1H-indazol-3-yl]-4 {[4-(propan-2-yl)piperazin-1-yl]carbonyl}-2-(tetrahydro-2H-pyran-1-ylamino)benzamide;
131. $N^1$-[5-(3,5-difluorobenzyl)-1H-indazol-3-yl]-$N^4$-[2-(dimethylamino)ethyl]-2-(tetrahydro-2H-pyran-4-ylamino)benzene-1,4-dicarboxamide;
132. N-[5-(3,5-difluorobenzyl)-1H-indazol-3-yl]-4-[(4-methylpiperazin-1-yl)carbonyl]-2-(tetrahydro-2H-pyran-4-ylamino)benzamide;
133. N-[5-(3,5-difluorobenzyl)-1H-indazol-3-yl]-4-{[4-(dimethylamino)piperidin-1-yl]carbonyl}-2-(tetrahydro-2H-pyran-4-ylamino)benzamide;
134. $N^1$-[5-(3,5-difluorobenzyl)-1H-indazol-3-yl]-$N^4$-(1-methyl piperidin-4-yl)-2-(tetrahydro-2H-pyran-4-ylamino)benzene-1,4-dicarboxamide;
135. N-[5-(2-methyl-5-fluoro-benzyl)-1H-indazol-3-yl]-4-(4-methyl-piperazin-1-yl)-2-(tetrahydro-pyran-4-ylamino)-benzamide;
136. 4-(4-methylpiperazin-1-yl)-N-[5-(pyridin-3-ylmethyl)-1H-indazol-3-yl]-2-(tetrahydro-2H-pyran-4-ylamino)benzamide;
137. N-[5-benzyl-1H-indazol-3-yl]-4-(4-methyl-piperazin-1-yl)-2-(tetrahydro-pyran-4-ylamino)-benzamide;
138. ethyl 4-{[2-{[5-(3,5-difluorobenzyl)-1H-indazol-3-yl]carbamoyl}-5-(4-methylpiperazin-1-yl)phenyl]amino}piperidine-1-carboxylate;
139. N-[5-(3,5-difluorobenzyl)-1H-indazol-3-yl]-4-(4-methylpiperazin-1-yl)-2-(piperidin-4-ylamino)benzamide;
140. ethyl 5-(3,5-difluorobenzyl)-3-({[4-(4-methylpiperazin-1-yl)-2-(tetrahydro-2H-pyran-4-ylamino)phenyl]carbonyl}amino)-1H-indazole-1-carboxylate;
141. N-[5-(3,5-difluoro-benzyl)-1H-indazol-3-yl]-2-((S)-2-methoxy-1-methyl-ethylamino)-4-(4-methyl-piperazin-1-yl)-benzamide;
142. N-[5-(3,5-difluorobenzyl)-1H-indazol-3-yl]-4-[(2R)-2-(pyrrolidin-1-ylmethyl)pyrrolidin-1-yl]-2-(tetrahydro-2H-pyran-4-ylamino)benzamide;
143. N-[5-(3,5-difluorobenzyl)-1H-indazol-3-yl]-4 {[(2R)-1-methylpyrrolidin-2-yl]methoxy}-2-(tetrahydro-2H-pyran-4-ylamino)benzamide;
144. N-[5-(3,5-difluorobenzyl)-1H-indazol-3-yl]-4-{[(3R)-1-methylpyrrolidin-3-yl]oxy}-2-(tetrahydro-2H-pyran-4-ylamino)benzamide;
145. N-[5-(3,5-difluorobenzyl)-1H-indazol-3-yl]-2-fluoro-5-{[(2R)-2-(pyrrolidin-1-ylmethyl)pyrrolidin-1-yl]methyl}benzamide, and
146. N-[5-(3,5-difluoro-benzyl)-1H-indazol-3-yl]-2-fluoro-5-((R)-2-pyrrolidin-1-ylmethyl-pyrrolidine-1-carbonyl)-benzamide.

Preferred specific compound of the invention is:

N-[5-(3,5-difluoro-benzyl)-1H-indazol-3-yl]-4-(4-methyl-piperazin-1-yl)-2-(tetrahydro-pyran-4-ylamino)-benzamide.

The present invention also provides a process for the preparation of a compound of formula (I) as defined above, characterized in that the process comprises:

i) reducing a carbonyl compound of formula (II):

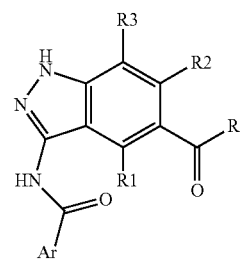

(II)

wherein Ar, R, R1, R2, and R3 are as defined above, to give a compound of formula ($I_A$), ($I_B$) or ($I_C$):

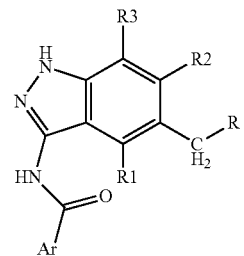

($I_A$)

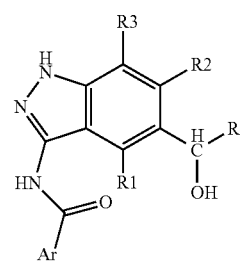

($I_B$)

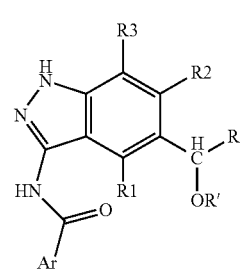

($I_C$)

wherein Ar, R, R1, R2, R3 and R' are as defined above; or i') reacting a compound of formula ($III_A$), ($III_B$), ($III_C$) or ($III_D$):

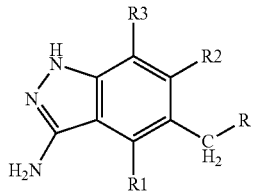
(III_A)

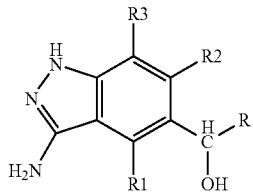
(III_B)

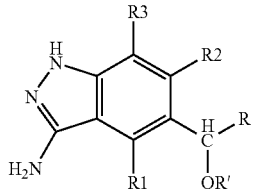
(III_C)

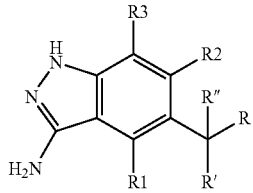
(III_D)

wherein R, R1, R2, R3, R' and R" are as defined above, with a compound of formula (IV):

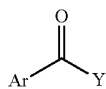
(IV)

wherein Ar is as defined above and Y represents hydroxy, or a suitable leaving group such as halogen, to give a compound of formula (I), as defined above;

or i") deprotecting a compound of formula (XXII_A), (XXII_C) or (XXII_D):

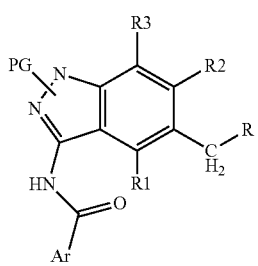
(XXII_A)

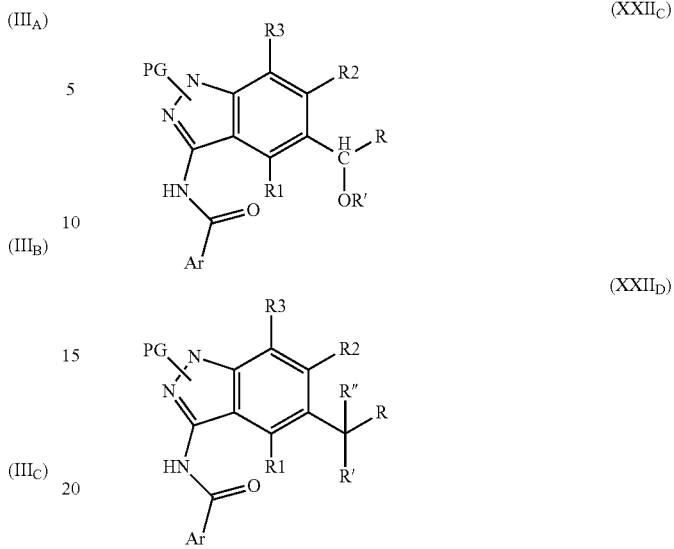
(XXII_C)
(XXII_D)

wherein Ar, R, R1, R2, R3, R' and R" are as defined above and PG is a suitable protecting group such as benzyl, p-methoxybenzyl, o,p-dimethoxybenzyl, or triphenylmethyl, to give a compound of formula (I_A), (I_C) or (I_D):

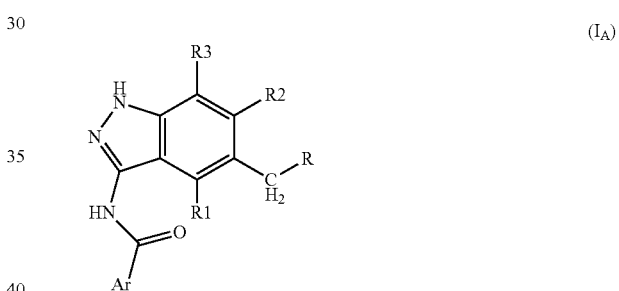
(I_A)

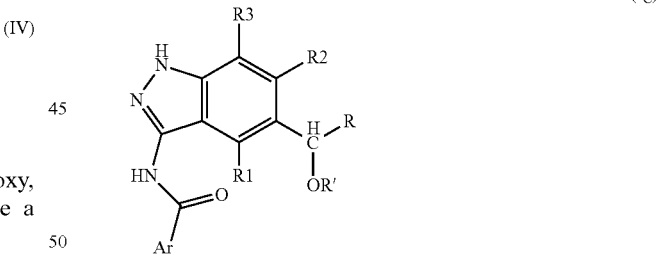
(I_C)

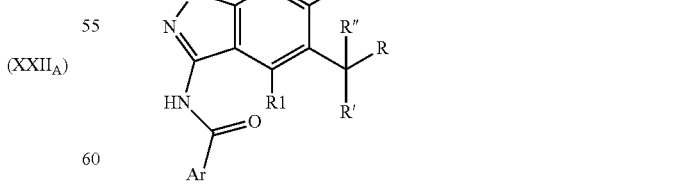
(I_D)

wherein Ar, R, R1, R2, R3, R' and R" are as defined above, optionally separating the resulting compound into the single isomers, converting the compound of formula (I) into a different compound of formula (I), and/or into a pharmaceutically acceptable salt if desired.

The present invention further provides a process for the preparation of a compound of formula (I$_A$), (I$_B$) or (I$_C$) as defined above, characterized in that the compound of formula (II) as defined above, is prepared according to the following steps:

a) reacting a compound of formula (XII):

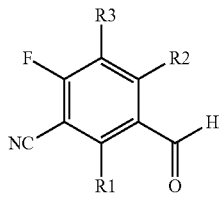
(XII)

wherein R1, R2 and R3 are as defined above, with an organometallic compound of formula RMgZ (XIII), namely a Grignard reagent, wherein R is as defined above and Z is halogen, to give a compound of formula (XI):

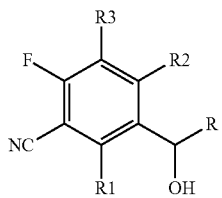
(XI)

wherein R, R1, R2 and R3 are as defined above;

b) oxidizing the resulting compound of formula (XI), to give a compound of formula (X):

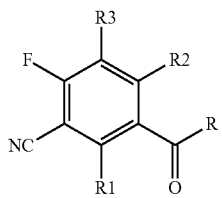
(X)

wherein R, R1, R2 and R3 are as defined above;

c) reacting the resulting compound of formula (X) with hydrazine hydrate, to give a compound of formula (IX):

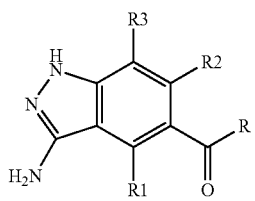
(IX)

wherein R, R1, R2 and R3 are as defined above;

d) protecting the resulting compound of formula (IX), to give a compound of formula (VIII):

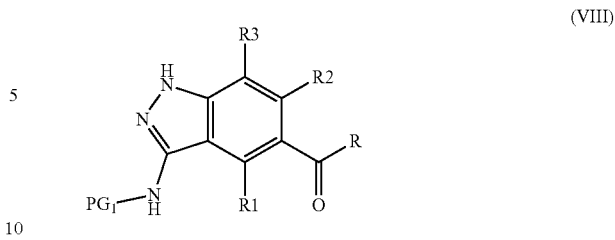
(VIII)

wherein R, R1, R2 and R3 are as defined above, and PG$_1$ is a suitable protecting group such as trifluoroacetyl group;

e) protecting the resulting compound of formula (VIII), to give a compound of formula (VII):

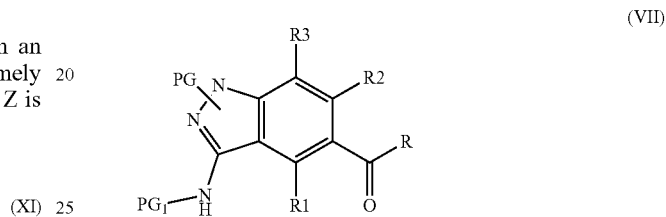
(VII)

wherein R, R1, R2, R3, PG and PG$_1$ are as defined above;

f) removing the protecting group PG$_1$ from the resulting compound of formula (VII), to give a compound of formula (VI):

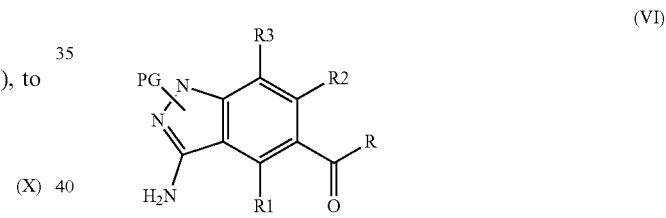
(VI)

wherein R, R1, R2, R3 and PG are as defined above;

g) reacting the resulting compound of formula (VI) with a compound of formula (IV) as defined above, to give a compound of formula (V):

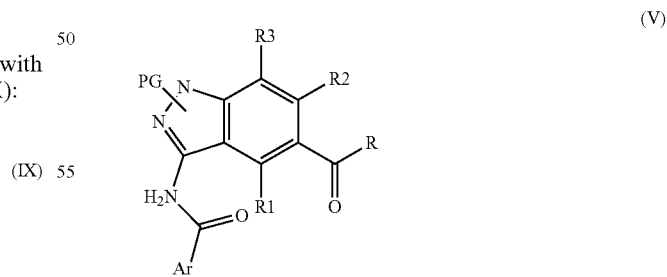
(V)

wherein Ar, R, R1, R2, R3 and PG are as defined above;

h) deprotecting the resulting compound of formula (V), to give a compound of formula (II) as defined above.

The present invention further provides a process for the preparation of a compound of formula (I$_A$) as defined above, characterized in that the compound of formula (III$_A$) as defined above, is prepared according to the following steps:

j) reducing a compound of formula (XI) as defined above, in the presence of a suitable reagent like for example NaI and Me₃SiCl, to give a compound of formula (XIV):

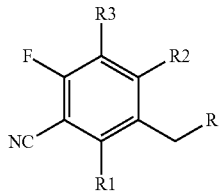

(XIV)

wherein R, R1, R2 and R3 are as defined above;
or
k) reacting a boronic acid compound of formula (XV):

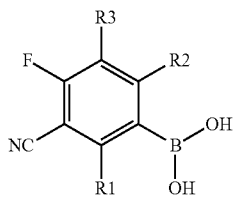

(XV)

wherein R1, R2 and R3 are as defined above, with a compound of formula (XVI):

(XVI)

wherein R is as defined above and W represents a halogen atom, such as bromine or iodine, or a suitable leaving group like sulphonates, such as methanesulphonate or trifluoromethanesulphonate, or phosphates in the presence of a suitable catalyst such as a Palladium catalyst, to give a compound of formula (XIV) as defined above;

l) reacting the resulting compound of formula (XIV) with hydrazine hydrate, to give a compound of formula (III$_A$) as defined above.

The present invention further provides a process for the preparation of a compound of formula (I$_B$) as defined above, characterized in that the compound of formula (III$_B$) as defined above, is prepared according to the following steps:

l') reacting a compound of formula (XI) as defined above with hydrazine hydrate, to give a compound of formula (III$_B$) as defined above.

The present invention further provides a process for the preparation of a compound of formula (I$_C$) as defined above, characterized in that the compound of formula (III$_C$) as defined above, is prepared according to the following steps:

m) reacting a compound of formula (XI) as defined above with an electrophilic alkylating agent of formula (XVIII):

(XVIII)

wherein R' is as defined above and W' represents a halogen atom such as chlorine, bromine or iodine or a suitable leaving group like sulphonates, such as methanesulphonate or trifluoromethanesulphonate, to give a compound of formula (XVII):

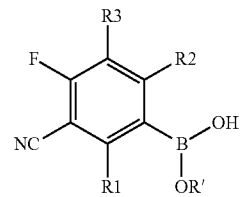

(XVII)

wherein R, R1, R2, R3 and R' are as defined above;

l'') reacting the resulting compound of formula (XVII) with hydrazine hydrate, to give a compound of formula (III$_C$) as defined above.

The present invention further provides a process for the preparation of a compound of formula (I$_D$) as defined above, characterized in that the compound of formula (III$_{D1}$) wherein R" is hydrogen, having the formula:

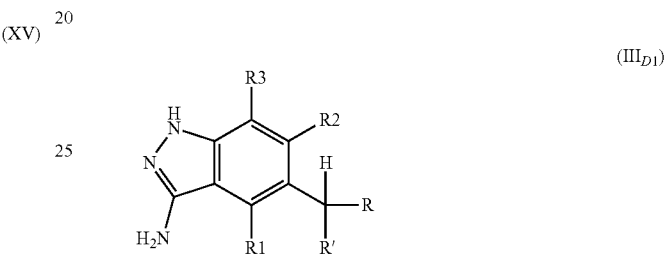

(III$_{D1}$)

wherein R, R1, R2, R3 and R' are as defined above, is prepared according to the following steps:

n) reacting a compound of formula (XIV) as defined above, with a compound of formula (XVIII) as defined above;

l''') reacting the resulting of formula (XIX$_{D1}$):

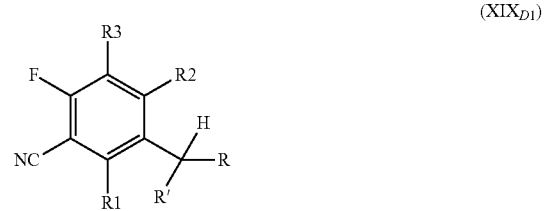

(XIX$_{D1}$)

wherein R, R1, R2, R3 and R' are as defined above, with hydrazine hydrate, to give a compound of formula (III$_{D1}$) as defined above;
or
o) reacting a compound of formula (XXI):

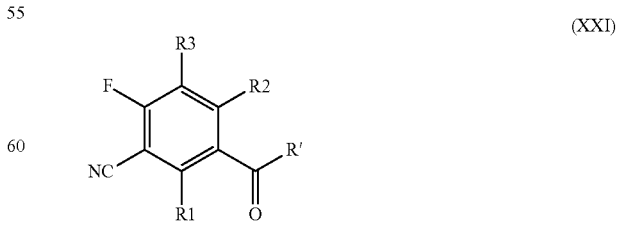

(XXI)

wherein R1, R2, R3 and R' are as defined above, with a compound of formula (XIII) as defined above, to give a compound of formula (XX):

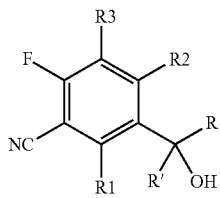
(XX)

wherein R, R1, R2, R3 and R' are as defined above;

p) reducing the resulting compound of formula (XX), to give a compound of formula XIX$_{D1}$ as defined before.

The present invention further provides a process for the preparation of a compound of formula (I$_D$) as defined above, characterized in that the compound of formula (III$_{D2}$) wherein R" is as defined above but not hydrogen, having the formula:

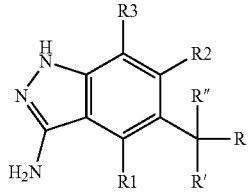
(III$_{D2}$)

wherein R, R1, R2, R3 and R' are as defined above, is prepared according to the following steps:

q) reacting a compound of formula (XIX$_{D1}$) as defined above, with an electrophilic alkylating agent of formula (XXIII):

R"—W'  (XIII)

wherein R" and W' are as defined above, to give a compound of formula (XIX$_{D2}$):

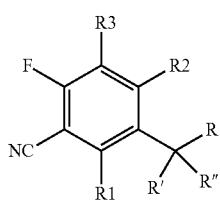
(XIX$_{D2}$)

wherein R, R1, R2, R3 and R' are as defined above and R" is as defined above but not hydrogen;

$1^{iv}$) reacting the resulting compound of formula (XIX$_{D2}$) with hydrazine hydrate, to give a compound of formula (III$_{D2}$) as defined above.

The present invention further provides a process for the preparation of a compound of formula (I$_A$), (I$_C$) or (I$_D$) as defined above, characterized in that a compound of formula (XXII$_A$), (XXII$_C$) or (XXII$_D$) as defined above, is prepared according to the following steps:

r) protecting a compound of formula (III$_A$), (III$_C$) or (III$_D$) as defined above, to give a compound of formula (XXIV$_A$), (XXIV$_C$) or (XXIV$_D$):

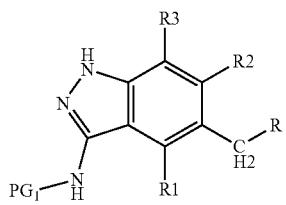
(XXIV$_A$)

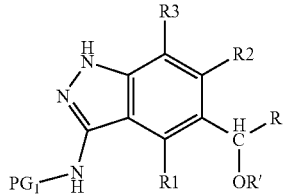
(XXIV$_C$)

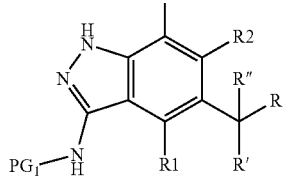
(XXIV$_D$)

wherein R, R1, R2, R3, R, R" and PG$_1$ are as defined above;

s) protecting the resulting compound of formula (XXIV$_A$), (XXIV$_C$) or (XXIV$_D$), to give a compound of formula (XXV$_A$), (XXV$_C$) or (XXV$_D$):

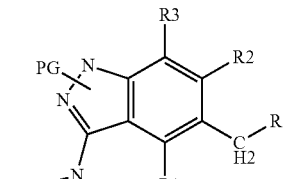
(XXV$_A$)

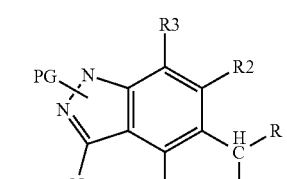
(XXV$_C$)

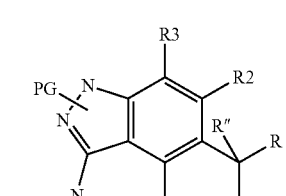
(XXV$_D$)

wherein R, R1, R2, R3, R, R", PG and PG$_1$ are as defined above;

t) removing the protecting group PG$_1$ from the resulting compound of formula (XXV$_A$), (XXV$_C$) or (XXV$_D$), to give a compound of formula (XXVI$_A$), (XXVI$_C$) or (XXVI$_D$):

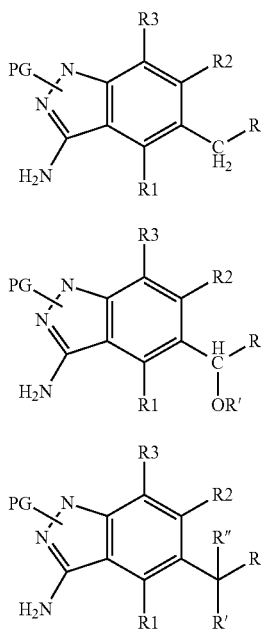

(XXVI$_A$)

(XXVI$_C$)

(XXVI$_D$)

wherein R, R1, R2, R3, R, R" and PG are as defined above;

u) reacting the resulting compound of formula (XXVI$_A$), (XXVI$_C$) or (XXVI$_D$) with a compound of formula (IV) as defined above, to give a compound of formula (XXII$_A$), (XXII$_C$) or (XXII$_D$) as defined above.

It is to be noted that a compound of formula (V), as defined above can be in any one of its isomeric forms a or b or a mixture of both:

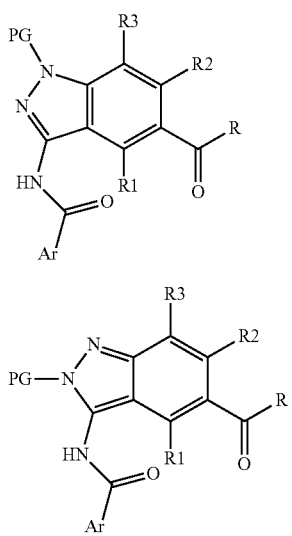

(Va)

(Vb)

Analogously, a compound of formula (XXII$_A$), (XXII$_C$), (XXII$_D$), (XXV$_A$), (XXV$_C$), (XXV$_D$), (XXVI$_A$), (XXVI$_C$) and (XXVI$_D$) as defined above, can be in any one of theirs isomeric forms a or b.

A compound of formula (II), (V), (XXII$_A$), (XXII$_C$), and (XXII$_D$), may be converted into another compound of formula (II), (V), (XXII$_A$), (XXII$_C$), and (XXII$_D$), said conversion is carried out by one or more of the following reactions:

1) reducing a compound of formula (II), (V, (XXII$_A$), (XXII$_C$) and (XXII$_D$) wherein Ar is a substituted aryl and one of the substituents is NO$_2$, for obtaining a compound of formula (II), (V), (XXII$_A$), (XXII$_C$), and (XXII$_D$) wherein such substituent is NH$_2$;

2) acylating a compound of formula (II), (V), (XXII$_A$), (XXII$_C$), and (XXII$_D$), wherein Ar is a substituted aryl and one of the substituents is NH$_2$, by reaction with an acylating agent of formula (XXVII) or (XXVIII):

(XXVII)

(XXVIII)

wherein R4 and Y are as defined above, for obtaining a compound of formula (II), (V), (XXII$_A$), (XXII$_C$), and (XXII$_D$) wherein such substituent is a NHCOR4 or NHSO$_2$R4 residue, wherein R4 is as defined above;

3) reacting a compound of formula (II), (V), (XXII$_A$), (XXII$_C$), and (XXII$_D$), wherein Ar is a substituted aryl and one of the substituents is NH$_2$, with a suitable aldehyde or ketone in the presence of a reducing agent, for obtaining a compound of formula (II), (V), (XXII$_A$), (XXII$_C$), and (XXII$_D$), wherein such substituent is a NR5R6 group, wherein one of the R5 or R6 is hydrogen and the other is an optionally further substituted straight or branched $C_1$-$C_6$ alkyl, $C_3$-$C_6$ cycloalkyl, heterocyclyl, aryl, R8R9N—$C_2$-$C_6$ alkyl, R8O—$C_2$-$C_6$ alkyl, wherein R8 and R9 are as defined above.

A compound of formula (I) may be converted into another compound of formula (I), said conversion is carried out by one or more of the following reactions: 4) reducing a compound of formula (I) wherein Ar is a substituted aryl and one of the substituents is NO$_2$, for obtaining a compound of formula (I) wherein such substituent is NH$_2$;

5) acylating a compound of formula (I), wherein Ar is a substituted aryl and one of the substituents is NH$_2$, by reaction with a compound of formula (XXVII) or (XXVIII) as defined above, followed by selective deprotection of the acyl group on the pyrazole ring for obtaining a compound of formula (I) wherein such substituent is a NHCOR4 or NHSO$_2$R4 residue, wherein R4 is as defined above;

6) reacting a compound of formula (I), wherein Ar is a substituted aryl and one of the substituents is NH$_2$, with a suitable aldehyde or ketone in the presence of a reducing agent, for obtaining a compound of formula (I), wherein such substituent is a NR5R6 group, wherein one of the R5 or R6 are defined as in conversion 3).

The synthesis of a compound of formula (I), according to the synthetic process described above, can be conducted in a stepwise manner, whereby each intermediate is isolated and purified by standard purification techniques, like, for example, column chromatography, before carrying out the subsequent reaction. Alternatively, two or more steps of the synthetic sequence can be carried out in a so-called "one-pot" procedure, as known in the art, whereby only the compound resulting from the two or more steps is isolated and purified.

Schemes 1-4 below show the preparation of a compound of formula (I) wherein X, Ar, R, R1, R2 and R3 have the above meanings.

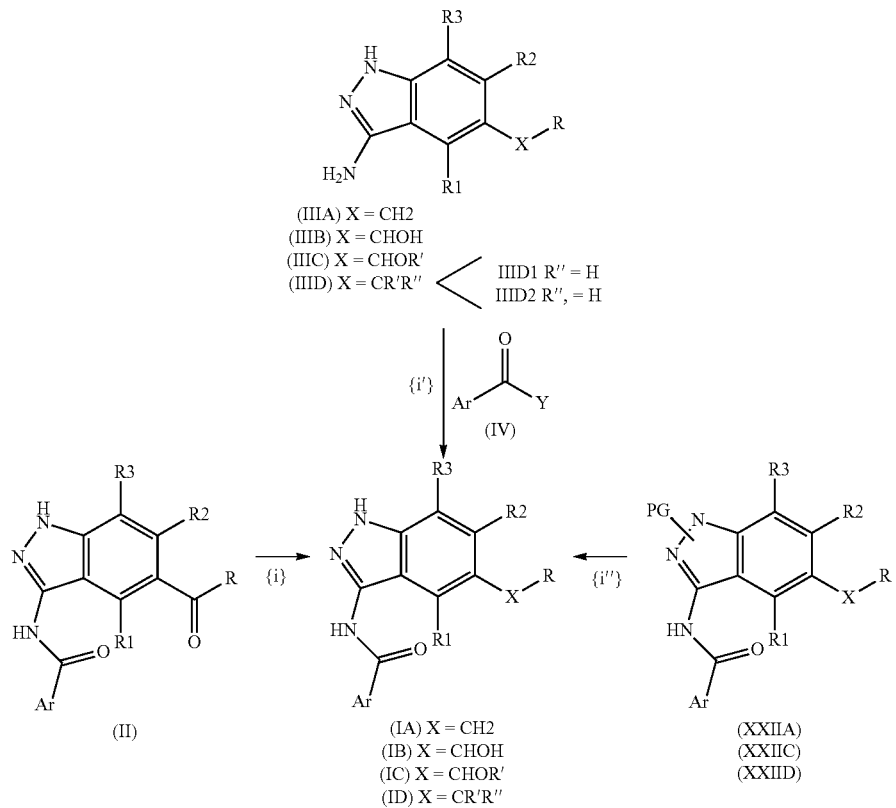
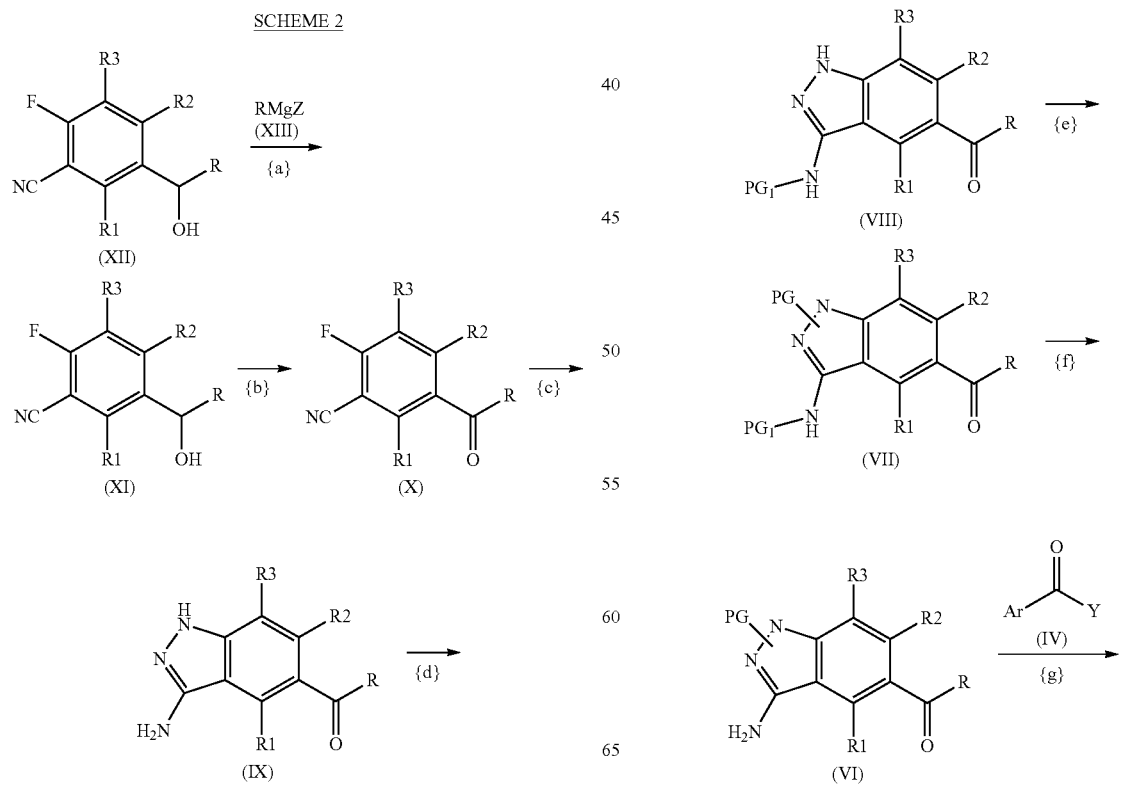

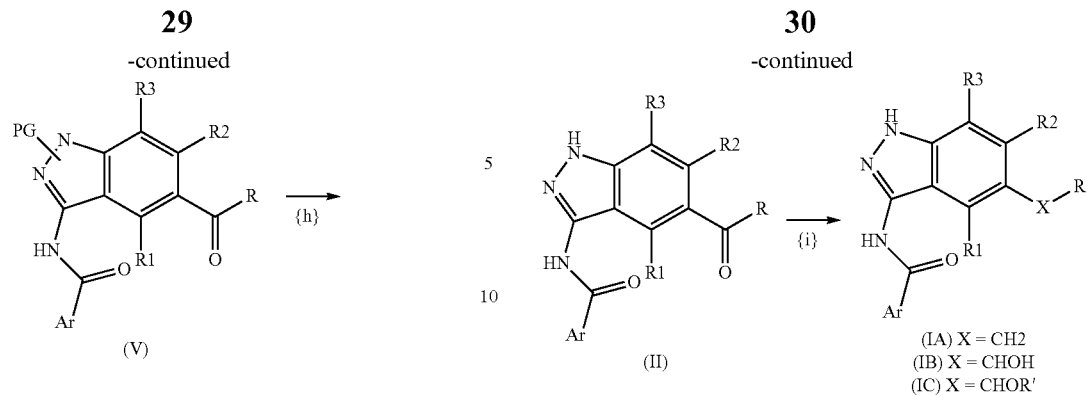
SCHEME 3
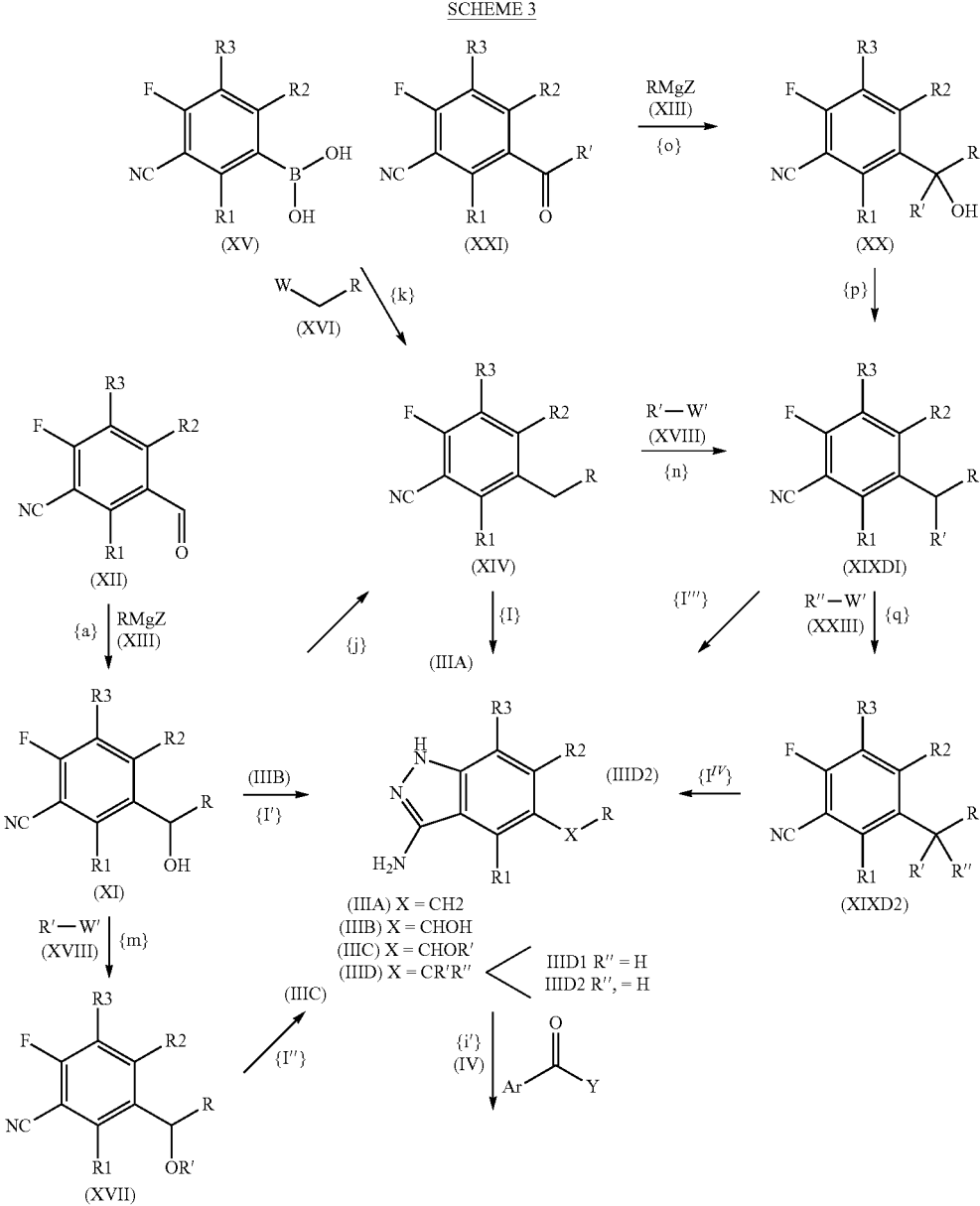

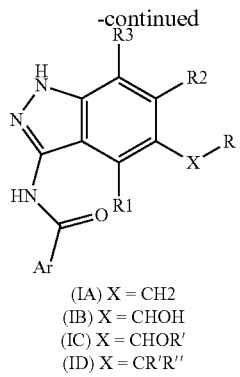

(IA) X = CH2
(IB) X = CHOH
(IC) X = CHOR'
(ID) X = CR'R''

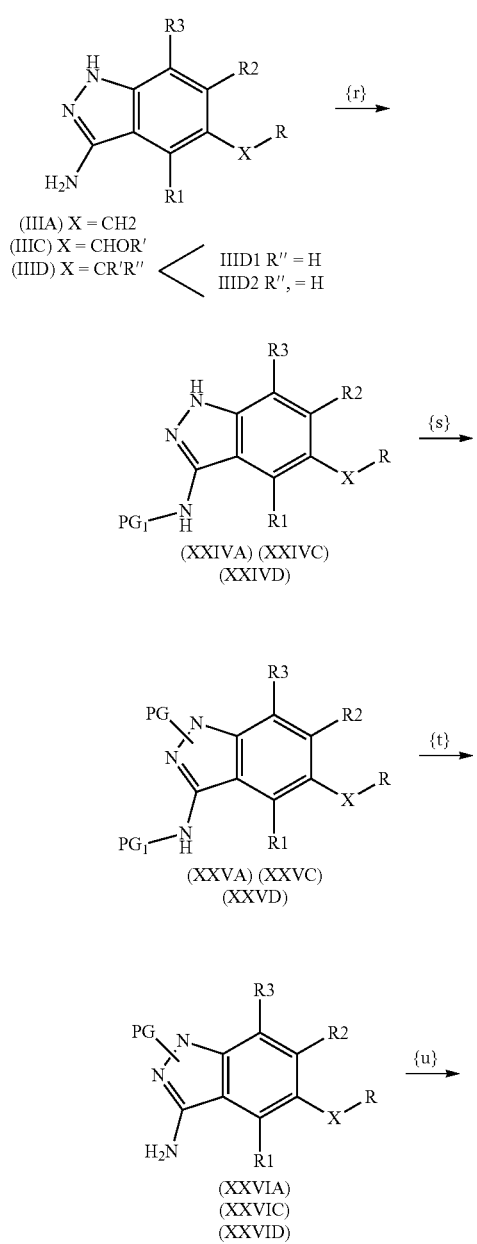

SCHEME 4

(IIIA) X = CH2
(IIIC) X = CHOR'
(IIID) X = CR'R''
 IIID1 R'' = H
 IIID2 R''' = H (XXIVA) (XXIVC)
(XXIVD)

(XXVA) (XXVC)
(XXVD)

(XXVIA)
(XXVIC)
(XXVID)

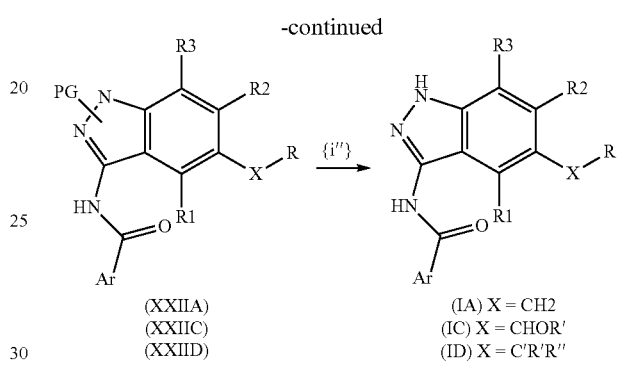

(XXIIA)
(XXIIC)
(XXIID)

(IA) X = CH2
(IC) X = CHOR'
(ID) X = C'R'R''

According to step i), a compound of formula $(I_A)$, $(I_B)$ or $(I_C)$ can be obtained by reducing a compound of formula (II) in a variety of ways and experimental conditions known in the art. Preferably this reduction is conducted in the presence of sodium borohydride, sodium cyanoborohydride, sodium borohydride/trifluoracetic acid, zinc/hydrochloric acid, tin chloride/acetic acid, in a suitable solvent, such as toluene, dichloromethane, chloroform, diethyl ether, tetrahydrofuran, 1,4-dioxan, methanol, ethanol, isopropanol, acetic acid at a temperature ranging from about −10° C. to reflux and for a period of time varying from about 1 hour to about 96 hours. According to the experimental conditions, a compound of formula $(I_A)$, $(I_B)$ or $(I_C)$ can be isolated as major product.

According to step i') a compound of formula $(I_A)$, $(I_B)$, $(I_C)$ or $(I_D)$ can be obtained by reacting a compound of formula $(III_A)$, $(III_B)$, $(III_C)$ or $(III_D)$ with a compound of formula (IV) in a variety of ways and experimental conditions, which are widely known in the art for condensation reactions. Preferably a compound of formula (IV) wherein Y is hydroxy is converted into its corresponding acyl chloride wherein Y is chlorine in the presence of thionyl chloride or oxalyl chloride, in a suitable solvent, such as toluene, dichloromethane, chloroform, diethyl ether, tetrahydrofuran, 1,4-dioxane, at a temperature ranging from about −10° C. to reflux and for a period of time varying from about 1 hour to about 96 hours. The acyl chloride is isolated by evaporation of the solvent and further reacted with $(III_A)$, $(III_B)$, $(III_C)$ or $(III_D)$ in the presence of a base such a pyridine, triethylamine or N-ethyldiisopropylamine in a suitable solvent, such as toluene, dichloromethane, chloroform, diethyl ether, tetrahydrofuran, 1,4-dioxane, at a temperature ranging from about −40° C. to reflux and for a period of time varying from about 1 hour to about 96 hours. Alternatively, a compound of formula (IV) is reacted with a compound of formula $(III_A)$, $(III_B)$, $(III_C)$ or $(III_D)$ in the presence of an activating agent such as hydroxybenzotriazole, dicyclohexyl carbodiimide, diisopropyl carbodiimide, 1-ethyl-3-(3'-dimethylamino)carbodiimide hydrochloric acid salt. Preferably, this reaction is carried out in a suitable solvent such as, for instance, tetrahydrofuran, dichloromethane, toluene, 1,4-dioxane, and in the presence of a proton scavenger such as, for example, pyridine, triethylamine, N,N-diisopropylethylamine, at a temperature ranging from room temperature to reflux, for a time ranging from about 30 min. to about 96 hours.

According to step i") a compound of formula ($I_A$), ($I_C$) or ($I_D$) can be obtained by deprotecting a compound of formula ($XXII_A$), ($XXII_C$) or ($XXII_D$) in a variety of ways and experimental conditions, which are widely known in the art. Preferably in the case of an acyl residue, this reaction is be carried out under basic conditions, for instance in the presence of sodium hydroxide, potassium hydroxide, lithium hydroxide or barium hydroxide, or of a tertiary amine such as triethylamine or diisopropylethylamine, or of hydrazine, and in a suitable solvent such as methanol, ethanol, tetrahydrofuran, N,N-dimethylformamide, water and mixtures thereof. Typically, the reaction is carried out at a temperature ranging from room temperature to reflux and for a time varying from about 30 minutes to about 96 hours. In the case of PG represents a suitable protecting group such as benzyl, p-methoxybenzyl, o,p-dimethoxybenzyl, or triphenylmethyl the transformation can be carried out under conditions analogous to that reported in step h).

According to step a), the transformation of a compound of formula (XII) into a compound of formula (XI) can be accomplished in a variety of ways and experimental conditions, according to conventional methods, which are widely known in the literature by using Grignard reagents of formula (XIII). Preferably the reaction of a compound of formula (XII) with organometallic reagents is carried out in a suitable solvent such as, for instance, tetrahydrofuran, 1,4-dioxane, and diethylether at a temperature ranging from −78° C. to room temperature and for a time varying from about 30 minutes to about 96 hours.

According to step b), the oxidation of a compound of formula (XI) to a compound of formula (X) can be carried out in a variety of ways, according to conventional methods for oxidizing alcohols to ketones. Preferably this reaction is carried out in a suitable solvent such as, for instance, methanol, ethanol, tert-butanol, water, tetrahydrofuran, 1,4-dioxane, toluene, acetic acid, trifluoroacetic acid, dichloromethane, dichloroethane, acetonitrile, dimethylsulfoxide, or a mixture thereof, in the presence of a suitable oxidizing agent, such as, for instance, 3-chloroperbenzoic acid, hydrogen peroxide, Dess-Martin periodinane, oxone, potassium permanganate, sodium periodate, periodic acid and catalytic chromium (VI) oxide, tetrapropylammonium perrutenate, ruthenium chloride. Typically, the reaction is carried out at a temperature ranging from −78° C. to reflux and for a time varying from about 30 minutes to about 96 hours.

According to step c), the transformation of a compound of formula (X) into a compound of formula (IX) can be accomplished in a variety of ways and experimental conditions, which are widely known in the art for the preparation of 3-aminoindazoles. Preferably the reaction of a compound of formula (X) with hydrazine is carried out in a suitable solvent such as, for instance, toluene, tetrahydrofuran, 1,4-dioxane, dimethyl sulfoxide, acetonitrile, methanol, ethanol or n-butanol at a temperature ranging from 0° C. to reflux and for a period of time varying from about 1 hour to about 96 hours. The addition of an acid such as, preferably, hydrochloric acid or acetic acid, may be required in order to catalyse the reaction.

According to step d), a compound of formula (IX) may be transformed into a compound of formula (VIII) in a variety of ways and experimental conditions which are widely known in the art for protection of the primary amino group. Preferably the reaction is carried out by treatment with an excess of trifluoroacetic anhydride or trifluoroacetyl chloride in a suitable solvent such as acetonitrile, tetrahydrofuran, toluene, dichloromethane. Typically, the reaction is carried out at a temperature ranging from 0° C. to about 110° C. and for a time varying from about 30 minutes to about 96 hours. Work-up of the reaction mixture with a protic solvent, such as, for instance, water, methanol, ethanol or mixtures thereof, or with a water solution of sodium hydrogencarbonate leads to selective hydrolysis of the trifluoroacetyl group on the indazole ring. In the case of the preparation of phthalimido derivative, the reaction is carried out by treatment with phthalic anhydride, under basic conditions, for instance in the presence of 1,8-diazabicyclo[5.4.0]undec-7-ene, N,N-dimethylaminopyridine, pyridine, triethylamine, and in a suitable solvent such as acetonitrile, tetrahydrofuran, N,N-dimethylformamide, toluene, dichloromethane, water and mixtures thereof. Typically, the reaction is carried out at a temperature ranging from room temperature to about 110° C. and for a time varying from about 30 minutes to about 96 hours.

According to step e), the reaction of a compound of formula (VIII) to obtain a compound of formula (VII) may be carried out in a variety of ways and experimental conditions. Preferably when PG is a triphenylmethyl group the reaction is carried out by treatment with trityl chloride in a suitable solvent such as, for instance, tetrahydrofuran, dichloromethane, toluene, 1,4-dioxane, and in the presence of a proton scavenger such as, preferably, 1,8-diazabicyclo[5.4.0]undec-7-ene, triethylamine, N,N-diisopropylethylamine, pyridine, at a temperature ranging from room temperature to reflux, for a time ranging from about 30 min. to about 96 hours.

According to step f) a compound of formula (VII) can be transformed into a compound of formula (VI) by removal of a suitable protecting group such as the trifluoroacetyl group, according to conventional methods. Preferably the reaction is carried out by treatment with an organic or inorganic base such as potassium carbonate, sodium hydroxide, ammonia, triethylamine, N,N-diisopropylethylamine in a suitable solvent such as, for instance, tetrahydrofuran, dichloromethane, toluene, 1,4-dioxane, methanol, ethanol, water or mixtures thereof at a temperature ranging from room temperature to reflux, for a time ranging from about 30 min. to about 96 hours.

According to step g) a compound of formula (VI) can be transformed into a compound of formula (V) in a variety of ways and experimental conditions, which are widely known in the art for condensation reactions. Preferably it is carried out in a way analogous to that reported for step i').

According to step h), a compound of formula (V) can be transformed into a compound of formula (II) by deprotection of the endocyclic indazole nitrogen atom according to conventional methods enabling the selective hydrolysis of benzyl, 4-methoxybenzyl, 2,4-dimethoxybenzyl and triphenylmethyl protecting groups. Preferably this reaction is run under acidic conditions, preferably in the presence of an inorganic or organic acid such as hydrochloric, trifluoroacetic or methanesulfonic acid, in a suitable solvent such as dichloromethane, 1,4-dioxane, a lower alcohol, such as methanol or ethanol, at a temperature ranging from room temperature to about 80° C. and for a period of time varying from about 1 hour to about 48 hours. In alternative, this reaction is carried out under reducing condition, such as, for instance, in the presence of hydrogen and a hydrogenation catalyst in a suitable solvent such as ethanol, methanol, ethyl acetate, or a mixture thereof. The catalyst is usually a metal, most often a palladium derivative such as, for instance, palladium hydroxide or palladium black.

According to step j), the reduction of a compound of formula (XI) to a compound of formula (XIV) can be carried out in a variety of ways, according to conventional methods for reducing alcohols to alkane. Preferably this reaction is carried out in a suitable solvent such as, for instance, methanol, ethanol, tetrahydrofuran, 1,4-dioxane, acetic acid, dichloromethane, acetonitrile, or a mixture thereof, in the presence of a suitable reducing system, such as, for instance, trimethylsilyl chloride/sodium iodide, dichlorodimethylsilane/sodium iodide, triethylsilane/trifluoroacetic anhydride, sodiumborohydride/trifluoroacetic acid. Typically, the reaction is carried out at a temperature ranging from −10° C. to reflux and for a time varying from about 30 minutes to about 96 hours.

According to step k), the transformation of a compound of formula (XV) into a compound of formula (XIV) in the presence of a compound of formula (XVI), can be carried out in a variety of ways, according to conventional methods for boron-derivatives coupling, namely Suzuki-like reactions. Preferably, this reaction is carried out in a suitable solvent such as, for instance, ethanol, water, tetrahydrofuran, dioxane, acetone, N,N-dimethylformamide, dimethoxyethane, toluene, xylene, or a mixture thereof, in the presence of a suitable base, such as, for instance, triethylamine, diisopropylethylamine, sodium, potassium or cesium carbonate, potassium phosphate, sodium hydroxide or cesium fluoride, at a temperature ranging from −20° C. to reflux and for a time varying from about 1 hour to about 96 hours. The catalyst is usually a metal, most often a palladium derivative such as, for instance, palladium chloride or palladium acetate in the presence of a suitable ligand such as, for instance, triphenylphosphine.

According to step l), the transformation of a compound of formula (XIV) into a compound of formula (III$_A$) can be carried out in a variety of ways and experimental conditions. Preferably it is carried out in a way analogous to that reported for step c). According to step l') the transformation of a compound of formula (XI) into a compound of formula (III$_B$) can be carried out in a variety of ways and experimental conditions. Preferably it is carried out in a way analogous to that reported for step c). According to step m), the transformation of a compound of formula (XI) into a compound of formula (XVII) in the presence of a compound of formula (XVIII) can be carried out in a variety of ways, according to conventional methods for O-alkylation reactions. Preferably, this reaction is carried out in a suitable solvent such as, for instance, tetrahydrofuran, dioxane, N,N-dimethylformamide, dimethoxyethane, in the presence of a suitable base, such as, for instance, triethylamine, diisopropylethylamine, sodium, potassium or cesium carbonate, sodium hydride, at a temperature ranging from −78° C. to reflux and for a time varying from about 1 hour to about 96 hours. Alkylating agent is usually a halogen or a sulphonates derivative; most often the leaving group is iodo, bromo, triflate or mesylate.

According to step l") the transformation of a compound of formula (XVII) into a compound of formula (III$_C$) can be carried out in a variety of ways and experimental conditions. Preferably it is carried out in a way analogous to that reported for step c).

According to step n), the transformation of a compound of formula (XIV) into a compound of formula (XIX$_{D1}$) in the presence of a compound of formula (XVIII) can be carried out in a variety of ways, according to conventional methods for C-alkylation reactions. Preferably it is carried out in a way analogous to that reported for step m).

According to step l'") the transformation of a compound of formula (XIX$_{D1}$) into a compound of formula (III$_{D1}$) can be carried out in a variety of ways and experimental conditions. Preferably it is carried out in a way analogous to that reported for step c).

According to step o), the transformation of a compound of formula (XXI) into a compound of formula (XX) in the presence of a compound of formula (XIII) can be carried out in a variety of ways and experimental conditions. Preferably it is carried out in a way analogous to that reported for step a).

According to step p), the transformation of a compound of formula (XX) into a compound of formula (XIX$_{D1}$) can be carried out in a variety of ways and experimental conditions. Preferably it is carried out in a way analogous to that reported for step j).

According to step q) the transformation of a compound of formula (XIX$_{D1}$) into a compound of formula (XIX$_{D2}$) in the presence of a compound of formula (XXIII) can be carried out in a variety of ways and experimental conditions. Preferably it is carried out in a way analogous to that reported for step m).

According to Step l$^{iv}$), the transformation of a compound of formula (XIX$_{D2}$) into a compound of formula (III$_{D2}$) can be carried out in a variety of ways and experimental conditions. Preferably it is carried out in a way analogous to that reported for step c).

According to step r), a compound of formula (III$_A$), (III$_C$) or (III$_D$) may be transformed into a compound of formula (XXIV$_A$), (XXIV$_C$) or (XXIV$_D$) in a variety of ways and experimental conditions which are widely known in the art for protection of the primary amino group. Preferably it is carried out in a way analogous to that reported for step d).

According to step s), the reaction of a compound of formula (XXIV$_A$), (XXIV$_C$) or (XXIV$_D$) to obtain a compound of formula (XXV$_A$), (XXV$_C$) or (XXV$_D$) may be carried out in a variety of ways and experimental conditions. Preferably it is carried out in a way analogous to that reported for step e).

According to step t) a compound of formula (XXV$_A$), (XXV$_C$) or (XXV$_D$) can be transformed into a compound of formula (XXVI$_A$), (XXVI$_C$) or (XXVI$_D$) by removal of a suitable protecting group such as the trifluoroacetyl group, according to conventional methods. Preferably it is carried out in a way analogous to that reported for step f).

According to step u) a compound of formula (XXVI$_A$), (XXVI$_C$) or (XXVI$_D$) can be transformed into a compound of formula (XXII$_A$), (XXII$_C$) or (XXII$_D$) in a variety of ways and experimental conditions, which are widely known in the art for condensation reactions. Preferably it is carried out in a way analogous to that reported for step i').

According to the conversion described under 1) the reduction of a compound of formula (II), (V), (XXII$_A$), (XXII$_C$) or (XXII$_D$), wherein Ar is a substituted aryl and one of the substituents is nitro, to a compound of formula (II), (V), (XXII$_A$), (XXII$_C$) or (XXII$_D$), wherein such substituent is amino, can be carried out in a variety of ways, according to conventional methods well known in the literature. Preferably this conversion is carried out in a suitable solvent such as, for instance, methanol, ethanol, water, tetrahydrofuran, 1,4-dioxane, N,N-dimethylformamide, acetic acid, or a mixture thereof, in the presence of a suitable reducing agent, such as, for instance, hydrogen and a hydrogenation catalyst, or by treatment with cyclohexene or cyclohexadiene, or formic acid or ammonium formate and a hydrogenation catalyst, or a metal such as iron or zinc in the presence of an inorganic acid, such as hydrochloric acid, or by treatment with tin (II) chloride, at a temperature ranging from 0° C. to reflux and for a time varying from about 1 hour to about 96 hours. The hydrogenation catalyst is usually a metal, most often palladium, which can be used as such or supported on carbon.

According to the conversion described under 2) the acylation of a compound of formula (II), (V), (XXII$_A$), (XXII$_C$) or (XXII$_D$), wherein Ar is a substituted aryl and one of the substituents is amino, by reaction with an acetylating agent of formula (XXVII) or (XXVIII) to give a compound of formula (II), (V), (XXII$_A$), (XXII$_C$) or (XXII$_D$), wherein such substituent is a NHCOR4 or NHSO$_2$R4 residue, can be carried out in a variety of ways, according to conventional methods well known in the literature. Preferably this conversion is carried out under conditions analogous to that reported for step i').

According to the conversion described under 3) the reductive amination of a compound of formula (II), (V), (XXII$_A$), (XXII$_C$) or (XXII$_D$), wherein Ar is a substituted aryl and one of the substituents is amino, by reaction with a suitable aldehyde or ketone can be conducted in a variety of ways, according to conventional methods for carrying out reductive alkylations. Preferably, this reaction is carried out in a suitable solvent such as, for instance, methanol, N,N-dimethylformamide, dichloromethane, tetrahydrofuran, or a mixture thereof, in the presence of a suitable reducing agent such as, for instance, sodium borohydride, tetra-alkylammonium borohydride, sodium cyano borohydride, sodium triacetoxyborohydride, tetramethylammonium triacetoxy borohydride and in presence of an acid catalyst, such as, for instance, acetic acid or trifluoroacetic acid, at a temperature ranging from about 0° C. to reflux and for a time varying from about 1 hour to about 96 hours.

According to the conversion described under 4) the reduction of a compound of formula (I), wherein Ar is a substituted aryl and one of the substituents is nitro, to a compound of formula (I) wherein such substituent is amino, can be carried out in a variety of ways, according to conventional methods well known in the literature. Preferably this conversion is carried out under conditions analogous to that reported for conversion 1).

According to the conversion described under 5) the acylation of a compound of formula (I) wherein Ar is a substituted aryl and one of the substituents is amino, by reaction with an acetylating agent of formula (XXVII) or (XXVIII) to give a compound of formula (I) wherein such substituent is a NHCOR4 or NHSO$_2$R4 residue, can be carried out in a variety of ways, according to conventional methods well known in the literature. Preferably this conversion is carried out under conditions analogous to that reported for conversion 2).

According to the conversion described under 6) the reductive amination of a compound of formula (I) wherein Ar is a substituted aryl and one of the substituents is amino, by reaction with a suitable aldehyde or ketone can be conducted in a variety of ways, according to conventional methods for carrying out reductive alkylations. Preferably, this reaction is carried out under conditions analogous to that reported for conversion 3).

It is known to the skilled person that when a compound of formula (IV) or formula (XXVII) carries functional groups that may interfere in acylation reactions, such groups have to be protected before carrying out the reaction. In particular, when a compound of formula (IV) or formula (XXVII) is substituted by residues of general formula NR5R6, OR7, SR7, R8R9N—C$_1$-C$_6$ alkyl, or R8O—C$_1$-C$_6$ alkyl wherein R7 or at least one of R5 and R6 or at least one of R8 and R9 represent hydrogen, such groups may be protected as known in the art. It is also known to the skilled person that such protecting group may be removed just after the reaction or at a later stage in the synthetic process.

The deprotection of a compound of formula (I), (XXII$_A$), (XXII$_C$ or (XXII$_D$) wherein Ar is a substituted aryl and one of the substituents is a protected amino group can be made in a variety of ways according to conventional methods for deprotecting amino groups. Depending on the amino protecting group, this reaction can be conducted in different ways. In one aspect, such reaction can be carried out by treatment with an inorganic acid, such as hydrochloric, sulphuric or perchloric acid, or an organic acid, such as trifluoroacetic or methanesulfonic acid, in a suitable solvent, such as water, methanol, ethanol, 1,4-dioxane, tetrahydrofuran, diethyl ether, diisopropyl ether, acetonitrile, N,N-dimethylformamide, dichloromethane or mixtures thereof, at a temperature ranging from –10° C. to 80° C., and for a period of time ranging from 30 minutes to 48 hours. In another aspect, such reaction can be carried out by treatment with an inorganic base, such as lithium or sodium or potassium hydroxide, or sodium or potassium or caesium carbonate, or with an organic base, such as triethylamine or N,N-diisopropylethylamine, or with anhydrous hydrazine or hydrazine hydrate in a suitable solvent such as water, methanol, ethanol, 1,4-dioxane, tetrahydrofuran, diethyl ether, diisopropyl ether, acetonitrile, N,N-dimethylformamide, dichlorometane or mixtures thereof at a temperature ranging from –10° C. to 80° C., and for a period of time ranging from 30 minutes to 72 hours.

Substituted indazole derivatives can be prepared using standard procedures in organic synthesis as reported, for instance, in Smith, Michael—March's Advanced Organic Chemistry: reactions mechanisms and structure—5$^{th}$ Edition, Michael B. Smith and Jerry March, John Wiley & Sons Inc., New York (N.Y.), 2001. It is known to the skilled person that transformation of a chemical function into another may require that one or more reactive centers in the compound containing this function be protected in order to avoid undesired side reactions. Protection of such reactive centers, and subsequent deprotection at the end of the synthetic transformations, can be accomplished following standard procedures described, for instance, in: Green, Theodora W. and Wuts, Peter G. M.—Protective Groups in Organic Synthesis, Third Edition, John Wiley & Sons Inc., New York (N.Y.), 1999.

In cases where a compound of formula (I) contains one or more asymmetric centers, said compound can be separated into the single isomers by procedures known to those skilled in the art. Such procedures comprise standard chromatographic techniques, including chromatography using a chiral stationary phase, or crystallization. General methods for separation of compounds containing one or more asymmetric centers are reported, for instance, in Jacques, Jean;

Collet, André; Wilen, Samuel H.,—Enantiomers, Racemates, and Resolutions, John Wiley & Sons Inc., New York (N.Y.), 1981.

A compound of formula (I) can also be transformed into a pharmaceutically acceptable salt according to standard procedures that are known to those skilled in the art. Alternatively, a compound of formula (I) that is obtained as a salt can be transformed into the free base or the free acid according to standard procedures that are known to the skilled person.

The starting materials of the process of the present invention, i.e. compounds of formula (XII), (XIII), (XV), (XVI), (XVIII), (XXIII), and (XXI) are either commercially available or can be prepared by using well-known methods.

For example, the compounds of formula (XIII) can be easily obtained according to conventional procedures, which are widely known in the art for Grignard reagents formation, as reported in the following scheme:

RZ+Mg→RMgZ  (XIII)

For example, the compounds of formula (XV) can be easily prepared from the corresponding halogen derivatives, as reported in the following scheme (see for example WANG, X.-J. et al.; Org Lett 2006, 8 (2), 305-307):

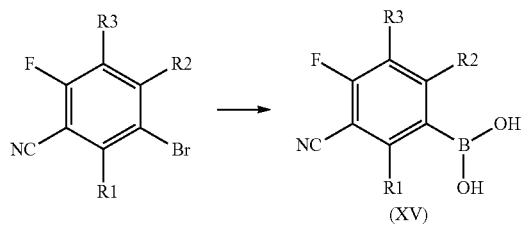

(XV)

For example, the compounds of formula (XVI) can be easily obtained by elaboration of the corresponding alcohols derivatives by working according to conventional synthetic methods.

For example, the compounds of formula (XXI) can be easily obtained by oxidation of the corresponding alcohols derivatives by working according to conventional synthetic methods.

Another object of the present invention is to provide an intermediate of formula (III$_{A'}$), (III$_{B'}$), (III$_{C'}$), or (III$_{D'}$):

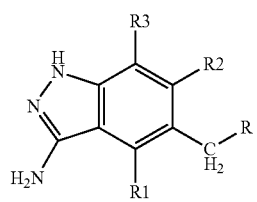

(III$_{A'}$)

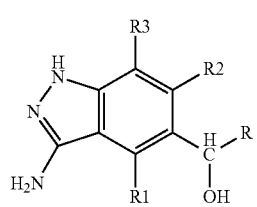

(III$_{B'}$)

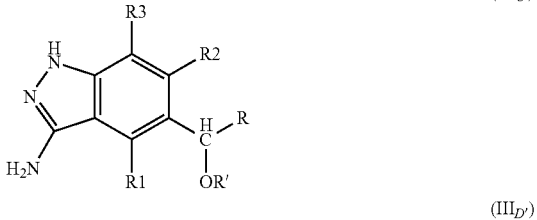

(III$_{C'}$)

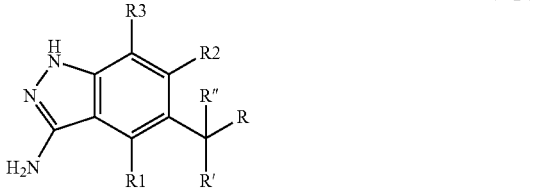

(III$_{D'}$)

wherein R is an optionally substituted $C_3$-$C_6$ cycloalkyl, aryl or heteroaryl, and R1, R2, R3, R' and R" are as defined above, with the proviso that the following compounds are excluded:

6-(3-amino-1H-indazol-5-ylmethyl)-3-isopropyl-1-(2,4,6-trichloro-phenyl)-1,7-dihydro-pyrazolo[3,4-d]pyrimidin-4-one and 1-[(3-amino-1H-indazol-5-yl)methyl]-3-({1-[2-(dimethylamino)ethyl]-1H-benzimidazol-2-yl}methyl)-1,3-dihydro-2H-benzimidazol-2-one.

Another object of the present invention is to provide an intermediate of formula of the formula (XII$_A$), (XXII$_C$) or (XXII$_D$):

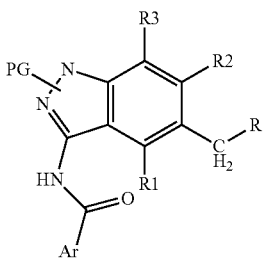

(XXII$_A$)

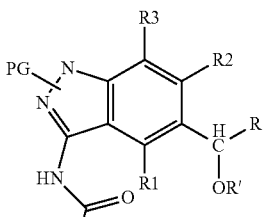

(XXII$_C$)

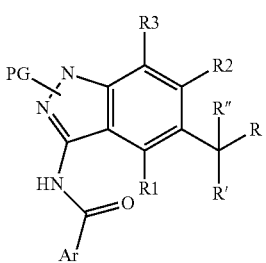

(XXII$_D$)

wherein Ar, R, R1, R2, R3, R', R" and PG are as defined above.

Another object of the present invention is to provide a compound of formula (XXVII):

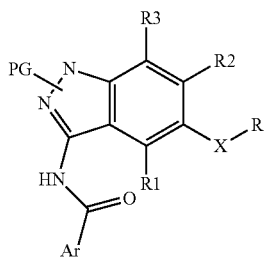

(XXVII)

wherein Ar, R, R1, R2 and R3 are as defined above and PG$_2$ is ethoxycarbonyl or 2-methoxymethylcarbonyl.

The present invention further provides a process for the preparation of a compound of formula (XXVII) as defined above, characterized in that the process comprises:

v) protecting a compound of formula (I) as defined above, to give a compound of formula (XXVII)

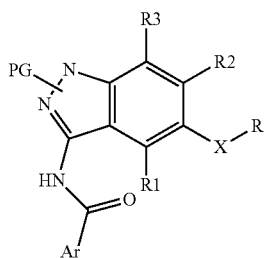

(XXVII)

wherein R, R1, R2, R3 and PG$_2$ are as defined above.

According to step v), the protection of a compound of formula (I) into a compound of formula (XXVII) can be accomplished in a variety of ways and experimental conditions. Preferably the reaction is carried out by treatment with a base such as lithium diisopropylamide, sodium hydride or lithium, sodium or potassium bis(trimethylsilyl)amide in a suitable solvent such as, for instance, toluene, tetrahydrofurane, 1,4-dioxane, diethylether, N,N-dimethylformamide, dimethoxyethane at a temperature ranging from −78° C. to room temperature and for a period of time varying from about 10 minutes to about 96 hours. The electrophile is usually a chloroformate derivative such as, for instance, ethyl chloroformate or 2-methoxyethyl chloroformate.

Pharmacology

The short forms and abbreviations used herein have the following meaning:
Ci Curie
DMSO dimethylsulfoxide
ID identity
KDa kiloDalton
microCi microCurie
mg milligram
microg microgram
mL milliliter
microL microliter
M molar
mM millimolar
microM micromolar
nM nanomolar Assays Compounds of the present invention were tested in biochemical assays, as described below.

Preparation of ALK Cytoplasmic Domain for Use in Biochemical Assay Cloning and Expression ALK cytoplasmic domain, corresponding to the residue 1060-1620 (the numbers of the amino acid residues refer to the Genbank accession number NP 004295.2) was PCR amplified from a human testis cDNA library.

Amplification was performed using the forward oligonucleotide:

(SEQ ID NO: 1)
5'GGGGACAAGTTTGTTACAAAAAAGCAGGCTTACTGGAAGTTCTGTTCC
AGGGGCCCCGCCGGAAGCACCAGGAGCTG-3' and the reverse oligonucleotide:

(SEQ ID NO: 2)
5'GGGGACCACTTTGTACAAGAAAGCTGGGTTTCAGGGCCCAGGCTGGTT
CATGCTATT-3'.

For cloning purposes, the oligonucleotides included attB sites in order to obtain an attB-flanked PCR product suitable for cloning using the Gateway technology (Invitrogen). Furthermore, for purification purposes, forward primer included a PreScission cleavage site (Amersham Biosciences). The resulting PCR product was cloned in the baculovirus expression vector pVL1393 (Invitrogen) Gateway-modified. For expression and purification purpose, a GST tag was added N-terminal to the ALK cytoplasmic domain. Cloning was performed according to the protocols described in the Gateway manual (Invitrogen).

Baculovirus was generated by cotransfecting Sf9 insect cells with expression vector and the viral DNA using the BaculoGold™ tranfection kit (Pharmingen). Viral supernatant was recovered after 5 days and subjected to 3 rounds of amplification to increase viral titer.

Recombinant protein was produced by infecting Sf21 insect cells at the density of 1×10$^6$ cells/mL with 30 mL viral supernatant per billion cells with shaking at 27° C. After 48 hours of infections the cells were recovered, pelletted and freezed at −80° C.

Protein Purification

Cells were resuspended in lysis buffer (Tris-HCl 50 mM pH8, NaCl 150 mM, CHAPS 0.2%, DTT 20 mM, glycerol 20%, "Complete" protease inhibitor cocktail (Roche Diagnostics), Na$_3$VO$_4$ 1 mM and lysed by liquid extrusion with a Gaulin homogenizer (Niro Soavi Italy). The lysate was cleared by centrifugation at 20000 g for 30 minutes and loaded on a Glutathione Sepharose 4B (Amersham Biosciences) column.

After extensive wash, recombinant protein was eluted with 10 mM Glutathione in 100 mM Tris-HCl pH8, 10% glycerol.

Affinity purified GST-ALK was loaded on a Heparin Sepharose™ FF (Amersham Biosciences) column and eluted with 50 mM NaCl, 25 mM TRIS pH 7.5, 2 mM DTT, 20% glycerol.

The eluted fractions were pooled and dialyzed against 150 mM NaCl, 50 mM Tris-HCl pH 7.4, 2 mM DTT, 20% glycerol.

Purified protein was stored at −80° C. prior its use in biochemical assay.

Biochemical Assay for Inhibitors of ALK Kinase Activity

ALK enzyme needs pre-activation in order to linearize reaction kinetics.

i. Kinase Buffer (KB) for ALK

Kinase buffer was composed of 50 mM HEPES pH 7.5 containing 1 mM $MnCl_2$, mM $MgCl_2$, 1 mM DTT, 3 microM $Na_3VO_4$, and 0.2 mg/mL BSA. 3×KB is buffer of the same composition and pH as KB, but with three times the concentration of each component.

ii. Assay Conditions

The kinase assay was run with a final enzyme concentration of 20 nM, in the presence of 8 microM ATP, 1 nM $^{33}$P-γ-ATP and 2 microM MBP. The MPB was purchased from Sigma-Aldrich, St. Louis, Mo., USA.

Cell-Based Assays for Inhibitors of ALK Kinase Activity

Western Blot Analysis of ALK and STAT3 Phosohorylation in Karpas-299, SR-786 and SUP-M2 Anaplastic Large Cell Lymphoma Cell Lines Karpas-299, SR-786 and SUP-M2 cells (DSMZ, Braunschwiegh, Germany) were seeded in 6-well tissue culture plates at $5 \times 10^5$ cells/mL in RPMI-1640 medium+2 mM glutamine+10% to 15% FCS (EuroClone, Italy), and incubated overnight at 37° C., 5% $CO_2$, 100% relative humidity. After this incubation, cells were treated with desired concentrations of compound for 2 hours at 37° C. Cells were collected by centrifugation at 248×g for 5 minutes, washed with cold PBS, centrifuged again at 248×g for 5 minutes and then lysed in 100 mM Tris-HCl pH 7.4, 2% SDS, 1 mM $Na_3VO_4$, protease inhibitor cocktail [Sigma-Aldrich product #P8340], phosphatase inhibitor cocktail [Sigma-Aldrich products #P2850+#P5726]). After brief sonication, cell lysates were cleared by centrifugation at 10,000×g for 20 minutes at room temperature and 20 microg/lane of cleared lysate protein were run on NuPAGE gels (NuPAGE 4-12% 10-lane Bis-Tris gels, Invitrogen) with MOPS running buffer, then transferred onto Hybond-ECL nitrocellulose filters (Amersham Biosciences, Little Chalfont, Buckinghamshire, UK) using Mini PROTEAN II chambers (Bio-Rad Laboratories, Hercules, Calif., USA). Filters bearing transferred protein were incubated for 1 hour in blocking buffer (TBS+5% Non-fat Dry Milk [#1706404 Bio-rad, Hercules, Calif., USA]+0.1% Tween 20), and probed over-night in TBS+5% BSA+0.1% Tween 20 at 4° C. containing 1/500 anti-phosho-ALK Tyr 1604 antibody (product #3341 Cell Signaling Technology, Beverly, Mass., USA) for dectection of phosphorylated ALK or 1/500 mouse anti-ALK antibody (product #35-4300, Zymed Laboratories, South San Francisco, Calif., USA) for the detection of total ALK or 1/500 mouse anti-phospho STAT3 Tyr 705 antibody (product #612357, BD Transduction Laboratories, Canada) for dectection of phosphorylated STAT3 or 1/1000 mouse anti-STAT3 antibody (product #610190 BD Transduction Laboratories, Canada) for detection of total STAT3.

In all cases, filters were then washed for 20 minutes with several changes of TBS+0.1% Tween 20, and incubated for 1 hour in TBS+5% Non-fat Dry Milk+0.1% Tween 20 containing 1/10000 dilution of horseradish peroxidase conjugated anti-rabbit or mouse IgG (Amersham, product #NA934), then were washed again and developed using the ECL chemiluminescence system (Amersham) according to manufacturer's recommendations. Unless otherwise stated, reagents used were from Sigma-Aldrich, St. Louis, Mo., USA.

In Vitro Cell Proliferation Assay for Inhibitors of ALK Kinase Activity

The human ALCL cell lines Karpas-299, SR-786 and SUP-M2 were seeded in 96 well plate (PerkinElmer, Wellesley, Mass., USA) $1 \times 10^5$ cells/mL in RPMI-1640 medium+2 mM glutamine+10% to 15% FCS (EuroClone, Italy), (100 microL/well) and maintained at 37° C., 5% $CO_2$, 100% relative humidity. The following day, plates were treated in duplicates with an appropriate dilution of compounds starting from a 10 mM stock solution in DMSO (final DMSO concentration: 0.1%). Eight untreated control wells were included in each plate. After 72 hours of treatment, 50 microL of CellTiter-Glo Assay (Promega, Madison, Wis., USA) were added to each well and after agitation the luminescence signal is measured using Envision Detector (PerkinElmer Wellesley, Mass., USA).

$IC_{50}$ values were calculated by LSW/Data Analysis using Microsoft Excel sigmoidal curve fitting.

Preparation of IGF-1R for Use in Biochemical Assay

Cloning and Expression

Human cDNA was used as template for amplification by polymerase chain reaction (PCR) of the predicted cytoplasmic portion of IGF-1R (amino acid residues 960-1367 of precursor protein; see NCBI Entrez Protein Accession #P08069) which includes the entire kinase domain. PCR was conducted using the forward primer sequence 5'-CTCG-GATCCAGAAAGAGAAATAACAGCAGGCTG-3' (SEQ ID NO:3) and the reverse primer sequence 5'-CTCGGATC-CTCAGCAGGTCGAAGACTGGGGCAGCGG-3' (SEQ ID NO:4). In order to facilitate subsequent cloning steps, both primers comprise a BamHI restriction endonuclease site sequence. This PCR product was cloned in frame using BamHI sticky ends into a transfer vector for the baculovirus expression system, pVL1392 (Pharmingen), previously modified by insertion into the pVL1392 multiple cloning site of sequences encoding Glutathione S-transferase (GST) fusion protein, PreScission protease cleavage site and partial MCS cassette derived from the pGex-6P plasmid (Amersham BioSciences). Insertion of the IGF-1R PCR product described above into the pGex-6P derived BamHI site of the modified pVL1392 vector results in an open reading frame corresponding to the pGEX-6P GST protein and PreScission peptide fused with the human IGF-1R cytoplasmic domain. In order to obtain fusion protein, Sf21 insect cells (Invitrogen) are cotransfected with 2 microg of purified plasmid and 1 microg of virus DNA (BaculoGold™ Transfection Kit, Pharmingen), as described in the Baculovirus Instruction manual (Pharmingen). A first amplification of the virus is performed using 600 microL of cotransfected virus on $6 \times 10^6$ Sf21 in a monolayer culture, in 12 mL of medium (TNM-FH Grace's medium—Pharmingen). After 3 days the medium is collected, centrifuged and transferred to a sterile tube. A second amplification is prepared with the same method using 2 mL on $3 \times 10^7$ cells, diluted in 40 mL of medium. For the third amplification of virus, 1 mL of supernatant from the second round are used per $3 \times 10^7$ cells diluted in 40 mL of medium.

Protein expression is performed in H5 insect cells infected with 14 mL virus/$1 \times 10^9$ insect cells (MOI=1.5) for 65 h with shaking at 27° C. Cells are harvested by centrifugation at 1200×g for 10 minutes.

Protein Purification

Cells were resuspended in phosphate buffered saline solution (PBS), 20 mM dithiothreitol (DTT), 0.2% CHAPS, 20% glycerol, 1 mM OVA, "Complete" protease inhibitor cocktail (1 tablet/50 mL buffer; Roche Diagnostics, Milan, Italy) and lysed by liquid extrusion with a Gaulin homogenizer (Niro Soavi, Italy). The lysate was centrifuged at 14000×g for 45 minutes and the supernatant was loaded onto a column containing 10 mL Glutathione Sepharose (Amersham Biosciences). The column was first washed with PBS buffer for 5 column volumes, then with 100 mM Tris pH 8.0, 20% glycerol for 5 column volumes, and lastly eluted with 10 mM glutathione in 100 mM Tris pH 8.0, 20% glycerol. Fractions of 10 mL were collected, and protein-rich fractions were pooled. Typically, 20 mg of fusion protein were recovered from $1 \times 10^9$ cells, and this was typically >85% pure as judged by SDS-PAGE followed by Coomassie staining. Purified protein was stored at −80° C. prior to its use in biochemical assays.

Biochemical Assay for Inhibitors of IGF-1R Kinase Activity

The inhibitory activity of putative kinase inhibitors and the potency of selected compounds were determined using a trans-phosphorylation assay.

A specific substrate was incubated with the kinase in appropriate buffer conditions in the presence of ATP traced with $^{33}P$-γ-ATP (gamma phosphate-labeled, Redivue™ Code Number AH9968, 1000-3000 Ci/mmole, Amersham Biosciences Piscataway, N.J., USA), optimal cofactors and test compound.

At the end of the phosphorylation reaction, more than 98% cold and radioactive ATP were captured by an excess of Dowex ion exchange resin. The resin was allowed to settle to the bottom of reaction wells by gravity. Supernatant, containing substrate peptide, was subsequently withdrawn and transferred into a counting plate, and radioactivity (corresponding to phosphate incorporated into peptide) was evaluated by β-counting.

Reagents/Assay Conditions i. Dowex Resin Preparation 500 g of wet resin (SIGMA, custom prepared DOWEX resin 1×8 200-400 mesh, 2.5 Kg) were weighed out and diluted to 2 L in 150 mM sodium formate, pH 3.00.

The resin was allowed to settle for several hours and then the supernatant was discarded. This washing procedure was repeated three times over two days. Finally, the resin was allowed to settle, supernatant was discarded and two volumes (with respect to the resin volume) of 150 mM sodium formate buffer were added. The final pH was circa 3.0. The washed resin was kept at 4° C. before use, and was stable for more than one week.

ii. Kinase Buffer (KB)

Kinase buffer was composed of 50 mM HEPES pH 7.9 containing 3 mM $MnCl_2$, 1 mM DTT, 3 microM $Na_3VO_4$, and 0.2 mg/mL BSA. 3×KB is buffer of the same composition and pH as KB, but with three times the concentration of each component.

iii. Enzyme pre-activation and preparation of 3× Enzyme Mix.

Prior to starting the kinase inhibition assay, IGF-1R was pre-phosphorylated in order to linearize reaction kinetics. To achieve this, the desired total quantity of enzyme was prepared at an enzyme concentration of 360 nM in KB containing 100 microM ATP, and this preparation was incubated for 30 min at 28° C. 3× Enzyme Mix was obtained by diluting this preactivated enzyme 20-fold in 3×KB.

iv. Assay Conditions

The kinase assay was run with a final enzyme concentration of 6 nM, in the presence of 6 microM ATP, 1 nM $^{33}P$-γ-ATP and 10 microM substrate, a carboxy-terminally biotinylated peptide of the following sequence: KKKSPGEYVNIEFGGGGGK-biotin (SEQ ID NO:5). The peptide was obtained in batches of >95% peptide purity from American Peptide Company, Inc. (Sunnyvale, Calif., USA).

Robotized Dowex Assay

Test reactions were performed in a total final volume of 21 microL consisting of:

a) 7 microL/well of 3× Enzyme Mix (18 nM preactivated enzyme in 3× kinase buffer), b) 7 microL/well of 3× substrate/ATP mix (30 microM substrate, 18 microM ATP, 3 nM $^{33}P$-γ-ATP in double-distilled water ($ddH_2O$), c) 7 microL/well 3× test compounds diluted into $ddH_2O$-3% DMSO.

Compound Dilution and Assay Scheme is Reported Below.

i. Dilution of Compounds 10 mM stock solutions of test compounds in 100% DMSO were distributed into 96 well 12×8 format microtiter plates.

For % inhibition studies, dilution plates at 1 mM, 100 microM and 10 microM were prepared in 100% DMSO, then diluted to 3× final desired concentration (30, 3 and 0.3 microM) in $ddH_2O$, 3% DMSO. A Multimek 96 (Beckman Coulter, Inc. 4300 N. Harbor Boulevard, P.O. Box 3100 Fullerton, Calif. 92834-3100 USA) was used for compound pipetting into test plates.

For IC50 determination, starting solutions of 30 microM compound in 3% DMSO were derived from 1 mM/100% DMSO stock solutions. These 30 microM starting solutions were used for generation of a further 9 serial ⅓ dilutions in $ddH_2O$, 3% DMSO, so as to generate a 10-point dilution curve at 3× the final assay concentration. Serial dilution was conducted in 96-well plates using a Biomek 2000 (Beckman Coulter) system. Dilution curves of 7 compounds/plate were prepared, and each plate also included a 10-point dilution curve of Staurosporine, as well as several negative and positive control wells.

ii. Assay Scheme 7 microL of each test compound dilution (or control) in $ddH_2O$, 3% DMSO were pipetted into each well of a 384-well, V-bottom assay plate, which was then transferred to a PlateTrak 12 robotized station (Perkin Elmer, 45 William Street Wellesley, Mass. 02481-4078, USA) equipped with one 384-tip pipetting head for starting the assay, plus one 96-tip head for dispensing the resin) prepared with reservoirs containing sufficient 3× Enzyme mix and 3×ATP mix (3×) to complete the assay run.

At the start of the assay the liquid handling system aspirates 7 microL of ATP mix, introduces an air gap inside the tips (5 microL) and then aspirates 7 microL of 3× Enzyme Mix. To start the reaction, tips contents were dispensed into the test wells already containing 7 microL test compound (at 3× desired final concentration), followed by 3 cycles of mixing, so as to restore desired final concentration for all reaction components.

Plates were incubated for 60 minutes at room temperature, and then the reaction was stopped by pipetting 70 microL of Dowex resin suspension into the reaction mix, followed by three cycles of mixing. After stopping the reaction, plates were allowed to rest for one hour in order to maximize ATP capture. At this point, 20 microL of supernatant were transferred from each well into wells of 384-Optiplates (Perkin Elmer) containing 70 microL/well of Microscint 40 (Perkin Elmer); after 5 min of orbital shaking the plates were read on a Perkin-Elmer Top Count radioactivity counter.

iii. Data Analysis

Data were analysed using a customized version of the "Assay Explorer" software package (Elsevier MDL, San Leandro, Calif. 94577). For single compound concentrations, inhibitory activity was typically expressed as % inhibition obtained in presence of compound, compared to total activity of enzyme obtained when inhibitor is omitted.

Compounds showing desired inhibition were further analysed in order to study the potency of the inhibitor through $IC_{50}$ calculation. In this case, inhibition data obtained using serial dilutions of the inhibitor were fitted by non-linear regression using the following equation:

$$v = v_0 + \frac{(v_0 - v_b)}{1 + 10^{n(\log IC_{50} - \log[I])}}$$

where $v_b$ is the baseline velocity, v is the observed reaction velocity, $v_o$ is the velocity in the absence of inhibitors, and [I] is the inhibitor concentration.

Cell-Based Assays for Inhibitors of IGF-1R Kinase Activity
Western Blot Analysis of Receptor Phosphorylation Following Stimulation with IGF-1 in MCF-7 Human Breast Cancer Cells MCF-7 cells (ATCC#HTB-22) were seeded in 12-well tissue culture plates at $2 \times 10^5$ cells/well in E-MEM medium (MEM+Earle's BSS+2 mM glutamine+0.1 mM non-essential amino acids)+10% FCS, and incubated overnight at 37° C., 5% CO2, 100% relative humidity. Cells were then starved by replacing E-MEM+10% FCS with E-MEM+0.1% BSA, and incubating overnight. After this incubation, wells were treated with desired concentrations of compound for 1 hour at 37° C., and were then stimulated with 10 nM recombinant human IGF-1 (Invitrogen, Carlsbad, Calif., USA) for 10 minutes at 37° C. Cells were then washed with PBS and lysed in 100 microL/well cell lysis buffer (M-PER Mammalian Protein Extraction Reagent [Product #78501, Pierce, Rockford, Ill., USA]+10 mM EDTA+Protease inhibitor cocktail [Sigma-Aldrich product #P8340]+phosphatase inhibitor cocktail [Sigma-Aldrich products #P2850+#P5726]). Cell lysates were cleared by centrifugation at 10,000×g for 5 minutes, and 10 microg/lane of cleared lysate protein were run on NuPAGE gels (NuPAGE 4-12% 10-lane Bis-Tris gels, Invitrogen) with MOPS running buffer, then transferred onto Hybond-ECL nitrocellulose filters (Amersham Biosciences, Little Chalfont, Buckinghamshire, UK) using Mini PROTEAN II chambers (Bio-Rad Laboratories, Hercules, Calif., USA). Filters bearing transferred protein were incubated for 1 hour in blocking buffer (TBS+5% BSA+0.15% Tween 20), and probed for 2 hours in the same buffer containing 1/1000 rabbit anti-phospho IGF-1R Tyr11131/InsR Tyr 1146 antibody (product #3021, Cell Signaling Technology, Beverly, Mass., USA) for the detection of phosphorylated IGF-1R, or 1/1000 dilution of rabbit IGF-Irβ(H-60) antibody (product #sc-9038, Santa Cruz Biotechnology, Inc., Santa Cruz, Calif., USA) for detecting total IGF-1R β chain. In either case, filters were then washed for 30 minutes with several changes of TBS+0.15% Tween 20, and incubated for 1 hour in washing buffer containing 1/5000 dilution of horseradish peroxidase conjugated anti-rabbit IgG (Amersham, product #NA934), then were washed again and developed using the ECL chemiluminescence system (Amersham) according to manufacturer's recommendations. Unless otherwise stated, reagents used were from Sigma-Aldrich, St. Louis, Mo., USA.

Growth Factor Induced S6 Ribosomal Protein Phosphorylation in Primary Human Fibroblasts Phosphorylation of S6 ribosomal protein in response to growth factor stimulation of normal human dermal fibroblasts (NHDF) was used to assess compound potency in inhibiting IGF-1 induced signal transduction in cells, and selectivity towards EGF and PDGF stimulus. NHDF cells obtained from PromoCell (Heidelberg, Germany), were maintained at 37° C. in a humidified atmosphere with 5% $CO_2$ in complete Fibroblast Growth Medium (PromoCell). For assay, NHDF were seeded in 384-well tissue culture plates (clear- and flat-bottomed black plates; Matrix Technologies Inc., Hudson, N.H., USA) at a density of 5000 cells/well in serum-free medium containing 0.1% bovine serum albumin (BSA) and incubated for 5 days. Starved cells were treated for 1 hour with desired doses of compounds and then stimulated for a further 2 hours with either 10 nM IGF-1 (Invitrogen Corp., CA, USA), 10 nM EGF (Gibco BRL, USA) or 1 nM PDGF-B/B (Roche Diagnostics GmbH, Germany). Cells were then fixed in PBS/3.7% paraformaldehyde for 20 minutes at room temperature, washed ×2 with PBS, and permeabilized with PBS/0.3% Triton X-100 for 15 minutes. Wells were then saturated with PBS/1% non-fat dry milk (Bio-Rad Laboratories, Hercules, Calif., USA) for 1 hour, and then probed for 1 hour at 37° C. with anti-phospho-S6 (Ser 235/236) antibody (Cell Signaling Technology, Beverly, Mass., USA, cat. #2211) at 1/200 dilution in PBS/1% milk/0.3% Tween 20. Wells were then washed twice with PBS, and incubated for 1 hour at 37° C. with PBS/1% milk/0.3% Tween 20+1 microg/mL DAPI (4,6-diamidino-2-phenylindole)+1/500 Goat anti-rabbit Cy5™-conjugated secondary antibody (Amersham Biosciences, Little Chalfont, Buckinghamshire, UK). Wells were then washed ×2 with PBS, and 40 microL PBS are left in each well for immunofluorescence analysis. Fluorescence images in the DAPI and Cy5™ channels were automatically acquired, stored and analysed using a Cellomics ArrayScan™ IV instrument (Cellomics, Pittsburgh, USA); the Cellomics Cytotoxicity Algorithm was used to quantify cytoplasmic fluorescence associated with phospho-S6 (Cy5™ signal parameter: "Mean Lyso Mass-pH") for each cell in 10 fields/well, and eventually expressed as a mean population value. Unless otherwise stated, reagents were obtained from Sigma-Aldrich, St. Louis, Mo., USA.

Biochemical Assay for Inhibitors of Aurora-2 Kinase Activity

The in vitro kinase inhibition assay was conducted in the same way as described for IGF-1R. At variance with IGF-1R, Aurora-2 enzyme does not need pre-activation.

i. Kinase Buffer (KB) for Aurora-2

The kinase buffer was composed of 50 mM HEPES, pH 7.0, 10 mM $MnCl_2$, 1 mM DTT, 3 microM $Na_3VO_4$, and 0.2 mg/mL BSA.

ii. Assay Conditions for Aurora-2 (Final Concentrations)

The kinase assay was run with an enzyme concentration of 2.5 nM, 10 microM ATP, 1 nM $^{33}$P-γ-ATP, and 8 microM substrate, composed of 4 LRRWSLG repeats.

Cell-Based Assays for Inhibitors of Aurora-2 Kinase Activity

In Vitro Cell Proliferation Assay for Inhibitors of Aurora-2 Kinase Activity

The human colon cancer cell line HCT-116 was seeded at 5000 cells/cm$^2$ in 24 wells plate (Costar) using F12 medium (Gibco) supplemented with 10% FCS (EuroClone, Italy) 2 mM L-glutamine and 1% penicillin/streptomycin and maintained at 37° C., 5% $CO_2$ and 96% relative humidity. The following day, plates were treated in duplicates with 5 mL of an appropriate dilution of compounds starting from a 10 mM stock in DMSO. Two untreated control wells were included in each plate. After 72 hours of treatment, medium was withdrawn and cells detached from each well using 0.5 mL of 0.05% (w/v) Trypsin, 0.02% (w/v) EDTA (Gibco). Samples were diluted with 9.5 mL of Isoton (Coulter) and counted using a Multisizer 3 cell counter (Beckman Coulter). Data were evaluated as percent of the control wells:

% of CTR=(Treated−Blank)/(Control−Blank).

$IC_{50}$ values were calculated by LSW/Data Analysis using Microsoft Excel sigmoidal curve fitting.

Given the above assays, the compounds of formula (I) of the invention resulted to possess a remarkable protein kinase inhibitory activity, typically with $IC_{50}$ lower than 10 μM.

See, as an example, the following Table I reporting the experimental data of some representative compounds of the invention being tested in biochemical assay as ALK, IGF-1R and Aurora-2 kinase inhibitors ($IC_{50}$ μM).

TABLE 1

| Cpd No. | ALK $IC_{50}$ (μM) Biochemical assay | IGF-1R $IC_{50}$ (μM) Biochemical assay | Aur2 $IC_{50}$ (μM) Biochemical assay |
|---|---|---|---|
| 11 | 0.055 | 0.263 | 0.338 |
| 4 | 0.207 | 2.350 | 0.484 |
| 26 | 0.411 | 1.103 | 0.568 |
| 18 | 1.771 | 6.070 | 3.234 |

From all of the above, the novel compounds of formula (I) of the invention appear to be particularly advantageous in the therapy of diseases caused by deregulated protein kinase activity such as cancer.

The compounds of the present invention can be administered either as single agents or, alternatively, in combination with known anticancer treatments such as radiation therapy or chemotherapy regimen in combination with, for example, antihormonal agents such as antiestrogens, antiandrogens and aromatase inhibitors, topoisomerase I inhibitors, topoisomerase II inhibitors, agents that target microtubules, platin-based agents, alkylating agents, DNA damaging or intercalating agents, antineoplastic antimetabolites, other kinase inhibitors, other anti-angiogenic agents, inhibitors of kinesins, therapeutic monoclonal antibodies, inhibitors of mTOR, histone deacetylase inhibitors, farnesyl transferase inhibitors, and inhibitors of hypoxic response.

If formulated as a fixed dose, such combination products employ the compounds of this invention within the dosage range described below and the other pharmaceutically active agent within the approved dosage range.

Compounds of formula (I) may be used sequentially with known anticancer agents when a combination formulation is inappropriate.

The compounds of formula (I) of the present invention, suitable for administration to a mammal, e.g., to humans, can be administered by the usual routes and the dosage level depends upon the age, weight, and conditions of the patient and administration route.

For example, a suitable dosage adopted for oral administration of a compound of formula (I) may range from about 10 to about 500 mg per dose, from 1 to 5 times daily. The compounds of the invention can be administered in a variety of dosage forms, e.g., orally, in the form tablets, capsules, sugar or film coated tablets, liquid solutions or suspensions; rectally in the form suppositories; parenterally, e.g., intramuscularly, or through intravenous and/or intrathecal and/or intraspinal injection or infusion.

The present invention also includes pharmaceutical compositions comprising a compound of formula (I) or a pharmaceutically acceptable salt thereof in association with a pharmaceutically acceptable excipient, which may be a carrier or a diluent.

The pharmaceutical compositions containing the compounds of the invention are usually prepared following conventional methods and are administered in a suitable pharmaceutical form.

For example, the solid oral forms may contain, together with the active compound, diluents, e.g., lactose, dextrose saccharose, sucrose, cellulose, corn starch or potato starch; lubricants, e.g., silica, talc, stearic acid, magnesium or calcium stearate, and/or polyethylene glycols; binding agents, e.g., starches, arabic gum, gelatine methylcellulose, carboxymethylcellulose or polyvinyl pyrrolidone; disintegrating agents, e.g., starch, alginic acid, alginates or sodium starch glycolate; effervescing mixtures; dyestuffs; sweeteners; wetting agents such as lecithin, polysorbates, laurylsulphates; and, in general, non-toxic and pharmacologically inactive substances used in pharmaceutical formulations. These pharmaceutical preparations may be manufactured in known manner, for example, by means of mixing, granulating, tabletting, sugar-coating, or film-coating processes.

The liquid dispersions for oral administration may be, e.g., syrups, emulsions and suspensions.

As an example the syrups may contain, as a carrier, saccharose or saccharose with glycerine and/or mannitol and sorbitol.

The suspensions and the emulsions may contain, as examples of carriers, natural gum, agar, sodium alginate, pectin, methylcellulose, carboxymethylcellulose, or polyvinyl alcohol.

The suspension or solutions for intramuscular injections may contain, together with the active compound, a pharmaceutically acceptable carrier, e.g., sterile water, olive oil, ethyl oleate, glycols, e.g., propylene glycol and, if desired, a suitable amount of lidocaine hydrochloride.

The solutions for intravenous injections or infusions may contain, as a carrier, sterile water or preferably they may be in the form of sterile, aqueous, isotonic, saline solutions or they may contain propylene glycol as a carrier.

The suppositories may contain, together with the active compound, a pharmaceutically acceptable carrier, e.g., cocoa butter, polyethylene glycol, a polyoxyethylene sorbitan fatty acid ester surfactant or lecithin.

EXPERIMENTAL SECTION

For a reference to any specific compound of formula (I) of the invention, optionally in the form of a pharmaceutically acceptable salt, see the experimental section and claims. Referring to the examples that follow, compounds of the present invention were synthesized using the methods described herein, or other methods, which are well known in the art.

The short forms and abbreviations used herein have the following meaning:
g (grams)
ml (milliliters)
μM (micromolar)
h (hours)
mm (millimeters)
M (molar)
mol (moles)
r.t. (room temperature)
TFA (trifluoroacetic acid)
DIPEA (N,N-diisopropyl-N-ethylamine)
THF (tetrahydrofuran)
MeOH (Methanol)
TIPS (triisopropylsilyl)
TBDMS (dimethyl-tert-butylsilyl)

BOC (tert-butyloxycarbonyl)
NaH=sodium hydride, 60% in mineral oil
mg (milligrams)
mM (millimolar)
mmol (millimoles)
MHz (Mega-Hertz)
Hz (Hertz)
min (minutes)
TLC (thin layer chromatography)
TEA (triethylamine)
DMF (N,N-dimethyl formamide)
DCM (dichloromethane)
Hex (hexane)
DMSO (dimethylsulfoxide)
bs (broad singlet)
Ac (acetyl)
$Ac_2O$ acetic anhydride
ESI=electrospray ionization
TBTU (2-(1H-benzotriazol-1-yl)-1,1,3,3-tetramethyluronium tetrafluoroborate
RP-HPLC (reverse phase high performance liquid chromatography) With the aim to better illustrate the present invention, without posing any limitation to it, the following examples are now given.

As used herein the symbols and conventions used in the processes, schemes and examples are consistent with those used in the contemporary scientific literature, for example, the *Journal of the American Chemical Society or the Journal of Biological Chemistry.*

Unless otherwise noted, all materials were obtained from commercial suppliers, of the best grade and used without further purification. Anhydrous solvent such as DMF, THF, $CH_2Cl_2$ and toluene were obtained from the Aldrich Chemical Company. All reactions involving air- or moisture-sensitive compounds were performed under nitrogen or argon atmosphere.

General Purification and Analytical Methods

Flash Chromatography was performed on silica gel (Merck grade 9395, 60A). HPLC was performed on Waters X Terra RP 18 (4.6×50 mm, 3.5 μm) column using a Waters 2790 HPLC system equipped with a 996 Waters PDA detector and Micromass mod. ZQ single quadrupole mass spectrometer, equipped with an electrospray (ESI) ion source. Mobile phase A was ammonium acetate 5 mM buffer (pH 5.5 with acetic acid-acetonitrile 95:5), and Mobile phase B was water-acetonitrile (5:95). Gradient from 10 to 90% B in 8 minutes, hold 90% B 2 minutes. UV detection at 220 nm and 254 nm. Flow rate 1 mL/min. Injection volume 10 microL. Full scan, mass range from 100 to 800 amu. Capillary voltage was 2.5 KV; source temperature was 120° C.; cone was 10 V. Retention times (HPLC r.t.) are given in minutes at 220 nm or at 254 nm. Mass are given as m/z ratio.

When necessary, compounds were purified by preparative HPLC on a Waters Symmetry C18 (19×50 mm, 5 um) column or on a Waters X Terra RP 18 (30×150 mm, 5 μm) column using a Waters preparative HPLC 600 equipped with a 996 Waters PDA detector and a Micromass mod. ZMD single quadrupole mass spectrometer, electron spray ionization, positive mode. Mobile phase A was water-0.01% trifluoroacetic acid, and mobile phase B was acetonitrile. Gradient from 10 to 90% B in 8 min, hold 90% B 2 min. Flow rate 20 mL/min. In alternative, mobile phase A was water-0.1% $NH_3$, and mobile phase B was acetonitrile. Gradient from 10 to 100% B in 8 min, hold 100% B 2 min. Flow rate 20 mL/min.

1H-NMR spectrometry was performed on a Mercury VX 400 operating at 400.45 MHz equipped with a 5 mm double resonance probe [1H (15N-31P) ID_PFG Varian].

Example 1

Step a

5-[(3,5-Difluoro-phenyl)-hydroxy-methyl]-2-fluoro-benzonitrile [(XI), R1=R2=R3=H, R=3,5-difluoro-phenyl]

To a stirred suspension of magnesium turnings (2.6 g, 109 mmol) in anhydrous tetrahydrofuran under argon (10 mL), a solution of 1-bromo-3,5-difluoro-benzene (21 g, 109 mmol) in dry tetrahydrofuran (90 mL) was slowly added. The reaction mixture was stirred and heated at 90° C. until all magnesium was consumed (1 hour). Thereafter, the reaction was cooled at −10° C. and a solution of 2-fluoro-5-formyl-benzonitrile (13.5 g, 90.6 mmol) in 100 mL of anhydrous tetrahydrofuran was added during 30 min. After 1 hour, the reaction mixture was quenched by adding dropwise 200 mL of 20% ammonium chloride solution. Ethyl acetate was added, the layers were separated, and the aqueous layer was extracted twice with ethyl acetate. Organic layers were collected, washed with brine, dried and evaporated. Crude was triturated with isopropyl ether/hexane 1:1 (100 mL), filtered and washed with the same mixture (50 mL) to afford 16 gr of final product. Purification of the resulting organic phase by chromatography over silica gel (hexane/EtOAc 4:1) afforded 4.5 g of the title compound (total amount 20.5 g, 87% yield).

1H-NMR (400 MHz), δ (ppm, DMSO-d6): 5.82 (d, J=4.02 Hz, 1H) 6.41 (d, J=4.02 Hz, 1H) 7.05-7.12 (m, 1H) 7.12-7.18 (m, 2H) 7.46-7.50 (m, 1H) 7.80 (td, J=5.76, 2.62 Hz, 1H) 7.97 (dd, J=6.34, 2.19 Hz, 1H)

Operating in an analogous way, the following compound was obtained:

5-(phenyl-hydroxy-methyl)-2-fluoro-benzonitrile [(XI), R1=R2=R3=H, R=phenyl]

ESI(+) MS: m/z 245 ($MNH_4^+$).

Step b 5-(3,5-Difluoro-benzoyl)-2-fluoro-benzonitrile [(X), R1=R2=R3=H, R=3,5-difluorophenyl]

A mixture of 5-[(3,5-Difluoro-phenyl)-hydroxy-methyl]-2-fluoro-benzonitrile (2.68 g, 10.2 mmol), 4-methylmorpholine N-oxide monohydrate (2.02 g, 15 mmol) and tetrapropylammonium perruthenate (35 mg, 0.1 mmol) in dry dichloromethane (50 mL) was stirred at room temperature for 2 hours. The reaction mixture was evaporated and the residue redissolved in ethyl acetate. The organic phase was washed with 10% sodium bisulphite and saturated ammonium chloride, dried and evaporated. Purification of the crude by chromatography over silica gel (EtOAc/hexane) afforded 2.05 g of the title compound (77% yield).

1H-NMR (400 MHz), δ (ppm, DMSO-d6): 7.43-7.50 (m, 2H) 7.61-7.68 (m, 1H) 7.72 (t, J=9.02 Hz, 1H) 8.17 (ddd, J=8.84, 5.30, 2.32 Hz, 1H) 8.35 (dd, J=6.22, 2.20 Hz, 1H)

Operating in an analogous way, the following compound was obtained:

5-Benzoyl-2-fluoro-benzonitrile [(X), R1=R2=R3=H, R=phenyl]

1H-NMR (400 MHz), δ (ppm, DMSO-d6): 7.59 (t, J=7.81 Hz, 2H) 7.72 (m, 2H) 7.78 (dd, J=8.30, 1.46 Hz, 2H) 8.13 (ddd, J=8.79, 5.37, 2.20 Hz, 1H) 8.28 (dd, J=6.10, 2.20 Hz, 1H)

Step c (3-Amino-1H-indazol-5-yl)-(3,5-difluoro-phenyl)-methanone [(IX), R1=R2=R3=H, R=3,5-difluorophenyl]

A mixture of 5-(3,5-difluoro-benzoyl)-2-fluoro-benzonitrile (2.05 g, 7.84 mmol) and hydrazine hydrate (0.73 mL, 15.7 mmol) in dry tetrahydrofuran (100 mL) was stirred at room temperature for 2 hours. The reaction mixture was treated with 37% hydrochloric acid (1.3 mL, 15.7 mmol) for 30 min and then the volatiles were partially evaporated. The reaction mixture was then diluted with water (100 mL) and aqueous $NH_3$ was added to reach neutral pH. The resulting solid was filtered, washed thoroughly with water and dried under vacuum at 60° C. The title compound was obtained as yellow solid (1.75 g, 80% yield).

1H-NMR (400 MHz), δ (ppm, DMSO-d6): 5.75 (br. s., 2H) 7.33-7.36 (m, 1H) 7.36-7.40 (m, 2H) 7.52-7.59 (m, 1H) 7.75 (dd, J=8.84, 1.65 Hz, 1H) 8.27 (dd, J=1.59, 0.73 Hz, 1H) 11.95 (br. s., 1H)

Operating in an analogous way, the following compounds were obtained:

(3-Amino-1H-indazol-5-yl)-(3-ethoxy-phenyl)-methanone [(IX), R1=R2=R3=H, R=3-ethoxyphenyl]

1H-NMR (400 MHz), δ (ppm, DMSO-d6): 1.36 (t, J=7.01 Hz, 3H) 4.11 (q, J=6.95 Hz, 2H) 7.20-7.24 (m, 2H) 7.25-7.28 (m, 1H) 7.41 (dd, J=8.84, 0.55 Hz, 1H) 7.48 (td, J=7.68, 0.61 Hz, 1H) 7.80 (dd, J=8.78, 1.59 Hz, 1H) 8.34 (d, J=0.85 Hz, 1H) 12.24 (br. s., 1H)

(3-Amino-1H-indazol-5-yl)-phenyl-methanone [(IX), R1=R2=R3=H, R=phenyl]

1H-NMR (400 MHz), δ (ppm, DMSO-d6): 7.40 (dd, J=8.78, 0.61 Hz, 1H) 7.57 (tt, J=7.68, 1.59 Hz, 2H) 7.66 (tt, J=7.32, 2.07 Hz, 2H) 7.72 (dt, J=6.83, 1.34 Hz, 2H) 7.78 (dd, J=8.78, 1.59 Hz, 1H) 8.31 (m, 1H) 12.15 (br. s., 1H)

Step d

N-[5-(3,5-Difluoro-benzoyl)-1H-indazol-3-yl]-2,2,2-trifluoro-acetamide [(VIII), R1=R2=R3=H, R=3,5-difluorophenyl, $PG_1$=trifluoroacethyl]

A suspension of (3-amino-1H-indazol-5-yl)-(3,5-difluoro-phenyl)-methanone (2.73 g, 10 mmol) in dry tetrahydrofuran (120 mL) was treated with trifluoroacetic anhydride (4.2 mL, 30 mmol) and stirred 1 hour at room temperature. The solution was evaporated, treated with methanol and further evaporated to dryness. The residue was redissolved in ethyl acetate and washed with aqueous bicarbonate. The organic phase was separated, dried and evaporated. The solid was triturated with a small amount of dichloromethane and filtered affording 3.25 g (88% yield) of title compound.

1H-NMR (400 MHz), δ (ppm, DMSO-d6): 7.39-7.46 (m, 2H) 7.56-7.64 (m, 1H) 7.68 (dd, J=8.84, 0.67 Hz, 1H) 7.86 (dd, J=8.84, 1.65 Hz, 1H) 8.28-8.32 (m, 1H) 12.16 (s, 1H) 13.50 (s, 1H)

Operating in an analogous way, the following compound was obtained:

N-[5-(3-Ethoxy-benzoyl)-1H-indazol-3-yl]-2,2,2-trifluoro-acetamide [(VIII), R1=R2=R3=H, R=3-ethoxyphenyl, $PG_1$=trifluoroacethyl]

1H-NMR (400 MHz), δ (ppm, DMSO-d6): 1.34 (t, J=6.95 Hz, 3H) 4.10 (q, J=6.95 Hz, 2H) 7.19-7.25 (m, 2H) 7.28 (d, J=7.56 Hz, 1H) 7.43-7.50 (m, 1H) 7.67 (d, J=8.90 Hz, 1H) 7.85 (dd, J=8.84, 1.52 Hz, 1H) 8.26 (s, 1H) 12.14 (s, 1H) 13.46 (s, 1H)

Step e

N-[5-(3,5-Difluoro-benzoyl)-1-trityl-1H-indazol-3-yl]-2,2,2-trifluoro-acetamide [(VII), R1=R2=R3=H, R=3,5-difluorophenyl, PG=triphenylmethyl, $PG_1$=trifluoroacethyl]

N-[5-(3,5-Difluoro-benzoyl)-1H-indazol-3-yl]-2,2,2-trifluoro-acetamide (19.11 g, 51.76 mmol) in dry dichloromethane (300 mL) was treated with chlorotriphenylmethane (14.72 g, 52.8 mmol) and triethylamine (14.55 mL, 103.5 mmol). After stirring at room temperature for two days, the reaction was washed with a solution of $NH_4Cl$, dried and evaporated. Purification of the crude by chromatography over silica gel (DCM/MeOH) afforded 27.32 g of the title compound (86% yield).

1H-NMR (400 MHz), δ (ppm, DMSO-d6): 6.57 (d, J=8.90 Hz, 1H) 7.20 (m, 6H) 7.29-7.40 (m, 11H) 7.58 (m, 2H) 8.22 (d, J=1.10 Hz, 1H) 12.27 (s, 1H)

Operating in an analogous way, the following compound was obtained:

N-[5-(3-Ethoxy-benzoyl)-1-trityl-1H-indazol-3-yl]-2,2,2-trifluoro-acetamide [(VII), R1=R2=R3=H, R=3-ethoxyphenyl, PG=triphenylmethyl, $PG_1$=trifluoroacethyl]

1H-NMR (400 MHz), δ (ppm, DMSO-d6): 1.33 (t, J=6.95 Hz, 3H) 4.10 (q, J=6.95 Hz, 2H) 6.56 (d, J=9.02 Hz, 1H) 7.17-7.39 (m, 18H) 7.41-7.47 (m, 1H) 7.54 (dd, J=9.08, 1.65 Hz, 1H) 8.18 (d, J=0.98 Hz, 1H) 12.25 (s, 1H)

Step f (3-Amino-1-trityl-1H-indazol-5-yl)-(3,5-difluoro-phenyl)-methanone [(VI), R1=R2=R3=H, R=3,5-difluorophenyl, PG=triphenylmethyl]

N-[5-(3,5-Difluoro-benzoyl)-1-trityl-1H-indazol-3-yl]-2,2,2-trifluoro-acetamide (6.12 g, 10 mmol) was heated at 100° C. in a mixture isopropanol/tetrahydrofuran 8:2 (100 mL) and triethylamine (12.2 mL) for 48 hours. The volatiles were partially evaporated and the resulting mixture cooled and filtered. The solid was washed with diethyl ether. After drying under vacuum at 70° C. the title compound was obtained as a white solid (5.1 g, 99% yield).

1H-NMR (400 MHz), δ (ppm, DMSO-d6): 5.98 (br. s., 2H) 6.35 (d, J=8.90 Hz, 1H) 7.20-7.37 (m, 17H) 7.48 (dd, J=9.08, 1.77 Hz, 1H) 7.50-7.57 (m, 1H) 8.23 (d, J=1.10 Hz, 1H)

Operating in an analogous way, the following compound was obtained:

(3-Amino-1-trityl-1H-indazol-5-yl)-(3-ethoxy-phenyl)-methanone [(VI), R1=R2=R3=H, R=3-ethoxyphenyl, PG=triphenylmethyl]

1H-NMR (400 MHz), δ (ppm, DMSO-d6): 1.33 (t, J=6.95 Hz, 3H) 4.07 (q, J=6.95 Hz, 2H) 5.93 (s, 2H) 6.36 (d, J=9.02 Hz, 1H) 7.12-7.34 (m, 18H) 7.40-7.46 (m, 2H) 8.22 (d, J=1.10 Hz, 1H)

Step g

N-[5-(3,5-Difluoro-benzoyl)-1-trityl-1H-indazol-3-yl]-4-(4-methyl-piperazin-1-yl-2-nitro-benzamide [(V), R1=R2=R3=H, R=3,5-difluorophenyl, Ar=4-(4-methyl-piperazin-1-yl)-2-nitro-phenyl, PG=triphenylmethyl]

To a suspension of 4-(4-methyl-piperazin-1-yl)-2-nitro-benzoic acid hydrochloride (1.5 g, 4.97 mmol) in dry tetrahydrofuran (80 mL) were added oxalyl chloride (1.4 mL, 19.9 mmol) and N,N-dimethylformamide (1-2 drops). The mixture was stirred at room temperature overnight and then evaporated to dryness. The resulting crude acyl chloride was taken-up with toluene and evaporated again then dissolved in dry tetrahydrofuran (180 mL). A solution of (3-amino-1-trityl-1H-indazol-5-yl)-(3,5-difluoro-phenyl)-methanone (1.83 g. 3.55 mmol) and N,N-diisopropylethylamine (2.5 mL, 14.22 mmol) in dry tetrahydrofuran (15 mL) was added to the reaction mixture. The mixture was stirred at room temperature overnight and then at 75° C. for 2 hours. The volatiles were evaporated and the residue taken up with dichloromethane and washed with brine. The organic phase was dried over sodium sulfate and evaporated to dryness. Purification of the crude by chromatography over silica gel (DCM/MeOH) afforded 2.51 g of the title compound as yellow powder (92% yield).

1H-NMR (400 MHz), δ (ppm, DMSO-d6): 2.22 (s, 3H) 2.40-2.45 (m, 4H) 3.26-3.36 (m, 4H) 6.50 (d, J=8.17 Hz, 1H) 7.19-7.50 (m, 21H) 7.56 (dd, J=9.15, 1.71 Hz, 1H) 8.28-8.30 (m, 1H) 11.22 (br. s., 1H)

Operating in an analogous way, the following compound was obtained:

N-[5-(3-Ethoxy-benzoyl)-1-trityl-1H-indazol-3-yl]-4-(4-methyl-piperazin-1-yl)-2-nitro-benzamide [(V), R1=R2=R3=H, R=3-ethoxyphenyl, Ar=4-(4-methyl-piperazin-1-yl)-2-nitro-phenyl, PG=triphenylmethyl]

1H-NMR (400 MHz), δ (ppm, DMSO-d6): 1.34 (t, J=6.95 Hz, 3H) 2.24 (m, 3H) 2.45 (m, 4H) 3.27 (m, 4H) 4.08 (q, J=6.95 Hz, 2H) 6.51 (d, J=8.17 Hz, 1H) 7.20-7.46 (m, 22H) 7.53 (dd, J=9.15, 1.71 Hz, 1H) 8.30 (m, 1H) 11.22 (br. s., 1H)

Step h

N-[5-(3,5-Difluoro-benzoyl)-1H-indazol-3-yl]-4-(4-methyl-piperazin-1-yl)-2-nitro-benzamide [(II), R1=R2=R3=H, R=3,5-difluorophenyl, Ar=4-(4-methyl-piperazin-1-yl)-2-nitro-phenyl]

A mixture of N-[5-(3,5-Difluoro-benzoyl)-1-trityl-1H-indazol-3-yl]-4-(4-methyl-piperazin-1-yl)-2-nitro-benzamide (2.76 g, 3.62 mmol), trifluoroacetic acid (5.6 mL) and dichloromethane (56 mL) was stirred at room temperature for 2 hours. The volatiles were evaporated and the residue taken up with dichloromethane and washed with a saturated solution of sodium hydrogen-carbonate. The organic phase was evaporated to dryness. The residue was redissolved in ethyl acetate and washed twice with brine. The resulting organic phase was dried over sodium sulfate and evaporated to dryness. Purification of the crude by chromatography over silica gel (DCM/MeOH) and trituration of the so obtained compound from diethyl ether afforded 1.47 g of the title compound (78% yield).

1H-NMR (400 MHz), δ (ppm, DMSO-d6): 2.25 (br. s., 3H) 2.47 (br. s., 4H) 3.29-3.38 (m, 4H) 7.26 (dd, J=8.84, 2.50 Hz, 1H) 7.37-7.43 (m, 2H) 7.45 (d, J=2.44 Hz, 1H) 7.51-7.59 (m, 1H) 7.63 (dd, J=8.84, 0.55 Hz, 1H) 7.66 (br. s., 1H) 7.86 (dd, J=8.84, 1.65 Hz, 1H) 8.36 (s, 1H) 11.13 (s, 1H) 13.21 (s, 1H)

Operating in an analogous way, the following compounds were obtained:

N-[5-(3-Ethoxy-benzoyl)-1H-indazol-3-yl]-4-(4-methyl-piperazin-1-yl)-2-nitro-benzamide [(II), R1=R2=R3=H, R=3-ethoxyphenyl, Ar=4-(4-methyl-piperazin-1-yl)-2-nitro-phenyl]

1H-NMR (400 MHz), δ (ppm, DMSO-d6): 1.34 (t, J=6.95 Hz, 3H) 2.26-2.34 (m, 3H) 2.46-2.59 (m, 4H) 3.28-3.35 (m, 4H) 4.10 (q, J=6.95 Hz, 2H) 7.18-7.21 (m, 1H) 7.24-7.26 (m, 1H) 7.27 (dd, J=9.33, 1.89 Hz, 1H) 7.29-7.32 (m, 1H) 7.45 (t, J=7.87 Hz, 1H) 7.46 (d, J=2.32 Hz, 1H) 7.62 (d, J=9.02 Hz, 1H) 7.66 (d, J=9.88 Hz, 1H) 7.84 (dd, J=8.78, 1.59 Hz, 1H) 8.39 (s, 1H) 11.13 (br. s., 1H) 13.17 (s, 1H)

4-[(3-Dimethylamino-propyl)-methyl-amino]-N-[5-(3-ethoxy-benzoyl)-1H-indazol-3-yl]-2-nitro-benzamide [(II), R1=R2=R3=H, R=3-ethoxyphenyl, Ar=4-[(3-dimethylamino-propyl)-methyl-amino]-2-nitro-phenyl]

1H-NMR (400 MHz), δ (ppm, DMSO-d6): 1.33 (t, J=6.95 Hz, 3H) 1.60-1.78 (m, 2H) 2.22 (s, 6H) 2.29-2.37 (m, 2H) 3.01 (s, 3H) 3.48 (t, J=7.01 Hz, 2H) 4.09 (q, J=6.99 Hz, 2H) 6.98 (dd, J=8.84, 2.50 Hz, 1H) 7.16-7.21 (m, 2H) 7.22-7.25 (m, 1H) 7.27-7.32 (m, 1H) 7.45 (t, J=7.93 Hz, 1H) 7.58-7.66 (m, 2H) 7.83 (dd, J=8.78, 1.59 Hz, 1H) 8.36 (s, 1H) 11.04 (s, 1H) 13.14 (s, 1H)

Step i

N-[5-(3,5-Difluoro-benzyl)-1H-indazol-3-yl]-4-(4-methyl-piperazin-1-yl)-2-nitro-benzamide [(I$_A$), R1=R2=R3=H, R=3,5-difluorophenyl, Ar=4-(4-methyl-piperazin-1-yl)-2-nitro-phenyl] cpd. 6

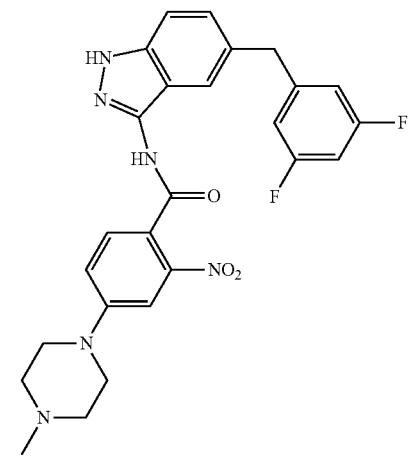 [SMILES: CN1CCN(c2ccc(C(=O)Nc3n[nH]c4ccc(Cc5cc(F)cc(F)c5)cc34)c([N+](=O)[O-])c2)CC1]

N-[5-(3,5-Difluoro-benzoyl)-1H-indazol-3-yl]-4-(4-methyl-piperazin-1-yl)-2-nitro-benzamide (3.61 g, 6.93 mmol) was dissolved in DCM (150 mL) in argon atmosphere and trifluoroacetic acid (150 mL) is added under stirring. Sodium borohydride pellets (2.62 gr, 69.3 mmol) is gradually added over a period of 72 hours. The reaction mixture was evaporated, taken up with a mixture MeOH/acetone and stirred for 1 hour. The resulting mixture was evaporated to dryness, redissolved in MeOH and NaOH 8N was added till basic pH was reached. Crude was evaporated and ice/water was added, the solid thus formed was filtered, washed with water and dried under vacuum at 80° C. affording 3.22 g of title compound (92% yield).

1H-NMR (400 MHz), δ (ppm, DMSO-d6): 2.23 (s, 3H) 2.42-2.47 (m, 4H) 3.33-3.38 (m, 4H) 4.05 (s, 2H) 6.91-6.97 (m, 2H) 6.97-7.05 (m, 1H) 7.24 (dd, J=8.60, 1.52 Hz, 1H) 7.27 (br. s., 1H) 7.41 (d, J=8.66 Hz, 1H) 7.44 (br. s., 1H) 7.63 (s, 1H) 7.66-7.73 (m, 1H) 10.81 (br. s., 1H) 12.70 (s, 1H)

Operating in an analogous way, the following compounds were obtained:

4-[(3-Dimethylamino-propyl)-methyl-amino]-N-[5-(3-ethoxy-benzyl)-1H-indazol-3-yl]-2-nitro-benzamide [(I$_A$), R1=R2=R3=H, R=3-ethoxyphenyl, Ar=4-[(3-dimethylamino-propyl)-methyl-amino]-2-nitro-phenyl] cpd. 53

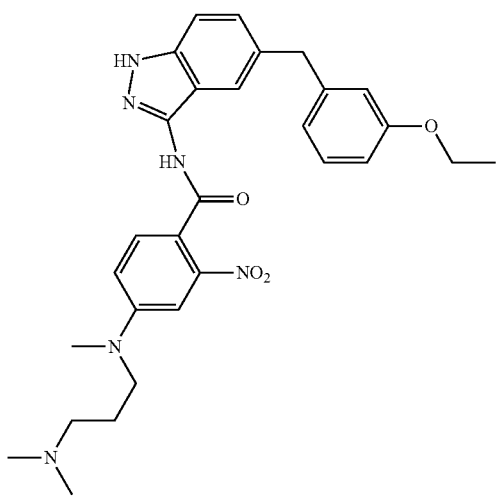 [SMILES: CCOc1cccc(Cc2ccc3[nH]nc(NC(=O)c4ccc(N(C)CCCN(C)C)cc4[N+](=O)[O-])c3c2)c1]

1H-NMR (400 MHz), δ (ppm, DMSO-d6): 1.26-1.31 (m, 3H) 1.69 (t, J=6.77 Hz, 2H) 2.19 (s, 6H) 2.28 (br. s., 2H) 3.02 (s, 3H) 3.45-3.51 (m, 2H) 3.93-4.00 (m, 2H) 3.96 (s, 2H) 6.70-6.73 (m, 1H) 6.76-6.80 (m, 1H) 6.77 (d, J=1.59 Hz, 1H) 6.98 (d, J=8.90 Hz, 1H) 7.14-7.19 (m, 1H) 7.19-7.23 (m, 2H) 7.38 (d, J=8.66 Hz, 1H) 7.61 (s, 1H) 7.67 (d, J=10.00 Hz, 1H) 10.72 (br. s., 1H) 12.65 (s, 1H)

N-{5-[(3,5-Difluoro-phenyl)-hydroxy-methyl]-1H-indazol-3-yl}-4-(4-methyl-piperazin-1-yl)-2-(tetrahydro-pyran-4-ylamino)-benzamide [(I$_B$), R1=R2=R3=H, R=3,5-difluorophenyl, Ar=4-(4-methyl-piperazin-1-yl)-2-(tetrahydro-pyran-4-ylamino)-phenyl] cpd. 60

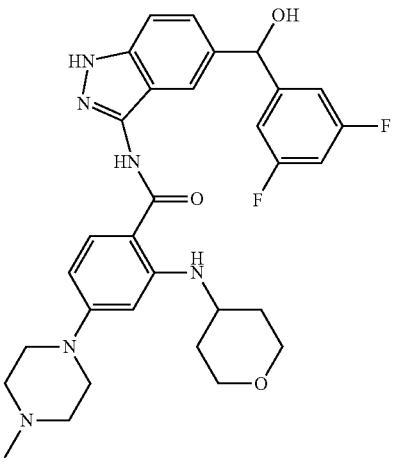 [SMILES: CN1CCN(c2ccc(C(=O)Nc3n[nH]c4ccc(C(O)c5cc(F)cc(F)c5)cc34)c(NC3CCOCC3)c2)CC1]

A mixture of N-[5-(3,5-Difluoro-benzoyl)-1H-indazol-3-yl]-4-(4-methyl-piperazin-1-yl)-2-(tetrahydro-pyran-4-ylamino)-benzamide (130 mg, 0.226 mmol) and sodium borohydride (15 mg, 0.39 mmol) was dissolved at room temperature in i-propanol (20 mL). The reaction mixture was stirred for 4 hours, quenched with methanol and evaporated to dryness. Crude material was redissolved in DCM and washed with brine. After trituration with diethyl ether, 59 mg of the title compound were recovered (45% yield).

1H-NMR (400 MHz), δ (ppm, DMSO-d6): 1.26-1.41 (m, 2H) 1.89-1.99 (m, 2H) 2.23 (s, 3H) 2.39-2.47 (m, 4H) 3.21-3.29 (m, 4H) 3.45-3.55 (m, 2H) 3.63-3.74 (m, 1H) 3.76-3.86 (m, 2H) 5.81 (d, J=4.15 Hz, 1H) 6.12 (d, J=4.15 Hz, 1H) 6.14 (d, J=2.07 Hz, 1H) 6.24 (dd, J=9.08, 2.26 Hz, 1H) 6.96-7.04 (m, 1H) 7.05-7.12 (m, 2H) 7.27-7.36 (m, 1H) 7.37-7.43 (m, 1H) 7.64 (s, 1H) 7.80 (d, J=9.15 Hz, 1H) 8.31 (d, J=7.56 Hz, 1H) 10.09 (s, 1H) 12.63 (s, 1H)

N-{5-[(3-Ethoxy-phenyl)-hydroxy-methyl]-1H-indazol-3-yl}-4-(4-methyl-piperazin-1-yl)-2-nitro-benzamide [(I$_B$), R1=R2=R3=H, R=3-ethoxyphenyl, Ar=4-(4-methyl-piperazin-1-yl)-2-nitro-phenyl] cpd. 67

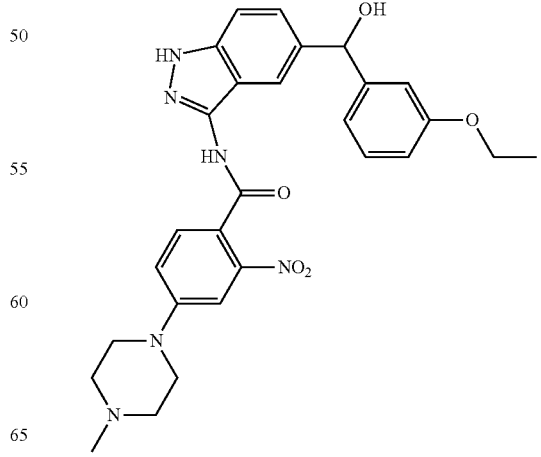

1H-NMR (400 MHz), δ (ppm, DMSO-d6): 1.29 (t, J=6.95 Hz, 3H) 2.24 (s, 3H) 2.42-2.47 (m, 4H) 3.36 (m, 4H) 3.97 (q, J=6.95 Hz, 2H) 5.70 (d, J=3.90 Hz, 1H) 5.85 (d, J=3.90 Hz, 1H) 6.72 (ddd, J=8.17, 2.56, 0.73 Hz, 1H) 6.90 (d, J=7.68 Hz, 1H) 6.93 (dd, J=2.20, 1.46 Hz, 1H) 7.17 (t, J=7.87 Hz, 1H) 7.26 (d, J=8.78 Hz, 1H) 7.28 (dd, J=8.72, 1.40 Hz, 1H) 7.36 (d, J=8.78 Hz, 1H) 7.44 (d, J=2.07 Hz, 1H) 7.70 (d, J=6.71 Hz, 1H) 7.81 (br. s., 1H) 10.80 (br. s., 1H) 12.65 (s, 1H).

Example 2

Step j 5-(3,5-Difluoro-benzyl)-2-fluoro-benzonitrile
[(XIV), R1=R2=R3=H, R=3,5-difluorophenyl]

5-[(3,5-Difluoro-phenyl)-hydroxy-methyl]-2-fluoro-benzonitrile (3.5 g, 13.3 mmol) and sodium iodide (20 g, 133 mmol) are stirred in acetonitrile (50 mL) under nitrogen at 60° C. To the reaction mixture is gradually added chlorotrimethylsilane (17 mL, 134 mmol) over a period of 8 hours. The mixture is diluted with ethyl acetate and washed with water, saturated aqueous sodium bicarbonate, 10% aqueous sodium thiosulfate and brine. Purification of the crude by chromatography over silica gel (EtOAc/hexane 5:100) afforded 3.1 g of the title compound (88% yield).

1H-NMR (400 MHz), δ (ppm, DMSO-d6): 4.02 (s, 2H) 7.02-7.11 (m, 3H) 7.47 (t, J=9.08 Hz, 1H) 7.68-7.74 (m, 1H) 7.90 (dd, J=6.22, 2.19 Hz, 1H)

Operating in an analogous way, the following compound was obtained:

5-benzyl-2-fluoro-benzonitrile [(XIV), R1=R2=R3=H, R=phenyl]

ESI(+) MS: m/z 229 (MNH$_4^+$).

Step k 5-(3,5-Difluoro-benzyl)-2-fluoro-benzonitrile
[(XIV), R1=R2=R3=H, R=3,5-difluorophenyl]

3-Cyano-4-fluorophenylboronic acid (1.649 g, 10 mmol), powdered potassium phosphate (4.254 g, 20 mmol) and Pd(PPh$_3$)$_4$ (231 mg, 0.2 mmol) were charged in an oven-dried flask under argon atmosphere. The flask was evacuated and back-filled with argon thrice and then toluene (30 mL) and 3,5-difluorobenzyl bromide (1.295 mL, 10 mmol) were added by means of a syringe through a lattice stopper, under good stirring.

The reaction mixture was heated to 100° C. in half an hour and maintained at that temperature for 1.5 hours. The black mixture was taken up with diethylether (200 mL), washed with saturated aqueous ammonium chloride (2×20 mL), brine (3×30 mL), dried over sodium sulphate and evaporated to dryness to afford 3.21 g of yellow oil. The crude was purified by flash chromatography on silica gel eluting with n-hexane/ethyl acetate 95:5 to yield 1.89 g (yield 76.4%) of whitish solid.

1H-NMR (400 MHz), δ (ppm, DMSO-d6): 4.02 (s, 2H) 7.02-7.11 (m, 3H) 7.47 (t, J=9.08 Hz, 1H) 7.68-7.74 (m, 1H) 7.90 (dd, J=6.22, 2.19 Hz, 1H)

Following an analogous procedure the compounds listed below were prepared:

5-(2,5-Difluoro-benzyl)-2-fluoro-benzonitrile

1H-NMR (400 MHz), δ (ppm, DMSO-d6): 4.01 (s, 2H), 7.09-7.17 (m, 1H), 7.20-7.27 (m, 2H), 7.46 (t, J=9.08 Hz, 1H), 7.64 (m, 1H), 7.82 (dd, J=6.22, 2.19 Hz, 1H)

2-Fluoro-5-(5-fluoro-2-methyl-benzyl)-benzonitrile

1H-NMR (400 MHz), δ (ppm, DMSO-d6): 2.18 (s, 3H), 4.01 (s, 2H), 7.00 (m, 2H), 7.22 (m, 1H), 7.48 (t, J=9.08 Hz, 1H), 7.56 (m, 1H), 7.75 (dd, J=6.22, 2.19 Hz, 1H)

2-Fluoro-5-(3-fluoro-benzyl)-benzonitrile

1H-NMR (400 MHz), δ (ppm, DMSO-d6): 3.98 (s, 2H), 6.95-7.15 (m, 3H), 7.27-7.38 (m, 1H), 7.38-7.48 (t, 1H), 7.61-7.70 (m, 1H), 7.81-7.87 (dd, J=6.22, 2.19 Hz. 1H).

2-Fluoro-5-pyridin-3-ylmethyl-benzonitrile

1H-NMR (400 MHz), δ (ppm, DMSO-d6): 4.03 (s, 2H) 7.33 (ddd, J=7.83, 4.79, 0.79 Hz, 1H) 7.47 (t, J=9.02 Hz, 1H) 7.65-7.68 (m, 1H) 7.68-7.72 (m, 1H) 7.89 (dd, J=6.28, 2.01 Hz, 1H) 8.44 (dd, J=4.76, 1.59 Hz, 1H) 8.54 (d, J=1.71 Hz, 1H)

Step l 5-(3,5-Difluoro-benzyl)-1H-indazol-3-ylamine
[(III$_A$), R1=R2=R3=H, R=3,5-difluorophenyl]

A mixture of 5-(3,5-difluoro-benzyl)-2-fluoro-benzonitrile (20 g, 80.9 mmol) and hydrazine hydrate (19.6 mL, 404 mmol) in n-butanol (200 mL) was heated at 120° C. overnight. The reaction mixture was diluted with water/ethyl acetate and the organic phase washed twice with brine, dried and evaporated. Crude was triturated with diethyl ether and filtered to afford 13 gr of final product. Purification of the resulting organic phase by chromatography over silica gel (DCM/EtOH 95:5) afforded further 6.3 g of the title compound (total amount 19.2 g, 92% yield).

1H-NMR (400 MHz), δ (ppm, DMSO-d6): 4.01 (s, 2H) 5.23 (s, 2H) 6.89-6.98 (m, 2H) 7.03 (tt, J=9.43, 2.33 Hz, 1H) 7.11-7.15 (m, 1H) 7.16-7.20 (m, 1H) 7.53 (s, 1H) 11.30 (s, 1H)

Following an analogous procedure the compounds listed below were prepared:

5-(2,5-Difluoro-benzyl)-1H-indazol-3-ylamine

1H-NMR (400 MHz), δ (ppm, DMSO-d6): 3.99 (s, 2H), 5.28 (m, 2H), 7.05-7.25 (m, 5H), 7.51 (s, 1H), 11.30 (bs, 1H).

5-(5-Fluoro-2-methyl-benzyl)-1H-indazol-3-ylamine

1H-NMR (400 MHz), δ (ppm, DMSO-d6): 2.21 (s, 3H), 3.97 (s, 2H), 5.22 (bs, 2H), 7.43 (s, 1H), 7.14-7.20 (m, 2H), 7.06 (dd, 1H), 6.87-6.97 (m, 2H), 11.27 (bs, 1H).

5-(3-Fluoro-benzyl)-1H-indazol-3-ylamine

1H-NMR (400 MHz), δ (ppm, DMSO-d6): 4.00 (s, 2H), 5.22 (bs, 2H), 6.96-7.09 (m, 3H), 7.11 (m, 1H), 7.15 (m, 1H), 7.29-7.37 (m, 1H), 7.53 (s, 1H), 11.27 (s, 1H).

5-Pyridin-3-ylmethyl-1H-indazol-3-ylamine

1H-NMR (400 MHz), δ (ppm, DMSO-d6): 4.01 (s, 2H) 5.23 (br. s., 2H) 7.08-7.15 (m, 1H) 7.15-7.19 (m, 1H) 7.25-7.34 (m, 1H) 7.53 (s, 1H) 7.60 (dt, J=7.86, 1.92 Hz, 1H) 8.40 (dd, J=4.69, 1.65 Hz, 1H) 8.51 (d, J=1.83 Hz, 1H) 11.28 (s, 1H)

5-benzyl-1H-indazol-3-ylamine

1H-NMR (400 MHz), δ (ppm, DMSO-d6): 3.97 (s, 2H) 5.21 (s, 2H) 7.07-7.11 (m, 1H) 7.13-7.16 (m, 1H) 7.16-7.20 (m, 1H) 7.20-7.24 (m, 2H) 7.25-7.31 (m, 2H) 7.52 (s, 1H) 11.25 (s, 1H).

Step n

5-[1-(3,5-Difluoro-phenyl)ethyl]-2-fluoro-benzonitrile [(XIXD$_1$), R1=R2=R3=H, R=3,5-difluorophenyl, R'=methyl]

5-(3,5-Difluoro-benzyl)-2-fluoro-benzonitrile (450 mg, 1.82 mmol) was dissolved in THF dry (14 mL) in nitrogen atmosphere at −20° C. and methyl iodide (0.17 mL, 2.73 mmol) was added under stirring. Bis-(trimethylsilyl)-lithiumamid, 1.0 M in THF (0.684 ml, 3.64 mmol) was gradually added. After 20 minutes the reaction was quenched by adding a solution of KHSO$_4$ 10% and extracted with ethyl acetate. The organic phase was washed with aqueous KHSO$_4$ 10% and brine, dried over sodium sulfate and evaporated to dryness. The crude was purified by flash chromatography on silica gel using hexane/ethyl acetate 98/2 as the eluant. The title product was isolated as an oil (400 mg, 84% yield).

1H-NMR (400 MHz), δ (ppm, DMSO-d6): 1.59 (d, J=7.32 Hz, 3H) 4.31 (q, J=7.19 Hz, 1H) 7.08 (m, 3H) 7.46 (t, J=9.15 Hz, 1H) 7.73 (m, 1H) 7.95 (dd, J=6.22, 2.44 Hz, 1H)

Step l'''

5-[1-(3,5-Difluoro-phenyl)-ethyl]-1H-indazol-3-ylamine [(IIID$_1$), R1=R2=R3=H, R=3,5-difluorophenyl, R'=methyl]

5-[1-(3,5-Difluoro-phenyl)-ethyl]-2-fluoro-benzonitrile (324 mg, 1.24 mmol) was dissolved in n-butanol (3 mL) and hydrazine hydrate (0.301 mL, 6.20 mmol) was added. The reaction mixture was stirred at 120° C. for 22 hours then quenched by adding water/ethyl acetate. The organic phase separated was washed with water and brine, dried over sodium sulfate and evaporated to dryness. The crude was purified by chromatography on silica gel with a gradient elution of DCM/EtOH from 99/1 to 98/2. Title product was isolated as an oil (96 mg, 39% yield).

1H-NMR (400 MHz), δ (ppm, DMSO-d6): 1.61 (d, J=7.19 Hz, 3H) 4.25 (q, J=7.32 Hz, 1H) 5.26 (br. s, 5.26, 2H) 6.99 (m, 3H) 7.12 (dd, J=8.66, 1.59 Hz, 1H) 7.16 (dd, J=8.54, 0.73 Hz, 1H) 7.62 (br. s, 1H) 11.29 (s, 1H)

Step i'

N-[5-(3,5-Difluoro-benzyl)-1H-indazol-3-yl]-4-(4-methyl-piperazin-1-yl)-2-(tetrahydro-pyran-4-ylamino)-benzamide [(I$_A$), R1=R2=R3=H, R=3,5-difluorophenyl, Ar=4-(4-methyl-piperazin-1-yl)-2-(tetrahydro-pyran-4-ylamino)-phenyl] cpd. 11

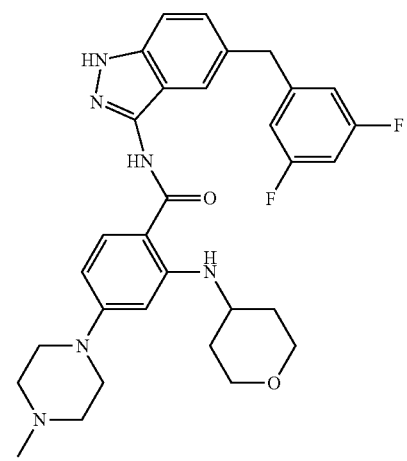 [SMILES: CN1CCN(c2ccc(C(=O)Nc3n[nH]c4ccc(Cc5cc(F)cc(F)c5)cc34)c(NC3CCOCC3)c2)CC1]

To a suspension of 4-(4-methyl-piperazin-1-yl)-2-[(tetrahydro-pyran-4-yl)-(2,2,2-trifluoro-acetyl)-amino]-benzoic acid trifluoroacetate (10 g, 22.1 mmol) in dry dichloromethane (300 mL) oxalyl chloride (3.58 mL, 42.3 mmol) and N,N-dimethylformamide (1-2 drops) were added. The mixture was stirred at room temperature for 2 hours then evaporated to dryness. The resulting crude acyl chloride was taken-up with toluene and evaporated again then dissolved in dry tetrahydrofuran (130 mL) at −20° C. A solution of 5-(3,5-difluoro-benzyl)-1H-indazol-3-ylamine (5 g. 19.28 mmol) and N,N-diisopropylethylamine (12.8 mL, 73.3 mmol) in dry THF (40 mL) was added to the cooled reaction mixture. The mixture was stirred at −20° C. for 4 hours then quenched by adding water/ethyl acetate. The organic phase was washed with a saturated solution of sodium hydrogenocarbonate, dried over sodium sulfate and evaporated to dryness.

The crude can be purified by flash chromatography on silica gel using dichloromethane/ethanol 100:10 as the eluant, affording intermediate N-[5-(3,5-Difluoro-benzyl)-1H-indazol-3-yl]-4-(4-methyl-piperazin-1-yl)-2-[(tetrahydropyran-4-yl)-(2,2,2-trifluoro-acetyl)-amino]-benzamide as a pale yellow solid.

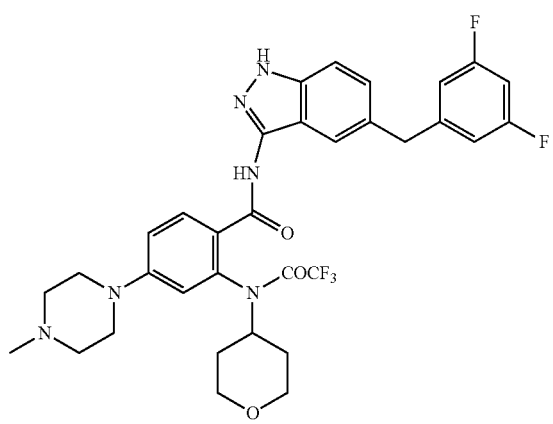

1H-NMR (400 MHz), δ (ppm, DMSO-d6): 1.25-1.41 (m, 1H) 1.48-1.61 (m, 1H) 1.66 (d, J=9.02 Hz, 1H) 1.92 (d, J=9.15 Hz, 1H) 2.25 (s, 3H) 2.43-2.49 (m, 4H) 3.23-3.41 (m, 6H) 3.77 (dd, J=10.91, 4.21 Hz, 1H) 3.87 (dd, J=11.65, 3.96 Hz, 1H) 4.02 (s, 2H) 4.37-4.49 (m, 1H) 6.89 (d, J=2.44 Hz, 1H) 6.90-6.98 (m, 2H) 7.02 (tt, J=9.42, 2.29 Hz, 1H) 7.09 (dd, J=8.78, 2.44 Hz, 1H) 7.27 (dd, J=8.72, 1.40 Hz, 1H) 7.41-7.43 (m, 2H) 7.83 (d, J=8.78 Hz, 1H) 10.52 (s, 1H) 12.69 (s, 1H)

Alternatively, not previously purified crude reaction mixture can be dissolved in methanol (375 mL) in the presence of triethylamine (60 mL) and stirred at 65° C. for 2 hours. The solvents were removed under reduced pressure and the residue treated with water/ethyl acetate. Organic phase was dried over sodium sulfate and evaporated to dryness. Purification of the crude by chromatography over silica gel (DCM/EtOH/NH₃ 5N in MeOH=1000/50/5) and crystallisation of the so obtained compound from EtOAc/hexane afforded 8.4 g of the title compound as a white solid (78% yield).

1H-NMR (400 MHz), δ (ppm, DMSO-d6): 1.26-1.43 (m, 2H) 1.86-2.02 (m, 2H) 2.23 (s, 3H) 2.42-2.46 (m, 4H) 3.23-3.29 (m, 4H) 3.45-3.54 (m, 2H) 3.62-3.75 (m, 1H) 3.82 (dt, J=11.61, 3.83 Hz, 2H) 4.05 (s, 2H) 6.14 (d, J=2.07 Hz, 1H) 6.24 (dd, J=8.90, 2.19 Hz, 1H) 6.94-7.06 (m, 3H) 7.26 (dd, J=8.66, 1.46 Hz, 1H) 7.41 (d, J=8.66 Hz, 1H) 7.50 (d, 1H) 7.80 (d, J=9.15 Hz, 1H) 8.29 (d, J=7.68 Hz, 1H) 10.08 (s, 1H) 12.63 (s, 1H).

Operating in an analogous way, the following compounds were obtained:

N-[5-(3,5-Difluoro-benzyl)-1H-indazol-3-yl]-2-(3-methoxy-propylamino)-4-(4-methyl-piperazin-1-yl)-benzamide [(I$_A$), R1=R2=R3=H, R=3,5-difluorophenyl, Ar=4-(4-methyl-piperazin-1-yl)-2-(3-methoxy-propylamino)-phenyl] cpd. 36

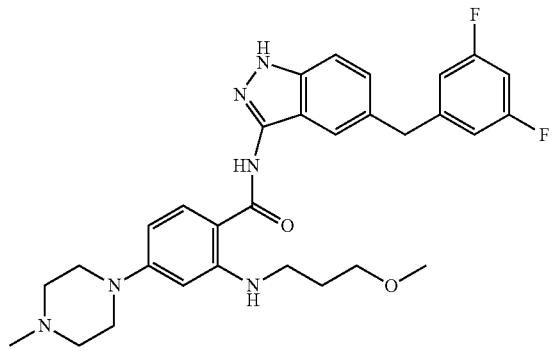 [SMILES: COCCCNc1cc(N2CCN(C)CC2)ccc1C(=O)Nc1n[nH]c2ccc(Cc3cc(F)cc(F)c3)cc12]

1H-NMR (400 MHz), δ (ppm, DMSO-d6): 1.14 (d, J=6.34 Hz, 3H) 2.23 (s, 3H) 2.41-2.47 (m, 4H) 3.24-3.31 (m, 4H) 3.27 (s, 3H) 3.32-3.40 (m, 2H) 3.74-3.83 (m, 1H) 4.05 (s, 2H) 6.13 (d, J=2.19 Hz, 1H) 6.24 (dd, J=9.02, 2.20 Hz, 1H) 6.94-7.04 (m, 3H) 7.25 (dd, J=8.66, 1.59 Hz, 1H) 7.41

1H-NMR (400 MHz), δ (ppm, DMSO-d6): 1.80 (quin, J=6.49 Hz, 2H) 2.24 (s, 3H) 2.42-2.47 (m, 4H) 3.16-3.21 (m, 2H) 3.23 (s, 3H) 3.26-3.32 (m, 4H) 3.41 (t, J=6.16 Hz, 2H) 4.04 (s, 2H) 6.07 (d, J=2.19 Hz, 1H) 6.24 (dd, J=9.02, 2.19 Hz, 1H) 6.95-7.00 (m, 2H) 6.99-7.04 (m, 1H) 7.24 (dd, J=8.66, 1.59 Hz, 1H) 7.41 (d, J=8.54 Hz, 1H) 7.51 (s, 1H) 7.80 (d, J=9.15 Hz, 1H) 8.19 (t, J=5.12 Hz, 1H) 10.07 (s, 1H) 12.62 (s, 1H)

N-[5-(3,5-Difluoro-benzyl)-1H-indazol-3-yl]-4-(4-methyl-piperazin-1-yl)-benzamide[(I$_A$), R1=R2=R3=H, R=3,5-difluorophenyl, Ar=4-(4-methyl-piperazin-1-yl)-phenyl] cpd. 4

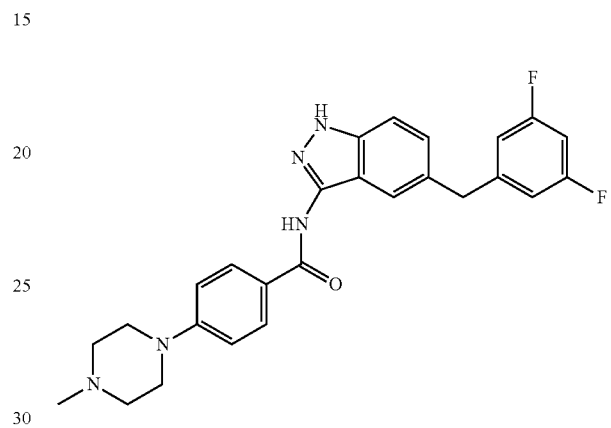

1H-NMR (400 MHz), δ (ppm, DMSO-d6): 2.23 (s, 3H) 2.44-2.49 (m, 4H) 3.28-3.32 (m, 4H) 4.05 (s, 2H) 6.90-7.00 (m, 3H) 7.02 (d, J=9.15 Hz, 2H) 7.24 (dd, J=8.66, 1.59 Hz, 1H) 7.41 (d, J=0.49 Hz, 1H) 7.59 (s, 1H) 7.97 (d, J=9.02 Hz, 2H) 10.39 (s, 1H) 12.67 (s, 1H)

N-[5-(3,5-Difluoro-benzyl)-1H-indazol-3-yl]-2-((R)-2-methoxy-1-methyl-ethylamino)-4-(4-methyl-piperazin-1-yl)-benzamide [(I$_A$), R1=R2=R3=H, R=3,5-difluorophenyl, Ar=4-(4-methyl-piperazin-1-yl)-2-((R)-2-methoxy-1-methyl-ethylamino)-phenyl] cpd. 32

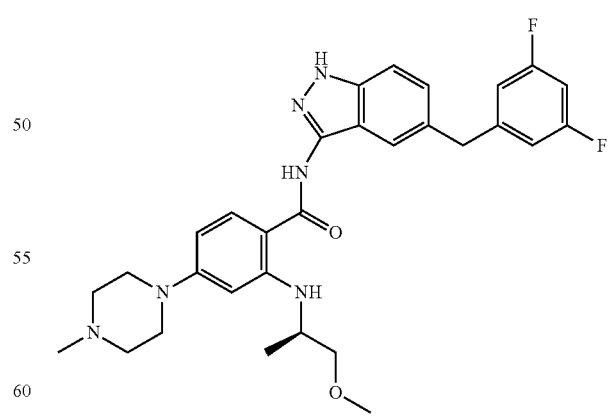

(d, J=8.54 Hz, 1H) 7.49 (s, 1H) 7.78 (d, J=9.02 Hz, 1H) 8.20 (d, J=7.68 Hz, 1H) 10.04 (s, 1H) 12.63 (s, 1H)

N-[5-(3,5-Difluoro-benzyl)-1H-indazol-3-yl]-2-(2-methoxy-ethylamino)-4-(4-methyl-piperazin-1-yl)-benzamide [(I$_A$), R1=R2=R3=H, R=3,5-difluoro-phenyl, Ar=4-(4-methyl-piperazin-1-yl)-2-(2-methoxy-ethylamino)-phenyl] cpd. 26

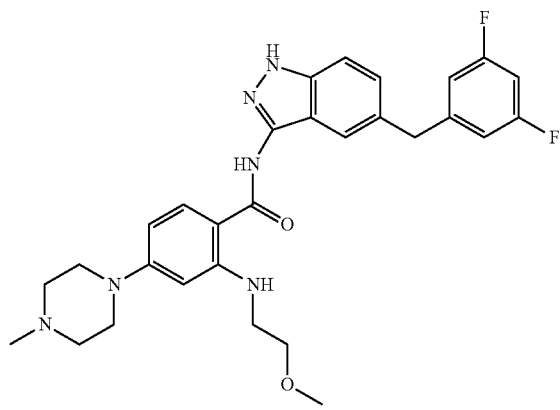 [SMILES: COCCNc1cc(N2CCN(C)CC2)ccc1C(=O)Nc1n[nH]c2ccc(Cc3cc(F)cc(F)c3)cc12]

1H-NMR (400 MHz), δ (ppm, DMSO-d6): 2.25 (s, 3H) 2.44-2.49 (m, 4H) 3.26 (s, 3H) 3.27-3.31 (m, 6H) 3.54 (t, J=5.37 Hz, 2H) 4.05 (s, 2H) 6.09 (d, J=1.95 Hz, 1H) 6.25 (dd, J=8.96, 2.01 Hz, 1H) 6.94-7.00 (m, 2H) 6.99-7.05 (m, 1H) 7.24 (dd, J=8.60, 1.52 Hz, 1H) 7.41 (d, J=8.66 Hz, 1H) 7.51 (s, 1H) 7.79 (d, J=9.15 Hz, 1H) 8.23 (t, J=5.12 Hz, 1H) 10.06 (s, 1H) 12.63 (s, 1H)

N-[5-(3,5-Difluoro-benzyl)-1H-indazol-3-yl]-4-[(3-dimethylamino-propyl)-methyl-amino]-2-nitro-benzamide [(I$_A$), R1=R2=R3=H, R=3,5-difluorophenyl, Ar=4-[(3-dimethylamino-propyl)-methyl-amino]-2-nitro-phenyl] cpd. 59

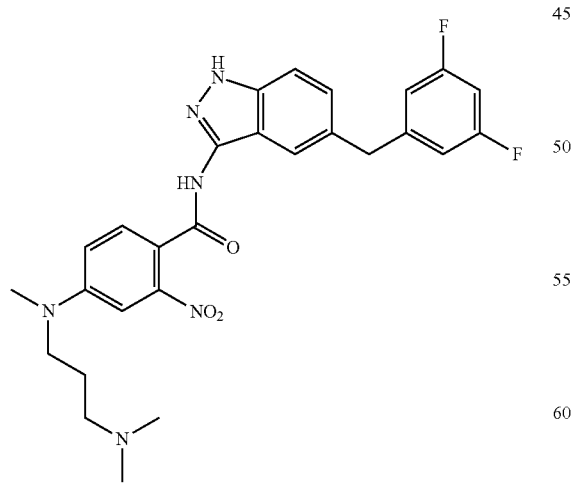

1H-NMR (400 MHz), δ (ppm, DMSO-d6): 1.68 (m, 2H) 2.15 (m, 6H) 2.25 (t, J=6.58 Hz, 2H) 3.02 (s, 3H) 3.48 (t, J=7.07 Hz, 2H) 4.05 (s, 2H) 6.93-7.05 (m, 4H) 7.19 (d, J=2.44 Hz, 1H) 7.26 (dd, J=8.54, 1.46 Hz, 1H) 7.42 (d, J=8.54 Hz, 1H) 7.62 (s, 1H) 7.68 (bs, 1H) 10.73 (s, 1H) 12.69 (s, 1H)

2-Cyclohexylamino-N-[5-(3,5-difluoro-benzyl)-1H-indazol-3-yl]-4-(4-methyl-piperazin-1-yl)-benzamide [(I$_A$), R1=R2=R3=H, R=3,5-difluorophenyl, Ar=4-(4-methyl-piperazin-1-yl)-2-cyclohexylamino-phenyl] cpd. 18

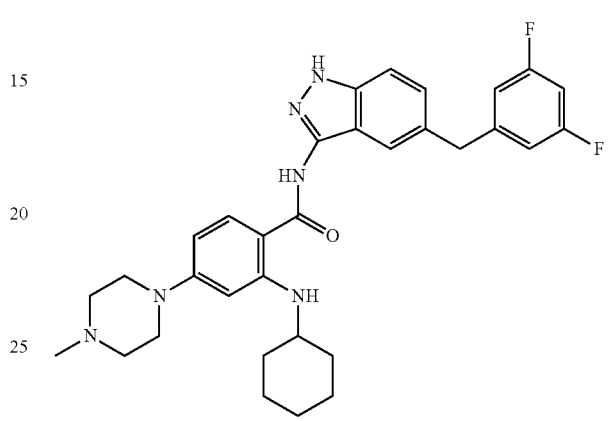

1H-NMR (400 MHz), δ (ppm, DMSO-d6): 12.61 (s, 1H) 10.04 (s, 1H) 8.26 (d, 1H) 7.77 (d, 1H) 7.48 (s, 1H) 7.40 (d, 1H) 7.25 (dd, 1H) 6.90-7.00 (m, 3H) 6.21 (dd, 1H) 6.08 (d, 1H) 4.03 (s, 2H) 3.45 (m, 1H) 3.25 (m, 4H) 2.45 (bs, 4H) 2.24 (s, 3H) 1.88-1.23 (m, 10H)

N-{5-[1-(3,5-Difluoro-phenyl)ethyl]-1H-indazol-3-yl}-4-(4-methyl-piperazin-1-yl)-2-(tetrahydro-pyran-4-ylamino)-benzamide [(ID), R1=R2=R3=R''=H, R=3,5-difluorophenyl, R'=methyl, Ar=4-(4-methyl-piperazin-1-yl)-2-(tetrahydro-pyran-4-ylamino)-phenyl] cpd. 75

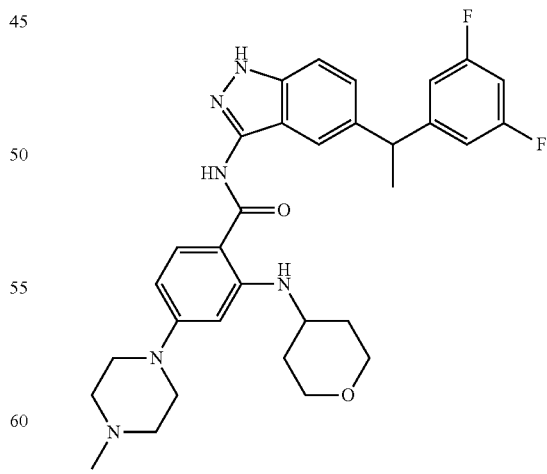

1H-NMR (400 MHz), δ (ppm, DMSO-d6): 1.29-1.43 (m, 2H) 1.60 (d, J=7.19 Hz, 3H) 1.89-1.99 (m, 2H) 2.29 (br. s., 3H) 2.45-2.57 (m, 4H) 3.22-3.38 (m, 4H) 3.45-3.55 (m, 2H) 3.64-3.76 (m, 1H) 3.78-3.85 (m, 2H) 4.31 (q, J=7.40 Hz, 1H)

6.15 (d, J=1.95 Hz, 1H) 6.25 (dd, J=8.90, 2.19 Hz, 1H) 6.94-7.06 (m, 3H) 7.28 (dd, J=8.78, 1.59 Hz, 1H) 7.40 (d, J=8.54 Hz, 1H) 7.52 (s, 1H) 7.81 (d, J=9.15 Hz, 1H) 8.32 (d, J=7.68 Hz, 1H) 10.09 (s, 1H) 12.62 (s, 1H)

Single enantiomers have been obtained by preparative chiral-HPLC by using Daicel Chiralpak AD 250×20 mm 10 μm as column system and hexane/2-propanol 40:60 as eluant.

N-[5-(3,5-difluorobenzyl)-1H-indazol-3-yl]-2-[(1-methoxy-2-methylpropan-2-yl)amino]-4-(4-methyl-piperazin-1-yl)benzamide [($I_A$), R1=R2=R3=H, R=3,5-difluorophenyl, Ar=4-(4-methyl-piperazin-1-yl)-2-[(1-methoxy-2-methylpropan-2-yl)amino]-phenyl] cpd. 34

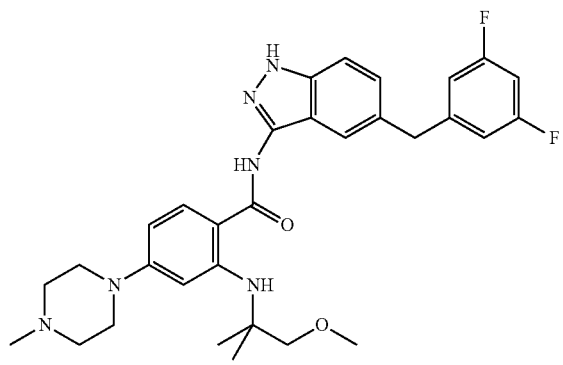 [SMILES: COCC(C)(C)Nc1cc(N2CCN(C)CC2)ccc1C(=O)Nc1n[nH]c2ccc(Cc3cc(F)cc(F)c3)cc12]

1H-NMR (400 MHz), δ (ppm, DMSO-d6): 1.31 (s, 6H) 2.27 (br. s., 3H) 2.50 (m, 4H) 3.26 (m, 7H) 3.35 (s, 2H) 4.05 (s, 2H) 6.27 (dd, J=9.02, 2.32 Hz, 1H) 6.31 (d, J=2.32 Hz, 1H) 6.93-7.05 (m, 3H) 7.25 (dd, J=8.60, 1.52 Hz, 1H) 7.41 (d, J=8.54 Hz, 1H) 7.51-7.53 (m, 1H) 7.76 (d, J=8.90 Hz, 1H) 8.26 (s, 1H) 10.14 (s, 1H) 12.63 (s, 1H)

N-[5-(3,5-Difluoro-benzyl)-1H-indazol-3-yl]-2-(2-methoxy-1-methoxymethyl-ethylamino)-4-(4-methyl-piperazin-1-yl)-benzamide [($I_A$), R1=R2=R3=H, R=3,5-difluorophenyl, Ar=4-(4-methyl-piperazin-1-yl)-2-(2-methoxy-1-methoxymethyl-ethyl-ethylamino)-phenyl] cpd. 16

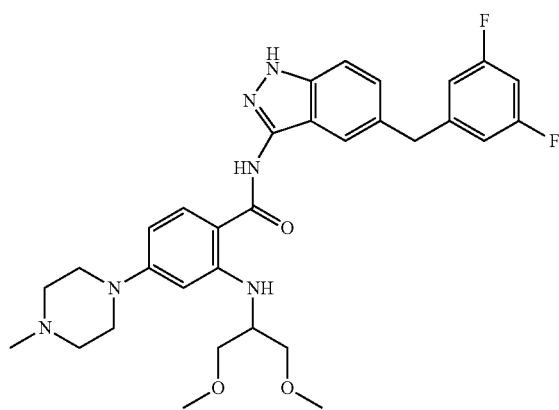 [SMILES: COCC(COC)Nc1cc(N2CCN(C)CC2)ccc1C(=O)Nc1n[nH]c2ccc(Cc3cc(F)cc(F)c3)cc12]

1H-NMR (400 MHz), δ (ppm, DMSO-d6): 2.42 (br. s., 3H) 2.70 (br. s., 4H) 3.26 (s, 6H) 3.30 (m, 4H) 3.41 (d, J=5.00 Hz, 4H) 3.85 (m, J=8.17, 5.00, 5.00, 5.00, 5.00 Hz, 1H) 4.04 (s, 2H) 6.20 (d, J=1.95 Hz, 1H) 6.26 (dd, J=8.96, 2.01 Hz, 1H) 6.94-7.04 (m, 3H) 7.24 (dd, J=8.66, 1.46 Hz, 1H) 7.41 (d, J=8.54 Hz, 1H) 7.48 (br. s., 1H) 7.79 (d, J=9.02 Hz, 1H) 8.32 (d, J=8.29 Hz, 1H) 10.06 (s, 1H) 12.64 (s, 1H)

2-Benzylamino-N-[5-(3,5-difluoro-benzyl)-1H-indazol-3-yl]-4-(4-methyl-piperazin-1-yl)-benzamide [($I_A$), R1=R2=R3=H, R=3,5-difluorophenyl, Ar=4-(4-methyl-piperazin-1-yl)-2-benzylamino-phenyl] cpd. 24

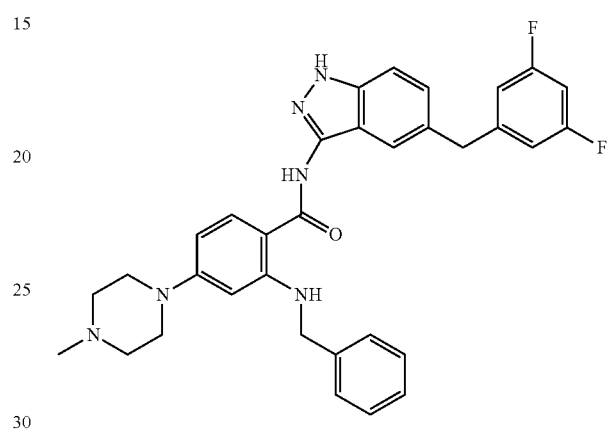

1H-NMR (400 MHz), δ (ppm, DMSO-d6): 2.22 (s, 3H) 2.41 (br. s., 4H) 3.19-3.24 (m, 4H) 4.04 (s, 2H) 4.39 (d, J=5.49 Hz, 2H) 6.09 (d, J=2.19 Hz, 1H) 6.26 (dd, J=9.02, 2.32 Hz, 1H) 6.92-6.98 (m, 2H) 6.98-7.04 (m, 1H) 7.21-7.27 (m, 2H) 7.30-7.36 (m, 2H) 7.36-7.39 (m, 2H) 7.40 (d, J=9.02 Hz, 1H) 7.51 (s, 1H) 7.81 (d, J=9.02 Hz, 1H) 8.60 (t, J=5.55 Hz, 1H) 10.11 (s, 1H) 12.63 (s, 1H)

N-[5-(3,5-Difluoro-benzyl)-1H-indazol-3-yl]-2-(2-fluoro-ethylamino)-4-(4-methyl-piperazin-1-yl)-benzamide [($I_A$), R1=R2=R3=H, R=3,5-difluorophenyl, Ar=4-(4-methyl-piperazin-1-yl)-2-(2-fluoro-ethylamino)-phenyl] cpd. 38

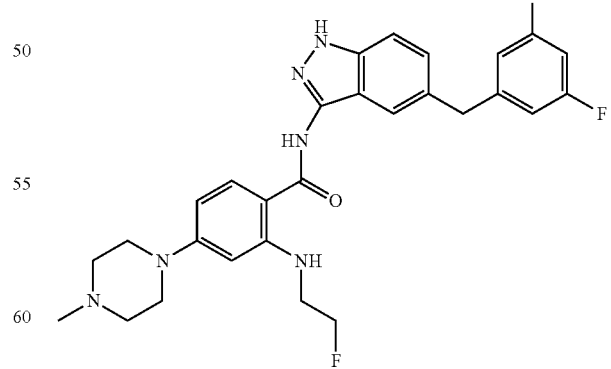

1H-NMR (400 MHz), δ (ppm, DMSO-d6): 2.24 (s, 3H) 2.43-2.48 (m, 4H) 3.26-3.31 (m, 4H) 3.49 (dq, J=27.68, 5.12 Hz, 2H) 4.04 (s, 2H) 4.60 (dt, J=47.68, 4.76 Hz, 2H) 6.12 (d, J=2.23 Hz, 1H) 6.28 (dd, J=8.99, 2.23 Hz, 1H) 6.94-7.00 (m, 2H) 6.99-7.04 (m, 1H) 7.24 (dd, J=8.57, 1.52 Hz, 1H) 7.41 (d, J=8.57 Hz, 1H) 7.51 (s, 1H) 7.81 (d, J=8.99 Hz, 1H) 8.37 (t, J=5.43 Hz, 1H) 10.11 (s, 1H) 12.63 (s, 1H)

N-[5-(3,5-Difluoro-benzyl)-1H-indazol-3-yl]-2-(2-fluoro-propylamino)-4-(4-methyl-piperazin-1-yl)-benzamide [(I_A), R1=R2=R3=H, R=3,5-difluoro-phenyl, Ar=4-(4-methyl-piperazin-1-yl)-2-(2-fluoro-propylamino)-phenyl] cpd. 40

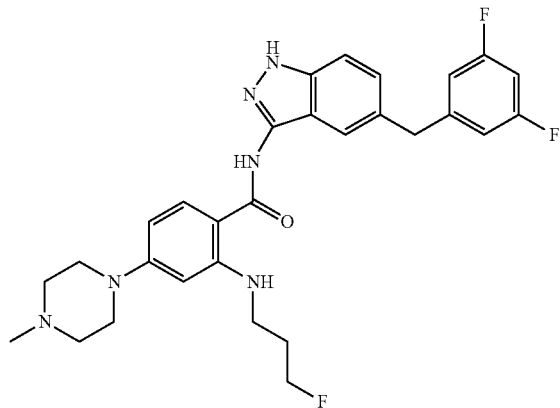 [SMILES: CN1CCN(c2ccc(C(=O)Nc3n[nH]c4ccc(Cc5cc(F)cc(F)c5)cc34)c(NCCCF)c2)CC1]

1H-NMR (400 MHz), δ (ppm, DMSO-d6): 1.86-2.04 (m, 2H) 2.26 (br. s., 3H) 2.48 (br. s., 4H) 3.21-3.37 (m, 6H) 4.04 (s, 2H) 4.44-4.66 (dt, J=47.43, 5.73 Hz, 2H) 6.09 (d, J=1.95 Hz, 1H) 6.26 (dd, J=9.02, 2.20 Hz, 1H) 6.94-7.05 (m, 3H) 7.25 (dd, J=8.60, 1.40 Hz, 1H) 7.41 (d, J=8.66 Hz, 1H) 7.50 (d, J=1.71 Hz, 1H) 7.81 (d, J=9.02 Hz, 1H) 8.22 (t, J=5.24 Hz, 1H) 10.09 (s, 1H) 12.63 (s, 1H)

N-[5-(3,5-Difluoro-benzyl)-1H-indazol-3-yl]-4-[(3-dimethylamino-propyl)-methyl-amino]-2-(tetra-hydro-pyran-4-ylamino)-benzamide [(I_A), R1=R2=R3=H, R=3,5-difluorophenyl, Ar=4-[(3-dimethylamino-propyl)-methyl-amino]-2-(tetra-hydro-pyran-4-ylamino)-phenyl] cpd. 55

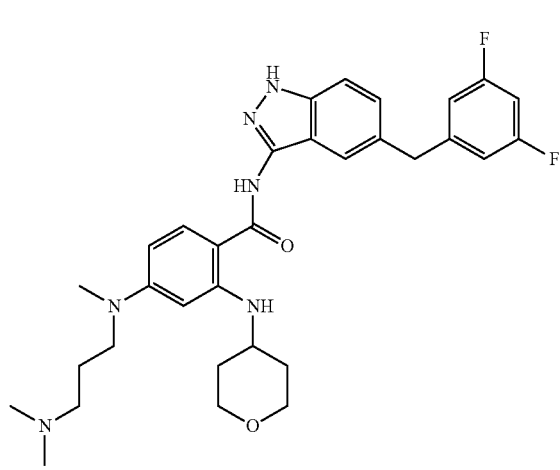 [SMILES: CN(C)CCCN(C)c1ccc(C(=O)Nc2n[nH]c3ccc(Cc4cc(F)cc(F)c4)cc23)c(NC2CCOCC2)c1]

1H-NMR (400 MHz), δ (ppm, DMSO-d6): 1.32-1.44 (m, 2H) 1.67 (quin, J=6.98 Hz, 2H) 1.93-1.98 (m, 2H) 2.17 (s, 6H) 2.26 (t, J=6.65 Hz, 2H) 2.96 (s, 3H) 3.36-3.43 (m, 2H) 3.44-3.53 (m, 2H) 3.58-3.69 (m, 1H) 3.79-3.87 (m, 2H) 4.05 (s, 2H) 5.87 (d, J=2.19 Hz, 1H) 6.04 (dd, J=9.02, 2.32 Hz, 1H) 6.96-7.05 (m, 3H) 7.25 (dd, J=8.60, 1.52 Hz, 1H) 7.41 (d, J=8.54 Hz, 1H) 7.49 (s, 1H) 7.77 (d, J=9.15 Hz, 1H) 8.35 (d, J=7.32 Hz, 1H) 9.96 (s, 1H) 12.60 (s, 1H)

N-[5-(3,5-Difluoro-benzyl)-1H-indazol-3-yl]-4-(4-methyl-piperazin-1-yl)-2-phenylamino-benzamide [(I_A) R1=R2=R3=H, R=3,5-difluorophenyl, Ar=4-(4-methyl-piperazin-1-yl)-2-phenylamino-phenyl] cpd. 42

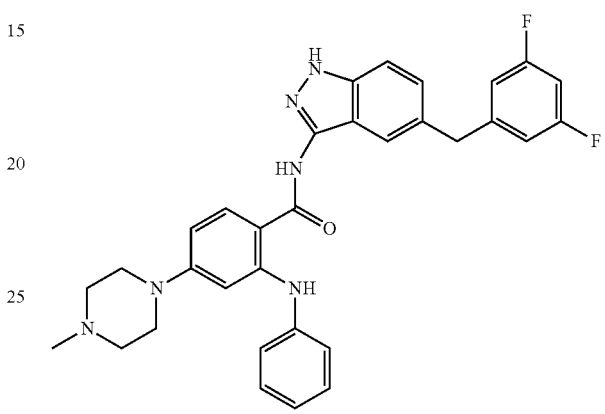

1H-NMR (400 MHz), δ (ppm, DMSO-d6): 2.24 (s, 3H) 2.46 (br. s., 4H) 3.22 (br. s., 4H) 4.05 (s, 2H) 6.53 (dd, J=9.02, 2.19 Hz, 1H) 6.74 (d, J=2.32 Hz, 1H) 6.95-7.02 (m, 4H) 7.19 (d, J=7.56 Hz, 2H) 7.25 (dd, J=8.66, 1.46 Hz, 1H) 7.29-7.35 (m, 2H) 7.40-7.44 (m, 1H) 7.55 (s, 1H) 7.91 (d, J=9.15 Hz, 1H) 10.03 (s, 1H) 10.39 (s, 1H) 12.69 (s, 1H)

N-[5-(3,5-difluorobenzyl)-1H-indazol-3-yl]-4-(4-methy-1,4-diazepan-1-yl)-2-(tetrabydro-2H-pyran-4-ylamino)benzamide [(I_A), R1=R2=R3=H, R=3,5-difluorophenyl, Ar=4-(4-methyl-1,4 diazepan-1-yl)-2-(tetrahydro-pyran-4-ylamino)-phenyl] cpd. 89

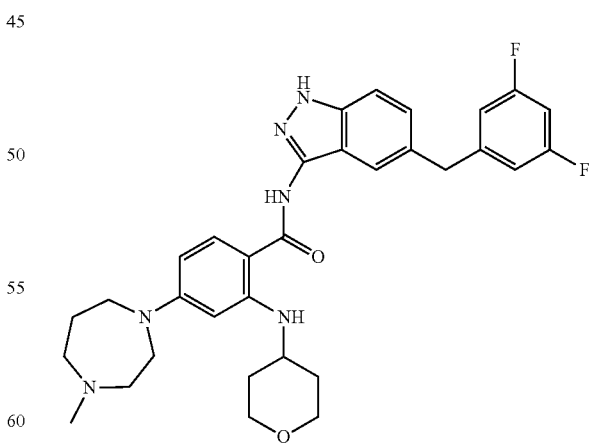

1H-NMR (400 MHz), δ (ppm, DMSO-d6): 1.31-1.42 (m, 2H) 1.83-1.98 (m, 4H) 2.28 (s, 3H) 2.44-2.49 (m, 2H) 2.63 (d, J=4.51 Hz, 2H) 3.44-3.59 (m, 6H) 3.65 (d, J=11.46 Hz, 1H) 3.78-3.85 (m, 2H) 4.04 (s, 2H) 5.87 (d, J=2.32 Hz, 1H) 6.05 (dd, J=9.08, 2.26 Hz, 1H) 6.96-7.04 (m, 3H) 7.25 (dd, J=8.59, 1.52 Hz, 1H) 7.41 (d, J=8.53 Hz, 1H) 7.49 (s, 1H) 7.77 (d, J=9.14 Hz, 1H) 8.36 (d, J=7.68 Hz, 1H) 9.96 (s, 1H) 12.60 (s, 1H)

N-[5-(3,5-Difluoro-benzyl)-1H-indazol-3-yl]-4-[(2-dimethylamino-ethyl)-methyl-amino]-2-(tetrahydro-pyran-4-ylamino)-benzamide [(I$_A$), R1=R2=R3=H, R=3,5-difluorophenyl, Ar=4-[(2-dimethylamino-ethyl)-methyl-amino]-2-(tetrahydro-pyran-4-ylamino)-phenyl] cpd. 90

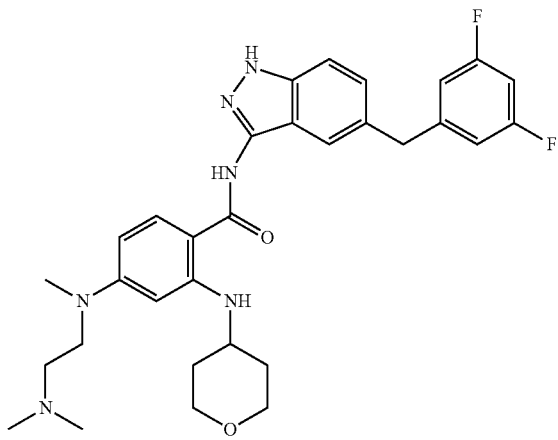 [SMILES: CN(C)CCN(C)c1ccc(C(=O)Nc2n[nH]c3ccc(Cc4cc(F)cc(F)c4)cc23)c(NC2CCOCC2)c1]

1H-NMR (400 MHz), δ (ppm, DMSO-d6): 1.32-1.43 (m, 2H) 1.96 (d, 1H) 2.19-2.22 (m, 6H) 2.40 (t, J=7.19 Hz, 2H) 2.98 (s, 3H) 3.41-3.51 (m, 4H) 3.56-3.65 (m, 1H) 3.80-3.87 (m, 2H) 4.04 (s, 2H) 5.87 (d, J=2.32 Hz, 1H) 6.02 (dd, J=9.08, 2.38 Hz, 1H) 6.96-7.04 (m, 3H) 7.25 (dd, J=8.59, 1.52 Hz, 1H) 7.41 (d, J=8.53 Hz, 1H) 7.49 (s, 1H) 7.78 (d, J=9.14 Hz, 1H) 8.35 (d, J=7.31 Hz, 1H) 9.97 (s, 1H) 12.60 (s, 1H)

N-[5-(3,5-difluorobenzyl)-1H-indazol-3-yl]-4-[4-(dimethylamino)piperidin-1-yl]-2-(tetrahydro-2H-pyran-4-ylamino)benzamide [(I$_A$), R1=R2=R3=H, R=3,5-difluorophenyl, Ar=4-[4-(dimethylamino)piperidin-1-yl]-2-(tetrahydro-pyran-4-ylamino)-phenyl] cpd. 91

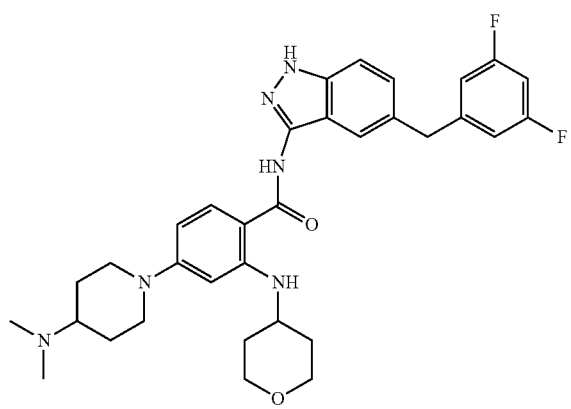 [SMILES: CN(C)C1CCN(c2ccc(C(=O)Nc3n[nH]c4ccc(Cc5cc(F)cc(F)c5)cc34)c(NC3CCOCC3)c2)CC1]

1H-NMR (400 MHz), δ (ppm, DMSO-d6): 1.43 (m, 4H) 1.82 (d, J=12.32 Hz, 2H) 1.93 (dq, J=12.74, 2.77 Hz, 2H) 2.20 (s, 6H) 2.29 (m, 1H) 2.78 (td, J=12.38, 2.19 Hz, 2H) 3.49 (ddd, J=11.86, 9.91, 2.26 Hz, 2H) 3.62-3.72 (m, 1H) 3.81 (dt, J=11.74, 4.07 Hz, 2H) 3.87 (d, J=12.56 Hz, 2H) 4.04 (s, 2H) 6.12 (d, J=2.19 Hz, 1H) 6.23 (dd, J=8.96, 2.26 Hz, 1H) 6.99 (m, 3H) 7.25 (dd, J=8.60, 1.52 Hz, 1H) 7.40 (d, J=8.54 Hz, 1H) 7.48 (br. s., 1H) 7.78 (d, J=9.15 Hz, 1H) 8.28 (d, J=7.56 Hz, 1H) 10.05 (s, 1H) 12.61 (s, 1H)

N-[5-(3,5-difluorobenzyl)-1H-indazol-3-yl]-4-[(2S)-2-(pyrrolidin-1-ylmethyl)pyrrolidin-1-yl]-2-(tetrahydro-2H-pyran-1-ylamino)benzamide [(I$_A$), R1=R2=R3=H, R=3,5-difluorophenyl, Ar=4-[(2S)-2-(pyrrolidin-1-ylmethyl)pyrrolidin-1-yl]-2-(tetrahydro-pyran-4-ylamino)-phenyl] cpd. 92

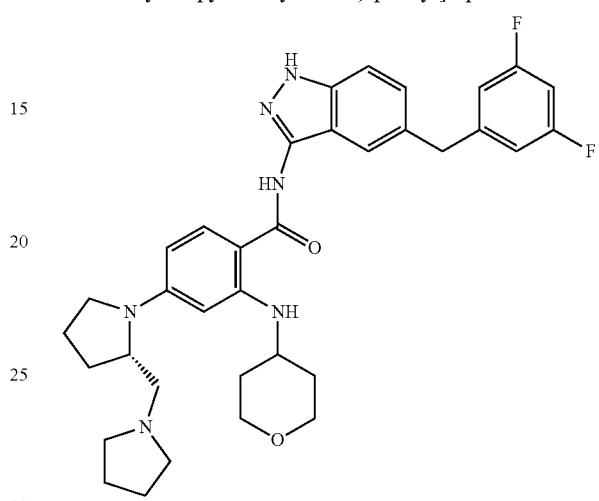

1H-NMR (400 MHz), δ (ppm, DMSO-d6): 1.36 (m, 2H) 1.72 (m, 4H) 1.99 (m, 6H) 2.43 (m, 3H) 2.63 (m, 2H) 3.16 (m, 2H) 3.39-3.47 (m, 3H) 3.58 (br. s., 1H) 3.82-3.90 (m, 2H) 3.90 (br. s., 1H) 4.04 (s, 2H) 5.82 (d, J=1.59 Hz, 1H) 5.90 (dd, J=8.90, 2.07 Hz, 1H) 6.98 (m, 3H) 7.24 (dd, J=8.60, 1.52 Hz, 1H) 7.40 (d, J=8.90 Hz, 1H) 7.48 (br. s., 1H) 7.77 (d, J=9.02 Hz, 1H) 8.36 (d, J=7.32 Hz, 1H) 9.95 (s, 1H) 12.60 (s, 1H)

N-[5-(3,5-difluorobenzyl)-1H-Indazol-3-yl]-3-(4-methylpiperazin-1-yl)benzamide [(I$_A$), R1=R2=R3=H, R=3,5-difluorophenyl, Ar=3-(4-methylpiperazin-1-yl)phenyl] cpd. 93

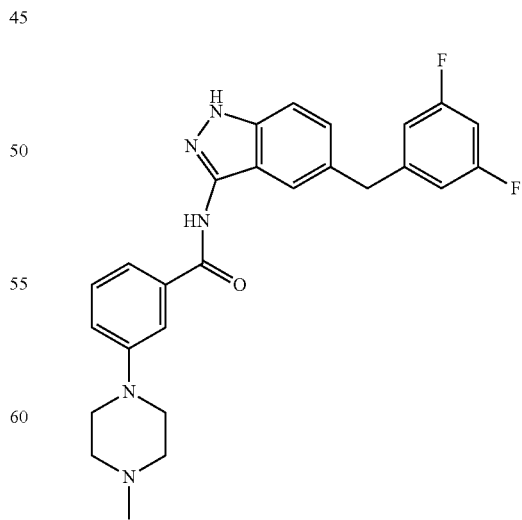

1H-NMR (400 MHz), δ (ppm, DMSO-d6): 2.26 (s, 3H) 2.47-2.54 (m, 4H) 3.22-3.27 (m, 4H) 4.06 (s, 2H) 6.92-6.99

(m, 2H) 6.99-7.06 (m, 1H) 7.15-7.20 (m, 1H) 7.26 (dd, J=8.66, 1.59 Hz, 1H) 7.36 (t, J=7.93 Hz, 1H) 7.42-7.45 (m, 1H) 7.47 (d, J=7.80 Hz, 1H) 7.60-7.63 (m, 2H) 10.65 (s, 1H) 12.73 (s, 1H)

N-[5-(3,5-difluorobenzyl)-1H-indazol-3-yl]-4-(piperazin-1-yl)-2-(tetrahydro-2H-pyran-4-ylamino)benzamide [(I$_A$), R1=R2=R3=H, R=3,5-difluorophenyl, Ar=4-(piperazin-1-yl)-2-(tetrahydro-2H-pyran-4-ylamino)phenyl] cpd. 98

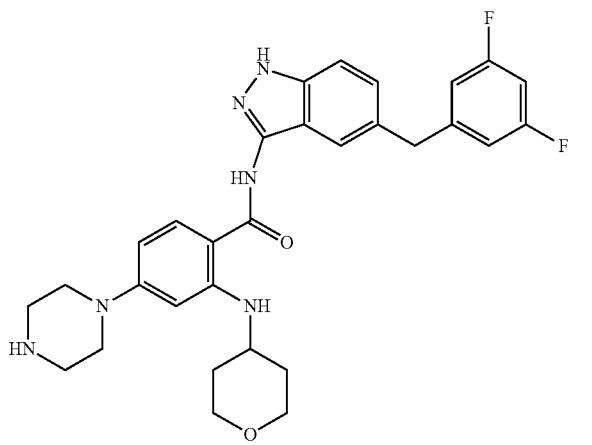 [SMILES: O=C(Nc1n[nH]c2ccc(Cc3cc(F)cc(F)c3)cc12)c1ccc(N2CCNCC2)cc1NC1CCOCC1]

1H-NMR (400 MHz), δ (ppm, DMSO-d6): 1.30-1.41 (m, 2H) 1.88-2.01 (m, 2H) 2.81-2.88 (m, 4H) 3.17-3.22 (m, 4H) 3.45-3.54 (m, 2H) 3.62-3.73 (m, 1H) 3.78-3.85 (m, 2H) 4.05 (s, 2H) 6.12 (d, J=2.19 Hz, 1H) 6.23 (dd, J=8.96, 2.26 Hz, 1H) 6.94-7.04 (m, 3H) 7.26 (dd, J=8.65, 1.58 Hz, 1H) 7.39-7.43 (m, 1H) 7.49 (s, 1H) 7.80 (d, J=9.02 Hz, 1H) 8.29 (d, J=7.68 Hz, 1H) 10.07 (s, 1H) 12.63 (s, 1H)

N-[5-(3,5-difluorobenzyl)-1H-Indazol-3-yl]-4-(4-methylpiperazin-1-yl)-2-{[cis-4-(trifluoromethyl)cyclohexyl]amino}benzamide [(I$_A$), R1=R2=R3=H, R=3,5-difluorophenyl, Ar=4-(4-methyl-piperazin-1-yl)-2-{[cis-4-(trifluoromethyl)cyclohexyl]amino}phenyl] cpd. 99

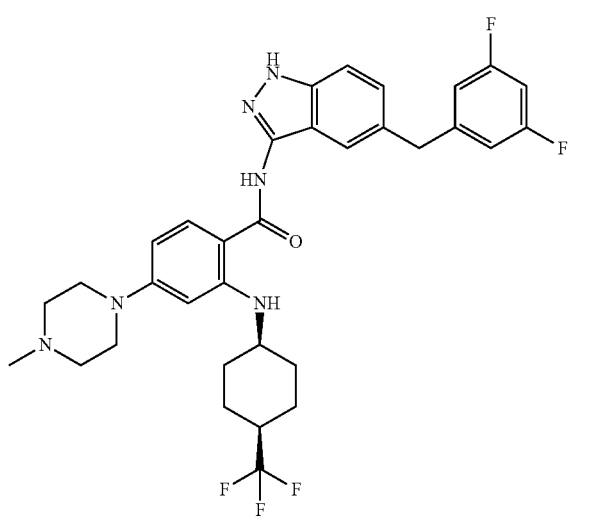 [SMILES: CN1CCN(c2ccc(C(=O)Nc3n[nH]c4ccc(Cc5cc(F)cc(F)c5)cc34)c(N[C@H]3CC[C@@H](C(F)(F)F)CC3)c2)CC1]

1H-NMR (400 MHz), δ (ppm, DMSO-d6): 1.39-1.53 (m, 2H) 1.58-1.73 (m, 4H) 1.84-1.91 (m, 2H) 2.25 (s, 3H) 2.28-2.40 (m, 1H) 2.47 (br. s., 4H) 3.25-3.33 (m, 4H) 3.82-3.90 (m, 1H) 4.01 (s, 2H) 6.10 (d, J=1.95 Hz, 1H) 6.24 (dd, J=9.15, 2.19 Hz, 1H) 6.90-6.96 (m, 2H) 6.96-7.03 (m, 1H) 7.24 (dd, J=8.60, 1.52 Hz, 1H) 7.42 (d, J=8.54 Hz, 1H) 7.52 (s, 1H) 7.83 (d, J=9.02 Hz, 1H) 8.69 (d, J=7.80 Hz, 1H) 10.10 (s, 1H) 12.65 (s, 1H)

N-[5-(3,5-difluorobenzyl)-1H-indazol-3-yl]-4-(4-methylpiperazin-1-yl)-2-{[trans-4-(trifluoromethyl)cyclohexyl]amino}benzamide [(I), R1=R2=R3=H, R=3,5-difluorophenyl, Ar=4-(4-methyl-piperazin-1-yl)-2-{[trans-4-(trifluoromethyl)cyclohexyl]amino}phenyl] cpd. 100

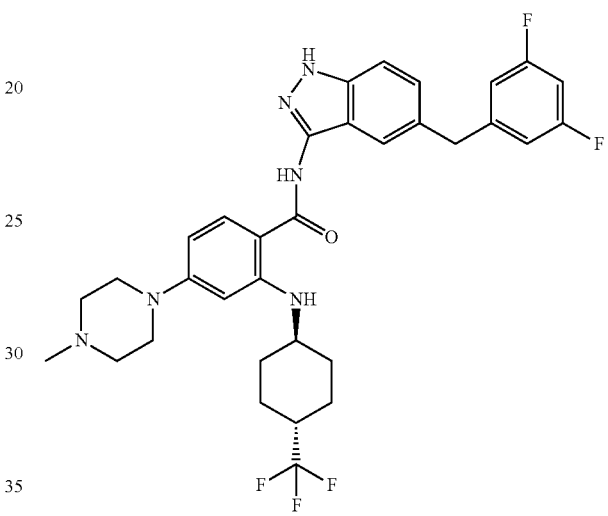

1H-NMR (400 MHz), δ (ppm, DMSO-d6): 1.10-1.23 (m, 2H) 1.44-1.57 (m, 2H) 1.86-1.94 (m, 2H) 2.06-2.15 (m, 2H) 2.25 (s, 3H) 2.29-2.34 (m, 1H) 2.46 (br. s., 4H) 3.24-3.31 (m, 4H) 3.39-3.51 (m, 1H) 4.05 (s, 2H) 6.15 (d, J=2.07 Hz, 1H) 6.23 (dd, J=8.90, 2.07 Hz, 1H) 6.95-7.00 (m, 2H) 7.00-7.06 (m, 1H) 7.25 (dd, J=8.60, 1.52 Hz, 1H) 7.41 (d, J=8.54 Hz, 1H) 7.48 (s, 1H) 7.78 (d, J=9.02 Hz, 1H) 8.14 (d, J=8.05 Hz, 1H) 10.05 (s, 1H) 12.62 (s, 1H)

N-[5-(3,5-difluorobenzyl)-1H-indazol-3-yl]-2-fluoro-4-(4-methylpiperazin-1-yl)benzamide [(I$_A$), R1=R2=R3=H, R=3,5-difluorophenyl, Ar=4-(4-methyl-piperazin-1-yl)-2-fluoro-phenyl] cpd. 101

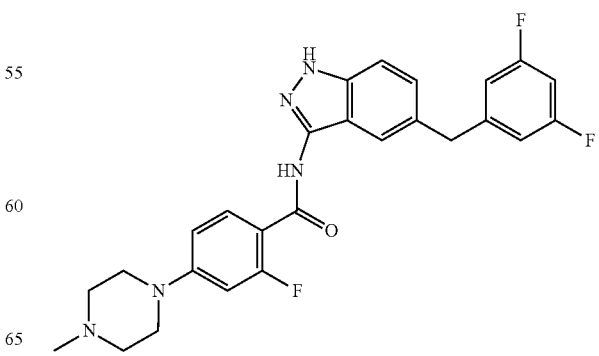

1H-NMR (400 MHz), δ (ppm, DMSO-d6): 2.26 (s, 3H) 2.45-2.50 (m, 4H) 3.29-3.36 (m, 4H) 4.06 (s, 2H) 6.78-6.89 (m, 2H) 6.94-6.98 (m, 2H) 6.98-7.06 (m, 1H) 7.25 (dd, J=8.54, 1.59 Hz, 1H) 7.42 (d, J=8.66 Hz, 1H) 7.64 (s, 1H) 7.68 (t, J=8.90 Hz, 1H) 10.08 (d, J=3.41 Hz, 1H) 12.68 (s, 1H)

N-[5-(3,5-difluorobenzyl)-1H-indazol-3-yl]-2-[(1-methylpiperidin-4-yl)amino]benzamide [(I$_A$), R1=R2=R3=H, R=3,5-difluorophenyl, Ar=2-[(1-methylpiperidin-4-yl)amino]-phenyl] cpd. 110

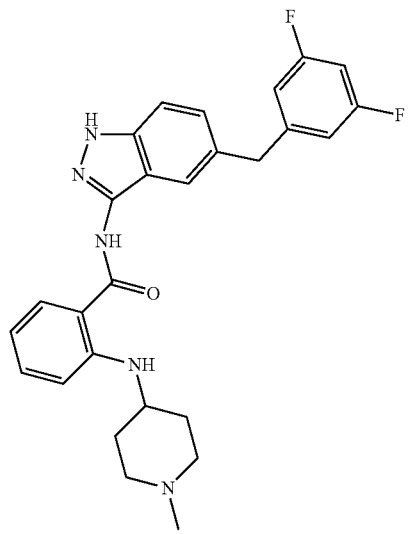 [SMILES: CN1CCC(Nc2ccccc2C(=O)Nc2n[nH]c3ccc(Cc4cc(F)cc(F)c4)cc23)CC1]

1H-NMR (400 MHz), δ (ppm, DMSO-d6): 1.35-1.49 (m, H) 1.94 (d, H) 2.20 (br. s., 5H) 2.60-2.73 (m, 2H) 3.38-3.47 (m, 1H) 4.05 (s, 2H) 6.58-6.64 (m, 1H) 6.80 (d, J=8.29 Hz, 1H) 6.95-7.00 (m, 2H) 7.00-7.05 (m, 1H) 7.27 (dd, J=8.65, 1.58 Hz, 1H) 7.32-7.37 (m, 1H) 7.44 (d, J=8.53 Hz, 1H) 7.53 (s, 1H) 7.85-7.88 (m, 1H) 7.89 (dd, J=8.05, 1.34 Hz, 1H) 10.44 (s, 1H) 12.72 (s, 1H)

N-[5-(3,5-difluorobenzyl)-1H-indazol-3-yl]-2-[(1-methylpiperidin-1-yl)amino]4-(morpholin-4-yl)benzamide [(I$_A$), R1=R2=R3=H, R=3,5-difluorophenyl, Ar=4-(morpholin-4-yl)-2-[(1-methylpiperidin-4-yl)amino]-phenyl] cpd. 111

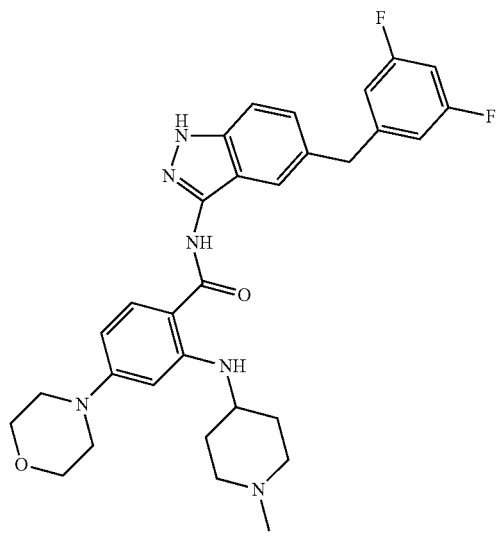 [SMILES: CN1CCC(Nc2cc(N3CCOCC3)ccc2C(=O)Nc2n[nH]c3ccc(Cc4cc(F)cc(F)c4)cc23)CC1]

1H-NMR (400 MHz), δ (ppm, DMSO-d6): 1.38-1.50 (m, 2H) 1.91-2.01 (m, 2H) 2.27 (m, 5H) 2.72 (m, 2H) 3.20-3.26 (m, 4H) 3.50 (br. s., 1H) 3.72-3.78 (m, 4H) 4.05 (s, 2H) 6.11 (d, J=2.19 Hz, 1H) 6.25 (dd, J=9.08, 2.13 Hz, 1H) 6.92-7.08 (m, 3H) 7.26 (dd, J=8.59, 1.52 Hz, 1H) 7.42 (d, J=8.53 Hz, 1H) 7.50 (s, 1H) 7.82 (d, J=9.02 Hz, 1H) 8.28 (d, J=7.31 Hz, 1H) 10.10 (s, 1H) 12.64 (s, 1H)

N-[5-(3,5-difluorobenzyl)-1H-indazol-3-yl]-2-methoxy-4-(4-methylpiperazin-1-yl)benzamide [(I$_A$), R1=R2=R3=H, R=3,5-difluorophenyl, Ar=4-(4-methyl-piperazin-1-yl)-2-methoxy-amino}phenyl] cpd. 112

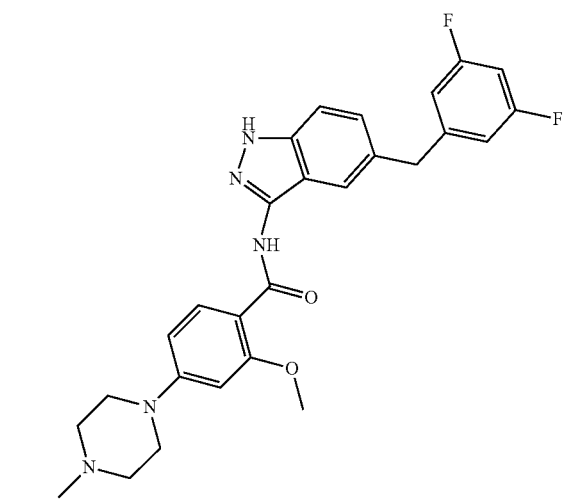 [SMILES: COc1cc(N2CCN(C)CC2)ccc1C(=O)Nc1n[nH]c2ccc(Cc3cc(F)cc(F)c3)cc12]

1H-NMR (400 MHz), δ (ppm, DMSO-d6): 2.25 (s, 3H) 2.47 (br. s., 4H) 3.33-3.38 (m, 4H) 4.02 (s, 3H) 4.06 (s, 2H) 6.63 (d, J=1.95 Hz, 1H) 6.67 (dd, J=8.96, 2.13 Hz, 1H) 6.96 (dd, J=8.72, 2.13 Hz, 2H) 6.99-7.05 (m, 1H) 7.24 (dd, J=8.66, 1.59 Hz, 1H) 7.40 (d, J=8.66 Hz, 1H) 7.76 (s, 1H) 7.88 (d, J=8.78 Hz, 1H) 9.99 (s, 1H) 12.65 (s, 1H)

N-[5-(2,5-Difluoro-benzyl)-1H-indazol-3-yl]-4-(4-methyl-piperazin-1-yl)-2-(tetrahydro-pyran-4-ylamino)-benzamide [(I), R1=R2=R3=H, R=2,5-difluorophenyl, Ar=4-(4-methyl-piperazin-1-yl)-2-(tetrahydro-pyran-4-ylamino)-phenyl] cpd. 10

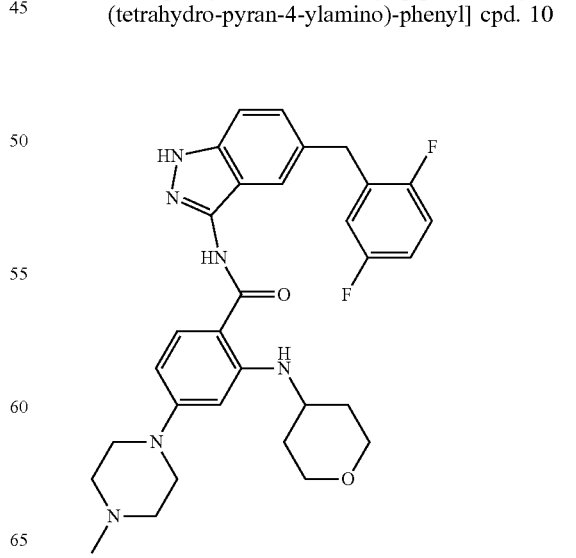

1H-NMR (400 MHz), δ (ppm, DMSO-d6): 1.29-1.42 (m, 2H) 1.90-1.98 (m, 2H) 2.27 (br. s., 3H) 2.49 (br. s., 4H) 3.24-3.32 (m, 4H) 3.45-3.56 (m, 2H) 3.64-3.74 (m, 1H) 3.82 (ddd, J=11.80, 3.96, 3.75 Hz, 2H) 4.04 (s, 2H) 6.14 (d, J=1.83 Hz, 1H) 6.24 (dd, J=8.90, 1.95 Hz, 1H) 7.04-7.12 (m, 1H) 7.15-7.23 (m, 2H) 7.24-7.27 (m, 1H) 7.41 (d, J=8.66 Hz, 1H) 7.46 (s, 1H) 7.80 (d, J=9.02 Hz, 1H) 8.30 (d, J=7.68 Hz, 1H) 10.08 (s, 1H) 12.63 (s, 1H)

N-[5-(2-methyl-5-fluoro-benzyl)-1H-indazol-3-yl]-4-(4-methyl-piperazin-1-yl)-2-(tetrahydro-pyran-4-ylamino)-benzamide [(I$_A$), R1=R2=R3=H, R=2-methyl-5-fluorophenyl, Ar=4-(4-methyl-piperazin-1-yl)-2-(tetrahydro-pyran-4-ylamino)-phenyl] cpd. 135

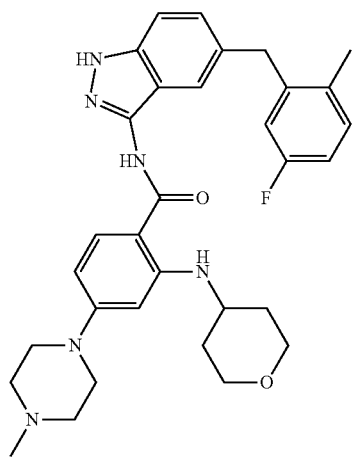 [SMILES: Cc1ccc(F)cc1Cc1ccc2[nH]nc(NC(=O)c3ccc(N4CCN(C)CC4)cc3NC3CCOCC3)c2c1]

1H-NMR (400 MHz), δ (ppm, DMSO-d6): 1.29-1.41 (m, 2H) 1.94 (dd, J=13.35, 2.86 Hz, 2H) 2.22 (s, 3H) 2.25 (s, 3H) 2.46 (br. s., 4H) 3.24-3.30 (m, 4H) 3.46-3.54 (m, 2H) 3.63-3.73 (m, 1H) 3.78-3.86 (m, 2H) 4.03 (s, 2H) 6.13 (d, J=1.95 Hz, 1H) 6.23 (dd, J=9.02, 2.07 Hz, 1H) 6.89-6.98 (m, 2H) 7.14-7.21 (m, 2H) 7.38 (s, 1H) 7.41 (d, J=8.65 Hz, 1H) 7.79 (d, J=9.02 Hz, 1H) 8.31 (d, J=7.80 Hz, 1H) 10.07 (s, 1H) 12.61 (s, 1H)

N-[5-(2-fluoro-benzyl)-1H-indazol-3-yl]-4-(4-methyl-piperazin-1-yl)-2-(tetrahydro-pyran-4-ylamino)-benzamide [(I$_A$), R1=R2=R3=H, R=2-fluorophenyl, Ar=4-(4-methyl-piperazin-1-yl)-2-(tetrahydro-pyran-4-ylamino)-phenyl] cpd. 9

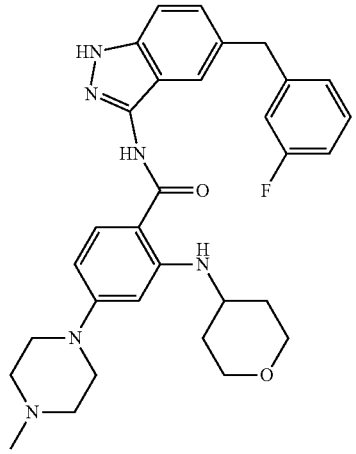 [SMILES: CN1CCN(c2ccc(C(=O)Nc3n[nH]c4ccc(Cc5cccc(F)c5)cc34)c(NC3CCOCC3)c2)CC1]

1H-NMR (400 MHz), δ (ppm, DMSO-d6): 1.29-1.42 (m, 2H) 1.89-1.98 (m, 2H) 2.24 (s, 3H) 2.45 (br. s., 4H) 3.24-3.30 (m, 4H) 3.47-3.55 (m, 2H) 3.64-3.74 (m, 1H) 3.77-3.87 (m, 2H) 4.04 (s, 2H) 6.14 (d, J=2.19 Hz, 1H) 6.24 (dd, J=8.96, 2.26 Hz, 1H) 6.95-7.02 (m, 1H) 7.04-7.09 (m, 1H) 7.10 (d, J=7.56 Hz, 1H) 7.24 (dd, J=8.66, 1.46 Hz, 1H) 7.31 (td, J=7.80, 6.34 Hz, 1H) 7.40 (d, J=8.53 Hz, 1H) 7.46 (s, 1H) 7.79 (d, J=9.02 Hz, 1H) 8.28 (d, J=7.80 Hz, 1H) 10.07 (s, 1H) 12.61 (s, 1H)

4-(4-methylpiperazin-1-yl)-N-[5-(pyridin-3-ylmethyl)-1H-indazol-3-yl]-2-(tetrahydro-2H-pyran-4-ylamino)benzamide [(I$_A$), R1=R2=R3=H, R=pyridin-3-yl, Ar=4-(4-methyl-piperazin-1-yl)-2-(tetrahydro-pyran-4-ylamino)-phenyl] cpd. 136

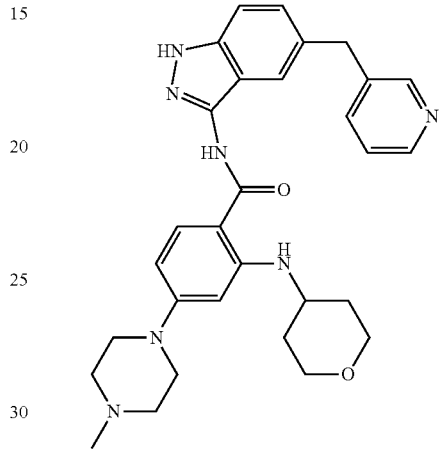

1H-NMR (400 MHz), δ (ppm, DMSO-d6): 1.30-1.42 (m, 2H) 1.95 (d, 2H) 2.26 (s, 3H) 2.47 (br. s., 4H) 3.25-3.30 (m, 4H) 3.47-3.54 (m, 2H) 3.64-3.74 (m, 1H) 3.79-3.86 (m, 2H) 4.05 (s, 2H) 6.14 (d, J=2.07 Hz, 1H) 6.24 (dd, J=8.90, 2.19 Hz, 1H) 7.24 (dd, J=8.60, 1.52 Hz, 1H) 7.29 (ddd, J=7.80, 4.76, 0.73 Hz, 1H) 7.41 (d, J=8.90 Hz, 1H) 7.47 (s, 1H) 7.63 (dt, J=7.87, 1.92 Hz, 1H) 7.79 (d, J=9.15 Hz, 1H) 8.27 (d, J=7.80 Hz, 1H) 8.39 (dd, J=4.76, 1.59 Hz, 1H) 8.52 (d, J=1.71 Hz, 1H) 10.07 (s, 1H) 12.62 (s, 1H)

N-[5-benzyl-1H-indazol-3-yl]-4-(4-methyl-piperazin-1-yl)-2-(tetrahydro-pyran-4-ylamino)-benzamide [(I$_A$), R1=R2=R3=H, R=phenyl, Ar=4-(4-methyl-piperazin-1-yl)-2-(tetrahydro-pyran-4-ylamino)-phenyl] cpd. 137

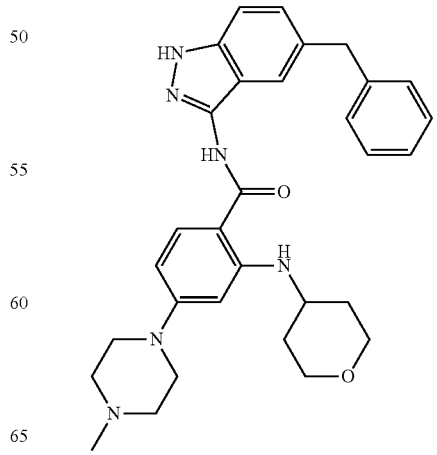

1H-NMR (400 MHz), δ (ppm, DMSO-d6): 1.31-1.42 (m, 2H) 1.90-1.99 (m, 2H) 2.24 (s, 3H) 2.42-2.47 (m, 4H) 3.24-3.31 (m, 4H) 3.46-3.55 (m, 2H) 3.64-3.76 (m, 1H) 3.78-3.87 (m, 2H) 4.01 (s, 2H) 6.14 (d, J=2.07 Hz, 1H) 6.24 (dd, J=8.96, 2.26 Hz, 1H) 7.17-7.27 (m, 6H) 7.38 (d, J=8.90 Hz, 1H) 7.44 (s, 1H) 7.79 (d, J=9.02 Hz, 1H) 8.28 (d, J=7.68 Hz, 1H) 10.05 (s, 1H) 12.59 (s, 1H).

Example 3

Step r

N-[5-(3,5-Difluoro-benzyl)-1H-indazol-3-yl]-2,2,2-trifluoro-acetamide [(XXIV$_A$), R1=R2=R3=H, R=3,5-difluorophenyl, PG$_1$=trifluoroacethyl]

To a suspension of 5-(3,5-difluoro-benzyl)-1H-indazol-3-ylamine (0.5 g, 1.93 mmol) in anhydrous dichloromethane (20 mL), under vigorous stirring and cooled to 0° C., trifluoroacetic anhydride was added dropwise and the dense slurry was stirred for 3.5 hours. The reaction mixture was poured into 3% NaHCO$_3$ solution and extracted with dichloromethane. The organic layer was washed with brine, dried over Na$_2$SO$_4$ and concentrated to yield a crude white solid that was directly used in the next step.
ESI (+) MS m/z 356 (100, MH$^+$); HRMS (ESI) calcd for C$_{16}$H$_{10}$F$_5$N$_3$O+H$^+$356.0817. found 356.0820.

Step s

N-[5-(3,5-Difluoro-benzyl)-1-trityl-1H-indazol-3-yl]-2,2,2-trifluoro-acetamide [(XXV$_A$), R1=R2=R3=H, R=3,5-difluorophenyl, PG-triphenylmethyl, PG$_1$=trifluoroacethyl]

Crude N-[5-(3,5-difluoro-benzyl)-1H-indazol-3-yl]-2,2,2-trifluoro-acetamide was suspended in dichloromethane (25 mL) and treated with trityl chloride (0.72 g, 2.58 mmol) under stirring. The suspension was cooled to 0° C. and neat 1,8-diazabicyclo[5.4.0]undec-7-ene (0.42 mL, 2.78 mmol) was added, producing immediate solubilization. After stirring at 0° C. for 3 hours the reaction mixture was poured into 50 mL of ice containing 1N HCl (5 mL) and extracted with dichloromethane. The organic layer was washed with NaHCO$_3$, brine, dried and concentrated to a crude material that was purified by flash chromatography (eluant: DCM). The desired product was obtained as a white solid (450 mg, yield 40% over two steps)
1H-NMR (400 MHz), δ (ppm, DMSO-d6): 3.98 (s, 2H) 6.34 (d, J=8.78 Hz, 1H) 6.93-7.07 (m, 4H) 7.16-7.20 (m, 6H) 7.25-7.39 (m, 9H) 7.52 (s, 1H) 11.99 (s, 1H)

Step t 5-(3,5-Difluoro-benzyl)-1-trityl-1H-indazol-3-ylamine [(XXVI$_A$), R1=R2=R3=H, R=3,5-difluorophenyl, PG=triphenylmethyl]

N-[5-(3,5-Difluoro-benzyl)-1-trityl-1H-indazol-3-yl]-2,2,2-trifluoro-acetamide (450 mg, 0.75 mmol) was dissolved in methanol (6 mL) and triethylamine (1.5 mL) and the solution was refluxed for 3 hours. The solvents were removed under reduced pressure and the residue was purified by flash chromatography (eluant: DCM). Title compound was isolated as white foam (300 mg, yield 80%).
1H-NMR (400 MHz), δ (ppm, DMSO-d6): 3.91 (s, 2H) 5.53 (s, 2H) 6.24 (d, J=8.78 Hz, 1H) 6.87-6.93 (m, 3H) 6.97-7.07 (m, 1H) 7.17-7.23 (m, 3H) 7.27 (t, J=7.50 Hz, 6H) 7.34 (d, J=1.59 Hz, 6H) 7.48 (s, 1H)

Step u

N-[5-(3,5-Difluoro-benzyl)-1-trityl-1H-indazol-3-yl]-4-(4-methyl-piperazin-1-yl)-2-nitro-benzamide [(XXII$_A$), R1=R2=R3=H, R=3,5-difluorophenyl, Ar=4-(4-methyl-piperazin-1-yl)-2-nitro-phenyl, PG=triphenylmethyl]

4-(4-Methyl-piperazin-1-yl)-2-nitro-benzoic acid (150 mg, 0.5 mmol) was suspended in anhydrous dichloromethane (10 mL), a drop of DMF was added, followed by oxalyl chloride (0.2 mL, 2 mmol). After stirring at room temperature for 2 hours the mixture was thoroughly dried under reduced pressure to give the acyl chloride as a white powder. 120 mg of the acyl chloride (0.4 mmol) were dissolved in anhydrous tetrahydrofuran (3 mL) and 5-(3,5-difluoro-benzyl)-1-trityl-1H-indazol-3-ylamine (200 mg, 0.4 mmol) was added. The resulting solution was cooled to 0° C. under stirring. After addition of diisopropyethylamine (0.2 mL, 1.2 mmol), the reaction mixture was stirred for 18 hours, while temperature was gradually increasing from 0° C. to room temperature. After evaporation of the volatiles, the crude residue was purified by flash chromatography (eluant: DCM/MeOH 10:1). Title compound was isolated as a bright yellow solid (200 mg, yield 67%).
1H-NMR (400 MHz), δ (ppm, DMSO-d6): 2.24 (s, 3H) 2.45 (br. s., 4H) 3.31-3.39 (m, 4H) 3.96 (s, 2H) 6.29 (br. s., 1H) 6.98 (m, 4H) 7.29 (m, 17H) 7.58 (s, 1H) 7.70 (br. s., 1H) 10.96 (br. s., 1H)

Step i"

N-[5-(3,5-Difluoro-benzyl)-1H-indazol-3-yl]-4-(4-methyl-piperazin-1-yl)-2-nitro-benzamide hydrochloride [(I$_A$), R1=R2=R3=H, R=3,5-difluorophenyl, Ar=4-(4-methyl-piperazin-1-yl)-2-nitro-phenyl] cpd. 6

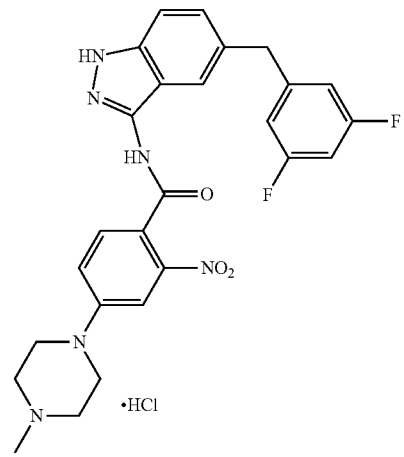 [SMILES: CN1CCN(c2ccc(C(=O)Nc3n[nH]c4ccc(Cc5cc(F)cc(F)c5)cc34)c([N+](=O)[O-])c2)CC1 ; Cl]

To a solution of N-[5-(3,5-difluoro-benzyl)-1-trityl-1H-indazol-3-yl]-4-(4-methyl-piperazin-1-yl)-2-nitro-benzamide (28.5 mg, 0.04 mmol) in dioxane (1 mL), 4 M HCl in dioxane (0.1 mL) was added and the mixture was stirred at room temperature for 1 hour. After concentration the residue was suspended in diethyl ether/MeOH 1:1, stirred for 20 min., filtered, washed with the same solvent mixture and dried. The desired product was obtained as hydrochloride derivative (19 mg, 87%).

1H-NMR (400 MHz), δ (ppm, DMSO-d6): 2.85 (d, J=4.02 Hz, 3H) 3.08-3.31 (m, 4H) 3.53 (d, J=11.71 Hz, 2H) 4.06 (s, 2H) 4.13 (d, J=13.17 Hz, 2H) 6.91-6.99 (m, 2H) 6.99-7.08 (m, 1H) 7.26 (dd, J=8.54, 1.34 Hz, 1H) 7.37 (d, J=6.95 Hz, 1H) 7.43 (d, J=8.66 Hz, 1H) 7.58 (br. s., 1H) 7.64 (s, 1H) 7.78 (d, J=7.44 Hz, 1H) 10.39 (br. s., 1H) 10.91 (br. s., 1H) 12.74 (br. s., 1H)

Operating in an analogous way, the following compound was obtained:

2-Amino-N-[5-(3,5-difluoro-benzyl)-1H-indazol-3-yl]-4-(4-methyl-piperazin-1-yl)-benzamide hydrochloride [(I$_A$), R1=R2=R3=H, R=3,5-difluorophenyl, Ar=4-(4-methyl-piperazin-1-yl)-2-amino-phenyl] cpd. 8

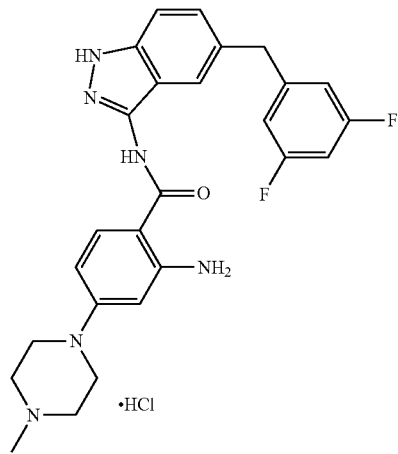

1H-NMR (400 MHz), δ (ppm, DMSO-d6): 2.84 (d, J=4.39 Hz, 3H) 3.05-3.20 (m, 4H) 3.44-3.53 (m, 2H) 3.85-3.94 (m, 2H) 4.05 (s, 2H) 6.30 (d, J=1.95 Hz, 1H) 6.36 (dd, J=8.96, 2.13 Hz, 1H) 6.93-7.00 (m, 2H) 6.99-7.05 (m, 1H) 7.24 (dd, J=8.66, 1.46 Hz, 1H) 7.41 (d, J=8.41 Hz, 1H) 7.53 (s, 1H) 7.81 (d, J=9.02 Hz, 1H) 10.11 (br. s., 1H) 10.37 (br. s., 1H) 12.66 (br. s., 1H)

Example 4

Conversion 1

2-Amino-N-[5-(3,5-difluoro-benzyl)-1-trityl-1H-indazol-3-yl]-4-(4-methyl-piperazin-1-yl)-benzamide [(XXII$_A$), R1=R2=R3=H, R=3,5-difluorophenyl, Ar=4-(4-methyl-piperazin-1-yl)-2-amino-phenyl, PG-triphenylmethyl]

A mixture of N-[5-(3,5-difluoro-benzyl)-1-trityl-1H-indazol-3-yl]-4-(4-methyl-piperazin-1-yl)-2-nitro-benzamide (170 mg, 0.236 mmol), 10% Pd—C (10 mg) and ammonium formate (25 mg, 0.4 mmol) in methanol (5 mL) was stirred for 18 hours at room temperature. The catalyst was filtered off and the solution was concentrated. The residue was dissolved in dichloromethane, washed with aqueous solution of NaHCO$_3$, dried and concentrated to yield title compound (145 mg, 87%).

ESI (+) MS m/z 243 (100, trityl$^+$), 719 (16, MH$^+$); HRMS (ESI) calcd for C$_{45}$H$_{40}$F$_2$N$_6$O+H$^+$ 719.3304. found 719.3309.

Operating in an analogous way, the following compounds were obtained:

2-Amino-N-[5-(3-ethoxy-benzoyl)-1H-indazol-3-yl]-4-(4-methyl-piperazin-1-yl)-benzamide [(II), R1=R2=R3=H, R=3-ethoxyphenyl, Ar=4-(4-methyl-piperazin-1-yl)-2-amino-phenyl]

1H-NMR (400 MHz), δ (ppm, DMSO-d6): 1.33 (t, J=6.95 Hz, 3H) 2.22 (s, 3H) 2.40-2.45 (m, 4H) 3.16-3.22 (m, 4H) 4.09 (q, J=6.95 Hz, 2H) 6.17 (d, J=2.44 Hz, 1H) 6.23 (dd, J=9.02, 2.44 Hz, 1H) 6.53 (s, 2H) 7.18 (ddd, J=8.23, 2.62, 0.85 Hz, 1H) 7.24 (dd, J=2.44, 1.46 Hz, 1H) 7.29 (dt, J=7.68, 1.10 Hz, 1H) 7.44 (t, J=7.93 Hz, 1H) 7.59 (dd, J=8.84, 0.55 Hz, 1H) 7.71 (d, J=9.15 Hz, 1H) 7.83 (dd, J=8.78, 1.59 Hz, 1H) 8.20 (br. s., 1H) 10.30 (s, 1H) 13.05 (s, 1H)

2-Amino-N-[5-(3,5-difluoro-benzoyl)-1H-indazol-3-yl]4-(4-methyl-piperazin-1-yl)-benzamide [(II), R1=R2=R3=H, R=3,5-difluorophenyl, Ar=4-(4-methyl-piperazin-1-yl)-2-amino-phenyl]

1H-NMR (400 MHz), δ (ppm, DMSO-d6): 2.30 (br. s., 3H) 2.56 (m, 4H) 3.22 (m, 4H) 6.18 (d, J=2.32 Hz, 1H) 6.24 (dd, J=9.08, 2.38 Hz, 1H) 6.57 (s, 2H) 7.42 (m, 2H) 7.54 (tt, J=9.15, 2.38 Hz, 1H) 7.61 (dd, J=8.90, 0.61 Hz, 1H) 7.73 (d, J=9.02 Hz, 1H) 7.83 (dd, J=8.84, 1.65 Hz, 1H) 8.26 (d, J=0.98 Hz, 1H) 10.36 (s, 1H) 13.11 (s, 1H)

Example 5

Conversion 2+Step i"

N-[5-(3,5-Difluoro-benzyl)-1H-indazol-3-yl]-2-methanesulfonylamino-4-(4-methyl-piperazin-1-yl)-benzamide hydrochloride [(I$_A$), R1=R2=R3=H, R=3,5-difluorophenyl, Ar=4-(4-methyl-piperazin-1-yl)-2-methanesulfonylamino-phenyl] cpd. 48

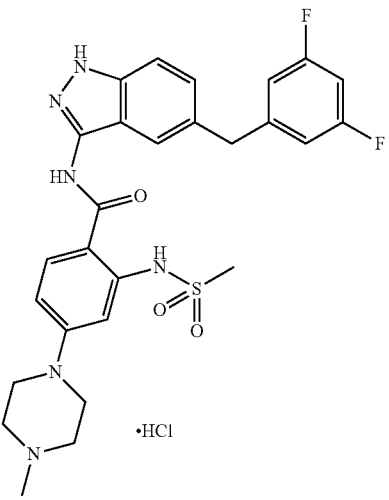 [SMILES: CN1CCN(c2ccc(C(=O)Nc3n[nH]c4ccc(Cc5cc(F)cc(F)c5)cc34)c(NS(C)(=O)=O)c2)CC1 ; Cl]

To a solution of 2-amino-N-[5-(3,5-difluoro-benzyl)-1-trityl-1H-indazol-3-yl]4-(4-methyl-piperazin-1-yl)-benzamide (29 mg, 0.04 mmol) in anhydrous dichloromethane (2 mL) and dry pyridine (0.05 mL), methanesulfonyl chloride (14.7 mg, 0.01 mL, 0.13 mmol) was added and the reaction mixture was stirred at room temperature for 8 hours. The mixture was poured into ice and was extracted with dichloromethane. The organic layer was washed with 0.1N HCl, then with water, dried over anhydrous $Na_2SO_4$ and concentrated to yield a crude whitish solid that was suspended in dioxane (1 mL). After adding 4M HCl in dioxane (0.1 mL) the suspension was stirred overnight. After concentration the residue was suspended in diethyl ether/MeOH 1:1, stirred for 20 min., filtered, washed with the same solvent mixture and dried. The desired product was obtained as the hydrochloride (15 mg, 0.025 mmol, 63%).

1H-NMR (400 MHz), δ (ppm, DMSO-d6): 2.86 (d, J=4.27 Hz, 3H) 3.17 (s, 3H) 3.14-3.27 (m, 4H) 3.55 (m, 2H) 4.02 (m, 2H) 4.06 (s, 2H) 6.92 (dd, J=9.02, 2.32 Hz, 1H) 6.97-7.03 (m, 3H) 7.05 (d, J=2.56 Hz, 1H) 7.28 (dd, J=8.66, 1.46 Hz, 1H) 7.45 (d, J=8.54 Hz, 1H) 7.55 (s, 1H) 8.12 (d, J=9.15 Hz, 1H) 10.56 (s, 1H) 10.76 (s, 1H) 11.42 (s, 1H) 12.84 (s, 1H)

Operating in an analogous way, the following compounds were obtained:

N-[2-{[5-(3,5-difluorobenzyl)-1H-indazol-3-yl]carbamoyl}-5-(4-methylpiperazin-1-yl)phenyl]-1H-pyrrole-2-carboxamide hydrochloride [(I$_A$), R1=R2=R3=H, R=3,5-difluorophenyl, Ar=4-(4-methylpiperazin-1-yl)-2-(1H-pyrrole-2-carbamoyl)-phenyl] cpd. 44

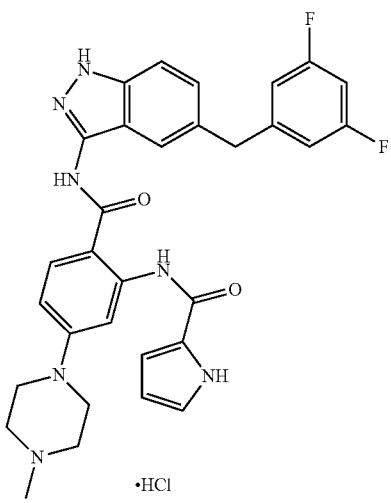 [SMILES: CN1CCN(c2ccc(C(=O)Nc3n[nH]c4ccc(Cc5cc(F)cc(F)c5)cc34)c(NC(=O)c3ccc[nH]3)c2)CC1 ; Cl]

1H-NMR (400 MHz), δ (ppm, DMSO-d6): 2.74 (br. s., 3H) 4.04 (s, 2H) 6.09 (dt, J=3.60, 2.41 Hz, 1H) 6.65 (dt, J=3.87, 1.78 Hz, 1H) 6.82 (dd, J=9.02, 2.32 Hz, 1H) 6.97 (m, 4H) 7.28 (dd, J=8.66, 1.46 Hz, 1H) 7.46 (d, J=8.66 Hz, 1H) 7.59 (br. s., 1H) 8.09 (d, J=9.15 Hz, 1H) 8.38 (d, J=2.44 Hz, 1H) 9.99 (br. s., 1H) 10.71 (s, 1H) 11.69 (br. s., 1H) 12.51 (s, 1H) 12.82 (s, 1H)

Example 6

Conversion 4

2-Amino-N-[5-(3,5-difluoro-benzyl)-1H-indazol-3-yl]-4-(4-methyl-piperazin-1-yl)-benzamide [(I$_A$), R1=R2=R3=H, R=3,5-difluorophenyl, Ar=4-(4-methyl-piperazin-1-yl)-2-amino-phenyl] cpd. 8

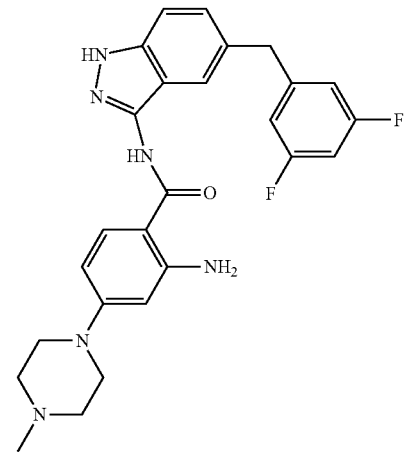

A mixture of N-[5-(3,5-difluoro-benzyl)-1H-indazol-3-yl]-4-(4-methyl-piperazin-1-yl)-2-nitro-benzamide (3.21 g, 6.33 mmol), cyclohexene (20 mL), dioxane (200 mL) and 10% Pd/C (0.8 g) was stirred at 100° C. for 2 hours. The reaction mixture was filtered over a celite pad washing thoroughly with THF and MeOH. After evaporation of the organic phase, purification of the crude by chromatography over silica gel (DCM/MeOH 95/5) gave 2.51 g of title compound (83% yield).

1H-NMR (400 MHz), δ (ppm, DMSO-d6): 2.23 (s, 3H) 2.44 (br. s., 4H) 3.20 (t, J=4.76 Hz, 4H) 4.04 (s, 2H) 6.18 (d, J=2.44 Hz, 1H) 6.24 (dd, J=8.96, 2.38 Hz, 1H) 6.53 (s, 2H) 6.97 (m, 3H) 7.22 (dd, J=8.66, 1.59 Hz, 1H) 7.39 (d, J=8.66 Hz, 1H) 7.52 (br. s., 1H) 7.72 (d, J=9.02 Hz, 1H) 10.01 (s, 1H) 12.60 (s, 1H)

Operating in an analogous way, the following compounds were obtained:

2-Amino-4-[(3-dimethylamino-propyl)-methyl-amino]-N-[5-(3-ethoxy-benzyl)-1H-indazol-3-yl]-benzamide [(I$_A$), R1=R2=R3=H, R=3-ethoxyphenyl, Ar=4-[(3-dimethylamino-propyl)-methyl-amino]-2-amino-phenyl] cpd. 54

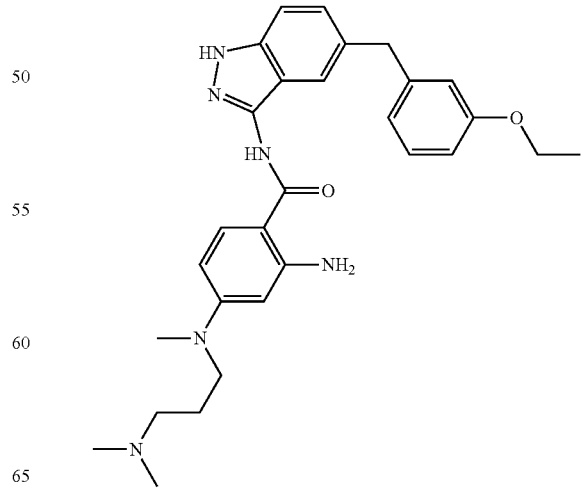

1H-NMR (400 MHz), δ (ppm, DMSO-d6): 1.27 (t, J=6.95 Hz, 3H) 1.67 (d, J=7.19 Hz, 2H) 2.19 (s, 6H) 2.28 (t, J=6.04 Hz, 2H) 2.90 (s, 3H) 3.24-3.40 (m, 2H) 3.96 (q, J=6.95 Hz, 2H) 3.95 (s, 2H) 5.94 (d, J=2.56 Hz, 1H) 6.04 (dd, J=9.02, 2.56 Hz, 1H) 6.52 (s, 2H) 6.68-6.72 (m, 1H) 6.76-6.79 (m, 1H) 6.77 (s, 1H) 7.13-7.17 (m, 1H) 7.18 (dd, J=8.60, 1.65 Hz, 1H) 7.33-7.38 (m, 1H) 7.47 (s, 1H) 7.69 (d, J=9.02 Hz, 1H) 9.88 (s, 1H) 12.53 (s, 1H)

2-amino-N-[5-(3,5-difluorobenzyl)-1H-indazol-3-yl]-4-{[(2S)-2-(pyrrolidin-1-ylmethyl)pyrrolidin-1-yl]carbonyl}benzamide 1H-NMR (400 MHz), δ (ppm, DMSO-d6): 3.29-3.48 (m, 2H) 4.06 (s, 2H) 4.29 (br. s., 1H) 6.63 (br. s., 3H) 6.85 (br. s., 1H) 6.92-7.05 (m, 3H) 7.26 (dd, J=8.66, 1.34 Hz, 1H) 7.43 (d, J=8.54 Hz, 1H) 7.57 (s, 1H) 7.85 (d, J=8.17 Hz, 1H) 10.46 (s, 1H) 12.72 (s, 1H)

2-amino-N-[5-(3,5-difluorobenzyl)-1H-indazol-3-yl]-4-{[(2R)-2-(pyrrolidin-1-ylmethyl)pyrrolidin-1-yl]carbonyl}benzamide ESI(+) MS: m/z 559 (MH⁺).

2-amino-N$^1$-[5-(3,5-difluorobenzyl)-1H-indazol-3-yl]-N$^4$-[2-(dimethylamino)ethyl]-N$^4$-methylbenzene-1,4-dicarboxamide ESI(+) MS: m/z 507 (MH⁺).

2-amino-N-[5-(3,5-difluorobenzyl)-1H-indazol-3-yl]-4-{[4-(propan-2-yl)piperazin-1-yl]carbonyl}benzamide 1H-NMR (400 MHz), δ (ppm, DMSO-d6): 0.99 (d, J=6.46 Hz, 6H) 2.43 (m, 4H) 2.70 (d, 1H) 3.58 (m, 4H) 4.06 (s, 2H) 6.54 (dd, J=8.05, 1.46 Hz, 1H) 6.65 (s, 2H) 6.75 (d, J=1.46 Hz, 1H) 6.92-7.01 (m, 2H) 6.99-7.05 (in, 1H) 7.26 (dd, J=8.59, 1.52 Hz, 1H) 7.43 (d, J=8.65 Hz, 1H) 7.57 (s, 1H) 7.85 (d, J=8.17 Hz, 1H) 10.45 (s, 11H) 12.71 (s, 1H)

2-amino-N$^1$-[5-(3,5-difluorobenzyl)-1H-indazol-3-yl]-N$^4$-[2-(dimethylamino)ethyl]benzene-1,4-dicarboxamide ESI(+) MS: m/z 493 (MH⁺).

2-amino-N-[5-(3,5-d fluorobenzyl)-1H-indazol-3-yl]-4-[(4-methylpiperazin-1-yl)carbonyl]benzamide 1H-NMR (400 MHz), δ (ppm, DMSO-d6): 4.06 (s, 2H) 6.60 (d, J=8.29 Hz, 1H) 6.68 (s, 2H) 6.80 (d, J=1.46 Hz, 1H) 6.93-7.00 (m, 2N) 7.00-7.06 (m, 1H) 7.26 (dd, J=8.53, 1.58 Hz, 1H) 7.44 (d, J=8.65 Hz, 1H) 7.55 (s, NH) 7.88 (d, J=8.17 Hz, 1H) 10.48 (s, 1H) 12.73 (s, 1H)

2-amino-N-[5-(3,5-difluorobenzyl)-1H-indazol-3-yl]-4-{[4-(dimethylamino)piperidin-1-yl]carbonyl}benzamide ESI(+) MS: m/z 533 (MH⁺).

2-amino-N$^1$-[5-(3,5-difluorobenzyl)-1H-indazol-3-yl]-N$^4$-(1-methylpiperidin-4-yl)benzene-1,4-dicarboxamide ESI(+) MS: m/z 519 (MH⁺).

Example 7

Conversion 6

N-[5-(3,5-Difluoro-benzyl)-1H-indazol-3-yl]-4-(4-methyl-piperazin-1-yl)-2-(tetrahydro-pyran-4-ylamino)-benzamide [(I$_A$), R1=R2=R3=H, R=3,5-difluorophenyl, Ar=4-(4-methyl-piperazin-1-yl)-2-(tetrahydro-pyran-4-ylamino)-phenyl] cpd. 11

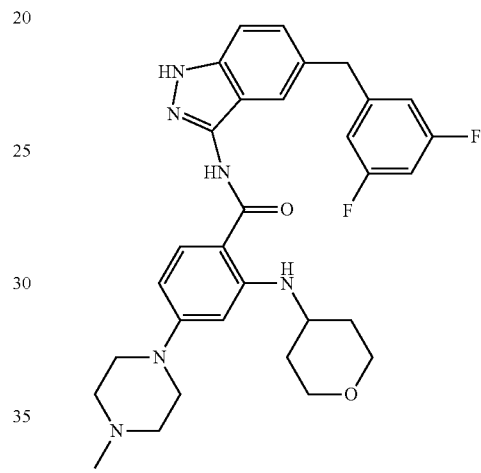

To a solution of 2-amino-N-[5-(3,5-difluoro-benzyl)-1H-indazol-3-yl]-4-(4-methyl-piperazin-1-yl)-benzamide (1.9 g, 3.98 mmol) in dichloromethane (80 mL) were added tetrahydro-pyran-4-one (0.55 mL, 5.98 mmol), trifluoroacetic acid (4 mL) and tetramethylammonium triacetoxyborohydride (1.57 g, 5.98 mmol). The mixture was stirred at room temperature overnight, and then more tetramethylammonium triacetoxyborohydride (1.57 g) was added. After stirring for additional 3 hours at room temperature the mixture was diluted with dichloromethane, washed with 2N sodium hydroxide and brine, dried over sodium sulfate and evaporated to dryness. The crude was purified by flash chromatography on silica gel using dichloromethane/methanol/NH$_3$ 5N in MeOH 96:4:0.5 as the eluant, affording 1.61 g of the title compound (72% yield).

1H-NMR (400 MHz), δ (ppm, DMSO-d6): 1.26-1.43 (m, 2H) 1.86-2.02 (m, 2H) 2.23 (s, 3H) 2.42-2.46 (m, 4H) 3.23-3.29 (m, 4H) 3.45-3.54 (m, 2H) 3.62-3.75 (m, 1H) 3.82 (dt, J=11.61, 3.83 Hz, 2H) 4.05 (s, 2H) 6.14 (d, J=2.07 Hz, 1H) 6.24 (dd, J=8.90, 2.19 Hz, 1H) 6.94-7.06 (m, 3H) 7.26 (dd, J=8.66, 1.46 Hz, 1H) 7.41 (d, J=8.66 Hz, 1H) 7.50 (d, 1H) 7.80 (d, J=9.15 Hz, 1H) 8.29 (d, J=7.68 Hz, 1H) 10.08 (s, 1H) 12.63 (s, 1H)

N-{5-[(3,5-Difluoro-phenyl)-methoxy-methyl]-1H-indazol-3-yl}-4-(4-methyl-piperazin-1-yl)-2-(tetrahydro-pyran-4-ylamino)-benzamide [(I$_C$), R1=R2=R3=H, R=3,5-difluorophenyl, R'=methyl, Ar=4-(4-methyl-piperazin-1-yl)-2-(tetrahydro-pyran-4-ylamino)-phenyl] cpd. 68

1-[4-{[5-(3,5-difluorobenzyl)-1H-indazol-3-yl]carbamoyl}-3-(tetrahydro-2H-pyran-4-ylamino)benzyl] piperidine trifluoroacetate [(I$_A$), R1=R2=R3=H, R=3,5-difluorophenyl, Ar=4-piperidin-1-ylmethyl-2-(tetrahydro-pyran-4-ylamino)-phenyl] cpd. 115

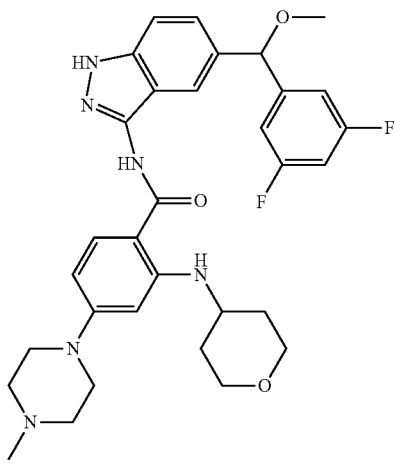 [SMILES: COC(c1cc(F)cc(F)c1)c1ccc2[nH]nc(NC(=O)c3ccc(N4CCN(C)CC4)cc3NC3CCOCC3)c2c1]

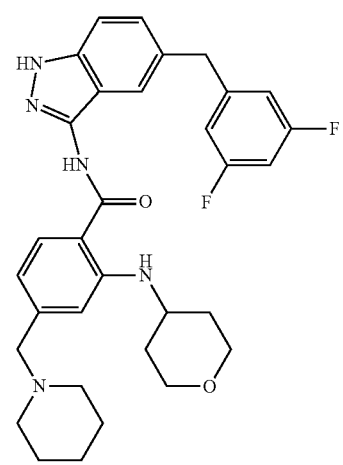 [SMILES: O=C(Nc1n[nH]c2ccc(Cc3cc(F)cc(F)c3)cc12)c1ccc(CN2CCCCC2)cc1NC1CCOCC1]

1H-NMR (400 MHz), δ (ppm, DMSO-d6): 1.32-1.46 (m, 3H) 1.65-1.93 (m, 5H) 1.96-2.04 (m, 2H) 2.81-2.96 (m, 2H) 3.32 (br. s., 2H) 3.44-3.54 (m, 2H) 3.63-3.74 (m, 1H) 3.82-3.91 (m, 2H) 4.06 (s, 2H) 4.23 (d, J=5.37 Hz, 2H) 6.75-6.81 (m, 1H) 6.94-7.06 (m, 2H) 7.13 (s, 1H) 7.29 (dd, J=8.66, 1.46 Hz, 1H) 7.45 (d, J=8.54 Hz, 1H) 7.50 (s, 1H) 7.96 (d, J=8.05 Hz, 1H) 8.00 (br. s., 1H) 10.14 (br. s., 1H) 10.54 (s, 1H) 12.77 (br. s., 1H)

N-[5-(3,5-difluorobenzyl)-1H-indazol-3-yl]-4-{[(2-methoxyethyl)(methyl)amino]methyl}-2-(tetrahydro-2H-pyran-4-ylamino)benzamide [(I$_A$), R1=R2=R3=H, R=3,5-difluorophenyl, Ar=4-{[(2-methoxyethyl)(methyl)amino]methyl}-2-(tetrahydro-pyran-4-ylamino)-phenyl] cpd. 116

Title compound was isolated as a by-product (about 15%) during preparative HPLC purification of the mixed fractions resulted from column chromatography purification of the previously reported preparation of N-[5-(3,5-difluoro-benzyl)-1H-indazol-3-yl]-4-(4-methyl-piperazin-1-yl)-2-(tetrahydro-pyran-4-ylamino)-benzamide 1H-NMR (400 MHz), δ (ppm, DMSO-d6): 1.31-1.44 (m, 2H) 1.91-2.01 (m, 2H) 2.79 (br. s., 3H) 3.32 (m, 11H) 3.45-3.56 (m, 2H) 3.68-3.78 (m, 1H) 3.80-3.88 (m, 2H) 5.48 (s, 1H) 6.22 (d, J=2.07 Hz, 1H) 6.30 (d, J=9.02 Hz, 1H) 7.04-7.12 (m, 3H) 7.32 (dd, J=8.78, 1.46 Hz, 1H) 7.45 (d, J=8.90 Hz, 1H) 7.64 (s, 1H) 7.86 (d, J=9.02 Hz, 1H) 8.35 (d, J=7.80 Hz, 1H) 10.20 (s, 1H) 12.73 (s, 1H) Operating in an analogous way, the following compounds were obtained:

2-[(2-{[tert-butyl(dimethyl)silyl]oxy}ethyl)amino]-N-[5-(3,5-difluorobenzyl)-1H-indazol-3-yl]-4-(4-methylpiperazin-1-yl)benzamide ESI(+) MS: m/z 635 (MH$^+$).

tert-butyl 3-({[2-{[5-(3,5-difluorobenzyl)-1H-indazol-3-yl]carbamoyl}-5-(4-methylpiperazin-1-yl)phenyl]amino}methyl)azetidine-1-carboxylate ESI(+) MS: m/z 646 (MH$^+$).

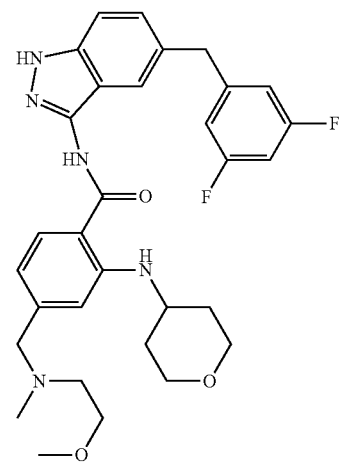 [SMILES: COCCN(C)Cc1ccc(C(=O)Nc2n[nH]c3ccc(Cc4cc(F)cc(F)c4)cc23)c(NC2CCOCC2)c1]

1H-NMR (400 MHz), δ (ppm, DMSO-d6): 1.31-1.45 (m, 2H) 1.95 (d, J=11.83 Hz, 2H) 2.22 (s, 3H) 2.52-2.57 (m, 2H) 3.26 (s, 3H) 3.43-3.53 (m, 6H) 3.64 (dd, J=6.95, 2.93 Hz, 1H) 3.80-3.88 (m, 2H) 4.05 (s, 2H) 6.58 (d, J=7.93 Hz, 1H)

6.79 (s, 1H) 6.95-7.06 (m, 3H) 7.27 (dd, J=8.66, 1.46 Hz, 1H) 7.43 (d, J=8.54 Hz, 1H) 7.52 (s, 1H) 7.86 (d, J=8.05 Hz, 1H) 7.96 (d, J=7.56 Hz, 1H) 10.39 (s, 1H) 12.71 (s, 1H)

N-[5-(3,5-difluorobenzyl)-1H-indazol-3-yl]-4-(pyrrolidin-1-ylmethyl)-2-(tetrahydro-2H-pyran-4-ylamino)benzamide [(I_A), R1=R2=R3=H, R=3,5-difluorophenyl, Ar=4-(pyrrolidin-1-ylmethyl)-2-(tetrahydro-pyran-4-ylamino)-phenyl] cpd. 117

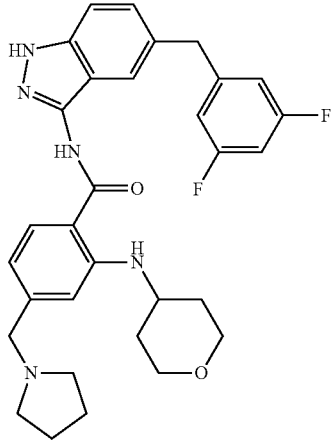 [SMILES: O=C(Nc1n[nH]c2ccc(Cc3cc(F)cc(F)c3)cc12)c1ccc(CN2CCCC2)cc1NC1CCOCC1]

1H-NMR (400 MHz), δ (ppm, DMSO-d6): 1.31-1.45 (m, 2H) 1.67-1.78 (m, 4H) 1.90-1.98 (m, 2H) 2.47 (br. s., 2H) 3.44-3.54 (m, 2H) 3.56 (br. s., 4H) 3.59-3.71 (m, 1H) 3.83 (dt, J=11.65, 3.69 Hz, 2H) 4.05 (s, 2H) 6.59 (d, J=8.66 Hz, 1H) 6.77 (s, 1H) 6.92-7.07 (m, 3H) 7.27 (dd, J=8.66, 1.59 Hz, 1H) 7.42 (d, J=0.49 Hz, 1H) 7.52 (s, 1H) 7.85 (d, J=8.17 Hz, 1H) 7.95 (d, J=7.80 Hz, 1H) 10.39 (s, 1H) 12.71 (s, 1H)

N-[5-(3,5-difluorobenzyl)-1H-indazol-3-yl]-4-(morpholin-4-ylmethyl)-2-(tetrahydro-2H-pyran-4-ylamino)benzamide [(I_A), R1=R2=R3=H, R=3,5-difluorophenyl, Ar=4-(morpholin-4-ylmethyl)-2-(tetrahydro-pyran-4-ylamino)-phenyl] cpd. 118

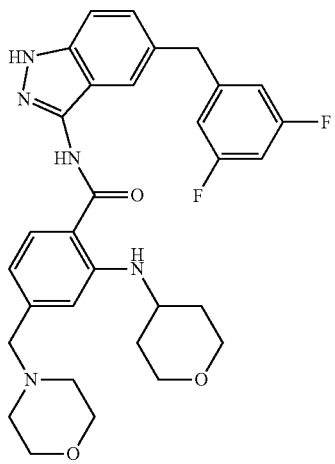 [SMILES: O=C(Nc1n[nH]c2ccc(Cc3cc(F)cc(F)c3)cc12)c1ccc(CN2CCOCC2)cc1NC1CCOCC1]

1H-NMR (400 MHz), δ (ppm, DMSO-d6): 1.30-1.44 (m, 2H) 1.88-2.01 (m, 2H) 2.39 (br. s., 4H) 3.45-3.46 (m, 2H) 3.46-3.54 (m, 2H) 3.61 (br. s., 4H) 3.65 (d, 1H) 3.84 (d, J=12.32 Hz, 2H) 4.05 (s, 2H) 6.60 (d, J=8.41 Hz, 1H) 6.79 (s, 1H) 6.89-7.09 (m, 3H) 7.28 (dd, J=8.72, 1.16 Hz, 1H) 7.43 (d, J=8.78 Hz, 1H) 7.51 (s, 1H) 7.87 (d, J=8.05 Hz, 1H) 7.95 (d, J=7.80 Hz, 1H) 10.40 (s, 1H) 12.71 (s, 1H)

4-(azetidin-1-ylmethyl)-N-[5-(3,5-difluorobenzyl)-1H-indazol-3-yl]-2-(tetrahydro-2H-pyran-4-ylamino)benzamide [(I_A), R1=R2=R3=H, R=3,5-difluorophenyl, Ar=4-(azetidin-1-ylmethyl)-2-(tetrahydro-pyran-4-ylamino)-phenyl] cpd. 119

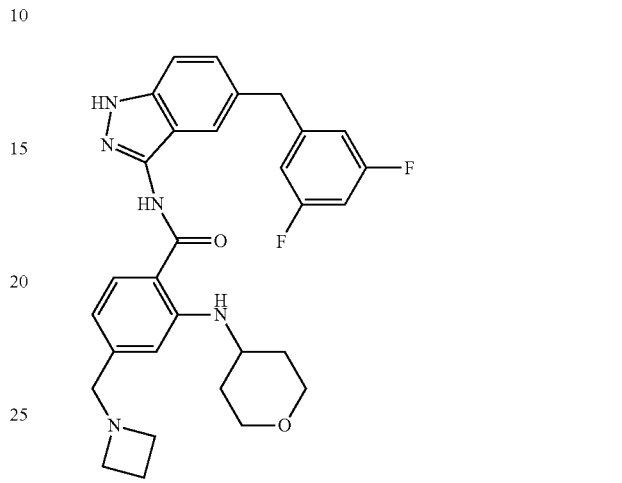

1H-NMR (400 MHz), δ (ppm, DMSO-d6): 1.31-1.43 (m, 2H) 1.90-1.98 (m, 2H) 1.98-2.06 (m, 2H) 3.15 (t, J=1.95 Hz, 4H) 3.46-3.54 (m, 4H) 3.61-3.70 (m, 1H) 3.79-3.88 (m, 2H) 4.05 (s, 2H) 6.53 (dd, J=8.11, 1.16 Hz, 1H) 6.72 (s, 1H) 6.94-7.05 (m, 3H) 7.27 (dd, J=8.60, 1.52 Hz, 1H) 7.43 (d, J=8.66 Hz, 1H) 7.51 (s, 1H) 7.83 (d, J=8.17 Hz, 1H) 7.94 (d, J=7.80 Hz, 1H) 10.38 (s, 1H) 12.70 (s, 1H)

N-[5-(3,5-difluorobenzyl)-1H-indazol-3-yl]-4-{[(2S)-2-(pyrrolidin-1-ylmethyl)pyrrolidin-1-yl]carbonyl}-2-(tetrahydro-2H-pyran-1-ylamino)benzamide [(I_A), R1=R2=R3=H, R=3,5-difluorophenyl, Ar=4-{[(2S)-2-(pyrrolidin-1-ylmethyl)pyrrolidin-1-yl]carbonyl}-2-(tetrahydro-pyran-4-ylamino)-phenyl] cpd. 127

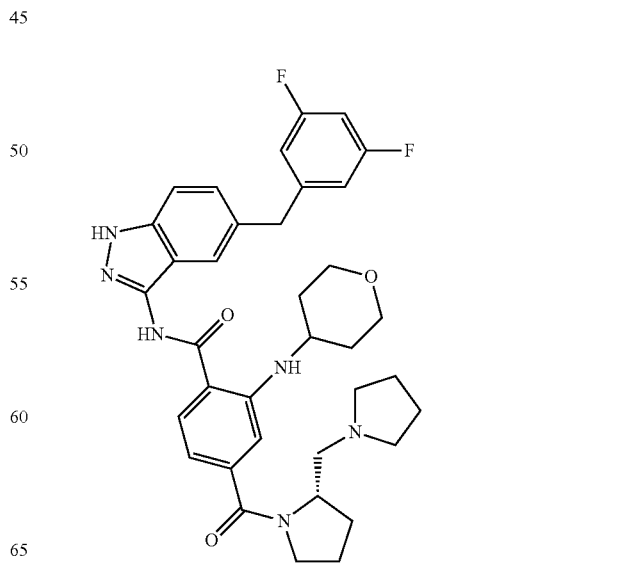

1H-NMR (400 MHz), δ (ppm, DMSO-d6): ppm 3.44-3.56 (m, 2H) 3.61-3.75 (m, 1H) 3.78-3.88 (m, 2H) 4.06 (s, 2H) 4.26 (br. s., 1H) 6.66 (s, 1H) 6.83 (s, 1H) 6.95-7.06 (m, 3H) 7.28 (dd, J=8.66, 1.46 Hz, 1H) 7.44 (d, J=8.78 Hz, 1H) 7.53 (s, 1H) 7.93 (d, J=8.17 Hz, 1H) 7.97 (br. s., 1H) 10.55 (s, 1H) 12.75 (s, 1H)

N-[5-(3,5-difluorobenzyl)-1H-Indazol-3-yl]-4-{[(2R)-2-(pyrrolidin-1-ylmethyl)pyrrolin-1-yl]carbonyl}-2-(tetrahydro-2H-pyran-4-ylamino)benzamide [(I$_A$) R1=R2=R3=H, R=3,5-difluorophenyl, Ar=4-{[(2R)-2-(pyrrolidin-1-ylmethyl)pyrrolidin-1-yl]carbonyl}-2-(tetrahydro-pyran-4-ylamino)-phenyl] cpd. 128

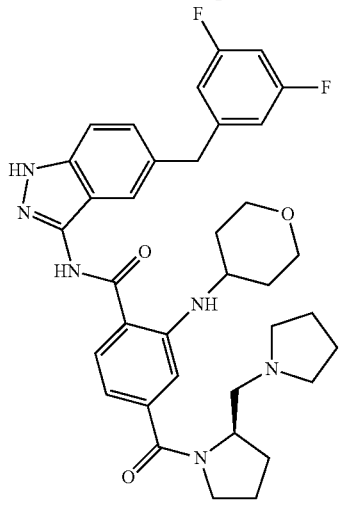 [SMILES: O=C(Nc1n[nH]c2ccc(Cc3cc(F)cc(F)c3)cc12)c1ccc(C(=O)N2CCC[C@@H]2CN2CCCC2)cc1NC1CCOCC1]

1H-NMR (400 MHz), δ (ppm, DMSO-d6): ppm 3.44-3.56 (m, 2H) 3.61-3.75 (m, 1H) 3.78-3.88 (m, 2H) 4.06 (s, 2H) 4.26 (br. s., 1H) 6.66 (s, 1H) 6.83 (s, 1H) 6.95-7.06 (m, 3H) 7.28 (dd, J=8.66, 1.46 Hz, 1H) 7.44 (d, J=8.78 Hz, 1H) 7.53 (s, 1H) 7.93 (d, J=8.17 Hz, 1H) 7.97 (br. s., 1H) 10.55 (s, 1H) 12.75 (s, 1H)

N$^1$-[5-(3,5-difluorobenzyl)-1H-indazol-3-yl]-N$^4$-[2-(dimethylamino)ethyl]-N$^4$-methyl-2-(tetrahydro-2H-pyran-4-ylamino)benzene-1,4-dicarboxamide [(I$_A$), R1=R2=R3=H, R=3,5-difluorophenyl, Ar=4-({N-[2-(dimethylamino)ethyl]-N-methyl}carbonyl)-2-(tetrahydro-pyran-4-ylamino)-phenyl] cpd. 129

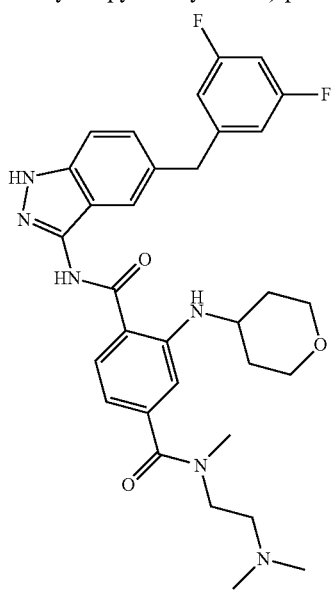

1H-NMR (400 MHz), δ (ppm, DMSO-d6): mixture of rotamers 1.31-1.44 (m, 2H) 1.87-1.97 (m, 2H) 3.45-3.52 (m, 2H) 3.62-3.72 (m, 1H) 3.79-3.88 (m, 2H) 4.06 (s, 2H) 6.56 (d, J=7.68 Hz, 1H) 6.76 (br. s., 1H) 6.95-7.05 (m, 3H) 7.28 (dd, J=8.59, 1.52 Hz, 1H) 7.44 (d, J=8.65 Hz, 1H) 7.54 (s, 1H) 7.91-7.99 (m, 2H) 10.56 (s, 1H) 12.75 (s, 1H)

N-[5-(3,5-difluorobenzyl)-1H-indazol-3-yl]-4-{[4-(propan-2-yl)piperazin-1-yl]carbonyl}-2-(tetrahydro-2H-pyran-4-ylamino)benzamide [(I$_A$), R1=R2=R3=H, R=3,5-difluorophenyl, Ar=4-{[4-(propan-2-yl)piperazin-1-yl]carbonyl}-2-(tetrahydro-pyran-4-ylamino)-phenyl] cpd. 130

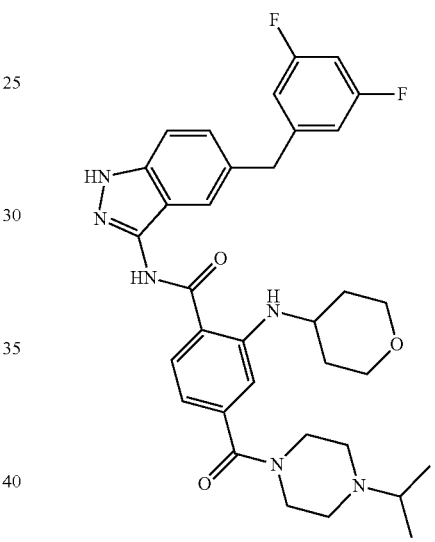

1H-NMR (400 MHz), δ (ppm, DMSO-d6): 0.99 (d, J=6.46 Hz, 6H) 1.32-1.43 (m, 2H) 1.89-1.97 (m, 2H) 2.36-2.54 (m, 4H) 2.66-2.75 (m, 1H) 3.28-3.37 (m, 2H) 3.49 (td, J=1.18, 2.13 Hz, 2H) 3.61 (br. s., 2H) 3.65-3.74 (m, 1H) 3.80-3.87 (m, 2H) 4.06 (s, 2H) 6.58 (dd, J=7.98, 1.28 Hz, 1H) 6.77 (d, J=0.85 Hz, 1H) 6.95-7.05 (m, 3H) 7.28 (dd, J=8.59, 1.52 Hz, 1H) 7.44 (d, J=8.65 Hz, 1H) 7.53 (s, 1H) 7.91-7.95 (m, 1H) 7.94-7.96 (m, 1H) 10.56 (s, 1H) 12.75 (s, 1H)

N¹-[5-(3,5-difluorobenzyl)-1H-indazol-3-yl]-N⁴-[2-(dimethylamino)ethyl]-2-(tetrahydro-2H-pyran-4-ylamino)benzene-1,4-dicarboxamide [(I$_A$), R1=R2=R3=H, R=3,5-difluorophenyl, Ar=4-({N-[2-(dimethylamino)ethyl]}carbonyl)-2-(tetrahydro-pyran-4-ylamino)-phenyl] cpd. 131

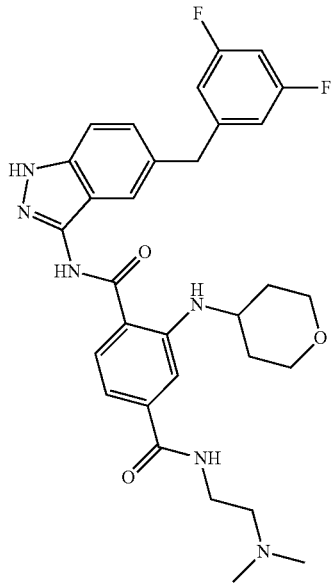 [SMILES: CN(C)CCNC(=O)c1ccc(C(=O)Nc2n[nH]c3ccc(Cc4cc(F)cc(F)c4)cc23)c(NC2CCOCC2)c1]

1H-NMR (400 MHz), δ (ppm, DMSO-d6): 1.33-1.47 (m, 2H) 1.93-2.00 (m, 2H) 2.30 (br. s., 6H) 2.51-2.60 (m, 2H) 3.37-3.44 (m, 2H) 3.46-3.54 (m, 2H) 3.73 (d, 1H) 3.85 (dt, J=11.61, 3.76 Hz, 2H) 4.06 (s, 2H) 6.95-7.05 (m, 3H) 7.07 (dd, J=8.17, 1.46 Hz, 1H) 7.23 (d, J=1.22 Hz, 1H) 7.28 (dd, J=8.65, 1.58 Hz, 1H) 7.44 (d, J=8.53 Hz, 1H) 7.54 (s, 1H) 7.93 (d, J=7.68 Hz, 1H) 7.96 (d, J=8.29 Hz, 1H) 8.47 (t, J=4.94 Hz, 1H) 10.60 (s, 1H) 12.76 (s, 1H)

N-[5-(3,5-difluorobenzyl)-1H-indazol-3-yl]-4-[(4-methylpiperazin-1-yl)carbonyl]-2-(tetrahydro-2H-pyran-4-ylamino)benzamide [(I$_A$), R1=R2=R3=H, R=3,5-difluorophenyl, Ar=4-[(4-methylpiperazin-1-yl)carbonyl]-2-(tetrahydro-pyran-4-ylamino)-phenyl] cpd. 132

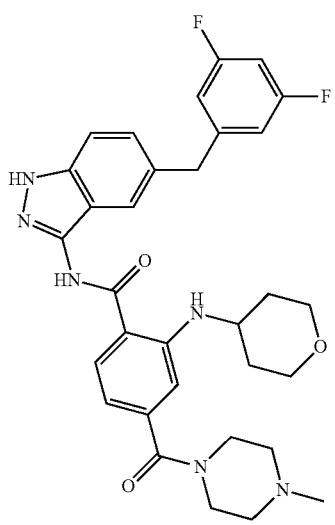 [SMILES: CN1CCN(C(=O)c2ccc(C(=O)Nc3n[nH]c4ccc(Cc5cc(F)cc(F)c5)cc34)c(NC3CCOCC3)c2)CC1]

1H-NMR (400 MHz), δ (ppm, DMSO-d6): 1.32-1.43 (m, 2H) 1.93 (d, J=11.70 Hz, 2H) 2.22 (s, 3H) 2.33 (m, 4H) 3.45-3.53 (m, 2H) 3.65-3.73 (m, 1H) 3.80-3.86 (m, 2H) 4.06 (s, 2H) 6.57 (dd, J=7.98, 1.28 Hz, 1H) 6.77 (d, J=0.98 Hz, 1H) 6.96-7.05 (m, 3H) 7.28 (dd, J=8.59, 1.52 Hz, 1H) 7.44 (d, J=8.53 Hz, 1H) 7.52 (s, 1H) 7.92-7.95 (m, 1H) 7.94-7.97 (m, 1H) 10.56 (s, 1H) 12.75 (s, 1H)

N-[5-(3,5-difluorobenzyl)-1H-indazol-3-yl]-4-{[4-(dimethylamino)piperidin-1-yl]carbonyl}-2-(tetrahydro-2H-pyran-4-ylamino)benzamide [(I$_A$), R1=R2=R3=H, R=3,5-difluorophenyl, Ar=4-{[4-(dimethylamino)piperidin-1-yl]carbonyl}-2-(tetrahydro-pyran-4-ylamino)-phenyl] cpd. 133

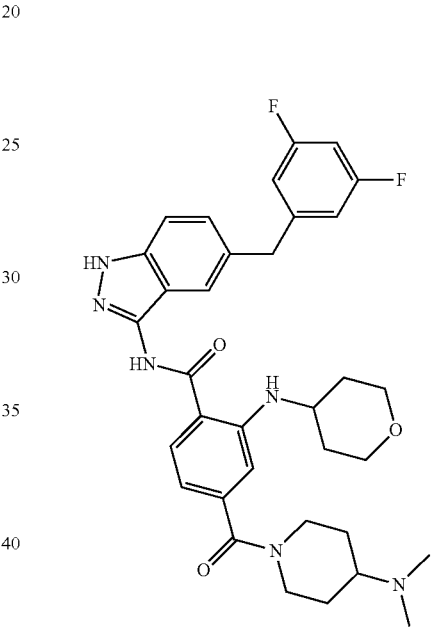

1H-NMR (400 MHz), δ (ppm, DMSO-d6): 1.25-1.46 (m, 4H) 1.73 (m, 1H) 1.84 (m, 1H) 1.93 (d, J=11.46 Hz, 2H) 2.20 (s, 6H) 2.34 (m, 1H) 2.82 (m, 1H) 3.04 (m, 1H) 3.42-3.55 (m, 2H) 3.65-3.76 (m, 2H) 3.78-3.88 (m, 2H) 4.06 (s, 2H) 4.43 (m, 1H) 6.58 (dd, J=8.05, 1.34 Hz, 1H) 6.78 (d, J=0.85 Hz, 1H) 6.94-7.06 (m, 3H) 7.28 (dd, J=8.65, 1.58 Hz, 1H) 7.44 (d, J=8.53 Hz, 1H) 7.53 (s, 1H) 7.90-7.96 (m, 2H) 10.55 (s, 1H) 12.74 (s, 1H)

N[1]-[5-(3,5-difluorobenzyl)-1H-indazol-3-yl]-N[4]-(1-methylpiperidin-4-yl)-2-(tetrahydro-2H-pyran-4-ylamino)benzene-1,4-dicarboxamide [(I$_A$), R1=R2=R3=H, R=3,5-difluorophenyl, Ar=4-[N-(1-methylpiperidin-4-yl)-carbonyl]-2-(tetrahydro-pyran-4-ylamino)-phenyl] cpd. 134

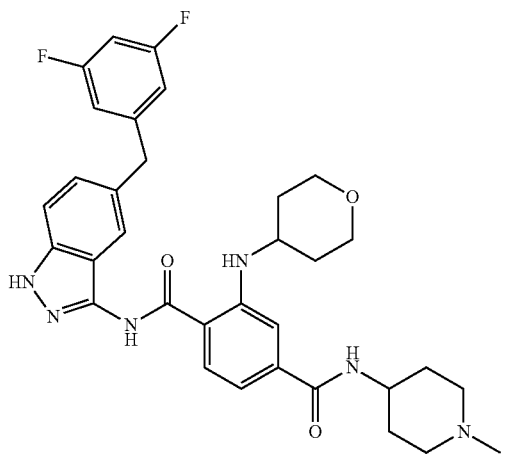 [SMILES: CN1CCC(NC(=O)c2ccc(C(=O)Nc3n[nH]c4ccc(Cc5cc(F)cc(F)c5)cc34)c(NC3CCOCC3)c2)CC1]

1H-NMR (400 MHz), δ (ppm, DMSO-d6): 1.32-1.47 (m, 2H) 1.56-1.70 (m, 2H) 1.74-1.83 (m, 2H) 1.92-1.99 (m, 2H) 2.02 (br. s., 2H) 2.21 (s, 3H) 2.82 (d, J=13.17 Hz, 2H) 3.46-3.54 (m, 2H) 3.67-3.80 (m, 2H) 3.79-3.88 (m, 2H) 4.06 (s, 2H) 6.96-7.05 (m, 3H) 7.08 (dd, J=8.17, 1.46 Hz, 1H) 7.21 (d, J=1.22 Hz, 1H) 7.28 (dd, J=8.65, 1.46 Hz, 1H) 7.42-7.46 (m, 1H) 7.54 (s, 1H) 7.92-7.97 (m, 2H) 8.26 (d, J=7.80 Hz, 1H) 10.60 (s, 1H) 12.77 (s, 1H).

Example 8

Preparation of tert-butyl 4-{[(2S)-1-methylpyrrolidin-2-yl]methoxy}-2-nitrobenzoate In a round bottomed three neck flask under argon atmosphere were added toluene (15 ml), CsCO$_3$ (1.6 gr, 5 mmol), phosphine ligand 2-(di-tert-butylphosphino)-1,1'-binaphthyl (331 mg, 0.83 mmol) and Pd(dba)$_2$ (380 mgr, 0.66 mmol). The mixture was degassed bubbling argon for five minutes. Then 4-bromo-2-nitrobenzoic acid tert butyl ester (1 gr, 3.31 mmol) and (S)-(−)-1-methyl-2-pyrrolidinemethanol (0.78 ml, 6.62 mmol) were added and the mixture was heated to 100° C. for 18 hr. The reaction was cooled to room temperature, quenched with 30 ml of water and extracted twice with 25 ml of AcOEt. The organic phases were collected, dried over Na$_2$SO$_4$ and the solvents evaporated to obtain a red oil which was subjected to chromatography purification on a Biotage SP1 automated system (90:10 DCM/MeOH (isocratic) to yield the pure title compound as a yellowish oil (460 mgr, 1.36 mmol, 41% yield).

ESI(+) MS: m/z 337 (MH$^+$).

Operating in an analogous way, the following compounds were obtained:

tert-butyl 4-[(1-methylpiperidin-4-yl)oxy]-2-nitrobenzoate

1H-NMR (400 MHz), δ (ppm, DMSO-d6): 1.48 (9H, s) 1.68 (m, 2H) 1.95 (m, 2H) 2.20 (m, 5H) 2.61 (m, 2H) 4.60 (m, 1H) 7.30 (dd, J=8.78, 2.56 Hz, 1H) 7.54 (d, J=2.56 Hz, 1H) 7.79 (d, J=8.78 Hz, 1H)

tert-butyl 4-[2-(dimethylamino)ethoxy]-2-nitrobenzoate

1H-NMR (400 MHz), δ (ppm, DMSO-d6): 1.49 (9H, s) 2.22 (s, 6H) 2.65 (t, J=5.61 Hz, 2H) 4.21 (t, J=5.63 Hz, 2H) 7.30 (dd, J=8.78, 2.56 Hz, 1H) 7.52 (d, J=2.56 Hz, 1H) 7.80 (d, J=8.78 Hz, 1H)

tert-butyl 4-{[(3S)-1-methylpyrrolidin-3-yl]oxy}-2-nitrobenzoate

ESI(+) MS: m/z 323 (MH$^+$).

Preparation of tert-butyl 2-amino-4-{[(2S)-1-methylpyrrolidin-2-yl]methoxy}benzoate Nitro-derivative tert-butyl 4-{[(2S)-1-methylpyrrolidin-2-yl]methoxy}-2-nitrobenzoate (460 mgr, 1.37 mmol) was dissolved in 20 ml of MeOH, 130 mg of Pd/C 5% and 700 mg (6.3 mmol) of HCOONH$_4$ were added under argon atmosphere. The mixture was refluxed at 80° C. for 1 hr then cooled to room temperature and filtered through a small pad of celite washing with MeOH. The solvent was then distilled off and the residue was dissolved in 20 ml of DCM and washed twice with 20 ml of NaHCO$_3$ (10%). The collected organic extracts were dried over Na$_2$SO$_4$, filtered and evaporated to dryness to yield a brown oil (400 mgr, 1.31 mmol, 95% yield), which was used in the next step without any further purification.

ESI(+) MS: m/z 307 (MH$^+$).

Operating in an analogous way, the following compounds were obtained:

tert-butyl 2-amino-4-[(1-methylpiperidin-4-yl)oxy]benzoate

ESI(+) MS: m/z 307 (MH$^+$).

tert-butyl 2-amino-4-[2-(dimethylamino)ethoxy]benzoate

1NMR (400 MHz), δ (ppm, DMSO-d6): 1.51 (s, 9H) 2.21 (s, 6H) 2.61 (t, J=5.79 Hz, 2H) 4.00 (t, J=5.79 Hz, 2H) 6.11 (dd, J=8.96, 2.50 Hz, 1H) 6.25 (d, J=2.56 Hz, 1H) 6.60 (s, 2H) 7.56 (d, J=8.90 Hz, 1H)

tert-butyl 2-amino-4-{[(3S)-1-methylpyrrolidin-3-yl]oxy}benzoate

ESI(+) MS: m/z 293 (MH$^+$).

Preparation of tert-butyl 4-{[(2S)-1-methylpyrrolidin-2-yl]methoxy}-2-(tetrahydro-2H-pyran-4-ylamino)benzoate Tert-butyl 2-amino-4-{[(2S)-1-methylpyrrolidin-2-yl]methoxy}benzoate (400 mg, 1.3 mmol) was dissolved in 20 ml of DCM under argon atmosphere. Tetrahydro-4H-pyran-4-one (0.19 ml, 2.05 mmol), TFA (0.29 ml, 3.69 mmol) and Me₄BH(OAc)₃, (540 mg, 2.05 mmol) were added. The resulting slurry was stirred overnight at room temperature then quenched with 15 ml of NaHCO₃ 10% and extracted twice with 20 ml of DCM. The organic layers were then dried over Na₂SO₄, filtered off and concentrated to yield a yellow oil (448 mg, 1.15 mmol, 88%) which was used in the next step without any further purification.

ESI(+) MS: m/z 391 (MH⁺).

Operating in an analogous way, the following compounds were obtained:

tert-butyl 4-[(1-methylpiperidin-4-yl)oxy]-2-(tetra-hydro-2H-pyran-4-ylamino)benzoate ESI(+) MS: m/z 391 (MH⁺).

tert-butyl 4-[2-(dimethylamino)ethoxy]-2-(tetra-hydro-2H-pyran-4-ylamino)benzoate ESI(+) MS: m/z 365 (MH⁺).

tert-butyl 4-{[(3S)-1-methylpyrrolidin-3-yl]oxy}-2-(tetrahydro-2H-pyran-4-ylamino)benzoate ESI(+) MS: m/z 377 (MH⁺).

Preparation of tert-butyl 4-{[(2S)-1-methylpyrrolidin-2-yl]methoxy}-2-[tetrahydro-2H-pyran-4-yl(trifluoroacetyl)amino]benzoate Tert-butyl 4-{[(2S)-1-methylpyrrolidin-2-yl]methoxy}-2-(tetrahydro-2H-pyran-4-ylamino)benzoate (448 mg, 1.15 mmol) was dissolved in 20 ml of DCM. TEA (0.18 ml, 1.3 mmol) and TFAA (0.27 ml, 1.7 mmol) were added and the reaction mixture was stirred at room temperature for 2 hours and quenched with 15 ml of NaHCO₃ 10%. The resulting mixture was extracted twice with 20 ml of DCM, dried over Na₂SO₄, filtered and concentrated under vacuum. The crude product was subjected to silica gel chromatographic purification (DCM/MeOH 95:5) to yield a yellow oil (481 mg, 1 mmol, 87%).

1H-NMR (400 MHz), δ (ppm, DMSO-d6): 1.00 (qd, J=12.25, 4.82 Hz, 1H) 1.47 (s, 9H) 1.51-1.64 (m, 1H) 1.98 (d, J=12.68 Hz, 2H) 3.83 (ddd, J=31.46, 11.34, 4.02 Hz, 2H) 4.51 (tt, J=11.95, 3.90 Hz, 1H) 7.02 (br. s., 1H) 7.21 (d, J=6.95 Hz, 1H) 7.95 (d, J=8.78 Hz, 1H)

Operating in an analogous way, the following compounds were obtained:

tert-butyl 4-[(1-methylpiperidin-4-yl)oxy]-2-[tetra-hydro-2H-pyran-4-yl(trifluoroacetyl)amino]benzoate ESI(+) MS: m/z 487 (MH⁺).

tert-butyl 4-[2-(dimethylamino)ethoxy]-2-[tetra-hydro-2H-pyran-4-yl(trifluoroacetyl)amino]benzoate ESI(+) MS: m/z 461 (MH⁺).

tert-butyl 4-{[(3S)-1-methylpyrrolidin-3-yl]oxy}-2-[tetrahydro-2H-pyran-4-yl(trifluoroacetyl)amino] benzoate ESI(+) MS: m/z 473 (MH⁺).

Preparation of 4-{[(2S)-1-methylpyrrolidin-2-yl]methoxy}-2-[tetrahydro-2H-pyran-4-yl(trifluoroacetyl)amino]benzoic acid trifluoroacetate Tert-butyl 4-{[(2S)-1-methylpyrrolidin-2-yl]methoxy}-2-[tetrahydro-2H-pyran-4- yl(trifluoroacetyl)amino]benzoate (480 mg, 1 mmol) was dissolved in 20 ml of DCM. Anhydrous HCl 4M in dioxane was added (2.5 ml, 10 mmol). The reaction was stirred at room temperature for 5 days after that the HPLC analysis showed the formation of the desired product but with almost 30% of the detrifluoroacetylated by-product. Solvents were removed under vacuum and the resulting yellow powder was suspended in 15 ml of DCM and TFAA (0.28 ml, 2 mmol) was added. The solid immediately dissolved and the mixture was stirred for 2 hours after that the HPLC analysis showed the complete disappearance of the by product. Solvents were evaporated to dryness to yield a dark yellow solid which was used in the next synthetic step without any further purification.

ESI(+) MS: m/z 431 (MH⁺).

Operating in an analogous way, the following compounds were obtained:

tert-butyl 4-[(1-methylpiperidin-4-yl)oxy-2-tetra-hydro-2H-pyran-4-yl(trifluoroacetyl)amino]benzoic acid trifluoroacetate ESI(+) MS: m/z 431 (MH⁺).

tert-butyl 4-[2-(dimethylamino)ethoxy]-2-[tetra-hydro-2H-pyran-4-yl(trifluoroacetyl)amino]benzoic acid trifluoroacetate ESI(+) MS: m/z 405 (MH⁺).

tert-butyl 4-{[(3S)-1-methylpyrrolidin-3-yl]oxy}-2-[tetrahydro-2H-pyran-4-yl(trifluoroacetyl)amino] benzoic acid trifluoroacetate ESI(+) MS: m/z 417 (MH⁺).

Step i'

Preparation of N-[5-(3,5-difluorobenzyl)-1H-indazol-3-yl]-4-{[(2S)-1-methylpyrrolidin-2-yl]methoxy}-2-(tetrahydro-2H-pyran-4-ylamino)benzamide [(I_A), R1=R2=R3=H, R=3,5-difluorophenyl, Ar=4-{[(2S)-1-methylpyrrolidin-2-yl]methoxy}-2-(tetrahydro-2H-pyran-4-ylamino)-phenyl] cpd. 94

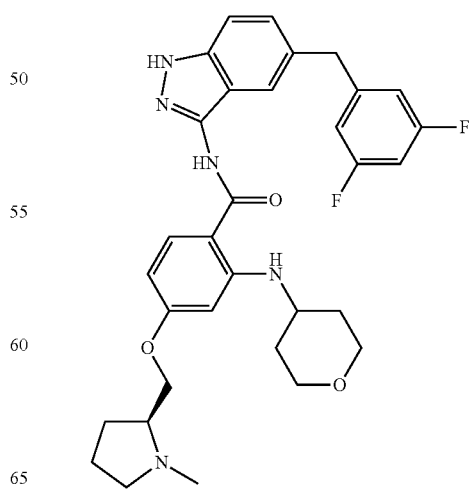

4-{[(2S)-1-methylpyrrolidin-2-yl]methoxy}-2-[tetrahydro-2H-pyran-4-yl(trifluoroacetyl)amino]benzoic acid trifluoroacetate (1 mmol, 531 mg) was dissolved in DCM and two drops of anhydrous DMF under nitrogen atmosphere. Oxalyl chloride (0.17 ml, 2 mmol) was added and the mixture was stirred at room temperature for 2 hours.

Solvents were evaporated to obtain a yellow powder. The solid was redissolved in THF under an argon atmosphere and cooled at −20° C. DIPEA (0.56 ml, 3.2 mmol) was added. 5-(3,5-Difluorobenzyl)-1H-indazol-3-amine, dissolved in 10 mL of dry THF was then added dropwise in 15'. The reaction mixture was kept at −20° C. for 6 hours then the temperature was allowed to raise at room temperature overnight. The reaction was quenched with 15 mL of NaHCO$_3$ 5% and extracted twice with AcOEt (15 ml). Solvents were then evaporated and the residue was redissolved in 20 ml of MeOH. TEA (10 mmol, 1.5 ml) was added and the mixture was heated to 65° C. for 3 hr. Then the reaction was cooled to room temperature and the solvents removed to yield the crude product which was purificated by means of silica gel flash chromatography (AcOEt/MeOH/NH$_3$Aq. 85:15:05) to yield the title compound as a white powder (258 mg, 0.45 mmol, 45%).

1H-NMR (400 MHz), δ (ppm, DMSO-d6): 1.28-1.44 (m, 2H) 1.94 (d, J=12.07 Hz, 2H) 3.44-3.56 (m, 3H) 3.59-3.73 (m, 1H) 3.77-3.87 (m, 2H) 4.05 (s, 2H) 6.23 (dd, 1H) 6.28 (d, J=2.19 Hz, 1H) 6.92-7.06 (m, 3H) 7.27 (dd, J=8.66, 1.59 Hz, 1H) 7.42 (d, J=8.90 Hz, 1H) 7.50 (s, 1H) 7.88 (d, J=8.90 Hz, 1H) 8.27 (d, J=7.80 Hz, 1H) 10.24 (s, 1H) 12.68 (s, 1H)

Operating in an analogous way, the following compounds were obtained:

N-[5-(3,5-difluorobenzyl)-1H-indazol-3-yl]-4-[(1-methylpiperidin-4-yl)oxy]-2-(tetrahydro-2H-pyran-4-ylamino)benzamide [(I$_A$), R=R2=R3=H, R=3,5-difluorophenyl, Ar=4-[(1-methylpiperidin-4-yl)oxy]-2-(tetrahydro-2H-pyran-4-ylamino)-phenyl] cpd. 95

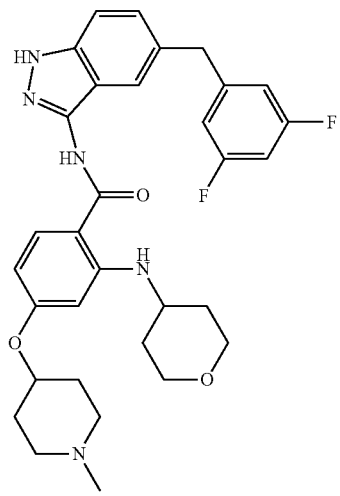 [SMILES: CN1CCC(Oc2ccc(C(=O)Nc3n[nH]c4ccc(Cc5cc(F)cc(F)c5)cc34)c(NC3CCOCC3)c2)CC1]

1H-NMR (400 MHz), δ (ppm, DMSO-d6): 1.36 (ddd, J=9.82, 3.66, 3.48 Hz, 2H) 1.70 (m, 2H) 1.85-2.00 (m, 4H) 2.22-2.30 (m, 5H) 2.64-2.79 (m, 2H) 3.44-3.54 (m, 2H) 3.58-3.72 (m, 1H) 3.82 (dt, J=11.65, 3.69 Hz, 2H) 4.05 (s, 2H) 4.51 (br. s., 1H) 6.20-6.30 (m, 2H) 6.94-7.07 (m, 3H) 7.27 (dd, J=8.60, 1.52 Hz, 1H) 7.42 (d, J=8.54 Hz, 1H) 7.50 (d, J=2.32 Hz, 1H) 7.88 (d, J=9.51 Hz, 1H) 8.22 (d, J=7.68 Hz, 1H) 10.24 (s, 1H) 12.68 (s, 1H)

N-[5-(3,5-difluorobenzyl)-1H-indazol-3-yl]4-[2-(dimethylamino)ethoxy]-2-(tetrahydro-2H-pyran-4-ylamino)benzamide [(I$_A$), R1=R2=R3=H, R=3,5-difluorophenyl, Ar=4-[2-(dimethylamino)ethoxy]-2-(tetrahydro-2H-pyran-4-ylamino)-phenyl] cpd. 96

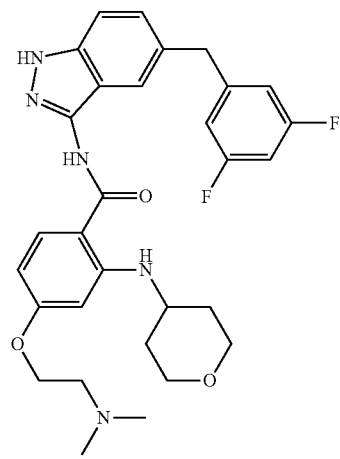 [SMILES: CN(C)CCOc1ccc(C(=O)Nc2n[nH]c3ccc(Cc4cc(F)cc(F)c4)cc23)c(NC2CCOCC2)c1]

1H-NMR (400 MHz), δ (ppm, DMSO-d6): 1.31-1.44 (m, 2H) 1.94 (d, J=10.73 Hz, 2H) 2.42 (br. s., 6H) 2.89 (br. s., 2H) 3.49 (t, J=9.88 Hz, 2H) 3.60-3.73 (m, 1H) 3.78-3.88 (m, 2H) 4.05 (s, 2H) 4.19 (t, J=5.24 Hz, 2H) 6.25 (dd, J=8.84, 2.38 Hz, 1H) 6.29 (d, J=2.32 Hz, 1H) 6.93-7.06 (m, 3H) 7.27 (dd, J=8.60, 1.52 Hz, 1H) 7.43 (d, J=8.78 Hz, 1H) 7.50 (s, 1H) 7.90 (d, J=8.78 Hz, 1H) 8.27 (d, J=7.44 Hz, 1H) 10.26 (s, 1H) 12.68 (s, 1H).

N-[5-(3,5-difluorobenzyl)-1H-indazol-3-yl]-4-{[(3S)-1-methylpyrrolidin-3-yl]oxy}-2-(tetrahydro-2H-pyran-4-ylamino)benzamide [(I$_A$), R1=R2=R3=H, R=3,5-difluorophenyl, Ar=4-{[(3S)-1-methylpyrrolidin-3-yl]oxy}-2-(tetrahydro-2H-pyran-4-ylamino)-phenyl] cpd. 97

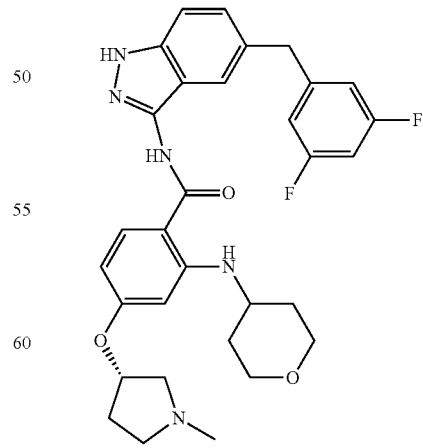

1H-NMR (400 MHz), δ (ppm, DMSO-d6): 1.29-1.44 (m, 2H) 1.75-1.86 (m, 1H) 1.93 (d, J=10.49 Hz, 2H) 2.32 (s, 4H)

2.44 (br. s., 1H) 2.65-2.78 (m, 2H) 2.79-2.88 (m, 1H) 3.44-3.54 (m, 2H) 3.58-3.71 (m, 1H) 3.82 (d, J=11.58 Hz, 2H) 4.05 (s, 2H) 4.96-5.01 (m, 1H) 6.15-6.19 (m, 1H) 6.19-6.20 (m, 1H) 6.94-7.06 (m, 3H) 7.26 (dd, J=8.66, 1.59 Hz, 1H) 7.42 (d, J=8.54 Hz, 1H) 7.50 (d, J=1.59 Hz, 1H) 7.87 (d, J=8.90 Hz, 1H) 8.23 (d, J=7.68 Hz, 1H) 10.24 (s, 1H) 12.67 (s, 1H).

Example 9

Step u

Preparation of N-[5-(3,5-Difluoro-benzyl)-1-trityl-1H-indazol-3-yl]-2-fluoro-5-formyl-benzamide 2-Fluoro-5-formyl-benzoic acid (368 mg, 2.187 mmol) in toluene (22 mL) was treated with thionyl chloride (1.59 mL, 21.87 mmol) and stirred under reflux temperature for 4 hours. The volatiles were evaporated, the residue was taken up with toluene (4 mL) and evaporated to dryness leaving an off white solid which was dissolved in dry THF (5 mL) and added drop-wise to a solution of 5-(3,5-difluoro-benzyl)-1-trityl-1H-indazol-3-ylamine (843 mg, 1.68 mmol) and DIPEA (0.88 mL, 5.04 mmol) in THF (10 mL), cooled to 4° C. The reaction was gradually brought to room temperature. After one night, the volatiles were evaporated. The crude was dissolved in DCM (150 mL) and washed with aqueous NaHCO₃ (100 mL) then with water and finally with brine. After drying over sodium sulphate, evaporation and purification over silica gel (eluent: DCM) 868 mg of title compound as a white solid in 79% yield were obtained.

1H-NMR (400 MHz), δ (ppm, DMSO-d6): 3.98 (s, 2H) 6.34 (d, J=8.66 Hz, 1H) 6.89-7.09 (m, 3H) 7.22-7.34 (m, 15H) 7.53-7.64 (m, 1H) 7.66 (s, 1H) 8.14 (br. s., 1H) 8.32 (d, J=4.51 Hz, 1H) 10.05 (s, 1H) 11.08 (br. s., 1H).

Step i'''

Preparation of N-[5-(3,5-Difluoro-benzyl)-1H-indazol-3-yl]-2-fluoro-5-formyl-benzamide N-[5-(3,5-Difluoro-benzyl)-1-trityl-1H-indazol-3-yl]-2-fluoro-5-formyl-benzamide (740 mg, 1.137 mmol) in dry dioxan (25 mL) was treated with 4N HCl in dioxan (2.8 mL). The reaction was stirred at room temperature for two days. The volatile components were evaporated to dryness and the residue was taken up with Et₂O (10 mL), stirred for 1 hour, filtered with suction, washed with Et₂O (10 mL), dried at 50° C. under vacuum to afford 358 mg of title compound as a white solid in 77% yield.

1H-NMR (400 MHz), δ (ppm, DMSO-d6): 4.08 (s, 2H) 6.88-7.09 (m, 3H) 7.22-7.31 (m, 1H) 7.45 (d, J=8.41 Hz, 1H) 7.62 (t, J=9.57 Hz, 1H) 7.71 (s, 1H) 8.12-8.19 (m, 1H) 8.35 (d, J=5.61 Hz, 1H) 10.08 (s, 1H) 10.92 (s, 1H) 12.80 (br. s., 1H)

Preparation of N-[5-(3,5-Difluoro-benzyl)-1H-indazol-3-yl]-2-fluoro-5-(4-methyl-piperazin-1-ylmethyl)-benzamide [(I_A), R1=R2=R3=H, R=3,5-difluorophenyl, Ar=2-fluoro-5-(4-methyl-piperazin-1-ylmethyl)-phenyl] cpd. 120

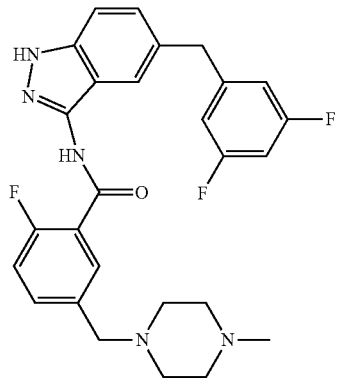 [SMILES: CN1CCN(Cc2ccc(F)c(C(=O)Nc3n[nH]c4ccc(Cc5cc(F)cc(F)c5)cc34)c2)CC1]

N-[5-(3,5-Difluoro-benzyl)-1H-indazol-3-yl]-2-fluoro-5-formyl-benzamide (150 mg, 0.367 mmol) in THF (4 mL), under a nitrogen atmosphere, at room temperature was treated with N-methylpiperazine ((0.039 mL, 0.367 mmol) and then with acetic acid (0.024 mL, 0.422 mmol). After 0.5 hours sodium triacetoxyborohydride was added and the reaction was stirred over night. EtOAc (25 mL) and water (25 mL) were added, pH was adjusted to 11 with concentrated NH₄OH. The organic layer was separated and the aqueous layer was extracted twice with EtOAc (2×10 mL). The combines organic extracts were dried over sodium sulphate, evaporated to dryness and purified over silica gel (Eluent: DCM: 7N NH₃ in MeOH 96:4) affording 177 mg of title compound.

1H-NMR (400 MHz), δ (ppm, DMSO-d6): 2.18 (br. s., 3H) 2.30-2.46 (m, 8H) 3.51 (br. s., 2H) 4.07 (s, 2H) 6.92-7.00 (m, 2H) 6.99-7.06 (m, 1H) 7.28 (s, 1H) 7.28-7.35 (m, 1H) 7.44 (d, J=8.53 Hz, 1H) 7.47-7.54 (m, 1H) 7.65 (br. s., 1H) 7.67 (br. s., 1H) 10.66 (br. s., 1H) 12.75 (br. s., 1H)

Operating in an analogous way, the following compounds were obtained:

N-[5-(3,5-difluorobenzyl)-1H-indazol-3-yl]-2-fluoro-5-{[(2S)-2-(pyrrolidin-1-ylmethyl)pyrrolidin-1-yl]methyl}benzamide [(I_A), R1=R2=R3=H, R=3,5-difluorophenyl, Ar=2-fluoro-5-{[(2S)-2-(pyrrolidin-1-ylmethyl)pyrrolidin-1-yl]methyl}-phenyl] cpd. 121

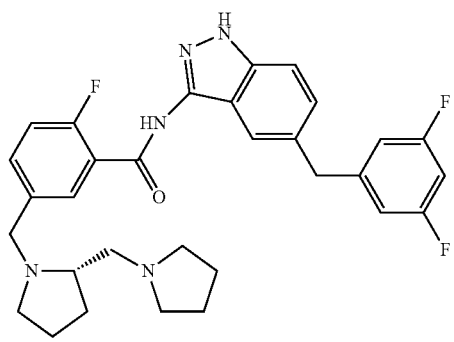 [SMILES: O=C(Nc1n[nH]c2ccc(Cc3cc(F)cc(F)c3)cc12)c1cc(CN2CCC[C@H]2CN2CCCC2)ccc1F]

1H-NMR (400 MHz), δ (ppm, DMSO-d6): 1.67 (m, 6H) 1.92 (m, 1H) 2.14 (m, 1H) 2.63 (m, 2H) 2.82 (m, 1H) 3.23-3.37 (m, 2H) 4.07 (s, 2H) 4.17 (d, J=14.26 Hz, 1H) 6.93-6.99 (m, 2H) 6.99-7.07 (m, 1H) 7.25-7.28 (m, 1H) 7.28-7.33 (m, 1H) 7.44 (d, J=8.65 Hz, 1H) 7.50 (br. s., 1H) 7.66 (br. s., 2H) 10.64 (br. s., 1H) 12.75 (br. s., 1H)

N-[5-(3,5-difluorobenzyl)-1H-indazol-3-yl]-2-fluoro-5-(morpholin-4-ylmethyl)benzamide [(I$_A$), R1=R2=R3=H, R=3,5-difluorophenyl, Ar=2-fluoro-5-(morpholin-4-ylmethyl)-phenyl] cpd. 122

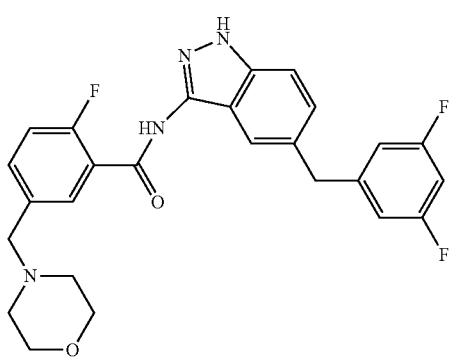 [SMILES: O=C(Nc1n[nH]c2ccc(Cc3cc(F)cc(F)c3)cc12)c1cc(CN2CCOCC2)ccc1F]

1H-NMR (400 MHz), δ (ppm, DMSO-d6): 2.40 (br. s., 4H) 3.52 (br. s., 2H) 3.60 (br. s., 4H) 4.07 (s, 2H) 6.94-6.99 (m, 2H) 6.99-7.07 (m, 1H) 7.27 (d, J=8.65 Hz, 1H) 7.33 (d, J=8.53 Hz, 1H) 7.44 (d, J=8.53 Hz, 1H) 7.53 (br. s., 1H) 7.67 (br. s., 2H) 10.67 (br. s., 1H) 12.75 (br. s., 1H).

Example 10

Preparation of N-[5-(3,5-Difluoro-benzyl)-1-trityl-1H-indazol-3-yl]-4-fluoro-isophthalamic acid N-[5-(3,5-Difluoro-benzyl)-1-trityl-1H-indazol-3-yl]-2-fluoro-5-formyl-benzamide (88 mg, 0.135 mmol) in tert-butanol (1.8 mL) at room temperature was treated first with 2-methyl-2-butene (0.079 mL, 1.082 mmol) and then with sodium chlorite (37 mg, 0.405 mmol) and sodium dihydrogenphosphate in water (0.8 mL) drop-wise. The reaction was stirred over-night, EtOAc was then added (30 mL) and washed with water (25 mL). The aqueous layer was extracted twice with EtOAc (2×10 mL). The combined organic layers were washed with brine, evaporated to dryness to leave 106 mg of title compound which was employed in the following step with no need of further purification.

1H-NMR (400 MHz), δ (ppm, DMSO-d6): 3.98 (s, 2H) 6.33 (d, J=8.53 Hz, 1H) 6.78 (br. s., 1H) 6.90-7.07 (m, 3H) 7.20-7.35 (m, 15H) 7.43-7.54 (m, 1H) 7.65 (br. s., 1H) 8.13 (br. s., 1H) 8.29 (d, J=3.66 Hz, 1H) 11.01 (s, 1H) 13.12 (br. s., 1H)

Preparation of N-[5-(3,5-Difluoro-benzyl)-1-trityl-1H-indazol-3-yl]-2-fluoro-5-((S)-2-pyrrolidin-1-ylmethyl-pyrrolidine-1-carbonyl)-benzamide N-[5-(3,5-Difluoro-benzyl)-1-trityl-1H-indazol-3-yl]-4-fluoro-isophthalamic acid (93 mg, 0.139 mmol) in DCM (1.4 mL) was treated with 1-hydroxybenzotriazole (25 mg, 0.181 mmol), EDCI (35 mg, 0.181 mmol) and (S)-(+)-1-(2-pyrrolidinylmethyl)pyrrolidine (0.03 mL, 0.1813 mmol).

After 1 hour the reaction was diluted with DCM (25 mL) and washed with aqueous NaHCO₃ (5 mL), water (5 mL) and finally with brine. After drying over sodium sulphate, evaporation of the solvent and purification over silica gel (eluent: DCM, 7N NH₃ in MeOH 95:5) 92 mg of title compound were obtained in 85% yield over two steps.

1H-NMR (400 MHz), δ (ppm, DMSO-d6): 3.97 (s, 2H) 4.26 (br. s., 1H) 6.33 (d, J=8.41 Hz, 1H) 6.86-7.09 (m, 4H) 7.15-7.35 (m, 15H) 7.38-7.46 (m, 1H) 7.63 (s, 1H) 7.68 (br. s., 1H) 7.82 (br. s., 1H) 10.96 (br. s., 1H)

Step i"

N-[5-(3,5-Difluoro-benzyl)-1H-indazol-3-yl]-2-fluoro-5-((S)-2-pyrrolidin-1-ylmethyl-pyrrolidine-1-carbonyl)-benzamide [(I$_A$), R1=R2=R3=H, R=3,5-difluorophenyl, Ar=2-fluoro-5-((S)-2-pyrrolidin-1-ylmethyl-pyrrolidine-1-carbonyl)-phenyl] cpd. 123

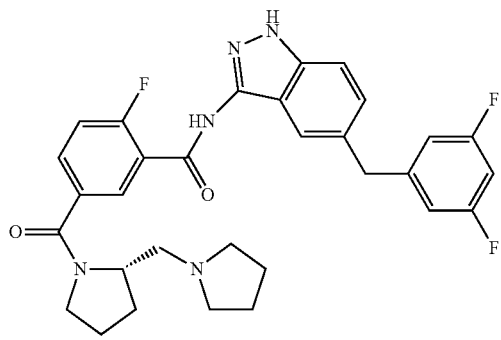 [SMILES: O=C(Nc1n[nH]c2ccc(Cc3cc(F)cc(F)c3)cc12)c1cc(C(=O)N2CCC[C@H]2CN2CCCC2)ccc1F]

N-[5-(3,5-Difluoro-benzyl)-1-trityl-1H-indazol-3-yl]-2-fluoro-5-((S)-2-pyrrolidin-1-ylmethyl-pyrrolidine-1-carbonyl)-benzamide (90 mg, 0.112 mmol) in DCM (1 mL) was treated with TFA (0.17 mL, 2.24 mmol). After two hours at room temperature, DCM was added (25 mL) and the organic phase was washed with aqueous NaHCO₃, water and brine. Drying over sodium sulphate, evaporation and purification of the crude over silica gel (eluent: DCM, MeOH, 7N NH₃ in MeOH 9:1:0.1) afforded 42 mg of title compound.

1H-NMR (400 MHz), δ (ppm, DMSO-d6): 4.07 (s, 2H) 4.29 (br. s., 1H) 6.93-6.99 (m, 2H) 6.99-7.06 (m, 1H) 7.27 (dd, J=8.53, 1.34 Hz, 1H) 7.42 (br. s., 1H) 7.65-7.74 (m, 2H) 7.85 (br. s., 1H) 10.80 (br. s., 1H) 12.77 (br. s., 1H).

Example 11

Step i'

Preparation of methyl 4-{[5-(3,5-difluorobenzyl)-1H-indazol-3-yl]carbamoyl}-3-nitrobenzoate 4-(methoxycarbonyl)-2-nitrobenzoic acid (4.8 gr, 21.3 mmol) and thionyl chloride (15.5 mL) were stirred in THF dry (130 mL) at 70° C. for 2 hours. Volatiles were evaporated and the residue dissolved in dry pyridine (100 mL) at 0° C. A solution of 5-(3,5-difluoro-benzyl)-1H-indazol-3-ylamine (4.6 mg, 17.76 mmol) in dry pyridine (10 mL) was added to the cooled reaction mixture. Temperature was allowed to reach room temperature overnight. Reaction was quenched with NaHCO₃ sat. sol and extracted with ethyl acetate. Collected organic phases were dried over Na₂SO₄, filtered and evaporated to dryness. Residue was purified by column chromatography over silica gel (DCM/EtOH/7N NH$_3$ in MeOH=95/5/0.5) affording 5.4 gr (65% yield) of the title compound.

1H-NMR (400 MHz), δ (ppm, DMSO-d$_6$): 3.97 (s, 3H) 4.08 (s, 2H) 6.89-7.00 (m, 2H) 6.99-7.07 (m, 1H) 7.29 (dd, J=8.66, 1.46 Hz, 1H) 7.45 (d, J=8.66 Hz, 1H) 7.76 (s, 1H) 8.01 (d, J=7.93 Hz, 1H) 8.40 (dd, J=7.93, 1.59 Hz, 1H) 8.58 (d, J=1.46 Hz, 1H) 11.22 (s, 1H) 12.81 (s, 1H)

Operating in an analogous way, the following compound was obtained:

methyl 4-{[5-(3,5-difluorobenzyl)-1H-indazol-3-yl]carbamoyl}benzoate

ESI(+) MS: m/z 422 (MH$^+$).

Preparation of 4-{[5-(3,5-difluorobenzyl)-1H-indazol-3-yl]carbamoyl}-3-nitrobenzoic acid Methyl 4-{[5-(3,5-difluorobenzyl)-1H-indazol-3-yl]carbamoyl}-3-nitrobenzoate (5.4 gr, 11.6 mmol) was dissolved in THF (78 mL) and water (52 mL) and treated at room temperature with LiOH hydrate (730 mg) for 24 hours. THF was evaporated and the resulting aqueous phase was treated with 5% KHSO$_4$ aqueous solution (100 mL). The so obtained precipitated was filtered off and dried under vacuum at 60° C. affording the title compound without any further purification.

1H-NMR (400 MHz), δ (ppm, DMSO-d$_6$): 4.08 (s, 2H) 6.92-7.00 (m, 2H) 7.00-7.07 (m, 1H) 7.27 (dd, J=8.59, 1.40 Hz, 1H) 7.44 (d, J=8.65 Hz, 1H) 7.76 (s, 1H) 7.85 (d, J=7.68 Hz, 1H) 8.30 (dd, J=7.74, 1.28 Hz, 1H) 8.50 (d, J=1.22 Hz, 1H) 11.08 (s, 1H) 12.77 (s, 1H)

Operating in an analogous way, the following compound was obtained:

4-{[5-(3,5-difluorobenzyl)-1H-indazol-3-yl]carbamoyl}benzoic acid

ESI(+) MS: m/z 408 (MH$^+$).

Preparation of N-[5-(3,5-Difluoro-benzyl)-1H-indazol-3-yl]-4-(4-methyl-piperazine-1-carbonyl)-2-nitro-benzamide 4-{[5-(3,5-difluorobenzyl)-1H-indazol-3-yl]carbamoyl}-3-nitrobenzoic acid (500 mg, 1.11 mmol) in DMF (10 mL) was treated with 1-hydroxybenzotriazole (195 mg, 1.44 mmol), EDCI (276 mg, 1.44 mmol) and 1-methylpiperazine (0.16 mL, 1.44 mmol). The reaction was left at room temperature over night. The volatiles were removed by evaporation, the residue was added drop-wise to iced-water (25 mL) with stirring. A yellow solid was obtained which was extracted with DCM (2×25 mL). The combined organic layers were dried over sodium sulphate and evaporated leaving 590 mg of title compound which was employed in the following step without any further purification.

1H-NMR (400 MHz), δ (ppm, DMSO-d$_6$): 2.23 (s, 3H) 2.34 (m, 2H) 2.45 (m, 2H) 3.39 (m, 2H) 3.67 (m, 2H) 4.08 (s, 2H) 6.93-6.99 (m, 2H) 6.99-7.07 (m, 1H) 7.28 (dd, J=8.59, 1.40 Hz, 1H) 7.45 (d, J=8.53 Hz, 1H) 7.74 (s, 1H) 7.87-7.90 (m, 1H) 7.90-7.93 (m, 1H) 8.15 (d, J=0.85 Hz, 1H) 11.10 (s, 1H) 12.78 (s, 1H)

Operating in an analogous way, the following compounds were obtained:

N-[5-(3,5-difluorobenzyl)-1H-indazol-3-yl]-4-{[(2R)-2-(pyrrolidin-1-ylmethyl)pyrrolidin-1-yl]carbonyl}benzamide [(I$_A$), R1=R2=R3=H, R=3,5-difluorophenyl, Ar=4-{[(2R)-2-(pyrrolidin-1-ylmethyl)pyrrolidin-1-yl]carbonyl}-phenyl] cpd. 124

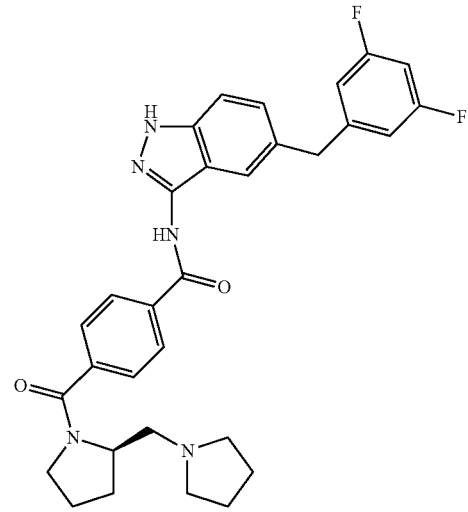 [SMILES: O=C(Nc1n[nH]c2ccc(Cc3cc(F)cc(F)c3)cc12)c1ccc(C(=O)N2CCC[C@@H]2CN2CCCC2)cc1]

1H-NMR (400 MHz), δ (ppm, DMSO-d6): 4.06 (s, 2H) 4.30 (br. s., 1H) 6.94-7.00 (m, 2H) 6.99-7.06 (m, 1H) 7.27 (dd, J=8.66, 1.59 Hz, 1H) 7.44 (d, J=8.54 Hz, 1H) 7.61 (d, 2H) 7.63 (s, 1H) 8.11 (d, J=8.29 Hz, 2H) 10.81 (s, 1H) 12.77 (s, 1H)

N-[5-(3,5-difluorobenzyl)-1H-indazol-3-yl]-4-{[(2S)-2-(pyrrolidin-1-ylmethyl)pyrrolidin-1-yl]carbonyl}benzamide [(I$_A$), R1=R2=R3=H, R=3,5-difluorophenyl, Ar=4-{[(2S)-2-(pyrrolidin-1-ylmethyl)pyrrolidin-1-yl]carbonyl}-phenyl] cpd. 125

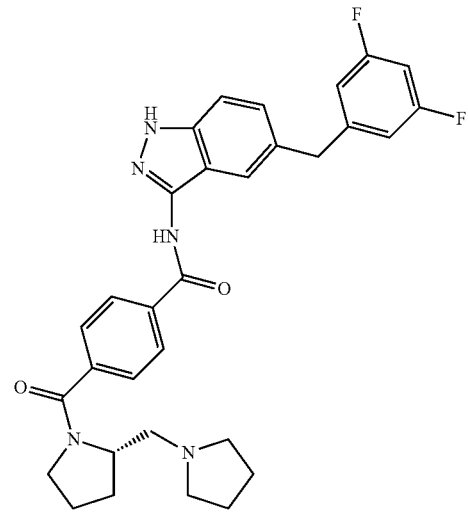 [SMILES: O=C(Nc1n[nH]c2ccc(Cc3cc(F)cc(F)c3)cc12)c1ccc(C(=O)N2CCC[C@H]2CN2CCCC2)cc1]

1H-NMR (400 MHz), δ (ppm, DMSO-d6): 4.06 (s, 2H) 4.30 (br. s., 1H) 6.94-7.00 (m, 2H) 6.99-7.06 (m, 1H) 7.27

(dd, J=8.60, 1.52 Hz, 1H) 7.44 (d, J=8.90 Hz, 1H) 7.59-7.65 (m, 3H) 8.11 (d, J=8.17 Hz, 2H) 10.81 (s, 1H) 12.77 (s, 1H)

N-[5-(3,5-difluorobenzyl)-1H-indazol-3-yl]-4-{[4-(pyrrolidin-1-yl)piperidin-1-yl]carbonyl}benzamide [($I_4$), R1=R2=R3=H, R=3,5-difluorophenyl, Ar=4-{[4-(pyrrolidin-1-yl)piperidin-1-yl]carbonyl}-phenyl] cpd. 126

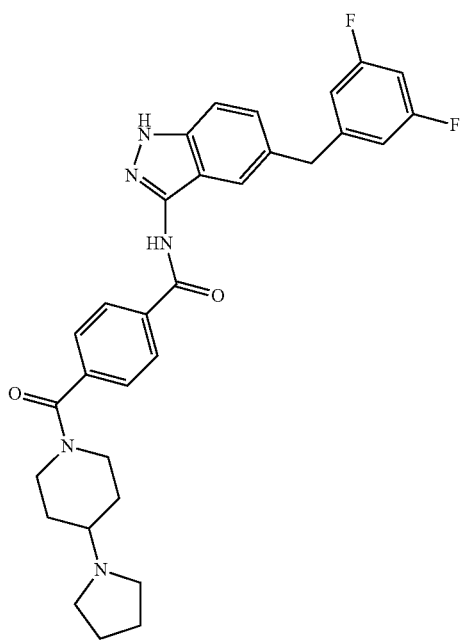 [SMILES: O=C(Nc1n[nH]c2ccc(Cc3cc(F)cc(F)c3)cc12)c1ccc(C(=O)N2CCC(N3CCCC3)CC2)cc1]

1H-NMR (400 MHz), δ (ppm, DMSO-d6): 1.41 (m, 2H) 1.70 (m, 4H) 1.94 (m, 2H) 2.33 (m, 1H) 2.53 (m, 4H) 3.06 (m, 2H) 3.52 (m, 1H) 4.06 (s, 2H) 4.30 m, 1H) 6.94-7.00 (m, 2H) 7.00-7.05 (m, 1H) 7.27 (dd, J=8.66, 1.59 Hz, 1H) 7.42-7.46 (m, 1H) 7.54 (d, J=8.29 Hz, 2H) 7.62 (s, 1H) 8.12 (d, J=8.17 Hz, 2H) 10.81 (s, 1H) 12.77 (s, 1H).

Example 12

Preparation of 2-nitro-terephthalic acid 1-tert-butyl ester 4-methyl ester

Commercially available 2-nitro-terephthalic acid 4-methyl ester (4.84 g, 21.49 mmol) in DCM (54 mL) was treated with tert-butanol (4.05 mL, 42.99 mmol), di-tert-butyl dicarbonate (12.19 g, 55.87 g) and DMAP (0.79 g, 6.45 mmol). After 4 days at room temperature, the reaction was diluted with DCM (100 mL), washed with 1N HCl (100 mL), aqueous NaHCO$_3$ and finally with water. After drying over sodium sulphate and evaporation of the volatiles, the title compound was obtained as a brownish oil in more than quantitative yield (6.51 g). The crude was employed in the following step with no further purification.
ESI(+) MS: m/z 282 (MH$^+$).

Preparation of 2-nitro-terephthalic acid 1-tert-butyl ester

2-Nitro-terephthalic acid 1-tert-butyl ester 4-methyl ester (21.49 mmol) was dissolved in THF (143 mL) and treated with lithium hydroxide monohydrate (1.35 g, 32.24 mmol) in water (97 mL). The reaction was stirred at room temperature for 2 hours then partially evaporated, cooled with an ice/water bath and treated with 1N HCl dropwise (35 mL). Precipitation of a solid occurred. The mixture was then extracted with DCM (150 mL and 2×50 mL). The aqueous phase was further treated with 1N HCl (10 mL) and extracted with DCM (2×50 mL). The combined organic layers were then washed with water and finally with brine. After drying over sodium sulphate and evaporation, 5.34 g of title compound were obtained as a reddish solid in 93% overall yield.
1H-NMR (400 MHz), δ (ppm, DMSO-d$_6$): 1.53 (s, 9H) 7.93 (d, J=7.92 Hz, 1H) 8.31 (dd, J=7.92, 1.58 Hz, 1H) 8.42 (d, J=1.34 Hz, 1H) 13.78 (s, 1H)

Preparation of 2-Nitro-4-(piperidine-1-carbonyl)-benzoic acid tert-butyl ester

2-Nitro-terephthalic acid 1-tert-butyl ester (500 mg, 1.88 mmol) in DCM (18 mL), was treated with 1-hydroxybenzotriazole (0.39 g, 2.43 mmol), EDCI (0.47 g, 2.43 mmol) and piperidine (0.24 mL, 2.43 mmol). After 3 hours the reaction was diluted with DCM (50 mL) and washed with aqueous NaHCO$_3$ (30 mL), water (30 mL) and finally with brine. After drying over sodium sulphate and evaporation of the solvent the title compound was obtained as a colourless oil in quantitative yield. The crude was employed in the following reaction without any further purification.
1H-NMR (400 MHz), δ (ppm, DMSO-d$_6$): 1.45 (br. s., 6H) 1.51 (s, 9H) 3.19-3.27 (m, 2H) 3.59 (br. s., 2H) 7.76-7.81 (m, 1H) 7.85-7.89 (m, 1H) 8.01 (d, J=1.22 Hz, 1H)

Operating in a way analogous to that described above, the following compounds were obtained:

tert-butyl 4-[(2-methoxyethyl)methyl)carbamoyl]-2-nitrobenzoate

1H-NMR (400 MHz), δ (ppm, DMSO-d$_6$): mixture of rotamers 1.52 (s, 9H) 7.77-7.83 (m, 1H) 7.84-7.91 (m, 1H) 8.03 (d, J=0.61 Hz, 1H)

tert-butyl 2-nitro-4-(pyrrolidin-1-ylcarbonyl)benzoate

1H-NMR (400 MHz), δ (ppm, DMSO-d$_6$): 1.52 (s, 9H) 1.78-1.94 (m, 4H) 3.37-3.43 (m, 2H) 3.49 (t, J=6.70 Hz, 2H) 7.84-7.90 (m, 1H) 7.91-7.96 (m, 1H) 8.12 (d, J=1.34 Hz, 1H)

tert-butyl 4-(azetidin-1-ylcarbonyl)-2-nitrobenzoate

1H-NMR (400 MHz), δ (ppm, DMSO-d$_6$): 1.52 (s, 9H) 2.29 (dt, J=15.51, 7.79 Hz, 2H) 4.06-4.12 (m, 2H) 4.31-4.38 (m, 2H) 7.88 (d, J=7.92 Hz, 1H) 8.01 (dd, J=7.92, 1.58 Hz, 1H) 8.16 (d, J=1.34 Hz, 1H)

tert-butyl 4-(morpholin-4-ylcarbonyl)-2-nitrobenzoate

ESI(+) MS: m/z 337 (MH$^+$).

Preparation of 2-nitro-4-piperidin-1-ylmethyl-benzoic acid hydrochloride

2-Nitro-4-(piperidine-1-carbonyl)-benzoic acid tert-butyl ester (1.87 mmol) was dissolved in dry THF and added drop-wise to 3.7 mL of borane tetrahydrofuran complex 1.0 M solution, at room temperature, under nitrogen, with stirring. The reaction was then refluxed for six hours, cooled to room temperature and treated carefully with 2N HCl (10 mL). After stirring for 15 minutes, solid $K_2CO_3$ was added in portions (1.75 g). The mixture was extracted with EtOAc (3×25 mL). The combined organic layers were dried over sodium sulphate and evaporated leaving an oil that by HPLC-MS analysis resulted a 4:6 mixture of the tertiary amine and the corresponding borane complex. The mixture was dissolved in DCM (1 mL) and treated with 4N HCl in dioxane (7 mL). After 4 days at room temperature, an off white was formed which was filtered, washed with dioxane (5 mL) and dried at 50° C. under vacuum. 0.40 g of title compound were obtained in 70% overall yield.

1H-NMR (400 MHz), δ (ppm, DMSO-$d_6$): 1.37-1.80 (m, 5H) 2.90 (br. s., 4H) 4.42 (s, 2H) 7.92-7.99 (m, 2H) 8.24 (d, J=0.85 Hz, 1H) 9.99 (br. s., 1H)

4-{[(2-methoxyethyl)(methyl)amino]methyl}-2-nitrobenzoic acid hydrochloride

ESI(+) MS: m/z 269 (MH$^+$).

2-nitro-4-(pyrrolidin-1-ylmethyl)benzoic acid hydrochloride

ESI(+) MS: m/z 251 (MH$^+$).

4-(morpholin-4-ylmethyl)-2-nitrobenzoic acid hydrochloride

1H-NMR (400 MHz), δ (ppm, DMSO-$d_6$): 2.39 (t, J=4.51 Hz, 4H) 3.59 (t, J=4.63 Hz, 4H) 3.62 (s, 2H) 7.72 (dd, J=7.87, 1.28 Hz, 1H) 7.82 (d, J=7.80 Hz, 1H) 7.87 (d, J=0.98 Hz, 1H)

4-(azetidin-1-ylmethyl)-2-nitrobenzoic acid hydrochloride

ESI(+) MS: m/z 237 (MH$^+$).

Step i'

Preparation of N-[5-(3,5-difluorobenzyl)-1H-indazol-3-yl]-2-nitro-4-(piperidin-1-ylmethyl)benzamide 2-Nitro-4-piperidin-1-ylmethyl-benzoic acid hydrochloride (440 mg, 1.46 mmol) was treated with thionyl chloride (5 mL) and refluxed for 1 hour. Excess of reagent was removed by evaporation followed by evaporation from toluene (2×5 mL). The solid was further died under vacuum. The acid chloride was treated with dry pyridine (7 mL), cooled to 4° C. and added with 5-(3,5-difluoro-benzyl)-1H-indazol-3-ylamine (315 mg, 1.22 mmol) in dry pyridine (3 mL) under a nitrogen atmosphere, with stirring. After stirring for a few hours the reaction was left at 0° C. over-night. EtOAc (50 mL) and water (50 mL) were added, pH was adjusted to 9 with concentrated $NH_4OH$. The organic layer was separated, dried over sodium sulphate, evaporated to dryness and purified over silica gel (DCM: MeOH 95:5) affording 266 mg of title compound in 43% yield.

1H-NMR (400 MHz), δ (ppm, DMSO-$d_6$): 1.54 (br. s., 6H) 2.39 (br. s., 4H) 3.61 (s, 2H) 4.07 (s, 2H) 6.92-6.99 (m, 2H) 6.99-7.06 (m, 1H) 7.26-7.29 (m, 1H) 7.44 (d, J=8.53 Hz, 1H) 7.73 (s, 1H) 7.79 (s, 2H) 8.04 (s, 1H) 11.01 (s, 1H) 12.75 (s, 1H)

Operating in a way analogous to that described above, the following compounds were obtained:

N-[5-(3,5-difluorobenzyl)-1H-indazol-3-yl]-4-{[(2-methoxyethyl)(methyl)amino]methyl}-2-nitrobenzamide 1H-NMR (400 MHz), δ (ppm, DMSO-$d_6$): 2.24 (s, 3H) 2.60 (t, J=5.67 Hz, 2H) 3.26 (s, 3H) 3.50 (t, J=5.73 Hz, 2H) 3.70 (s, 2H) 4.07 (s, 2H) 6.96 (d, J=6.70 Hz, 2H) 6.99-7.07 (m, 1H) 7.24-7.30 (m, 1H) 7.44 (d, J=8.53 Hz, 1H) 7.73 (s, 1H) 7.80 (s, 2H) 8.07 (s, 1H) 11.02 (s, 1H) 12.75 (s, 1H)

N-[5-(3,5-difluorobenzyl)-1H-indazol-3-yl]-2-nitro-4-(pyrrolidin-1-ylmethyl)benzamide 1H-NMR (400 MHz), δ (ppm, DMSO-$d_6$): 1.75 (br. s., 4H) 2.46-2.56 (m, 4H) 3.77 (br. s., 2H) 4.07 (s, 2H) 6.96 (d, J=6.58 Hz, 2H) 6.99-7.06 (m, 1H) 7.25-7.30 (m, 1H) 7.44 (d, J=8.54 Hz, 1H) 7.73 (s, 1H) 7.80 (s, 2H) 8.05 (s, 1H) 11.02 (s, 1H) 12.75 (s, 1H)

N-[5-(3,5-difluorobenzyl)-1H-indazol-3-yl]-4-(morpholin-4-ylmethyl)-2-nitrobenzamide 1H-NMR (400 MHz), δ (ppm, DMSO-$d_6$): 2.40-2.46 (m, 4H) 3.60-3.65 (m, 4H) 3.66 (s, 2H) 4.07 (s, 2H) 6.90-6.99 (m, 2H) 6.99-7.07 (m, 1H) 7.24-7.29 (m, 1H) 7.44 (d, J=8.54 Hz, 1H) 7.73 (s, 1H) 7.81 (s, 2H) 8.07 (s, 1H) 11.02 (s, 1H) 12.75 (s, 1H)

4-(azetidin-1-ylmethyl)-N-[5-(3,5-difluorobenzyl)-1H-indazol-3-yl]-2-nitrobenzamide ESI(+) MS: m/z 478 (MH$^+$).

Conversion 4

Preparation of 2-Amino-N-[5-(3,5-difluoro-benzyl)-1H-indazol-3-yl]-4-piperidin-1-ylmethyl benzamide N-[5-(3,5-Difluoro-benzyl)-1H-indazol-3-yl]-2-nitro-4-piperidin-1-ylmethyl-benzamide (255 mg, 0.505 mmol) was suspended in DCM (7 mL) and treated with $nBu_4NCl$ (95 mg, 0.343 mmol). $Na_2S_2O_4$ (659 mg, 3.029 mmol) in water (3.4 mL) was added drop-wise, with stirring. After 2 hours, the volatiles were removed by evaporation, a solid was filtered from the aqueous phase and dried under vacuum. The solid was treated with 4N HCl in dioxane (12 mL) and the solvent was then removed by evaporation. The solid was dissolved in DCM (100 mL), washed with aqueous $K_2CO_3$ and then with brine. After drying over sodium sulphate and removal of the solvent, 248 mg of title compound were obtained in more than quantitative yield. The crude was employed in the following step with no further purification.

ESI(+) MS: m/z 476 (MH$^+$).

Operating in a way analogous to that described above, the following compounds were obtained:

2-Amino-N-[5-(3,5-difluorobenzyl)-1H-indazol-3-yl]-4-{[(2-methoxyethyl)(methyl)amino]methyl}-benzamide ESI(+) MS: m/z 480 (MH$^+$).

2-Amino-N-[5-(3,5-difluorobenzyl)-1H-indazol-3-yl]-4-(pyrrolidin-1-ylmethyl)benzamide ESI(+) MS: m/z 462 (MH$^+$).

2-Amino-N-[5-(3,5-difluorobenzyl)-1H-indazol-3-yl]-4-(morpholin-4-ylmethyl)-benzamide ESI(+) MS: m/z 478 (MH$^+$).

2-Amino-4-(azetidin-1-ylmethyl)-N-[5-(3,5-difluorobenzyl)-1H-indazol-3-yl]-benzamide ESI(+) MS: m/z 448 (MH$^+$).

Example 13

Preparation of tert-butyl 4-(4-methylpiperazin-1-yl)-2-[(1-methylpiperidin-4-yl)amino]benzoate tert-Butyl 2-amino-4-(4-methylpiperazin-1-yl)benzoate (1.5 g, 5.15 mmol) was dissolved in dry dioxane (25 mL) under a nitrogen atmosphere. N-methylpiperidone (0.72 g, 6.18 mmol, 1.2 eq) was added, followed by trifluoroacetic acid (1.03 mL, 13.39 mmol, 2.6 eq) and sodium triacetoxyborohydride (1.72 g, 7.73 mmol, 1.5 eq). The mixture was stirred at room temperature for 26 hours. During this time extra portions of N-methylpiperidone (0.5 mL, 0.75 eq) and sodium triacetoxyborohydride (1.72 g, 7.73 mmol, 1.5 eq) were added. A saturated aqueous solution of NaHCO$_3$ was then added and the reaction mixture was concentrated under reduced pressure. 10% ammonium hydroxide was added until pH 10 and the aqueous phase was extracted with dichloromethane. The organic phase was washed with brine, dried over Na$_2$SO$_4$ and evaporated under reduced pressure. After purification by chromatography over silica gel (DCM/MeOH/NH$_3$ 7% in MeOH 90:8:2) 1.025 g of title compound were obtained as off-white solid (51% yield).

1H-NMR (400 MHz), δ (ppm, DMSO-d$_6$): 1.36-1.47 (m, 2H) 1.50 (s, 9H) 1.88-1.98 (m, 2H) 2.09-2.16 (m, 2H) 2.18 (s, 3H) 2.21 (s, 3H) 2.38-2.44 (m, 4H) 2.59-2.68 (m, 2H) 3.20-3.26 (m, 4H) 3.37-3.50 (m, 1H) 6.01 (d, J=1.95 Hz, 1H) 6.18 (dd, J=9.08, 2.26 Hz, 1H) 7.56 (d, J=9.02 Hz, 1H) 7.68 (d, J=7.56 Hz, 1H)

Operating in an analogous way, the following compound was obtained:

ethyl 4-{[2-(tert-butoxycarbonyl)-5-(4-methylpiperazin-1-yl)phenyl]amino}piperidine-1-carboxylate 1H-NMR (400 MHz), δ (ppm, DMSO-d$_6$): 1.19 (t, J=7.50 Hz, 3H) 1.24-1.34 (m, 2H) 1.50 (s, 9H) 1.89-2.00 (m, 2H) 2.22 (s, 3H) 2.39-2.45 (m, 4H) 3.03-3.16 (m, 2H) 3.20-3.29 (m, 4H) 3.66-3.76 (m, 1H) 3.80-3.90 (m, 2H) 4.05 (q, J=7.07 Hz, 2H) 6.07 (d, J=2.07 Hz, 1H) 6.20 (dd, J=9.15, 2.19 Hz, 1H) 7.57 (d, J=9.02 Hz, 1H) 7.70 (d, J=7.93 Hz, 1H)

Preparation of tert-butyl 4-(4-methylpiperazin-1-yl)-2-[(1-methylpiperidin-4-yl)(trifluoroacetyl)amino]benzoate tert-butyl 4-(4-methylpiperazin-1-yl)-2-[(1-methylpiperidin-4-yl)amino]benzoate (1.02 g, 2.625 mmol) was dissolved in dry dichloromethane (10 mL) under nitrogen atmosphere and the solution was cooled to 0° C. Triethylamine (0.548 mL, 3.938 mmol, 1.5 eq) was added, followed by trifluoroacetic anhydride (0.445 mL, 3.15 mmol, 1.2 eq) and the mixture was stirred at 0° C. for 2 hours. It was then diluted with dichloromethane and washed twice with water. The aqueous phase was back-extracted with dichloromethane. The combined organic layers were dried over Na$_2$SO$_4$ and concentrated under reduced pressure to give 1.18 g of crude product (93% yield), which was used in the following step without further purification.

1H-NMR (400 MHz), δ (ppm, DMSO-d$_6$): 0.93-1.07 (m, 2H) 1.45 (s, 9H) 1.48-1.64 (m, 2H) 1.85-2.05 (m, 2H) 2.11 (s, 3H) 2.23 (s, 3H) 2.41-2.47 (m, 4H) 2.66-2.87 (m, 2H) 3.27-3.35 (m, 4H) 4.10-4.26 (m, 1H) 6.78 (d, J=2.44 Hz, 1H) 7.05 (dd, J=9.02, 2.56 Hz, 1H) 7.81 (d, J=9.02 Hz, 1H)

Operating in an analogous way, the following compound was obtained:

ethyl 4-{[2-(tert-butoxycarbonyl)-5-(4-methylpiperazin-1-yl)phenyl](trifluoroacetyl)amino}piperidine-1-carboxylate 1H-NMR (400 MHz), δ (ppm, DMSO-d$_6$): 0.77-0.93 (m, 1H) 1.13 (t, J=7.07 Hz, 3H) 1.34-1.44 (m, 1H) 1.46 (s, 9H) 1.56-1.63 (m, 1H) 2.01-2.10 (m, 1H) 2.22 (s, 3H) 2.40-2.44 (m, 4H) 2.78-2.97 (m, 2H) 3.27-3.36 (m, 4H) 3.91-4.06 (m, 2H) 3.94-4.01 (m, 2H) 4.37-4.47 (m, 1H) 6.78 (d, J=2.44 Hz, 1H) 7.04 (dd, J=9.02, 2.56 Hz, 1H) 7.81 (d, J=9.02 Hz, 1H)

Preparation of 4-(4-methylpiperazin-1-yl)-2-[(1-methylpiperidin-4-yl)(trifluoroacetyl)amino]benzoic acid dihydrochloride tert-Butyl 4-(4-methylpiperazin-1-yl)-2-[(1-methylpiperidin-4-yl)(trifluoroacetyl)amino]benzoate (1.18 g, 2.435 mmol) was dissolved in dry dichloromethane (3 mL) under nitrogen atmosphere. A 4 M solution of HCl in dioxane (9.1 mL, 36.4 mmol, 15 eq) was then added dropwise and the mixture was stirred for 1.5 hours. A sticky solid was formed. 5 more equivalents of HCl were added and the mixture was stirred for 2 more hours. The solid was filtered, washed with DCM (10 mL) and diethyl ether (10 mL) and dried under vacuum at 60° C. for 2 hours. 1.06 g of title compound were obtained as a beige powder (87% yield).

ESI(+) MS: m/z 429 (MH$^+$).

Operating in an analogous way, the following compound was obtained:

2-{[1-(ethoxycarbonyl)piperidin-4-yl](trifluoroacetyl)amino}-4-(4-methylpiperazin-1-yl)benzoic acid hydrochloride 1H-NMR (400 MHz), δ (ppm, DMSO-d$_6$): 0.83-0.98 (m, 1H) 1.13 (t, J=7.01 Hz, 3H) 1.34-1.47 (m, 1H) 1.63 (d, J=10.85 Hz, 1H) 2.04 (d, J=13.66 Hz, 1H) 2.84 (s, 3H) 2.88 (m, 2H) 3.16 (m, 4H) 3.52 (m, 2H) 3.94-4.02 (m, 2H) 4.05 (m, 4H) 4.34-4.48 (m, 1H) 6.96 (d, J=2.32 Hz, 1H) 7.11 (dd, J=8.90, 2.56 Hz, 1H) 7.91 (d, J=8.90 Hz, 1H) 10.26 (br. s., 1H) 12.79 (br. s., 1H)

Step i'

Preparation of N-[5-(3,5-difluorobenzyl)-1H-indazol-3-yl]-4-(4-methylpiperazin-1-yl)-2-[(1-methylpiperidin-4-yl)amino]benzamide [(I$_A$), R1=R2=R3=H, R=3,5-difluorophenyl, Ar=4-(4-methylpiperazin-1-yl)-2-[(1-methylpiperidin-4-yl]amino)-phenyl] cpd. 13

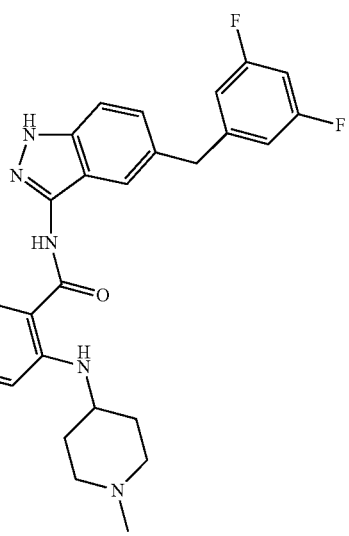

4-(4-Methylpiperazin-1-yl)-2-[(1-methylpiperidin-4-yl)(trifluoroacetyl)amino]benzoic acid dihydrochloride (251 mg, 0.501 mmol, 1.3 eq) was suspended in dry THF (4 mL) under nitrogen atmosphere. Thionyl chloride (0.365 mL, 1.0 mmol, 2.6 eq) was added and the mixture was stirred at 70° C. for 1.5 hours. The mixture was then evaporated to dryness, taken up with toluene, evaporated to dryness again and then left for 2 hours at room temperature under high vacuum. The acid chloride was then suspended in dry pyridine (2 mL) and cooled to 0° C. A solution of 5-(3,5-difluorobenzyl)-1H-indazol-3-amine (100 mg, 0.386 mmol, 1 eq) in dry pyridine (1.2 mL) was added dropwise and the mixture was stirred at 0° C. for 2 hours and then left at 4° C. overnight. It was then diluted with water and ethyl acetate. The aqueous phase was basified until pH 10 with 30% ammonium hydroxide and extracted with ethyl acetate. The combined organic layers were dried over Na$_2$SO$_4$ and evaporated to dryness to give 290 mg of crude trifluoroacetamide. The crude product was dissolved in methanol (7 mL), triethylamine was added (1.3 mL, 9.34 mmol, 24 eq) and the solution was refluxed for 1.5 hours. The reaction mixture was evaporated to dryness and purified by chromatography on silica gel (DCM/MeOH/NH$_3$ 7% in MeOH 83:17:1). The product was then slurried in diethyl ether (1 mL) for 30 minutes at room temperature, then filtered and dried at 45° C. under high vacuum for 3 hours. 153 mg of title compound were obtained as pale yellow powder (69% yield).

1H-NMR (400 MHz), δ (ppm, DMSO-d$_6$): 1.33-1.50 (m, 2H) 1.92 (dd, J=9.51, 4.02 Hz, 2H) 2.18 (br. s., 3H) 2.21 (br. s., 2H) 2.23 (s, 3H) 2.44 (t, J=4.60 Hz, 4H) 2.61 (br. s., 2H) 3.25 (t, J=4.90 Hz, 4H) 3.41-3.52 (m, 1H) 4.04 (s, 2H) 6.08 (d, J=1.95 Hz, 1H) 6.22 (dd, J=8.96, 2.13 Hz, 1H) 6.98 (m, 3H) 7.24 (dd, J=8.65, 1.46 Hz, 1H) 7.40 (d, J=8.53 Hz, 1H) 7.49 (s, 1H) 7.78 (d, J=9.02 Hz, 1H) 8.26 (d, J=7.44 Hz, 1H) 10.06 (s, 1H) 12.62 (s, 1H)

Operating in an analogous way, the following compound was obtained:

ethyl 4-{[2-{[5-(3,5-difluorobenzyl)-1H-indazol-3-yl]carbamoyl}-5-(4-methylpiperazin-1-yl)phenyl]amino}piperidine-1-carboxylate [(I$_A$), R1=R2=R3=H, R=3,5-difluorophenyl, Ar=4-(4-methylpiperazin-1-yl)-2-{(1-(ethoxycarbonyl)piperidin-4-yl]amino}-phenyl] cpd. 138

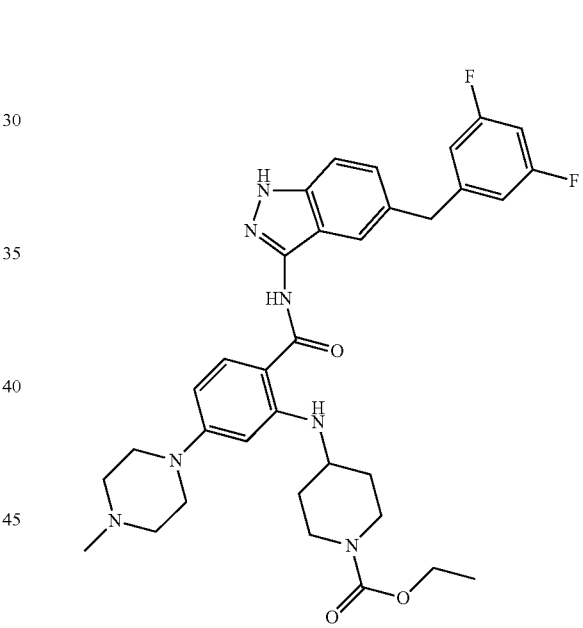

1H-NMR (400 MHz), δ (ppm, DMSO-d$_6$): 1.17 (t, J=7.07 Hz, 3H) 1.21-1.34 (m, 2H) 1.87-1.98 (m, 2H) 2.26 (br. s., 3H) 2.45-2.49 (m, 4H) 3.07-3.21 (m, 2H) 3.25-3.35 (m, 4H) 3.64-3.73 (m, 1H) 3.76 (ddd, J=13.57, 4.18, 3.96 Hz, 2H) 4.02 (q, J=7.03 Hz, 2H) 4.04 (s, 2H) 6.15 (d, J=2.10 Hz, 1H) 6.25 (dd, J=9.11, 2.10 Hz, 1H) 6.92-7.05 (m, 3H) 7.25 (dd, J=8.57, 1.52 Hz, 1H) 7.41 (d, J=8.57 Hz, 1H) 7.47 (s, 1H) 7.80 (d, J=9.11 Hz, 1H) 8.31 (d, J=7.93 Hz, 1H) 10.09 (s, 1H) 12.63 (s, 1H)

Preparation of N-[5-(3,5-difluorobenzyl)-1H-indazol-3-yl]-4-(4-methylpiperazin-1-yl)-2-(piperidin-4-ylamino)benzamide [(I$_A$), R1=R2=R3=H, R=3,5-difluorophenyl, Ar=4-(4-methylpiperazin-1-yl)-2-[(piperidin-4-yl)amino]-phenyl] cpd. 139

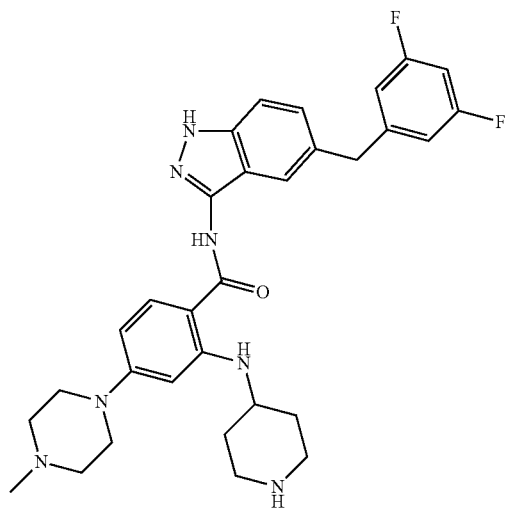 [SMILES: CN1CCN(c2ccc(C(=O)Nc3n[nH]c4ccc(Cc5cc(F)cc(F)c5)cc34)c(NC3CCNCC3)c2)CC1]

ethyl 4-{[2-{[5-(3,5-difluorobenzyl)-1H-indazol-3-yl]carbamoyl}-5-(4-methylpiperazin-1-yl)phenyl]amino}piperidine-1-carboxylate (198 mg, 0.313 mmol) were dissolved in 62% aqueous HBr (4 mL) in a screw cap pirex tube and stirred at 70° C. for 1 hour. The mixture was then diluted with water and 30% ammonium hydroxide and extracted with ethyl acetate. The organic phase was dried over Na$_2$SO$_4$ and concentrated to dryness. After purification by chromatography on silica gel (DCM/MeOH/NH$_3$ 7% in MeOH, 80:10:10) 127 mg of pure product were obtained (72% yield). The product was slurried with ethyl acetate, filtered, washed with n-hexane and dried at 45° C. under high vacuum for 3 hours to give 88 mg of title compound as white solid.

1H-NMR (400 MHz), δ (ppm, DMSO-d$_6$): 1.16-1.31 (m, J=12.50, 10.20, 10.20, 3.66 Hz, 2H) 1.89 (dq, J=12.50, 3.40 Hz, 2H) 2.22 (s, 3H) 2.43 (t, J=4.76 Hz, 4H) 2.63 (ddd, J=12.59, 10.27, 2.62 Hz, 2H) 2.92 (dt, J=12.53, 3.92 Hz, 2H) 3.25 (t, J=4.63 Hz, 4H) 3.46-3.57 (m, 1H) 4.04 (s, 2H) 6.09 (d, J=2.07 Hz, 1H) 6.22 (dd, J=9.02, 2.07 Hz, 1H) 6.93-7.04 (m, 3H) 7.24 (dd, J=8.66, 1.59 Hz, 1H) 7.40 (d, J=8.66 Hz, 1H) 7.48 (br. s., 1H) 7.78 (d, J=9.02 Hz, 1H) 8.24 (d, J=7.80 Hz, 1H) 10.04 (s, 1H) 12.62 (s, 1H).

Example 14

Preparation of 1-[1-(tert-butoxycarbonyl)piperidin-4-yl]-1H-pyrazole-4-carboxylic acid A mixture of ethyl 1H-pyrazole-4-carboxylate (700 mg, 5 mmol) and NaH 60% (6 mmol) was stirred under nitrogen at 0° C. for 1 hour in dry DMF (15 mL). tert-Butyl 4-[(methylsulfonyl)oxy]piperidine-1-carboxylate (1.53 gr, 5.5 mmol) dissolved in 4 mL of dry DMF was added and the resulting solution was heated at 100° C. overnight. Reaction mixture was quenched with water and extracted (×3) with ethyl acetate. Collected organic phases were dried over Na$_2$SO$_4$, filtered and evaporated to dryness. Residue was dissolved in MeOH (20 mL) and water (5 mL) and KOH (1.12 gr, 20 mmol) was added. The resulting solution was stirred at room temperature 24 hours, then solvents removed under reduced pressure. The residue was taken-up with AcOEt and KHSO$_4$ 5% solution. Aqueous phase was extracted with EtOAc several times. Collected organic phases were dried with Na$_2$SO$_4$, filtered and evaporated to dryness affording 600 mg of the title compound.

1H-NMR (400 MHz), δ (ppm, DMSO-d$_6$): 1.42 (s, 9H) 1.73-1.87 (m, 2H) 1.96-2.03 (m, 2H) 2.82-2.99 (m, 2H) 4.04 (d, J=12.93 Hz, 2H) 4.34-4.47 (m, 1H) 7.81 (s, 1H) 8.29 (s, 1H) 12.26 (br. s., 1H)

Step i'

Preparation of N-[5-(3,5-difluorobenzyl)-1H-indazol-3-yl]-1-(piperidin-4-yl)-1H-pyrazole-4-carboxamide hydrochloride [(I$_A$), R1=R2=R3=H, R=3,5-difluorophenyl, Ar=(piperidin-4-yl)-1H-pyrazole] cpd. 102

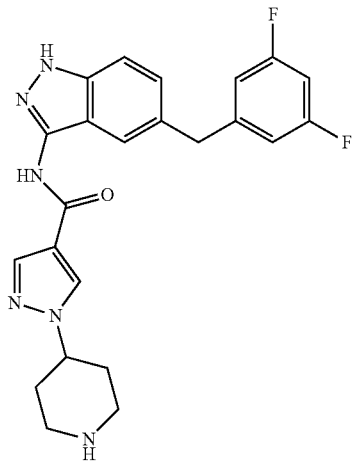 [SMILES: O=C(Nc1n[nH]c2ccc(Cc3cc(F)cc(F)c3)cc12)c1cnn(C2CCNCC2)c1]

1-[1-(tert-butoxycarbonyl)piperidin-4-yl]-1H-pyrazole-4-carboxylic acid (134 mg, 0.45 mmol) and oxalyl chloride (0.6 mmol) were stirred in DCM dry (5 mL) at room temperature overnight. Volatiles were evaporated and the residue dissolved in dry pyridine (5 mL) at 0° C. A solution of 5-(3,5-difluoro-benzyl)-1H-indazol-3-ylamine (100 mg, 0.38 mmol) in dry pyridine (2 mL) was added to the cooled reaction mixture. After 1 hour, reaction was quenched with NaHCO$_3$ sat. sol and extracted with ethyl acetate. Collected organic phases were dried over Na$_2$SO$_4$, filtered and evaporated to dryness. Residue was purified by column chromatography over silica gel (DCM/EtOH/NH$_3$ 5N in MeOH=1000/50/1) affording 87 mg of Boc-protected derivative which was dissolved in 2 mL of dioxane and treated with 0.4 mL of 4M HCl in dioxane. Volatiles were evaporated affording 65 mg of the title compound.

1H-NMR (400 MHz), δ (ppm, DMSO-d$_6$): 2.10-2.23 (m, 2H) 2.22-2.31 (m, 2H) 3.03-3.19 (m, 2H) 3.32-3.49 (m, 2H) 4.05 (s, 2H) 4.54-4.63 (m, 1H) 6.92-6.98 (m, 2H) 6.98-7.05 (m, 1H) 7.25 (dd, J=8.59, 1.65 Hz, 1H) 7.40-7.44 (m, 1H) 7.63 (d, J=0.61 Hz, 1H) 8.16 (s, 1H) 8.49 (s, 1H) 8.65-8.77 (m, 1H) 8.82-8.96 (m, 1H) 10.44 (s, 1H) 12.71 (br. s., 1H)

Example 15

Step i'

Preparation of N-[5-(3,5-difluorobenzyl)-1H-indazol-3-yl]-2-[(cis-4-hydroxycyclohexyl)amino]-4-(4-methylpiperazin-1-yl)benzamide [(I$_A$), R1=R2=R3=H, R=3,5-difluorophenyl, Ar=4-(4-methyl-piperazin-1-yl)-2-[(cis-4-hydroxycyclohexyl)amino]-phenyl] cpd. 103

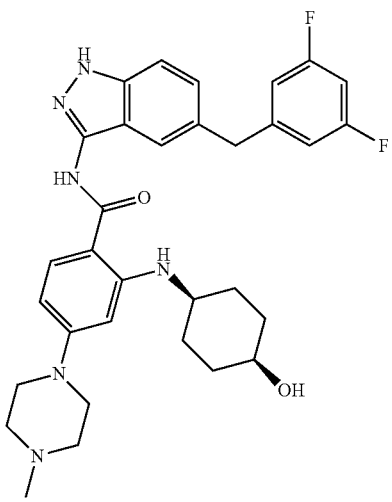 [SMILES: CN1CCN(c2ccc(C(=O)Nc3n[nH]c4ccc(Cc5cc(F)cc(F)c5)cc34)c(N[C@H]3CC[C@@H](O)CC3)c2)CC1]

4-(4-methylpiperazin-1-yl)-2-[{cis-4-[(phenylcarbonyl)oxy]cyclohexyl}(trifluoroacetyl)amino]benzoic acid hydrochloride (1.03 gr, 1.94 mmol) and oxalyl chloride (3.88 mmol) were stirred in DCM dry (20 mL) and a few drops of dry DMF at 0° C., temperature was allowed to reach room temperature in 2 hours. Volatiles were evaporated and the residue dissolved in dry pyridine (25 mL) at 0° C. A solution of 5-(3,5-difluoro-benzyl)-1H-indazol-3-ylamine (387 mg, 1.49 mmol) in dry pyridine (6 mL) was added to the cooled reaction mixture. Temperature was allowed to reach room temperature overnight Reaction was quenched with NaHCO$_3$ sat. sol and extracted with ethyl acetate. Collected organic phases were dried over Na$_2$SO$_4$, filtered and evaporated to dryness. Residue was purified by column chromatography over silica gel (DCM/AcOEt/EtOH=100/10/15). The so obtained derivative, was dissolved in MeOH (200 mL) and water (20 mL) and treated at 60° C. with LiOH hydrate (160 mg, 3.8 mmol) for 4 hours. MeOH was evaporated and the resulting aqueous phase was extracted with EtOAc. Collected organic phases were dried over Na$_2$SO$_4$, filtered and evaporated to dryness. Residue was purified by column chromatography over silica gel (DCM/EtOH/NH$_3$ 5N in MeOH=100/10/2) affording 233 mg of title compound.

1H-NMR (400 MHz), δ (ppm, DMSO-d$_6$): 1.41-1.70 (m, 8H) 2.24 (s, 3H) 2.45 (br. s., 4H) 3.22-3.29 (m, 4H) 3.58 (d, J=10.61 Hz, 2H) 4.05 (s, 2H) 4.43 (d, J=3.78 Hz, 1H) 6.09 (d, J=1.95 Hz, 1H) 6.22 (dd, J=8.96, 2.13 Hz, 1H) 6.94-7.04 (m, 3H) 7.25 (dd, J=8.65, 1.58 Hz, 1H) 7.41 (d, J=8.53 Hz, 1H) 7.51 (s, 1H) 7.79 (d, J=9.14 Hz, 1H) 8.39 (d, J=7.68 Hz, 1H) 10.04 (s, 1H) 12.63 (s, 1H)

Operating in a way analogous to that described above, the following compound was obtained:

N-[5-(3,5-difluorobenzyl)-1H-indazol-3-yl]-2-[(trans-4-hydroxycyclohexyl)amino]-4-(4-methyl-piperazin-1-yl)benzamide [(I$_A$), R1=R2=R3=H, R=3,5-difluorophenyl, Ar=4-(4-methyl-piperazin-1-yl)-2-[(trans-4-hydroxycyclohexyl)amino]-phenyl] cpd. 104

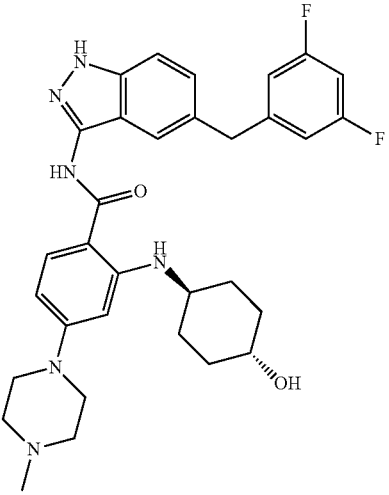 [SMILES: CN1CCN(c2ccc(C(=O)Nc3n[nH]c4ccc(Cc5cc(F)cc(F)c5)cc34)c(N[C@H]3CC[C@H](O)CC3)c2)CC1]

1H-NMR (400 MHz), δ (ppm, DMSO-d$_6$): 1.10-1.22 (m, 2H) 1.29-1.41 (m, 2H) 1.78-1.83 (m, 2H) 1.94-2.03 (m, 2H) 2.24 (s, 3H) 2.42-2.48 (m, 4H) 3.23-3.28 (m, 4H) 3.34-3.42 (m, 1H) 3.43-3.52 (m, 1H) 4.04 (s, 2H) 4.53 (d, J=4.14 Hz, 1H) 6.09 (d, J=2.07 Hz, 1H) 6.21 (dd, J=9.02, 2.19 Hz, 1H) 6.95-7.04 (m, 3H) 7.25 (dd, J=8.53, 1.58 Hz, 1H) 7.40 (d, J=8.53 Hz, 1H) 7.48 (s, 1H) 7.77 (d, J=9.14 Hz, 1H) 8.17 (d, J=7.80 Hz, 1H) 10.04 (s, 1H) 12.61 (s, 1H)

Example 16

Preparation of N-[5-(3,5-difluorobenzyl)-1H-indazol-3-yl]-2-[(2-hydroxyethyl)amino]-4-(4-methyl-piperazin-1-yl)benzamide [(I$_A$), R1=R2=R3=H, R=3,5-difluorophenyl, Ar=4-(4-methyl-piperazin-1-yl)-2-[(2-hydroxyethyl)amino]-phenyl] cpd. 105

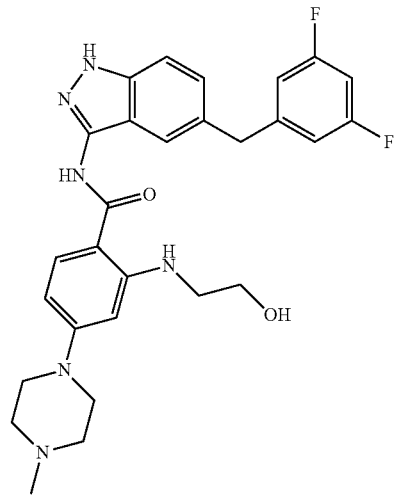 [SMILES: CN1CCN(c2ccc(C(=O)Nc3n[nH]c4ccc(Cc5cc(F)cc(F)c5)cc34)c(NCCO)c2)CC1]

2-[(2-{[tert-butyl(dimethyl)silyl]oxy}ethyl)amino]-N-[5-(3,5-difluorobenzyl)-1H-indazol-3-yl]-4-(4-methylpiperazin-1-yl)benzamide (126 mg, 0.2 mmol) was dissolved in dry THF (3 mL) and 1M TBAF in THF (0.24 mL) was added at 0° C. The resulting solution was stirred overnight at room temperature. Reaction was quenched with water and extracted with ethyl acetate. Collected organic phases were dried over $Na_2SO_4$, filtered and evaporated to dryness. Residue was purified by column chromatography over silica gel (DCM/EtOH/$NH_3$ 5N in MeOH=85/15/1) affording 83 mg of title compound.

1H-NMR (400 MHz), δ (ppm, DMSO-$d_6$): 2.34 (br. s., 3H) 2.51-2.65 (m, 4H) 3.20 (q, J=5.57 Hz, 2H) 3.25-3.36 (m, 4H) 3.60 (q, J=5.53 Hz, 2H) 4.05 (s, 2H) 4.74 (t, J=5.18 Hz, 1H) 6.09 (d, J=2.07 Hz, 1H) 6.25 (dd, J=8.90, 2.19 Hz, 1H) 6.94-6.99 (m, 2H) 6.99-7.04 (m, 1H) 7.23 (dd, J=8.66, 1.58 Hz, 1H) 7.41 (d, J=8.65 Hz, 1H) 7.51 (s, 1H) 7.79 (d, J=9.02 Hz, 1H) 8.22 (t, J=5.18 Hz, 1H) 10.06 (s, 1H) 12.62 (s, 1H).

Example 17

Preparation of 2-[(azetidin-3-ylmethyl)amino]-N-[5-(3,5-difluorobenzyl)-1H-indazol-3-yl]-4-(4-methyl-piperazin-1-yl)benzamide [($I_A$), R1=R2=R3=H, R=3,5-difluorophenyl, Ar=4-(4-methyl-piperazin-1-yl)-2-[(azetidin-3-ylmethyl)amino]-phenyl] cpd. 106

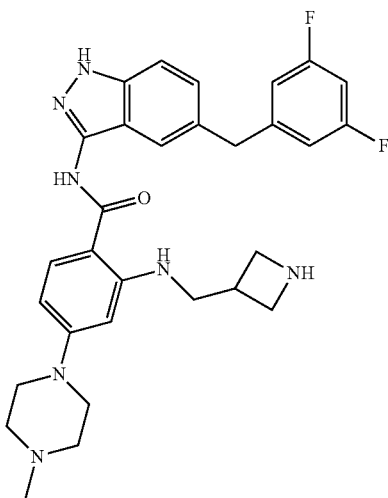 [SMILES: CN1CCN(c2ccc(C(=O)Nc3n[nH]c4ccc(Cc5cc(F)cc(F)c5)cc34)c(NCC3CNC3)c2)CC1]

tert-butyl 3-({[2-{[5-(3,5-difluorobenzyl)-1H-indazol-3-yl]carbamoyl}-5-(4-methylpiperazin-1-yl)phenyl]amino}methyl)azetidine-1-carboxylate (289 mg, 0.45 mmol) was dissolved in DCM (3 mL) and TFA (0.7 mL) was added. The resulting reaction solution was stirred overnight at room temperature. The mixture was diluted with DCM and extracted with 10% aqueous $NH_3$. Organic phase was evaporated. Reverse phase column chromatography purification afforded 104 mg of the title compound.

1H-NMR (400 MHz), δ (ppm, DMSO-$d_6$): 2.24 (s, 3H) 2.42-2.47 (m, 4H) 2.80-2.90 (m, 1H) 3.26-3.38 (m, 4H) 3.58 (t, J=7.86 Hz, 2H) 4.04 (s, 2H) 6.08 (d, J=2.32 Hz, 1H) 6.25 (dd, J=8.96, 2.13 Hz, 1H) 6.94-7.00 (m, 2H) 6.98-7.04 (m, 1H) 7.25 (dd, J=8.65, 1.58 Hz, 1H) 7.39-7.43 (m, 1H) 7.49 (d, J=0.61 Hz, 1H) 7.80 (d, J=8.90 Hz, 1H) 8.16 (t, J=5.06 Hz, 1H) 10.07 (br. s., 1H) 12.63 (br. s., 1H)

Preparation of N-[5-(3,5-difluorobenzyl)-1H-indazol-3-yl]-2-{[(1-methylazetidin-3-yl)methyl]amino}-4-(4-methylpiperazin-1-yl)benzamide [($I_A$), R1=R2=R3=H, R=3,5-difluorophenyl, Ar=4-(4-methyl-piperazin-1-yl)-2-[(1-methylazetidin-3-ylmethyl)amino]-phenyl] cpd. 107

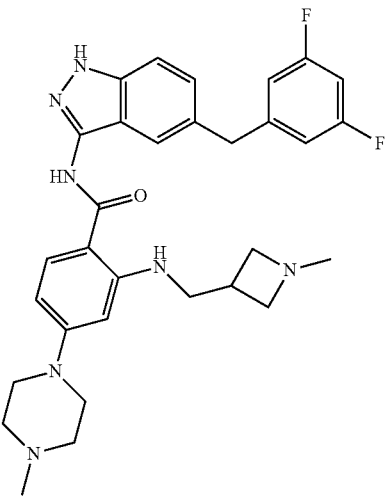 [SMILES: CN1CCN(c2ccc(C(=O)Nc3n[nH]c4ccc(Cc5cc(F)cc(F)c5)cc34)c(NCC3CN(C)C3)c2)CC1]

To a solution of 2-[(azetidin-3-ylmethyl)amino]-N-[5-(3,5-difluorobenzyl)-1H-indazol-3-yl]-4-(4-methylpiperazin-1-yl)benzamide (100 mg, 0.14 mmol) in dichloromethane (2 mL) were added formaldehyde 37 wt. % in water (0.014 mL, 0.168 mmol), TEA (0.4 mmol) and sodium triacetoxyborohydride (45 mg, 0.21 mmol). The mixture was stirred at room temperature overnight, diluted with dichloromethane, washed with aqueous $NaHCO_3$ sat.sol., water and brine. Organic phase was dried over sodium sulfate and evaporated to dryness. The crude was purified by flash chromatography on silica gel using dichloromethane/methanol/$NH_3$ 5N in MeOH 100:10:1 as the eluant, affording 5 mg of the title compound.

1H-NMR (400 MHz), δ (ppm, DMSO-$d_6$): 2.26 (s, 3H) 2.47 (br. s., 4H) 2.62 (s, 3H) 2.84-2.99 (m, 1H) 3.27-3.34 (m, 4H) 3.36-3.46 (m, 2H) 3.52-3.62 (m, 2H) 3.80-3.90 (m, 2H) 4.04 (s, 2H) 6.09 (d, J=2.07 Hz, 1H) 6.28 (dd, J=9.02, 2.07 Hz, 1H) 6.93-6.99 (m, 2H) 6.99-7.05 (m, 1H) 7.25 (dd, J=8.59, 1.52 Hz, 1H) 7.41 (d, J=8.65 Hz, 1H) 7.50 (s, 1H) 7.81 (d, J=9.14 Hz, 1H) 8.25 (t, J=5.49 Hz, 1H) 10.12 (s, 1H) 12.64 (s, 1H).

Example 18

Preparation of 4-nitro-2-(tetrahydro-pyran-4-ylamino)-benzoic acid

4-Nitro-2-(tetrahydro-pyran-4-ylamino)-benzoic acid ethyl ester (11.2 g, 38 mmol) was dissolved in 200 mL of ethanol at 60° C. then 2N NaOH was added (40 mL, 80 mmol). The mixture was stirred at 60° C. for 4 hours, then the solvent removed under reduced pressure. The residue was taken-up with 200 mL of water and the mixture brought to acidic pH with 2N HCl (35 mL). The precipitated yellow solid was filtered, washed with plenty of water and dried in oven at 40° C. affording the title compound (9.3 g).

1H-NMR (400 MHz), δ (ppm, DMSO-$d_6$): 13.49 (bs, 1H), 8.17 (bd, 1H), 8.04 (d, J=8.7 Hz, 1H), 7.54 (d, J=2.2 Hz, 1H), 7.32 (dd, J1=8.7 HZ, J2=2.2 Hz, 1H), 3.90-3.78 (m, 3H), 3.54 (m, 2H), 1.98 (m, 2H), 1.46 (m, 2H).

Preparation of 4-nitro-2-[(tetrahydro-pyran-4-yl)-(2,2,2-trifluoro-acetyl)-amino]-benzoic acid To 30 mL of trifluoroacetic anhydride was added 4-nitro-2-(tetrahydro-pyran-4-ylamino)-benzoic acid (9.1 g, 34.2 mmol) in small portions, at room temperature. The mixture was stirred at room temperature for 1 hour then evaporated to dryness. The residue (brown oil) was treated with 200 mL of water and vigorously stirred for 3 hours at room temperature. The white solid thus formed was filtered, washed with plenty of water and dried in oven at 40° C. affording the title compound (11.8 g).

1H-NMR (400 MHz), δ (ppm, DMSO-$d_6$): 13.52 (bs, 1H), 8.45 (dd, J1=8.5 Hz, J2=2.3 Hz, 1H), 8.32 (d, J=2.3 Hz, 1H), 8.26 (d, J=8.5 Hz, 1H), 4.58 (m, 1H), 3.84 (m, 2H), 3.45-3.2 (m, 2H), 1.98 (m, 1H), 1.59 (m, 1H), 1.49 (m, 1H), 1.14 (m, 1H).

Step i'

Preparation of N-[5-(3,5-difluorobenzyl)-1H-indazol-3-yl]-4-nitro-2-[tetrahydro-2H-pyran-4-yl(trifluoroacetyl)amino]benzamide 4-nitro-2-[(tetrahydro-pyran-4-yl)-(2,2,2-trifluoroacetyl)-amino]-benzoic acid (3.62 g, 10 mmol) and oxalyl chloride (3.8 mL, 30 mmol) were stirred in DCM dry (120 mL) and a few drops of dry DMF at room temperature for 2 hours Volatiles were evaporated and the residue dissolved in dry pyridine (50 mL) at 0° C. A solution of 5-(3,5-difluoro-benzyl)-1H-indazol-3-ylamine (2 gr, 7.72 mmol) in dry pyridine (20 mL) was added to the cooled reaction mixture under nitrogen atmosphere. The resulting mixture was allowed to react overnight at room temperature, then the solvent removed under reduced pressure. The residue was taken-up with EtOAc and washed with aqueous $NaHCO_3$ sat.sol., water and brine. Organic phase was dried over sodium sulfate and evaporated to dryness. The crude was purified by flash chromatography on silica gel using AcOEt/Hexane 7:3 as the eluant, affording 3.9 g of the title compound.

1H-NMR (400 MHz), δ (ppm, DMSO-$d_6$): 1.38-1.57 (m, 2H) 1.65-1.74 (m, 1H) 1.91-1.98 (m, 1H) 3.25-3.44 (m, 2H) 3.70-3.78 (m, 1H) 3.87 (dd, J=11.92, 4.09 Hz, 1H) 4.04 (s, 2H) 4.47-4.58 (m, 1H) 6.98 (d, J=1.34 Hz, 2H) 6.99-7.06 (m, 1H) 7.31 (dd, J=8.68, 1.47 Hz, 1H) 7.45 (d, J=8.56 Hz, 1H) 7.54 (s, 1H) 8.20 (d, J=8.56 Hz, 1H) 8.36 (d, J=2.32 Hz, 1H) 8.51 (dd, J=8.56, 2.08 Hz, 1H) 11.28 (s, 1H) 12.85 (s, 1H)

Conversion 4

Preparation of N-[5-(3,5-difluorobenzyl)-1H-indazol-3-yl]-4-amino-2-[tetrahydro-2H-pyran-4-yl(trifluoroacetyl)amino]benzamide A mixture of N-[5-(3,5-difluorobenzyl)-1H-indazol-3-yl]-4-nitro-2-[tetrahydro-2H-pyran-4-yl(trifluoroacetyl)amino]benzamide (3.86 g, 6.4 mmol), cyclohexene (10 mL), dioxane (70 mL) and 10% Pd/C (0.42 g) was stirred at 100° C. for 4 hours. The reaction mixture was filtered over a celite pad washing thoroughly with THF and MeOH. After evaporation of the organic phase, purification of the crude by chromatography over silica gel (DCM/EtOH 9/1) gave 2.75 g of title compound (82% yield).

1H-NMR (400 MHz), δ (ppm, DMSO-$d_6$): 1.29 (qd, J=12.28, 4.63 Hz, 1H) 1.56 (qd, J=12.19, 4.51 Hz, 1H) 1.62 (ddd, J=12.93, 3.47, 2.01 Hz, 1H) 1.84 (ddd, J=12.47, 3.93, 2.01 Hz, 1H) 3.33 (m, 2H) 3.77 (dd, J=11.58, 4.39 Hz, 1H) 3.88 (dd, J=11.65, 4.33 Hz, 1H) 4.00 (s, 2H) 4.43 (tt, J=11.93, 3.86 Hz, 1H) 5.96 (s, 2H) 6.50 (d, J=2.32 Hz, 1H) 6.68 (dd, J=8.47, 2.26 Hz, 1H) 6.89-6.97 (m, 2H) 7.01 (tt, J=9.43, 2.33 Hz, 1H) 7.25 (dd, 1H) 7.39 (m, 2H) 7.68 (d, J=8.54 Hz, 1H) 10.33 (s, 1H) 12.64 (s, 1H)

Conversion 6

Preparation of tert-butyl 3-{[(4-{[5-(3,5-difluorobenzyl)-1H-indazol-3-yl]carbamoyl}-3-[tetrahydro-2H-pyran-4-yl(trifluoroacetyl)amino]phenyl)amino]methyl}azetidine-1-carboxylate To a solution of N-[5-(3,5-difluorobenzyl)-1H-indazol-3-yl]-4-amino-2-[tetrahydro-2H-pyran-4-yl(trifluoroacetyl)amino]benzamide (240 mg, 0.42 mmol) in dichloromethane (20 mL) were added tert-butyl 3-formylazetidine-1-carboxylate (116 mg, 0.63 mmol), trifluoroacetic acid (0.32 mL) and tetramethylammonium triacetoxyborohydride (165 mg g, 0.63 mmol). The mixture was stirred at room temperature overnight, then diluted with dichloromethane, washed with $NaHCO_3$ sat.sol. and brine, dried over sodium sulfate and evaporated to dryness.

ESI(+) MS: m/z 743 (MH$^+$).

Operating in a way analogous to that described above, the following compound was obtained:

N-[5-(3,5-difluorobenzyl)-1H-indazol-3-yl]-4-[(1-methylpiperidin-4-yl)amino]-2-[tetrahydro-2H-pyran-4-yl(trifluoroacetyl)amino]benzamide ESI(+) MS: m/z 671 (MH$^+$).

Preparation of tert-butyl 3-({[4-{[5-(3,5-difluorobenzyl)-1H-indazol-3-yl]carbamoyl}-3-(tetrahydro-2H-pyran-4-ylamino)phenyl]amino}methyl) azetidine-1-carboxylate tert-butyl 3-{[(4-{[5-(3,5-difluorobenzyl)-1H-indazol-3-yl]carbamoyl}-3-[tetrahydro-2H-pyran-4-yl(trifluoroacetyl)amino]phenyl)amino]methyl}azetidine-1-carboxylate (760 mg, 1.02 mmol) was dissolved in MeOH (12 mL) and TEA (4 mL) and stirred at room temperature overnight. Volatiles were evaporated and the residue was taken-up with DCM and washed with brine. Organic phase was dried over sodium sulfate and evaporated to dryness.

ESI(+) MS: m/z 647 (MH$^+$).

Operating in a way analogous to that described above, the following compound was obtained:

N-[5-(3,5-difluorobenzyl)-1H-indazol-3-yl]-4-[1-methylpiperidin-4-yl)amino]-2-[tetrahydro-2H-pyran-ylamino]benzamide [(I$_A$), R1=R2=R3=H, R=3,5-difluorophenyl, Ar=4-[(1-methylpiperidin-4-yl)amino]-2-[tetrahydro-2H-pyran-4-ylamino]-phenyl] cpd. 108

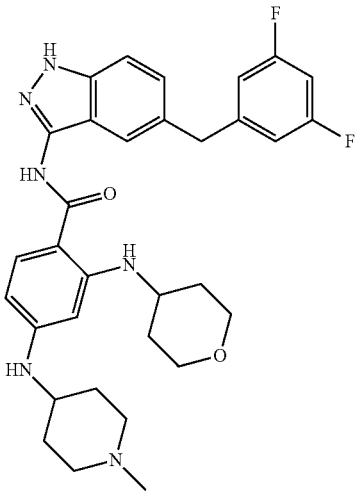 [SMILES: CN1CCC(Nc2ccc(C(=O)Nc3n[nH]c4ccc(Cc5cc(F)cc(F)c5)cc34)c(NC3CCOCC3)c2)CC1]

1H-NMR (400 MHz), δ (ppm, DMSO-d$_6$): 1.28-1.50 (m, 4H) 1.80-1.99 (m, 4H) 2.06 (t, J=12.54 Hz, 2H) 2.19 (s, 3H) 2.75 (d, J=12.19 Hz, 2H) 3.40 (m, 1H) 3.45 (ddd, J=11.83, 10.12, 2.32 Hz, 2H) 3.83 (dt, J=11.68, 3.86 Hz, 2H) 4.03 (s, 2H) 5.87 (d, J=1.71 Hz, 1H) 5.90 (dd, J=8.78, 1.95 Hz, 1H) 5.93 (d, J=7.93 Hz, 1H) 5.95 (s, 1H) 6.98 (m, 3H) 7.24 (dd, J=8.66, 1.59 Hz, 1H) 7.39 (d, J=8.54 Hz, 1H) 7.47 (br. s., 1H) 7.69 (d, J=8.90 Hz, 1H) 8.30 (d, J=7.44 Hz, 1H) 9.88 (s, 1H) 12.57 (s, 1H)

Preparation of 4-[(azetidin-3-ylmethyl)amino]-N-[5-(3,5-difluorobenzyl)-1H-indazol-3-yl]-2-(tetrahydro-2H-pyran-4-ylamino)benzamide [(I$_A$), R1=R2=R3=H, R=3,5-difluorophenyl, Ar=4-[(azetidin-3-ylmethyl)amino]-2-[tetrahydro-2H-pyran-4-ylamino]phenyl] cpd. 109

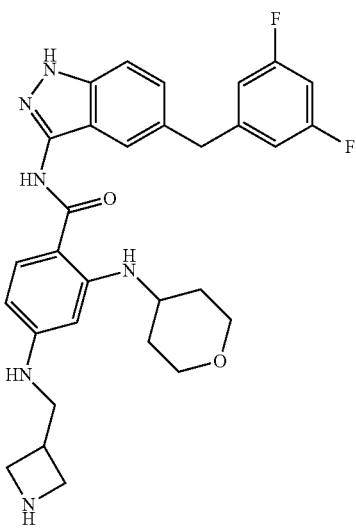 [SMILES: O=C(Nc1n[nH]c2ccc(Cc3cc(F)cc(F)c3)cc12)c1ccc(NCC2CNC2)cc1NC1CCOCC1]

tert-butyl 3-({[4-{[5-(3,5-difluorobenzyl)-1H-indazol-3-yl]carbamoyl}-3-(tetrahydro-2H-pyran-4-ylamino)phenyl]amino}methyl)azetidine-1-carboxylate (738 mg, 1.1 mmol) was dissolved in DCM (12 mL) and TFA (3 mL) was added. The resulting reaction solution was stirred for 3 hours at room temperature. The mixture was diluted with DCM and extracted with 10% aqueous NH$_3$. Aqueous phase was extracted several time with DCM. Collected organic phases were washed with brine, dried over sodium sulfate and evaporated to dryness. Column chromatography purification on silica gel using dichloromethane/methanol/NH$_3$ 5N in MeOH 70:30:1 as the eluant, afforded 150 mg of the title compound.

1H-NMR (400 MHz), δ (ppm, DMSO-d$_6$): 1.30-1.42 (m, 2H) 1.87-2.00 (m, 2H) 2.77-2.88 (m, 1H) 3.24-3.33 (m, 4H) 3.42-3.53 (m, 2H) 3.53-3.60 (m, 3H) 3.78-3.88 (m, 2H) 4.05 (s, 2H) 5.86 (s, 1H) 5.90 (d, J=8.66 Hz, 1H) 6.07-6.13 (m, 1H) 6.95-7.04 (m, 3H) 7.25 (dd, J=8.60, 1.52 Hz, 1H) 7.40 (d, J=8.66 Hz, 1H) 7.48 (s, 1H) 7.70 (d, J=8.78 Hz, 1H) 8.35 (d, J=7.19 Hz, 1H) 9.90 (s, 1H) 12.59 (br. s., 1H).

Example 19

Step i'

Preparation of 2,6-dichloro-N-[5-(3,5-difluorobenzyl)-1H-indazol-3-yl]pyridine-3-carboxamide 2,6-dichloropyridine-3-carboxylic acid (480 mg, 2.5 mmol) and thionyl chloride (0.28 mL, 3.75 mmol) were heated in toluene dry (120 mL) and a few drops of dry DMF at 90° C. for 2 hours Volatiles were evaporated and the residue dissolved in dry pyridine (15 mL) at 0° C. under nitrogen atmosphere. A solution of 5-(3,5-difluoro-benzyl)-1H-indazol-3-ylamine (518 mg, 2 mmol) in dry pyridine (7 mL) was added to the cooled reaction mixture. The resulting mixture was allowed to react overnight at room temperature, then the solvent removed under reduced pressure. The residue was taken-up with EtOAc and washed with aqueous NaHCO$_3$ sat.sol., water and brine. Organic phase was dried over sodium sulfate and evaporated to dryness. The crude was purified by flash chromatography on silica gel using DCM/EtOH 100:4 as the eluant, affording 300 mg of the title compound.

1H-NMR (400 MHz), δ (ppm, DMSO-d): 4.09 (s, 2H) 6.93-7.01 (m, 2H) 7.04 (tt, J=9.39, 2.32 Hz, 1H) 7.29 (dd, J=8.54, 1.34 Hz, 1H) 7.45 (d, J=8.54 Hz, 1H) 7.70 (s, 1H) 7.75 (d, J=8.05 Hz, 1H) 8.24 (d, J=7.93 Hz, 1H) 11.04 (s, 1H) 12.80 (s, 1H)

Operating in a way analogous to that described above, the following compound was obtained:

N-[5-(3,5-difluorobenzyl)-1H-indazol-3-yl]-3,5-difluoropyridine-2-carboxamide

1H-NMR (400 MHz), δ (ppm, DMSO-d$_6$): 4.07 (s, 2H) 6.93-6.99 (m, 2H) 6.99-7.06 (m, 1H) 7.28 (dd, J=8.66, 1.46 Hz, 1H) 7.45 (d, J=8.41 Hz, 1H) 7.68 (s, 1H) 8.12-8.23 (m, 1H) 8.68 (s, 1H) 10.78 (s, 1H) 12.81 (s, 1H)

Preparation of 6-chloro-N-[5-(3,5-difluorobenzyl)-1H-indazol-3-yl]-2-(tetrahydro-2H-pyran-4-ylamino)pyridine-3-carboxamide A solution of 2,6-dichloro-N-[5-(3,5-difluorobenzyl)-1H-indazol-3-yl]pyridine-3-carboxamide (80 mg, 0.18 mmol) in dioxane (1 mL) was heated at 100° C. for 24 hours in the presence of DIPEA (0.1 mL, 0.55 mmol) and tetrahydro-2H-pyran-4-amine. (28 mg, 0.28 mmol) Reaction mixture was diluted with EtOAc and washed with water. The organic layer was dried over sodium sulfate, filtered and evaporated. The crude was purified by flash chromatography on silica gel using DCM/EtOH 95:5 as the eluant, affording 57 mg of the title compound.

1H-NMR (400 MHz), δ (ppm, DMSO-d$_6$): 1.37-1.52 (m, 2H) 1.94 (dd, J=13.05, 2.80 Hz, 2H) 3.47 (td, J=11.16, 2.19 Hz, 2H) 3.80-3.87 (m, 2H) 4.06 (s, 2H) 4.07-4.15 (m, 1H) 6.73 (d, J=8.05 Hz, 1H) 6.93-7.07 (m, 3H) 7.28 (dd, J=8.66, 1.59 Hz, 1H) 7.44 (dd, J=8.54, 0.49 Hz, 1H) 7.55 (s, 1H) 8.29 (d, J=8.17 Hz, 1H) 8.60 (d, J=7.32 Hz, 1H) 10.74 (s, 1H) 12.79 (s, 1H)

Operating in a way analogous to that described above, the following compound was obtained:

N-[5-(3,5-difluorobenzyl)-1H-indazol-3-yl]-5-fluoro-3-(tetrahydro-2H-pyran-4-ylamino)pyridine-2-carboxamide 1H-NMR (400 MHz), δ (ppm, DMSO-d$_6$): 1.34-1.52 (m, 2H) 1.95 (d, J=10.36 Hz, 2H) 3.45-3.54 (m, 2H) 3.68-3.77 (m, 1H) 3.82-3.89 (m, 2H) 4.07 (s, 2H) 6.97-7.05 (m, 3H) 7.28 (dd, J=8.66, 1.59 Hz, 1H) 7.37 (dd, J=12.44, 2.32 Hz, 1H) 7.43 (d, J=8.54 Hz, 1H) 7.65 (s, 1H) 7.88 (d, J=2.32 Hz, 1H) 8.55 (d, J=6.95 Hz, 1H) 10.46 (s, 1H) 12.76 (s, 1H)

Preparation of N-[5-(3,5-difluorobenzyl)-1H-indazol-3-yl]-5-(4-methylpiperazin-1-yl)-3-(tetrahydro-2H-pyran-4-ylamino)pyridine-2-carboxamide [(I$_A$), R1=R2=R3=H, R=3,5-difluorophenyl, Ar=5-(4-methylpiperazin-1-yl)-3-(tetrahydro-2H-pyran-4-ylamino)pyridine] cpd. 113

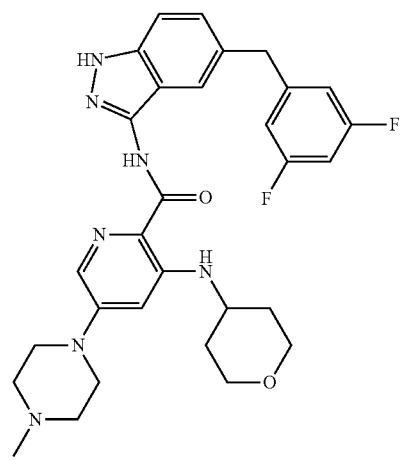 [SMILES: CN1CCN(c2cnc(C(=O)Nc3n[nH]c4ccc(Cc5cc(F)cc(F)c5)cc34)c(NC3CCOCC3)c2)CC1]

A solution of N-[5-(3,5-difluorobenzyl)-1H-indazol-3-yl]-5-fluoro-3-(tetrahydro-2H-pyran-4-ylamino)pyridine-2-carboxamide (925 mg, 1.92 mmol) and N-methylpiperazine (20 mL) was stirred at 60° C. for 48 hours. The reaction mixture was then diluted with EtOAc and washed with NaHCO$_3$ sat.sol. The organic layer was dried over sodium sulfate, filtered and evaporated. The crude was purified by flash chromatography on silica gel using DCM/EtOH/NH$_3$ 5N in MeOH 100:5:0.5 as the eluant, affording 600 mg of the title compound.

1H-NMR (400 MHz), δ (ppm, DMSO-d$_6$): 1.34-1.47 (m, 2H) 1.92-2.00 (m, 2H) 2.25 (s, 3H) 2.44-2.49 (m, 2H) 3.34-3.40 (m, 4H) 3.48-3.56 (m, 2H) 3.72-3.81 (m, 1H) 3.82-3.88 (m, 2H) 4.07 (s, 2H) 6.54 (d, J=2.20 Hz, 1H) 6.95-7.07 (m, 3H) 7.26 (dd, J=8.66, 1.59 Hz, 1H) 7.41 (d, J=8.54 Hz, 1H) 7.72 (s, 1H) 7.73 (d, J=2.32 Hz, 1H) 8.32 (d, J=8.05 Hz, 1H) 10.19 (s, 1H) 12.66 (s, 1H)

Operating in an analogous way, the following compound was obtained:

N-[5-(3,5-difluorobenzyl)-1H-indazol-3-yl]-6-(4-methylpiperazin-1-yl)-2-(tetrahydro-2H-pyran-4-ylamino)pyridine-3-carboxamide [(I$_A$), R1=R2=R3=H, R=3,5-difluorophenyl, Ar=6-(4-methylpiperazin-1-yl)-2-(tetrahydro-2H-pyran-4-ylamino)pyridine] cpd. 114

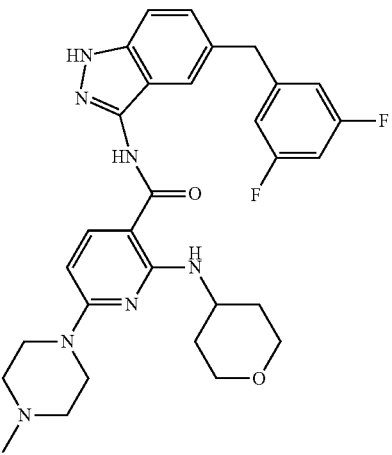 [SMILES: CN1CCN(c2ccc(C(=O)Nc3n[nH]c4ccc(Cc5cc(F)cc(F)c5)cc34)c(NC3CCOCC3)n2)CC1]

1H-NMR (400 MHz), δ (ppm, DMSO-d$_6$): 1.35-1.47 (m, 2H) 1.90-2.00 (m, 2H) 2.22 (s, 3H) 2.36-2.40 (m, 4H) 3.41-3.51 (m, 2H) 3.57-3.63 (m, 4H) 3.78-3.88 (m, 2H) 4.05 (s, 2H) 4.06-4.11 (m, 1H) 6.10 (d, J=8.90 Hz, 1H) 6.96-7.05 (m, 3H) 7.25 (dd, J=8.66, 1.59 Hz, 1H) 7.41 (d, J=8.66 Hz, 1H) 7.50 (s, 1H) 8.10 (d, J=9.02 Hz, 1H) 8.73 (d, J=6.95 Hz, 1H) 10.06 (s, 1H) 12.63 (s, 1H).

Example 20

Step v

Preparation of tert-butyl 4-[4-{[5-(3,5-difluorobenzyl)-1H-indazol-3-yl]carbamoyl}-3-(tetrahydro-2H-pyran-4-ylamino)phenyl]piperazine-1-carboxylate To a solution of N-[5-(3,5-difluoro-benzyl)-1H-indazol-3-yl]-4-piperazin-1-yl-2-(tetrahydro-pyran-4-ylamino)-benzamide (71.7 mg, 0.131 mmol) in anhydrous dichloromethane (3.0 mL) and triethylamine (0.052 mL, 38.1 mg, 0.377 mmol) di-tert-butyl-dicarbonate (34.5 mg, 0.157 mmol) was added, and the solution was stirred at room temperature for 40 minutes. The mixture was evaporated to dryness and purified by flash chromatography on silica gel eluting with dichloromethane/methanol 9:1. affording 60 mg of title compound.

1H-NMR (400 MHz), δ (ppm, DMSO-d$_6$): 1.28-1.41 (m, 2H) 1.44 (s, 9H) 1.90-1.99 (m, 2H) 3.24-3.30 (m, 4H) 3.46 (d, J=4.88 Hz, 4H) 3.48-3.54 (m, 2H) 3.64-3.74 (m, 1H) 3.79-3.86 (m, 2H) 4.05 (s, 2H) 6.16 (d, J=2.19 Hz, 1H) 6.25 (dd, J=8.90, 2.19 Hz, 1H) 6.95-7.04 (m, 3H) 7.26 (dd, J=8.66, 1.46 Hz, 1H) 7.41 (d, J=8.90 Hz, 1H) 7.49 (s, 1H) 7.82 (d, J=9.15 Hz, 1H) 8.29 (d, J=7.44 Hz, 1H) 10.10 (s, 1H) 12.64 (s, 1H)

Preparation of ethyl 5-(3,5-difluorobenzyl)-3-({[4-(piperazin-1-yl)-2-(tetrahydro-2H-pyran-4-ylamino)phenyl]carbonyl}amino)-1H-indazole-1-carboxylate To a solution of tert-butyl 4-[4-{[5-(3,5-difluorobenzyl)-1H-indazol-3-yl]carbamoyl}-3-(tetrahydro-2H-pyran-4-ylamino)phenyl]piperazine-1-carboxylate (0.013 mmol) in anhydrous tetrahydrofurane (1.0 mL) maintained at −50° C. under argon atmosphere a 1M solution of LiHMSD in anhydrous tetrahydrofurane (0.015 mL) was added. After stirring at that temperature for 5 minutes ethyl chlorocarbonate (0.002 mL, 1.63 mg, 0.015 mmol) was added. After 30 minutes at −50° C. the reaction was completed. After diluting with dichloromethane, the solution was washed with brine, dried over sodium sulphate and evaporated to dryness. The crude was dissolved in dichloromethane (1 mL), trifluoroacetic acid (0.1 mL) was added and the mixture was stirred at room temperature overnight. After diluting with dichloromethane, the solution was washed with sodium hydrogencarbonate, with brine, dried over sodium sulphate and evaporated to dryness.

The crude was purified by flash chromatography on silica gel eluting with dichloromethane/methanol 9:1 and a 0.5% of aq. 33% NH$_4$OH affording the title compound.

1H-NMR (400 MHz), δ (ppm, DMSO-d$_6$): 1.30-1.38 (m, 2H) 1.40 (t, J=7.13 Hz, 3H) 1.90-1.99 (m, 2H) 2.79-2.86 (m, 4H) 3.18-3.23 (m, 4H) 3.47-3.54 (m, 2H) 3.63-3.76 (m, 1H) 3.79-3.86 (m, 2H) 4.11 (s, 2H) 4.48 (q, J=7.15 Hz, 2H) 6.11 (d, J=2.07 Hz, 1H) 6.24 (dd, J=9.15, 2.19 Hz, 1H) 6.97-7.07 (m, 3H) 7.55 (dd, J=8.66, 1.59 Hz, 1H) 7.67 (d, J=0.73 Hz, 1H) 7.80 (d, J=9.02 Hz, 1H) 8.07 (d, J=8.66 Hz, 1H) 8.24 (d, J=7.56 Hz, 1H) 10.65 (br. s., 1H)

Preparation of 1-(acetyloxy)ethyl 4-[4-{[5-(3,5-difluorobenzyl)-1H-indazol-3-yl]carbamoyl}-3-(tetrahydro-2H-pyran-4-ylamino)phenyl]piperazine-1-carboxylate To a solution of N-[5-(3,5-Difluoro-benzyl)-1H-indazol-3-yl]-4-piperazin-1-yl-2-(tetrahydro-pyran-4-ylamino)-benzamide in chloroform (5.0 mL), cooled to 0° C. under nitrogen, 1,8-bis(dimethylamino)naphtalene (21.4 mg, 0.1 mmol) and (1-chloroethyl)chloroformate (0.011 mL, 14.3 mg, 0.1 mmol) were added. After stirring for 2 hours at room temperature the mixture was diluted with dichloromethane (30 mL), washed with saturated sodium hydrogencarbonate solution (3 mL), brine (3×5 mL), dried over sodium sulphate and evaporated to dryness. The crude was dissolved in glacial acetic acid (2.0 mL), mercury (II) acetate (31.9 mg, 0.1 mmol) was added and the mixture was stirred at room temperature for 1.5 hours. After removing the solvent, the crude was taken up with dichloromethane, washed with saturated sodium hydrogencarbonate solution (3×3 mL), brine (3×5 mL), dried over sodium sulphate and evaporated to dryness to yield 50 mg of yellowish foam that was purified by flash chromatography on silica gel eluting with ethyl acetate and a 0.5% of aq. 33% NH$_4$OH affording 35 mg of the title compound.

1H-NMR (400 MHz), δ (ppm, DMSO-d$_6$): 1.29-1.42 (m, 2H) 1.46 (d, J=5.49 Hz, 3H) 1.90-1.98 (m, 2H) 2.03-2.06 (m, 3H) 3.30-3.50 (m, 8H) 3.45-3.52 (m, 2H) 3.64-3.74 (m, 1H) 3.79-3.86 (m, 2H) 4.05 (s, 2H) 6.16 (d, J=2.07 Hz, 1H) 6.25 (dd, J=9.02, 2.07 Hz, 1H) 6.67-6.73 (m, 1H) 6.94-7.05 (m, 3H) 7.26 (dd, J=8.66, 1.59 Hz, 1H) 7.41 (d, J=8.66 Hz, 1H) 7.49 (s, 1H) 7.82 (d, J=9.02 Hz, 1H) 8.30 (d, J=7.68 Hz, 1H) 10.11 (s, 1H) 12.64 (s, 1H)

Preparation of ethyl 5-(3,5-difluorobenzyl)-3-({[4-(4-methylpiperazin-1-yl)-2-(tetrahydro-2H-pyran-4-ylamino)phenyl]carbonyl}amino)-1H-indazole-1-carboxylate [(XXVII), R1=R2=R3=H, R=3,5-difluorophenyl, Ar=4-(4-methylpiperazin-1-yl)-2-(tetrahydro-2H-pyran-4-ylamino)phenyl, PG=ethoxycarbonyl] cpd. 140

To a solution of N-[5-(3,5-difluoro-benzyl)-1H-indazol-3-yl]-4-(4-methyl-piperazin-1-yl)-2-(tetrahydro-pyran-4-ylamino)-benzamide (200 mg, 0.356 mmol) in anhydrous tetrahydrofurane (9 mL) maintained at −50° C. under nitrogen atmosphere a 1M solution of LiHMSD in anhydrous tetrahydrofurane (0.374 mL) was added. After stirring at that temperature for 5 minutes ethyl chloroformate (0.036 mL, 0.374 mmol) was added. After 1 hour at −50° C. the reaction was completed. Reaction mixture was diluted with water/EtOAc, washed with brine, dried over sodium sulphate and evaporated to dryness. The crude was purified by flash chromatography on silica gel eluting with DCM/ethanol 100:5, affording 140 mg (62% yield) of the title compound.

1H-NMR (400 MHz), δ (ppm, DMSO-d$_6$): 1.39 (t, J=7.07 Hz, 3H) 2.25 (br. s., 3H) 2.46 (br. s., 4H) 3.50 (ddd, J=11.83, 10.06, 2.26 Hz, 1H) 3.66-3.75 (m, 1H) 3.81 (dt, J=11.61, 3.76 Hz, 2H) 4.10 (s, 2H) 4.47 (q, J=7.15 Hz, 2H) 6.13 (d, J=1.95 Hz, 1H) 6.25 (dd, J=9.08, 2.13 Hz, 1H) 7.54 (dd, J=8.66, 1.59 Hz, 1H) 7.66 (dd, J=1.46, 0.73 Hz, 1H) 7.80 (d, J=9.15 Hz, 1H) 8.07 (d, J=8.66 Hz, 1H) 8.24 (d, J=7.68 Hz, 1H) 10.65 (s, 1H)

Operating in a way analogous to that described above, the following compounds were obtained:

2-methoxyethyl 5-(3,5-difluorobenzyl)-3-({[4-(4-methylpiperazin-1-yl)-2-(tetrahydro-2H-pyran-4-ylamino)phenyl]carbonyl}amino)-1H-indazole-1-carboxylate 1H-NMR (400 MHz), δ (ppm, DMSO-d$_6$): 1.30-1.43 (m, 2H) 1.90-2.00 (m, 2H) 2.26 (br. s., 3H) 2.47 (br. s., 4H) 3.27-3.33 (m, 7H) 3.46-3.55 (m, 2H) 3.67-3.74 (m, 3H) 3.79-3.85 (m, 2H) 4.11 (s, 2H) 4.54-4.59 (m, 2H) 6.14 (d, J=1.71 Hz, 1H) 6.26 (dd, J=9.02, 2.19 Hz, 1H) 6.97-7.09 (m, 3H) 7.56 (dd, J=8.72, 1.52 Hz, 1H) 7.67 (d, J=0.85 Hz, 1H) 7.81 (d, J=9.15 Hz, 1H) 8.07 (d, J=8.54 Hz, 1H) 8.25 (d, J=7.56 Hz, 1H) 10.68 (s, 1H)

ethyl 5-(3,5-difluorobenzyl)-3-[({4-[4-(ethoxycarbonyl)piperazin-1-yl]-2-(tetrahydro-2H-pyran-4-ylamino)phenyl}carbonyl)amino]-1H-indazole-1-carboxylate 1H-NMR (400 MHz), δ (ppm, DMSO-d$_6$): 1.22 (t, J=7.07 Hz, 3H) 1.30-1.38 (m, 2H) 1.40 (t, J=7.07 Hz, 3H) 1.90-2.00 (m, 2H) 3.48-3.54 (m, 2H) 3.71 (d, 1H) 3.78-3.86 (m, 2H) 4.05-4.10 (m, 2H) 4.11 (s, 2H) 4.48 (q, J=7.03 Hz, 2H) 6.15 (d, J=2.07 Hz, 1H) 6.26 (dd, J=9.15, 2.19 Hz, 1H) 6.95-7.07 (m, 2H) 7.55 (dd, J=8.66, 1.59 Hz, 1H) 7.67 (d, J=0.85 Hz, 1H) 7.83 (d, J=9.15 Hz, 1H) 8.08 (d, J=8.78 Hz, 1H) 8.25 (d, J=7.80 Hz, 1H) 10.68 (s, 1H)

Example 21

Preparation of 4-fluoro-2-nitro-benzoic acid tert-butyl ester

A solution of 4-fluoro-2-nitro benzoic acid (10 g, 54 mmol), (Boc)$_2$O (2 eq., 23.6 g, 108 mmol) and 4-(N,N- dimethylamino)pyridine (0.3 eq., 1.98 g, 16.2 mmol) in tert-butanol (100 mL) and dichloromethane (100 mL) was stirred at room temperature for 20 hours. The reaction mixture was then diluted with ethyl acetate (500 mL), washed with 1N HCl (500 mL), water (500 mL), brine (500 mL), dried over sodium sulfate and evaporated to dryness. The title compound was obtained as pale yellow oil (quantitative) and it was used in the next step without any further purification.

1H-NMR (400 MHz), δ (ppm, DMSO-$d_6$): 8.04 (dd, J=8.47, 2.50 Hz, 1H) 7.95 (dd, J=8.66, 5.37 Hz, 1H) 7.71 (ddd, J=8.66, 8.17, 2.56 Hz, 1H) 1.51 (s, 9H).

Preparation of 4-(4-methyl-piperazin-1-yl)-2-nitro-benzoic acid tert-butyl ester A solution of 4-fluoro-2-nitro-benzoic acid tert-butyl ester (13 g, 54 mmol) and N-methylpiperazine (17 mL) was stirred at room temperature for 6 hours. The reaction mixture was then diluted with water (800 mL) and maintained under magnetic stirring for 20 hours. The resulting solid was filtered, washed thoroughly with water and dried under vacuum at 40° C. The title compound was obtained as yellow solid (16.4 g, 94% yield) and it was used in the next step without any further purification.

1H-NMR (400 MHz), δ (ppm, DMSO-$d_6$): 7.69 (d, J=8.90 Hz, 1H) 7.29 (d, J=2.56 Hz, 1H), 7.15 (dd, J1=8.90 Hz, J2=2.56 Hz, 1H), 3.37 (m, 4H), 2.44 (m, 4H), 1.46 (s, 9H).

Operating in an analogous way, the following compounds were obtained:

4-[(2-Dimethylamino-ethyl)-methyl-amino]-2-nitro-benzoic acid tert-butyl ester

1H-NMR (400 MHz), δ (ppm, DMSO-$d_6$): 7.67 (d, J=8.9 Hz, 1H), 6.98 (d, J=2.6 Hz, 1H), 6.89 (dd, J1=8.9 Hz, J2=2.6 Hz, 1H), 3.54 (m, 2H), 3.02 (s, 3H), 2.40 (m, 2H), 2.19 (s, 6H), 1.46 (s, 9H).

4-(4-Dimethylamino-piperidin-1-yl)-2-nitro-benzoic acid tert-butyl ester

1H-NMR (400 MHz), δ (ppm, DMSO-$d_6$): 7.67 (d, J=9.0 Hz, 1H), 7.26 (d, J=2.6 Hz, 1H), 7.13 (dd, J1=9.0 Hz, J2=2.6 Hz, 1H), 3.96 (m, 2H), 2.93 (m, 2H), 2.36 (m, 1H), 2.20 (s, 6H), 1.82 (m, 2H), 1.46 (s, 9H), 1.40 (m, 2H).

4-[(3-Dimethylamino-propyl)-methyl-amino]-2-nitro-benzoic acid tert-butyl ester

1H-NMR (400 MHz), δ (ppm, DMSO-$d_6$): 7.67 (d, J=9.0 Hz, 1H), 7.02 (d, J=2.6 Hz, 1H), 6.90 (dd, J1=9.0 Hz, J2=2.6 Hz, 1H), 3.46 (m, 2H), 3.00 (s, 3H), 2.22 (m, 2H), 2.14 (s, 6H), 1.65 (m, 2H), 1.45 (s, 9H).

tert-butyl 4-(4-methyl-1,4-diazepan-1-yl)-2-nitrobenzoate

1H-NMR (400 MHz), δ (ppm, DMSO-$d_6$): 1.44 (s, 9H) 1.85 (m, 2H) 2.25 (s, 3H) 2.43 (m, 2H) 2.60 (m, 21) 3.51 (t, 2H) 3.60 (t, 2H) 6.91 (dd, J1=9.02 Hz, J2=2.66 Hz, 1H) 7.02 (d, J=2.56 Hz, 1H) 7.64 (d, J=8.90 Hz, 1H) tert-butyl 2-nitro-4-(piperazin-1-yl)benzoate 1H-NMR (400 MHz), δ (ppm, DMSO-$d_6$): 1.46 (m, 9H) 2.81 (m, 4H) 3.33 (m, 4H) 7.12 (dd, J1=8.90 Hz, J2=2.56 Hz, 1H) 7.25 (d, J=2.56 Hz, 1H) 7.65 (d, J=8.90 Hz, 1H)

tert-butyl 2-nitro-4-[(2S)-2-(pyrrolidin-1-ylmethyl)pyrrolidin-1-yl]benzoate

ESI(+) MS: m/z 376 (MH$^+$).

Preparation of 2-amino-4-(4-methyl-piperazin-1-yl)-benzoic acid tert-butyl ester A mixture of 4-(4-methyl-piperazin-1-yl)-2-nitro-benzoic acid tert-butyl ester (13.3 g, 41.5 mmol) cyclohexene (45 mL), ethanol (300 mL) and 10% Pd/C (0.4 g) was stirred at 80° C. for 7 hours. More 10% Pd/C was added (0.9 g) and the mixture stirred at 80° C. for additional 4 hours. The reaction mixture was filtered over a celite pad washing thoroughly with ethanol and the filtrate was evaporated to dryness affording the title compound as a pale yellow solid (11.5 g, 95% yield).

1H-NMR (400 MHz), δ (ppm, DMSO-$d_6$): 7.47 (d, J=9.0 Hz, 1H), 6.40 (bs, 2H), 6.18 (dd, J1=9.0 Hz, J2=2.4 Hz, 1H), 6.11 (d, J=2.4 Hz, 1H), 3.16 (m, 4H), 2.41 (m, 4H), 2.21 (s, 3H), 1.49 (s, 9H).

Operating in an analogous way, the following compounds were obtained:

2-Amino-4-[(2-dimethylamino-ethyl)-methyl-amino]-benzoic acid tert-butyl ester

ESI(+) MS: m/z 294 (MH$^+$).

2-Amino-4-[(3-dimethylamino-propyl)-methyl-amino]-benzoic acid tert-butyl ester

1H-NMR (400 MHz), δ (ppm, DMSO-$d_6$): 7.45 (d, J=9.0 Hz, 1H), 6.36 (bs, 2H), 5.99 (dd, J1=9.0 Hz, J2=2.6 Hz, 1H), 5.86 (d, J=2.6 Hz, 1H), 3.31 (m, 2H), 2.87 (s, 3H), 2.22 (m, 2H), 2.15 (s, 6H), 1.62 (m, 2H), 1.48 (s, 9H).

tert-butyl 2-amino-4-[4-(trifluoroacetyl)piperazin-1-yl]benzoate

1H-NMR (400 MHz), δ (ppm, DMSO-$d_6$): 1.51 (s, 9H) 3.28-3.35 (m, 4H) 3.66-3.74 (m, 4H) 6.15 (d, J=2.44 Hz, 1H) 6.21 (dd, J=9.14, 2.44 Hz, 1H) 6.47 (br. s., 2H) 7.50-7.53 (m, 1H)

tert-butyl 2-amino-4-[4-(dimethylamino)piperidin-1-yl]benzoate

1H-NMR (400 MHz), δ (ppm, DMSO-$d_6$): 1.31-1.45 (m, 2H) 1.49-1.52 (m, 9H) 1.75-1.81 (m, 2H) 2.17 (s, 6H) 2.20-2.30 (m, 1H) 2.69-2.79 (m, 2H) 3.71-3.80 (m, 2H) 6.12 (d, J=2.44 Hz, 1H) 6.18 (dd, J=9.14, 2.44 Hz, 1H) 6.39 (s, 2H) 7.46 (d, J=9.02 Hz, 1H)

tert-butyl 2-amino-4-(4-methyl-1,4-diazepan-1-yl)benzoate

ESI(+) MS: m/z 306 (MH$^+$).

tert-butyl 2-amino-4-[(2S)-2-(pyrrolidin-1-ylmethyl)pyrrolidin-1-yl]benzoate

ESI(+) MS: m/z 346 (MH$^+$).

tert-butyl 2-amino-4-(morpholin-4-yl)benzoate

ESI(+) MS: m/z 279 (MH$^+$).

Preparation of 4-(4-methyl-piperazin-1-yl)-2-tetrahydro-pyran-4-ylamino)-benzoic acid tert-butyl ester To a solution of 2-amino-4-(4-methyl-piperazin-1-yl)-benzoic acid tert-butyl ester (11.5 g, 39.5 mmol) in dichloromethane (340 mL) were added tetrahydro-pyran-4-one (4.5 mL, 49.3 mmol), trifluoroacetic acid (8.2 mL) and tetramethylammonium triacetoxyborohydride (15.57 g, 59.2 mmol). The mixture was stirred at room temperature for 2 hours then washed with 0.5N hydrochloric acid, with 0.5N NaOH and with a saturated solution of NaHCO$_3$. The organic layer was dried over sodium sulfate and evaporated to dryness affording the title compound as a pale yellow solid (13.3 g, 90% yield).

1H-NMR (400 MHz), δ (ppm, DMSO-d$_6$): 7.72 (d, J=7.7 Hz, 1H), 7.58 (d, J=9.1 Hz, 1H), 6.20 (dd, J1=9.1 Hz, J2=2.2 Hz, 1H), 6.08 (d, J=2.2 Hz, 1H), 3.85 (m, 2H), 3.70 (m, 1H), 3.50 (m, 2H), 3.27 (m, 4H), 2.47 (m, 4H), 2.26 (bt, 3H), 1.96 (m, 2H), 1.51 (s, 9H), 1.39 (m, 2H).

Operating in an analogous way, the following compounds were obtained:

4-[(2-Dimethylamino-ethyl)-methyl-amino]-2-(tetrahydro-pyran-4-ylamino)-benzoic acid tert-butyl ester ESI(+) MS: m/z 378 (MH$^+$).

4-[(3-Dimethylamino-propyl)-methyl-amino]-2-(tetrahydro-pyran-4-ylamino)-benzoic acid tert-butyl ester 1H-NMR (400 MHz), δ (ppm, DMSO-d$_6$): 7.70 (bd, J=7.4 Hz, 1H), 7.54 (d, J=9.0 Hz, 1H), 5.99 (dd, J1=9.0 Hz, J2=2.3 Hz, 1H), 5.79 (d, J=2.3 Hz, 1H), 3.86 (m, 2H), 3.62 (m, 1H), 3.47 (m, 2H), 3.36 (m, 2H), 2.93 (s, 3H), 2.28 (m, 2H), 2.18 (bs, 6H), 1.97 (m, 2H), 1.64 (m, 2H), 1.49 (s, 9H), 1.39 (m, 2H).

tert-butyl 2-(tetrahydro-2H-pyran-4-ylamino)-4-[4-(trifluoroacetyl)piperazin-1-yl]benzoate 1H-NMR (400 MHz), δ (ppm, DMSO-d$_6$): 1.33-1.45 (m, 2H) 1.51 (s, 9H) 1.92-2.00 (m, 2H) 3.36-3.42 (m, 4H) 3.50 (td, J=11.18, 2.13 Hz, 2H) 3.70 (d, J=3.05 Hz, 5H) 3.82-3.89 (m, 2H) 6.10 (d, J=2.32 Hz, 1H) 6.21 (dd, J=9.08, 2.26 Hz, 1H) 7.61 (d, J=9.02 Hz, 1H) 7.73 (d, J=7.68 Hz, 1H)

tert-butyl 4-[4-(dimethylamino)piperidin-1-yl]-2-(tetrahydro-2H-pyran-1-ylamino)benzoate ESI(+) MS: m/z 404 (MH$^+$).

tert-butyl 4-(4-methyl-1,4-diazepan-1-yl)-2-(tetrahydro-2H-pyran-4-ylamino)benzoate ESI(+) MS: m/z 390 (MH$^+$).

tert-butyl 4-[(2S)-2-(pyrrolidin-1-ylmethyl)pyrrolidin-1-yl]-2-(tetrahydro-2H-pyran-4-ylamino)benzoate ESI(+) MS: m/z 430 (MH$^+$).

tert-butyl 2-(cyclohexylamino)-4-(4-methylpiperazin-1-yl)benzoate

ESI(+) MS: m/z 374 (MH$^+$).

tert-butyl 2-[(1,3-dimethoxypropan-2-yl)amino]-4-(4-methylpiperazin-1-yl)benzoate ESI(+) MS: m/z 394 (MH$^+$).

tert-butyl 2-(benzylamino)-4-(4-methylpiperazin-1-yl)benzoate

ESI(+) MS: m/z 382 (MH$^+$).

tert-butyl 4-(4-methylpiperazin-1-yl)-2-{[cis-4-(trifluoromethyl)cyclohexyl]amino}benzoate 1H-NMR (400 MHz), δ (ppm, DMSO-d$_6$): 1.40-1.50 (m, 2H) 1.51 (s, 9H) 1.57-1.69 (m, 2H) 1.70-1.78 (m, 2H) 1.87 (d, J=14.27 Hz, 2H) 2.24 (s, 3H) 2.32-2.39 (m, 1H) 2.40-2.48 (m, 4H) 3.27 (br. s., 4H) 3.83-3.94 (m, 1H) 6.05 (d, J=1.95 Hz, 1H) 6.20 (dd, J=9.21, 2.26 Hz, 1H) 7.57 (d, J=9.02 Hz, 1H) 8.04 (d, J=8.05 Hz, 1H)

tert-butyl 4-(4-methylpiperazin-1-yl)-2-{[trans-4-(trifluoromethyl)cyclohexyl]amino}benzoate 1H-NMR (400 MHz), δ (ppm, DMSO-d$_6$): 1.18-1.31 (m, 2H) 1.44-1.57 (m, 2H) 1.50 (s, 9H) 1.87-1.94 (m, 2H) 2.07-2.13 (m, 2H) 2.25 (s, 3H) 2.28-2.38 (m, 1H) 2.44 (br. s., 4H) 3.26 (br. s., 4H) 3.40-3.53 (m, 1H) 6.07 (d, J=2.07 Hz, 1H) 6.18 (dd, J=9.08, 2.26 Hz, 1H) 7.54-7.58 (m, 1H) 7.62 (d, J=7.93 Hz, 1H)

tert-butyl 4-(4-methylpiperazin-1-yl)-2-({cis-4-[(phenylcarbonyl)oxy]cyclohexyl}amino)benzoate ESI(+) MS: m/z 494 (MH$^+$).

tert-butyl 4-(4-methylpiperazin-1-yl)-2-({trans-4-[(phenylcarbonyl)oxy]cyclohexyl}amino)benzoate ESI(+) MS: m/z 494 (MH$^+$).

tert-butyl 2-[(1-methylpiperidin-4-yl)amino]benzoate

ESI(+) MS: m/z 291 (MH$^+$).

tert-butyl 2-[(1-methylpiperidin-4-yl)amino]-4-(morpholin-4-yl)benzoate

ESI(+) MS: m/z 376 (MH$^+$).

Preparation of 4-(4-methyl-piperazin-1-yl)-2-[(tetrahydro-pyran-4-yl)-(2,2,2-trifluoro-acetyl)-amino]-benzoic acid tert-butyl ester To a solution of 4-(4-methyl-piperazin-1-yl)-2-(tetrahydro-pyran-4-ylamino)-benzoic acid tert-butyl ester (13.3 g, 35.4 mmol) in dry dichloromethane (350 mL), under argon, at 0° C., were added triethylamine (7.5 mL, 53.1 mmol) and trifluoroacetic anhydride (6.5 mL, 46.1 mmol). The mixture was stirred at 0° C. for 20 minutes, then water (350 mL) was dropped. The phases were separated and the organic phase washed with brine, dried over sodium sulfate and evaporated to dryness. The crude residue was purified by chromatography on silica gel using dichloromethane/ethanol 95:5 as the eluant, affording 12.1 g of the title compound as a pale yellow solid (73% yield).

1H-NMR (400 MHz), δ (ppm, DMSO-$d_6$): 7.83 (d, J=9.0 Hz, 1H), 7.06 (dd, J1=9.0 Hz, J2=2.5 Hz, 1H), 6.82 (J=2.5 Hz, 1H), 4.48 (m, 1H), 3.85 (m, 2H), 3.5-3.3 (m, 6H), 2.49 (m, 4H), 2.26 (bs, 3H), 2.0 (m, 1H), 1.59 (m, 1H), 1.51 (m, 1H), 1.46 (s, 9H), 1.03 (m, 1H).

Operating in an analogous way, the following compounds were obtained:

4-[(2-Dimethylamino-ethyl)-methyl-amino]-2-[(tetrahydro-pyran-4-yl)-(2,2,2-trifluoro-acetyl)-amino]-benzoic acid tert-butyl ester 1H-NMR (400 MHz), δ (ppm, DMSO-$d_6$): 7.80 (d, J=9.1 Hz, 1H), 6.79 (dd, J1=9.1 Hz, J2=2.6 Hz, 1H), 6.51 (d, J=2.6 Hz, 1H), 4.48 (m, 1H), 3.86 (m, 1H), 3.79 (m, 1H), 3.52 (m, 2H), 3.41-3.25 (m, 2H), 3.00 (s, 3H), 2.5-2.35 (m, 2H), 2.21 (s, 6H), 1.98 (m, 1H), 1.64-1.45 (m, 3H), 1.44 (s, 9H).

4-[(3-Dimethylamino-propyl)-methyl-amino]-2-[(tetrahydro-pyran-4-yl)-(2,2,2-trifluoro-acetyl)-amino]-benzoic acid tert-butyl ester 1H-NMR (400 MHz), δ (ppm, DMSO-$d_6$): 7.79 (d, J=9.1 Hz, 1H), 6.79 (dd, J1=9.1 Hz, J2=2.6 Hz, 1H), 6.52 (d, J=2.6 Hz, 1H), 4.48 (m, 1H), 3.87 (m, 1H), 3.79 (m, 1H), 3.51-3.32 (m, 4H), 2.98 (s, 3H), 2.22 (m, 2H), 2.12 (s, 6H), 1.99 (m, 1H), 1.70-1.46 (m, 4H), 1.44 (s, 9H), 1.03 (m, 1H).

tert-butyl 2-[tetrahydro-2H-pyran-4-yl(trifluoroacetyl)amino]-4-[4-(trifluoroacetyl)piperazin-1-yl]benzoate 1H-NMR (400 MHz), δ (ppm, DMSO-$d_6$): 1.45 (s, 9H) 1.60 (qd, J=12.21, 4.94 Hz, 2H) 3.73 (t, J=5.12 Hz, 4H) 4.48 (tt, J=11.96, 3.89 Hz, 1H) 6.84 (d, J=2.56 Hz, 1H) 7.07 (dd, J=8.96, 2.62 Hz, 1H) 7.85 (d, J=9.02 Hz, 1H)

tert-butyl 4-[4-(dimethylamino)piperidin-1-yl]-2-[tetrahydro-2H-pyran-4-yl(trifluoroacetyl)amino]benzoate ESI(+) MS: m/z 500 (MH$^+$).

tert-butyl 4-(4-methyl-1,4-diazepan-1-yl)-2-[tetrahydro-2H-pyran-4-yl(trifluoroacetyl)amino]benzoate ESI(+) MS: m/z 486 (MH$^+$).

tert-butyl 4-[(2S)-2-(pyrrolin-1-ylmethyl)pyrrolin-1-yl]-2-[tetrahydro-2H-pyran-4-yl(trifluoroacetyl)amino]benzoate ESI(+) MS: m/z 526 (MH$^+$).

tert-butyl 2-[cyclohexyl(trifluoroacetyl)amino]-4-(4-methylpiperazin-1-yl)benzoate ESI(+) MS: m/z 470 (MH$^+$).

tert-butyl 2-[(1,3-dimethoxypropan-2-yl)(trifluoroacetyl)amino]-4-(4-methylpiperazin-1-yl)benzoate ESI(+) MS: m/z 490 (MH$^+$).

tert-butyl 2-[benzyl(trifluoroacetyl)amino]-4-(4-methylpiperazin-1-yl)benzoate

ESI(+) MS: m/z 478 (MH$^+$).

tert-butyl 4-(4-methylpiperazin-1-yl)-2-{(trifluoroacetyl)[cis-4-(trifluoromethyl)cyclohexyl]amino}benzoate ESI(+) MS: m/z 538 (MH$^+$).

tert-butyl 4-(4-methylpiperazin-1-yl)-2-{(trifluoroacetyl)[trans-4-(trifluoromethyl)cyclohexyl]amino}benzoate ESI(+) MS: m/z 538 (MH$^+$).

tert-butyl 4-(4-methylpiperazin-1-yl)-2-[{cis-4-[(phenylcarbonyl)oxy]cyclohexyl}(trifluoroacetyl)amino]benzoate ESI(+) MS: m/z 590 (MH$^+$).

tert-butyl 4-(4-methylpiperazin-1-yl)-2-[{trans-4-[(phenylcarbonyl)oxy]cyclohexyl}(trifluoroacetyl)amino]benzoate ESI(+) MS: m/z 590 (MH$^+$).

tert-butyl 2-[(1-methylpiperidin-4-yl)(trifluoroacetyl)amino]benzoate

ESI(+) MS: m/z 387 (MH$^+$).

tert-butyl 2-[(1-methylpiperidin-4-yl)(trifluoroacetyl)amino]-4-(morpholin-4-yl)benzoate ESI(+) MS: m/z 472 (MH$^+$).

tert-butyl 4-(4-methylpiperazin-1-yl)-2-[phenyl(trifluoroacetyl)amino]benzoate

ESI(+) MS: m/z 464 (MH$^+$).

Preparation of 4-(4-methyl-piperazin-1-yl)-2-[(tetrahydro-pyran-4-yl)-(2,2,2-trifluoro-acetyl)-amino]-benzoic acid trifluoroacetate A mixture of 4-(4-methyl-piperazin-1-yl)-2-[(tetrahydro-pyran-4-yl)-(2,2,2-trifluoro-acetyl)-amino]-benzoic acid tert-butyl ester (12.1 g, 25.7 mmol), trifluoroacetic acid (48.5 mL) and dichloromethane (195 mL) was stirred at room temperature for 2 hours. The volatiles were then evaporated, the residue taken up with diethylether and evaporated again. The procedure was repeated for 5 times, then the solid was triturated with diethylether, filtered and dried in oven at 40° C. affording the title compound as a pale brown solid (13.4 g).

1H-NMR (400 MHz), δ (ppm, DMSO-$d_6$): 12.78 (bs, 1H), 9.74 (bs, 1H), 7.93 (d, J=8.8 Hz, 1H), 7.13 (dd, J1=8.8 Hz, J2=2.5 Hz, 1H), 6.98 (d, J=2.5 Hz, 1H), 4.49 (m, 1H), 4.11 (m, 2H), 3.84 (m, 2H), 3.6-3.0 (m, 8H), 2.89 (s, 3H), 1.98 (m, 1H), 1.59 (m, 1H), 1.53 (m, 1H), 1.08 (m, 1H).

Operating in an analogous way, the following compounds were obtained:

4-[(2-Dimethylamino-ethyl)-methyl-amino]-2-[(tetrahydro-pyran-4-yl)-(2,2,2-trifluoro-acetyl)-amino]-benzoic acid trifluoroacetate 1H-NMR (400 MHz), δ (ppm, DMSO-d$_6$): 12.56 (bs, 1H), 9.49 (bs, 1H), 7.88 (d, J=8.9 Hz, 1H), 8.92 (dd, J1=8.9 Hz, J2=2.6 Hz, 1H), 6.63 (d, J=2.6 Hz, 1H), 4.49 (m, 1H), 3.9-3.2 (m, 8H), 3.02 (s, 3H), 2.85 (s, 6H), 1.98 (m, 1H), 1.62-1.49 (m, 2H), 1.08 (m, 1H).

4-[(3-Dimethylamino-propyl)-methyl-amino]-2-[(tetrahydro-pyran-4-yl)-(2,2,2-trifluoro-acetyl)-amino]-benzoic acid trifluoroacetate ESI(+) MS: m/z 432 (MH$^+$).

2-[tetrahydro-2H-pyran-4-yl(trifluoroacetyl)amino]-4-[4-(trifluoroacetyl)piperazin-1-yl]benzoic acid 1H-NMR (400 MHz), δ (ppm, DMSO-d$_6$): 1.08 (m, J=12.35, 12.24, 12.24, 4.76 Hz, 1H) 1.47-1.55 (m, 1H) 1.56-1.67 (m, 1H) 1.91-2.01 (m, 1H) 3.38-3.53 (m) 3.73 (t, J=5.12 Hz, 4H) 3.78 (dd, J=11.52, 4.45 Hz, 1H) 3.86 (dd, J=11.40, 4.57 Hz, 1H) 4.46 (tt, J=11.87, 3.98 Hz, 1H) 6.85 (d, 1H) 7.06 (dd, J=8.90, 2.68 Hz, 1H) 7.89 (d, J=8.90 Hz, 1H) 12.67 (br. s., 1H)

4-(4-methyl-1,4-diazepan-1-yl)-2-[tetrahydro-2H-pyran-4-yl(trifluoroacetyl)amino]benzoic acid hydrochloride 1H-NMR (400 MHz), δ (ppm, DMSO-d$_6$): 4.42-4.55 (m, 1H) 6.91-6.96 (m, 1H) 7.89 (d, J=9.02 Hz, 1H) 10.14 (br. s., 1H) 12.56 (br. s., 1H)

4-[4-(dimethylamino)piperidin-1-yl]-2-[tetrahydro-2H-pyran-4-yl(trifluoroacetyl)amino]benzoic acid hydrochloride ESI(+) MS: m/z 444 (MH$^+$).

4-[(2S)-2-(pyrrolidin-1-ylmethyl)pyrrolidin-1-yl]-2-[tetrahydro-2H-pyran-4-yl(trifluoroacetyl)amino]benzoic acid hydrochloride ESI(+) MS: m/z 470 (MH$^+$).

2-[cyclohexyl(trifluoroacetyl)amino]-4-(4-methylpiperazin-1-yl)benzoic acid hydrochloride ESI(+) MS: m/z 414 (MH$^+$).

2-[(1,3-dimethoxypropan-2-yl)(trifluoroacetyl)amino]-4-(4-methylpiperazin-1-yl)benzoic acid hydrochloride ESI(+) MS: m/z 434 (MH$^+$).

2-[benzyl(trifluoroacetyl)amino]-4-(4-methylpiperazin-1-yl)benzoic acid hydrochloride ESI(+) MS: m/z 422 (MH$^+$).

4-(4-methylpiperazin-1-yl)-2-{(trifluoroacetyl)[cis-4-(trifluoromethyl)cyclohexyl]amino}benzoic acid trifluoroacetate 1H-NMR (400 MHz), δ (ppm, DMSO-d$_6$): 1.09-1.90 (4m, 8H) 2.36-2.46 (m, 1H) 2.88 (br. s., 3H) 2.99-3.25 (m, 4H) 3.49 (br. s., 2H) 3.96-4.16 (m, 2H) 4.27-4.37 (m, 1H) 7.00 (d, J=2.32 Hz, 1H) 7.12 (dd, J=8.90, 2.44 Hz, 1H) 7.92 (d, J=8.90 Hz, 1H) 9.67 (br. s., 1H) 12.80 (s, 1H)

4-(4-methylpiperazin-1-yl)-2-{(trifluoroacetyl)[trans-4-(trifluoromethyl)cyclohexyl]amino}benzoic acid trifluoroacetate ESI(+) MS: m/z 482 (MH$^+$).

4-(4-methylpiperazin-1-yl)-2-[{cis-4-[(phenylcarbonyl)oxy]cyclohexyl}(trifluoroacetyl)amino]benzoic acid hydrochloride ESI(+) MS: m/z 534 (MH$^+$).

4-(4-methylpiperazin-1-yl)-2-[{trans-4-[(phenylcarbonyl)oxy]cyclohexyl}(trifluoroacetyl)amino]benzoic acid hydrochloride ESI(+) MS: m/z 534 (MH$^+$).

2-[(1-methylpiperidin-4-yl)(trifluoroacetyl)amino]benzoic acid hydrochloride ESI(+) MS: m/z 331 (MH$^+$).

2-[(1-methylpiperidin-4-yl)(trifluoroacetyl)amino]-4-(morpholin-4-yl)benzoic acid hydrochloride ESI(+) MS: m/z 416 (MH$^+$).

4-(4-methylpiperazin-1-yl)-2-[phenyl(trifluoroacetyl)amino]benzoic acid hydrochloride ESI(+) MS: m/z 408 (MH$^+$).

Example 22

Preparation of 2,4-difluoro-benzoic acid tert-butyl ester

To a solution of 2,4-difluorobenzoic acid (5 g, 31.62 mmol) in a mixture of dichloromethane (100 mL) and t-BuOH (50 mL) were added (Boc)$_2$O (13.8 g, 63.24 mmol) and N,N-dimethylaminopyridine (1.16 g, 9.49 mmol). The solution was stirred at room temperature for 24 hours then diluted with dichloromethane and washed twice with 1N HCl, NaHCO$_3$ satured solution, water (3 times) and brine. The organic phase was dried over sodium sulfate, filtered and evaporated to give the title compound (5.70 g, 84%) as yellowish oil.

1H-NMR (400 MHz), δ (ppm, DMSO-d$_6$): 7.91 (m, 1H), 7.36 (m, 1H), 7.20 (m, 1H), 1.53 (s, 9H).

Preparation of 4-fluoro-2-((S)-2-methoxy-1-methyl-ethylamino)-benzoic acid tert-butyl ester A mixture of 2,4-difluoro-benzoic acid tert-butyl ester (30 g, 140.05 mmol) and (S)-2-methoxy-1-methyl-ethylamine (100 mL) was stirred at 65° C. for 2 days. A satured solution of NaHCO$_3$ was added and the mixture was extracted with dichloromethane (3 times). The organic phase was washed twice with water then with brine, dried over sodium sulfate filtered and evaporated to dryness to obtain a crude, which was purified by column chromatography on silica gel (exane/ethyl acetate 9:1). The title compound (33.38 g, 84%) was obtained as oil.

1H-NMR (400 MHz), δ (ppm, DMSO-$d_6$): 7.87 (d, J=7.80 Hz, 1H), 7.80 (t, J=7.19 Hz, 1H), 6.60 (dd, J1=13.05 Hz, J2=2.44 Hz, 1H), 6.36 (m, 1H), 3.80 (m, 1H), 3.40 (d, J=4.76 Hz, 2H), 3.30 (s, 3H), 1.53 (s, 9H), 1.17 (d, J=6.58 Hz, 3H).

Operating in a way analogous to that described above, the following compounds were obtained:

4-Fluoro-2-((R)-2-methoxy-1-methyl-ethylamino)-benzoic add tert-butyl ester

1H-NMR (400 MHz), δ (ppm, DMSO-$d_6$): 7.87 (d, J=7.80 Hz, 1H), 7.80 (t, J=7.19 Hz, 1H), 6.60 (dd, J1=13.05 Hz, J2=2.44 Hz, 1H), 6.36 (m, 1H), 3.80 (m, 1H), 3.40 (d, J=4.76 Hz, 2H), 3.30 (s, 3H), 1.53 (s, 9H), 1.17 (d, J=6.58 Hz, 3H).

4-Fluoro-2-(2-methoxy-ethylamino)-benzoic acid tert-butyl ester

1H-NMR (400 MHz), δ (ppm, DMSO-$d_6$): 7.89 (t, J=5.00 Hz, 1H), 7.80 (t, J=7.07 Hz, 1H), 6.56 (dd, J1=12.80 Hz, J2=2.56 Hz, 1H), 6.37 (m, 1H), 3.55 (t, J=5.37 Hz, 2H), 3.33 (m, 2H), 3.29 (s, 3H), 1.53 (s, 9H).

tert-butyl 4-fluoro-2-[(3-methoxypropyl)amino]benzoate

1H-NMR (400 MHz), δ (ppm, DMSO-$d_6$): 1.51-1.53 (m, 9H) 1.76-1.85 (m, 2H) 3.18-3.23 (m, 2H) 3.25 (s, 3H) 3.38-3.44 (m, 2H) 6.32-6.39 (m, 1H) 6.49 (dd, J=12.80, 2.44 Hz, 1H) 7.79 (dd, J=8.90, 7.07 Hz, 1H) 7.88 (br. s., 1H)

tert-butyl 4-fluoro-2-[(2-fluoroethyl)amino]benzoate

1H-NMR (400 MHz), δ (ppm, DMSO-$d_6$): 1.54 (s, 9H) 3.50 (dd, J=27.00, 5.00 Hz, 2H) 4.63 (dt, J=47.56, 4.88 Hz, 2H) 6.41 (td, J=8.57, 2.50 Hz, 1H) 6.62 (dd, J=12.62, 2.38 Hz, 1H) 7.82 (dd, J=8.90, 7.07 Hz, 1H) 8.05 (t, J=4.82 Hz, 1H)

tert-butyl 4-fluoro-2-[(3-fluoropropyl)amino]benzoate

ESI(+) MS: m/z 272 (MH+).

tert-butyl 4-fluoro-2-[(1-methoxy-2-methylpropan-2-yl)amino]benzoate

1H-NMR (400 MHz), δ (ppm, DMSO-$d_6$): 1.34 (s, 6H) 1.53 (s, 9H) 3.33 (br. s., 3H) 3.40 (s, 2H) 6.31-6.39 (m, 1H) 6.67 (dd, J=13.29, 2.44 Hz, 1H) 7.82 (dd, J=8.84, 7.38 Hz, 1H) 8.22 (s, 1H)

Preparation of 4-fluoro-2-[((S)-2-methoxy-1-methyl-ethyl)-(2,2,2-trifluoro-acetyl)-amino]-benzoic acid tert-butyl ester A solution of 4-fluoro-2-((S)-2-methoxy-1-methyl-ethyl-amino)-benzoic acid tert-butyl ester (1.54 g, 5.44 mmol) in dichloromethane (30 mL) was cooled to 0°-5° C. Triethylamine (1.11 mL, 8.16 mmol) and trifluoroacetic anhydride (1.15 mL, 8.16 mmol) were added. After 3 hours at 0°-5° C. the mixture was washed with $NaHCO_3$ saturated solution, water and brine. The organic layer was dried over sodium sulfate, filtered and evaporated to give the title compound as yellowish oil (2 g, 99%).

1H-NMR (400 MHz), δ (ppm, DMSO-$d_6$): (mixture of tautomers) 8.07 (m, 1H), 7.53 (m, 1H), 7.29 (dd, J1=9.39 Hz, J2=2.68 Hz, 1H), 4.83 (m, 1H), 3.44 (m, 1H), 3.30 (s, 3H), 1.49 (s, 9H), 0.86 (d, 3H).

Operating in a way analogous to that described above, the following compounds were obtained:

4-Fluoro-2-[((R)-2-methoxy-1-methyl-ethyl)-(2,2,2-trifluoro-acetyl)-amino]-benzoic acid tert-butyl ester 1H-NMR (400 MHz), δ (ppm, DMSO-$d_6$): (mixture of tautomers) 8.07 (m, 1H), 7.53 (m, 1H), 7.29 (dd, J1=9.39 Hz, J2=2.68 Hz, 1H), 4.83 (m, 1H), 3.44 (m, 1H), 3.30 (s, 3H), 1.49 (s, 9H), 0.86 (d, 3H).

4-Fluoro-2-[(2-methoxy-ethyl)-(2,2,2-trifluoro-acetyl)-amino]-benzoic acid tert-butyl ester 1H-NMR (400 MHz), δ (ppm, DMSO-$d_6$): 8.07 (m, 1H), 7.50 (m, 1H), 7.41 (dd, J1=9.39 Hz, J2=2.56 Hz, 1H), 4.28 (m, 1H), 3.55 (m, 1H), 3.46 (m, 1H), 3.38 (m, 1H), 3.18 (s, 3H), 1.49 (s, 9H).

tert-butyl 4-fluoro-2-[(3-methoxypropyl)trifluoroacetyl)amino]benzoate

1H-NMR (400 MHz), δ (ppm, DMSO-$d_6$): 1.48 (s, 9H) 1.68-1.83 (m, 2H) 3.18 (s, 3H) 3.21-3.29 (m, 1H) 3.33-3.38 (m, 2H) 4.06-4.18 (m, 1H) 7.46-7.52 (m, 1H) 7.56 (dd, J=9.27, 2.68 Hz, 1H) 8.06 (dd, J=8.84, 6.40 Hz, 1H)

tert-butyl 4-fluoro-2-[(2-fluoroethyl)(trifluoroacetyl)amino]benzoate

1H-NMR (400 MHz), δ (ppm, DMSO-$d_6$): 1.50 (s, 9H) 3.54-3.74 (m, 1H) 4.26-4.45 (m, 1H) 4.50-4.80 (m, 2H) 7.47-7.55 (m, 2H) 8.08 (dd, J=9.27, 6.46 Hz, 1H)

tert-butyl 4-fluoro-2-[(3-fluoropropyl)(trifluoroacetyl)amino]benzoate

1H-NMR (400 MHz), δ (ppm, DMSO-$d_6$): 1.50 (s, 9H) 1.80-2.07 (m, 2H) 3.26-3.42 (m, 1H) 4.21 (ddd, J=13.78, 8.90, 6.71 Hz, 1H) 4.42-4.60 (m, 2H) 7.48-7.55 (m, 1H) 7.60 (dd, J=9.27, 2.44 Hz, 1H) 8.09 (dd, J=8.84, 6.40 Hz, 1H)

tert-butyl 4-fluoro-2-[(1-methoxy-2-methylpropan-2-yl)(trifluoroacetyl)amino]benzoate 1H-NMR (400 MHz), δ (ppm, DMSO-$d_6$): 1.09 (s, 3H) 1.47 (s, 3H) 1.52 (s, 9H) 3.17 (s, 3H) 3.19 (d, J=9.75 Hz, 1H) 3.80 (d, J=9.63 Hz, 1H) 7.36 (dd, J=9.45, 2.62 Hz, 1H) 7.47 (td, J=8.41, 2.68 Hz, 1H) 7.93 (dd, J=8.78, 6.46 Hz, 1H)

Preparation of 2-[((S)-2-methoxy-1-methyl-ethyl)-(2,2,2-trifluoro-acetyl)-amino]-4-(4-methyl-piperazin-1-yl)-benzoic acid tert-butyl ester A solution of 4-fluoro-2-[((S)-2-methoxy-1-methyl-ethyl)-(2,2,2-trifluoro-acetyl)-amino]-benzoic acid tert-butyl ester (2 g, 5.28 mmol) and N-methylpiperazine (5.86 mL, 52.8 mmol) in tetrahydrofuran (20 mL) was stirred at 60° C. for 7 days. The solution was then evaporated, $NaHCO_3$ saturated solution was added and the mixture extracted with dichloromethane (3 times). The organic layer was washed with water, brine, dried over sodium sulfate filtered and evaporated to obtain a crude, which was purified by column chromatography on silica gel (dichloromethane-methanol 93:7). The title compound (2.04 g, 84%) was obtained as yellowish solid.

1H-NMR (400 MHz), δ (ppm, DMSO-$d_6$): (mixture of tautomers) 7.81 (d, J=9.15 Hz, 1H), 7.06 (dd, J1=9.15 Hz, J2=2.56 Hz, 1H), 6.79 (d, J=2.56 Hz, 1H), 4.80 (m, 1H), 3.39 (m, 2H), 3.34-3.28 (m, 7H), 2.55 (m, 4H), 2.29 (bs, 3H), 1.46 (s, 9H), 0.83 (d, 3H).

Operating in a way analogous to that described above, the following compounds were obtained:

2-[((R)-2-Methoxy-1-methyl-ethyl)-(2,2,2-trifluoro-acetyl)-amino]-4-(4-methyl-piperazin-1-yl)-benzoic acid tert-butyl ester 1H-NMR (400 MHz), δ (ppm, DMSO-$d_6$): (mixture of tautomers) 7.81 (d, J=9.15 Hz, 1H), 7.06 (dd, J1=9.15 Hz, J2=2.56 Hz, 1H), 6.79 (d, J=2.56 Hz, 1H), 4.80 (m, 1H), 3.39 (m, 2H), 3.34-3.28 (m, 7H), 2.55 (m, 4H), 2.29 (bs, 3H), 1.46 (s, 9H), 0.83 (d, 3H).

2-[(2-Methoxy-ethyl)-(2,2,2-trifluoro-acetyl-amino]-4-(4-methyl-piperazin-1-yl)-benzoic acid tert-butyl ester 1H-NMR (400 MHz), δ (ppm, DMSO-$d_6$): (mixture of tautomers) 7.83 (d, J=9.02 Hz, 1H), 7.05 (dd, J1=9.02 Hz, J2=2.68 Hz, 1H), 6.86 (d, J=2.68 Hz, 1H), 4.31 (m, 1H), 3.55 (m, 1H), 3.40 (m, 1H), 3.32 (m, 4H), 3.25 (m, 1H), 3.21 (s, 1H), 2.44 (t, J=5.12 Hz, 4H), 2.22 (bs, 3H), 1.46 (s, 9H).

4-[(2-Dimethylamino-ethyl)-methyl-amino]-2-[(2-methoxy-ethyl)-(2,2,2-trifluoro-acetyl)-amino]-benzoic acid tert-butyl ester 1H-NMR (400 MHz), δ (ppm, DMSO-$d_6$): 7.81 (d, J=8.9 Hz, 1H), 6.78 (dd, J1=8.9 Hz, J2=2.8 Hz, 1H), 6.60 (d, J=2.8 Hz, 1H), 4.40-4.31 (m, 1H), 3.59-3.39 (m, 4H), 3.23 (s, 3H), 3.22-3.15 (m, 1H), 3.00 (s, 3H), 2.40 (m, 2H), 2.19 (bs, 6H), 1.46 (s, 9H).

tert-butyl 2-[(3-methoxypropyl)(trifluoroacetyl)amino]-4-(4-methylpiperazin-1-yl)benzoate 1H-NMR (400 MHz), δ (ppm, DMSO-$d_6$): 1.45 (s, 9H) 1.68-1.84 (m, 2H) 2.26 (br. s., 3H) 2.44-2.60 (m, 4H) 3.12-3.23 (m, 1H) 3.18 (s, 3H) 3.25-3.48 (m, 6H) 4.08 (d, J=22.92 Hz, 1H) 6.92 (d, J=2.19 Hz, 1H) 7.02 (d, J=9.02, 2.44 Hz, 1H) 7.81 (d, J=9.02 Hz, 1H)

tert-butyl 2-[(2-fluoroethyl)(trifluoroacetyl)amino]-4-(4-methylpiperazin-1-yl)benzoate 1H-NMR (400 MHz), δ (ppm, DMSO-$d_6$): 1.46 (s, 9H) 2.22 (s, 3H) 2.43 (t, J=4.76 Hz, 4H) 3.25-3.31 (m, 4H) 3.41-3.59 (m, 1H) 4.27-4.46 (m, 1H) 4.46-4.78 (m, 2H) 6.90 (d, J=2.07 Hz, 1H) 7.05 (dd, J=9.02, 2.68 Hz, 1H) 7.83 (d, J=9.02 Hz, 1H)

tert-butyl 2-[(3-fluoropropyl)(trifluoroacetyl)amino]-4-(4-methylpiperazin-1-yl)benzoate 1H-NMR (400 MHz), δ (ppm, DMSO-$d_6$): 1.46 (s, 9H) 1.80-2.05 (m, 2H) 2.25 (br. s., 3H) 2.46 (br. s., 4H) 3.18-3.37 (m, 5H) 4.10-4.24 (m, 1H) 4.38-4.60 (m, 2H) 6.95 (d, J=2.44 Hz, 1H) 7.04 (dd, J=8.96, 2.62 Hz, 1H) 7.84 (d, J=9.02 Hz, 1H)

tert-butyl 2-[(1-methoxy-2-methylpropan-2-yl)(trifluoroacetyl)amino]-4-(4-methylpiperazin-1-yl)benzoate 1H-NMR (400 MHz), δ (ppm, DMSO-$d_6$): 1.04 (s, 3H) 1.45 (s, 3H) 1.49 (s, 9H) 2.22 (s, 3H) 2.44 (t, J=4.94 Hz, 4H) 3.20 (d, J=9.51 Hz, 1H) 3.23 (s, 3H) 3.25-3.30 (m, 4H) 3.93 (d, J=9.51 Hz, 1H) 6.89 (d, J=2.32 Hz, 1H) 7.00 (dd, J=8.96, 2.62 Hz, 1H) 7.70 (d, J=8.90 Hz, 1H)

Preparation of 2-[((S)-2-methoxy-1-methyl-ethyl)-(2,2,2-trifluoro-acetyl)-amino]-4-(4-methyl-piperazin-1-yl)-benzoic acid trifluoroacetate To a solution of 2-[((S)-2-methoxy-1-methyl-ethyl)-(2,2,2-trifluoro-acetyl)-amino]-4-(4-methyl-piperazin-1-yl)-benzoic acid tert-butyl ester (2.03 g, 4.42 mmol) in dichloromethane (15 mL) trifluoroacetic acid (3.4 mL, 44.2 mmol) was added. The mixture was stirred at room temperature for 15 hours then the solution was evaporated to dryness affording the title compound as oil that was used for the next step without any further purification.

1H-NMR (400 MHz), δ (ppm, DMSO-$d_6$): (mixture of tautomers) 12.10 (bs, 1H), 9.74 (bs, 1H), 7.90 (d, J=8.90 Hz, 1H), 7.15 (dd, J1=8.90 Hz, J2=2.56 Hz, 1H), 6.89 (d, J=2.56 Hz, 1H), 4.76 (m, 1H), 4.03 (t, 2H), 3.55 (m, 2H), 3.37 (m, 2H), 3.30 (s, 3H), 3.18 (m, 2H), 2.88 (bs, 3H), 0.85 (d, 3H).

Operating in a way analogous to that described above, the following compounds were obtained:

2-[((R)-2-Methoxy-1-methyl-ethyl)-(2,2,2-trifluoro-acetyl)-amino]-4-(4-methyl-piperazin-1-yl)-benzoic acid trifluoroacetate 1H-NMR (400 MHz), δ (ppm, DMSO-$d_6$): (mixture of tautomers) 12.10 (bs, 1H), 9.74 (bs, 1H), 7.90 (d, J=8.90 Hz, 1H), 7.15 (dd, J1=8.90 Hz, J2=2.56 Hz, 1H), 6.89 (d, J=2.56 Hz, 1H), 4.76 (m, 1H), 4.03 (t, 2H), 3.55 (m, 2H), 3.37 (m, 2H), 3.30 (s, 3H), 3.18 (m, 2H), 2.88 (bs, 3H), 0.85 (d, 3H).

2-[(2-Methoxy-ethyl)-(2,2,2-trifluoro-acetyl)-amino]-4-(4-methyl-piperazin-1-yl)-benzoic acid trifluoroacetate 1H-NMR (400 MHz), δ (ppm, DMSO-$d_6$): (mixture of tautomers) 12.76 (bs, 1H), 9.73 (bs, 1H), 7.91 (d, J=8.78 Hz, 1H), 7.10 (dd, J1=8.78 Hz, J2=2.68 Hz, 1H), 7.01 (d, J=2.68 Hz, 1H), 4.15 (m, 1H), 4.04 (m, 2H), 3.54 (m, 2H), 3.42 (m, 2H), 3.38 (m, 2H), 3.33 (m, 2H), 3.19 (s, 3H), 3.14 (m, 2H), 2.86 (bs, 3H).

4-[(2-Dimethylamino-ethyl)-methyl-amino]-2-[(2-methoxy-ethyl)-(2,2,2-trifluoro-acetyl)-amino]-benzoic acid hydrochloride 1H-NMR (400 MHz), δ (ppm, DMSO-$d_6$): 12.59 (bs, 1H), 10.00 (bs, 1H), 7.88 (d, J=8.9 Hz, 1H), 6.92 (dd, J1=8.9 Hz, J2=2.8 Hz, 1H), 6.74 (8d, J=2.8 Hz, 1H), 4.18 (m, 1H), 3.79 (m, 2H), 3.56 (m, 1H), 3.47-3.36 (m, 2H), 3.24 (m, 2H), 3.21 (s, 3H), 3.01 (s, 3H), 2.84 (bd, 6H).

2-[(3-methoxypropyl)(trifluoroacetyl)amino]-4-(4-methylpiperazin-1-yl)benzoic acid hydrochloride 1H-NMR (400 MHz), δ (ppm, DMSO-$d_6$): 1.70-1.81 (m, 2H) 2.84 (d, J=2.93 Hz, 3H) 3.06-3.40 (m, 7H) 3.19 (s, 3H)

3.52 (d, J=10.36 Hz, 2H) 3.96-4.06 (m, 1H) 4.09 (br. s., 2H) 7.07 (d, J=2.56 Hz, 1H) 7.10 (dd, J=8.90, 2.68 Hz, 1H) 7.93 (d, J=8.78 Hz, 1H) 10.27 (br. s., 1H) 12.76 (br. s., 1H)

2-[(2-fluoroethyl)(trifluoroacetyl)amino]-4-(4-methylpiperazin-1-yl)benzoic acid hydrochloride 1H-NMR (400 MHz), δ (ppm, DMSO-$d_6$): 2.84 (br. s., 3H) 3.04-3.30 (m, 4H) 3.47-3.56 (m, 2H) 3.54-3.67 (m, 1H) 4.06 (d, 2H) 4.18-4.40 (m, 1H) 4.46-4.79 (m, 2H) 7.07 (d, J=2.19 Hz, 1H) 7.12 (dd, J=8.96, 2.62 Hz, 1H) 7.91-7.97 (m, 1H) 10.33 (br. s., 1H) 12.83 (br. s., 1H)

2-[(3-fluoropropyl)(trifluoroacetyl)amino]-4-(4-methylpiperazin-1-yl)benzoic acid trifluoroacetate 1H-NMR (400 MHz), δ (ppm, DMSO-$d_6$): 1.82-2.02 (m, 2H) 2.87 (s, 3H) 3.14 (m, 5H) 3.44 (m) 4.09 (m, 3H) 4.40-4.59 (m, 2H) 7.08-7.15 (m, 2H) 7.95 (d, J=9.15 Hz, 1H) 9.72 (br. s., 1H) 12.81 (br. s., 1H)

2-[(1-methoxy-2-methylpropan-2-yl)(trifluoroacetyl)amino]-4-(4-methylpiperazin-1-yl)benzoic acid hydrochloride 1H-NMR (400 MHz), δ (ppm, DMSO-$d_6$): 1.07 (s, 3H) 1.43 (s, 3H) 2.84 (s, 3H) 3.10-3.38 (m, 5H) 3.25 (s, 3H) 3.47-3.57 (m, 2H) 3.92 (d, J=9.51 Hz, 1H) 3.95-4.02 (m, 2H) 7.00 (d, J=2.44 Hz, 1H) 7.10 (dd, J=8.84, 2.50 Hz, 1H) 7.84 (d, J=8.78 Hz, 1H) 10.25 (br. s., 1H) 12.77 (br. s., 1H)

Example 23

Preparation of tert-butyl 4-(4-acetylpiperazin-1-yl)-2-nitrobenzoate

To a solution of tert-butyl 2-amino-4-(piperazin-1-yl)benzoate (7.6 g, 24.7 mmol) in dichloromethane (120 mL), triethylamine (13.46 mL, 98.7 mmol) and trifluoroacetic anhydride (6.87 mL, 49.35 mmol) were added. After 1 hour the volatiles were evaporated and the crude was purified by column chromatography (EtOAc/hexane 3:7) affording 9.46 gr (yield 95%) of the title compound.
ESI(+) MS: m/z 404 (MH$^+$).

Example 24

Preparation of tert-butyl 4-(4-methylpiperazin-1-yl)-2-(phenylamino)benzoate

In a dry Schlenk tube under argon atmosphere tert-butyl 2-amino-4-(4-methylpiperazin-1-yl)benzoate (800 mg, 2.745 mmol) was dissolved in dry toluene (14 mL). Argon was bubbled through the mixture for a few minutes before adding bromobenzene (0.32 mL, 3.02 mmol, 1.1 eq), Cs$_2$CO$_3$ (1.34 g, 4.118 mmol, 1.5 eq), Pd(OAc)$_2$ (16 mg, 0.069 mmol, 2.5 mol %) and Rac-BINAP (88 mg, 0.137 mmol, 5 mol %). The mixture was then stirred at 100° C. for 21 hours. The mixture was allowed to cool to room temperature and diluted with dichloromethane. Salts were filtered over a Celite pad and the filtrate was concentrated under reduced pressure. The crude product was purified by chromatography over silica gel (DCM/EtOH/NH$_3$ 7% in methanol 95:5:0.5) to give 1.13 g of title compound (quant. yield) as off-white solid
1H-NMR (400 MHz), δ (ppm, DMSO-$d_6$): 1.54 (s, 9H) 2.21 (s, 3H) 2.37-2.43 (m, 4H) 3.15-3.20 (m, 4H) 6.43 (dd, J=9.15, 2.44 Hz, 1H) 6.60 (d, J=2.44 Hz, 1H) 7.02-7.07 (m, 1H) 7.23-7.27 (m, 2H) 7.33-7.38 (m, 2H) 7.69 (d, J=9.02 Hz, 1H) 9.50 (s, 1H)

Example 25

Preparation of methyl 2-methoxy-4-(4-methylpiperazin-1-yl)benzoate

Methyl 2-methoxy-4-fluoro-benzoate (1.6 gr, 9.7 mmol), K$_2$CO$_3$ (1.3 gr, 9.7 mmol) and N-methyl piperazine (1.3 mL, 11.7 mmol) were heated at 100° C. in DMSO (5 mL) for 20 hours. Reaction mixture was diluted with DCM and washed with water. Organic phase was dried over sodium sulfate and evaporated to dryness. Column chromatography purification on silica gel using dichloromethane/methanol 95:5 as the eluant, afforded 1.7 g (yield 66%) of the title compound.
1H-NMR (400 MHz), δ (ppm, DMSO-$d_6$): 2.25 (s, 3H) 2.45 (br. s., 4H) 3.26-3.34 (m, 4H) 3.70 (s, 3H) 3.80 (s, 3H) 6.49 (d, J=2.32 Hz, 1H) 6.53 (dd, J=8.84, 2.38 Hz, 1H) 7.61 (d, J=8.78 Hz, 1H)

Preparation of 2-methoxy-4-(4-methylpiperazin-1-yl)benzoic acid hydrochloride

Methyl 2-methoxy-4-(4-methylpiperazin-1-yl)benzoate (1.9 gr, 7.2 mmol) was heated at 40° C. in a mixture 2N NaOH (10 mL) and MeOH (10 mL) for 2 hours. MeOH was evaporated and the aqueous layer was acidified to pH=6 with 25% HCl and extracted with n-BuOH. Organic phase was dried over sodium sulfate and evaporated to dryness. affording 1.0 g (yield 61%) of the title compound.
1H-NMR (400 MHz), δ (ppm, DMSO-$d_6$): 2.82 (br. s., 3H) 2.99-3.31 (m, 4H) 3.47 (br. s., 2H) 3.83 (s, 3H) 4.04 (br. s., 2H) 6.61 (d, 1H) 6.59 (s, 1H) 7.66 (d, J=8.78 Hz, 1H) 10.49 (br. s., 1H) 11.91 (br. s., 1H)

Example 26

Preparation of 4-(4-methyl-piperazin-1-yl)-2-nitro benzoic acid hydrochloride

A mixture of 4-(4-methyl-piperazin-1-yl)-2-nitro-benzoic acid tert-butyl ester (16.4 g, 51 mmol) and 37% HCl (100 mL) in 1,4-dioxane (200 mL) was stirred at room temperature for 4 hours. The resulting solid was filtered, washed thoroughly with 1,4-dioxane and dried under vacuum at 45° C. The title compound was obtained as a pale yellow solid (13.45 g, 87.5% yield), and it was used in the next step without any further purification.
1H-NMR (400 MHz), δ (ppm, DMSO-$d_6$): 10.27 (bs, 1H), 7.81 (d, J=8.90 Hz, 1H), 7.40 (d, J=2.69 Hz, 1H), 7.24 (dd, J1=8.90 Hz, J2=2.69 Hz, 1H), 4.13 (bs, 2H), 3.55-3.06 (bs, 6H), 2.83 (s, 3H).
Operating in an analogous way, the following compounds were obtained:

4-[(3-Dimethylamino-propyl)-methyl-amino]-2-nitro-benzoic acid hydrochloride

1H-NMR (400 MHz), δ (ppm, DMSO-$d_6$): 13.07 (bs, 1H), 9.72 (bs, 1H), 7.76 (d, J=9.0 Hz, 1H), 7.03 (d, J=2.6 Hz, 1H), 6.93 (dd, J1=9.0 Hz, J2=2.6 Hz, 1H), 3.51 (m, 2H), 3.08 (m, 2H), 3.03 (s, 3H), 2.77 (s, 6H), 1.90 (m, 2H).

What is claimed is:

1. A method for treating a patient having a cancer selected from the group consisting of ovarian cancer, lung cancer, colon cancer and lymphoma, comprising administering to said patient an effective amount of N-[5-(3,5-difluorobenzyl)-1H-indazol-3-yl]-4-(4-methyl-piperazin-1-yl)-2-(tetrahydro-pyran-4-ylamino)-benzamide, or a pharmaceutically acceptable salt thereof, and an effective amount of at least one second therapeutic agent, wherein said at least one second therapeutic agent is selected from antihormonal agents, antiestrogens, antiandrogens, aromatase inhibitors, topoisomerase I inhibitors, topoisomerase II inhibitors, agents that target microtubules, platin-based agents, alkylating agents, DNA damaging agents, DNA intercalating agents, antineoplastic antimetabolites, kinase inhibitors, anti-angiogenic agents, inhibitors of kinesins, therapeutic monoclonal antibodies, mTOR inhibitors, histone deacetylase inhibitors, farnesyl transferase inhibitors, and hypoxic response inhibitors.

2. The method of claim 1, wherein said cancer is lung cancer.

3. The method of claim 1, wherein said cancer is colon cancer.

4. The method of claim 1, wherein said cancer is lymphoma.

5. The method of claim 1, wherein said cancer is ovarian cancer.

6. The method of claim 1, wherein said N-[5-(3,5-difluorobenzyl)-1H-indazol-3-yl]-4-(4-methyl-piperazin-1-yl)-2-(tetrahydro-pyran-4-ylamino)-benzamide, or a pharmaceutically acceptable salt thereof, and said at least one second therapeutic agent are simultaneously administered to said patient.

7. The method of claim 1, wherein said N-[5-(3,5-difluorobenzyl)-1H-indazol-3-yl]-4-(4-methyl- piperazin-1-yl)-2-(tetrahydro-pyran-4-ylamino)-benzamide, or a pharmaceutically acceptable salt thereof, and said at least one second therapeutic agent are sequentially administered to said patient.

8. The method according to claim 1, wherein said at least one second therapeutic agent is selected from kinase inhibitors.

9. The method according to claim 8, wherein said cancer is selected from lung cancer, colon cancer, ovarian cancer, and lymphoma.

10. The method of claim 9, wherein said cancer is lung cancer.

11. The method of claim 9, wherein said cancer is colon cancer.

12. The method of claim 9, wherein said cancer is ovarian cancer.

13. The method of claim 9, wherein said cancer is lymphoma.

* * * * *

SEQUENCE LISTING

```
<160> NUMBER OF SEQ ID NOS: 5

<210> SEQ ID NO 1
<211> LENGTH: 76
<212> TYPE: DNA
<213> ORGANISM: Artificial
<220> FEATURE:
<223> OTHER INFORMATION: Forward primer

<400> SEQUENCE: 1
ggggacaagt ttgtacaaaa aagcaggctt actggaagtt ctgttccagg ggccccgccg    60
gaagcaccag gagctg                                                   76

<210> SEQ ID NO 2
<211> LENGTH: 57
<212> TYPE: DNA
<213> ORGANISM: Artificial
<220> FEATURE:
<223> OTHER INFORMATION: Reverse primer

<400> SEQUENCE: 2
ggggaccact ttgtacaaga aagctgggtt tcagggccca ggctggttca tgctatt      57

<210> SEQ ID NO 3
<211> LENGTH: 33
<212> TYPE: DNA
<213> ORGANISM: Artificial
<220> FEATURE:
<223> OTHER INFORMATION: Forward primer

<400> SEQUENCE: 3
ctcggatcca gaaagagaaa taacagcagg ctg                                33

<210> SEQ ID NO 4
<211> LENGTH: 36
<212> TYPE: DNA
<213> ORGANISM: Artificial
<220> FEATURE:
<223> OTHER INFORMATION: Reverse primer

<400> SEQUENCE: 4
ctcggatcct cagcaggtcg aagactgggg cagcgg                             36

<210> SEQ ID NO 5
<211> LENGTH: 19
<212> TYPE: PRT
<213> ORGANISM: Artificial
<220> FEATURE:
<223> OTHER INFORMATION: Carboxy-terminally biotinylated peptide enzyme
      substrate

<400> SEQUENCE: 5

Lys Lys Lys Ser Pro Gly Glu Tyr Val Asn Ile Glu Phe Gly Gly Gly
1               5                   10                  15

Gly Gly Lys
```